US008080388B2

(12) United States Patent
Subjeck et al.

(10) Patent No.: US 8,080,388 B2

(45) Date of Patent: Dec. 20, 2011

(54) STRESS PROTEIN COMPOSITIONS AND METHODS FOR PREVENTION AND TREATMENT OF CANCER AND INFECTIOUS DISEASE

(75) Inventors: John R. Subjeck, Williamsville, NY (US); Robert A. Henderson, Seattle, WA (US); Elizabeth A. Repasky, Williamsville, NY (US); Latif Kazim, Amherst, NY (US); Xiang-Yang Wang, Buffalo, NY (US); Masoud H. Manjili, Williamsville, NY (US)

(73) Assignee: Health Research, Inc., Buffalo, NY (US)

(*) Notice: Subject to any disclaimer, the term of this patent is extended or adjusted under 35 U.S.C. 154(b) by 320 days.

(21) Appl. No.: 12/127,499

(22) Filed: May 27, 2008

(65) Prior Publication Data

US 2008/0293103 A1 Nov. 27, 2008

Related U.S. Application Data

(63) Continuation of application No. 10/161,028, filed on Jun. 3, 2002, now Pat. No. 7,378,096, which is a continuation-in-part of application No. 09/872,186, filed on Jun. 1, 2001, now abandoned, which is a continuation-in-part of application No. 09/676,340, filed on Sep. 29, 2000, now Pat. No. 6,984,384.

(60) Provisional application No. 60/156,821, filed on Sep. 30, 1999, provisional application No. 60/163,138, filed on Nov. 2, 1999, provisional application No. 60/215,497, filed on Jun. 30, 2000.

(51) Int. Cl.

| | |
|---|---|
| *C12N 15/09* | (2006.01) |
| *C12N 5/07* | (2010.01) |
| *C12N 5/09* | (2010.01) |
| *C12N 5/10* | (2006.01) |

(52) U.S. Cl. ..................... 435/69.1; 435/252.3; 435/325

(58) Field of Classification Search ........................ None
See application file for complete search history.

(56) References Cited

U.S. PATENT DOCUMENTS

| | | | | |
|---|---|---|---|---|
| 5,066,579 | A | 11/1991 | Reyes | |
| 5,550,214 | A | 8/1996 | Eberlein | |
| 5,726,023 | A | 3/1998 | Cheever | |
| 5,747,332 | A | 5/1998 | Wallen et al. | |
| 5,830,464 | A | 11/1998 | Srivastava | |
| 5,858,192 | A | 1/1999 | Becker | |
| 5,888,795 | A | 3/1999 | Hamilton | |
| 5,891,432 | A | 4/1999 | Hoo | |
| 5,961,979 | A | 10/1999 | Srivastava | |
| 5,981,706 | A | 11/1999 | Wallen et al. | |
| 6,015,567 | A | 1/2000 | Hudziak | |
| 6,017,540 | A | 1/2000 | Srivastava et al. | |
| 6,066,716 | A | 5/2000 | Wallen et al. | |
| 6,156,302 | A | 12/2000 | Srivastava | |
| 6,159,708 | A * | 12/2000 | Sogo et al. | 435/69.1 |
| 6,162,436 | A | 12/2000 | Srivastava | |
| 6,187,312 | B1 | 2/2001 | Srivastava | |
| 6,268,213 | B1 | 7/2001 | Samulski | |
| 6,322,790 | B1 | 11/2001 | Srivastava | |
| 6,331,299 | B1 | 12/2001 | Rothman et al. | |
| 6,403,095 | B1 | 6/2002 | Srivastava et al. | |
| 6,451,316 | B1 | 9/2002 | Srivastava et al. | |
| 7,157,089 | B1 | 1/2007 | Mizzen | |

FOREIGN PATENT DOCUMENTS

| | | |
|---|---|---|
| WO | WO 94/29459 | 12/1994 |
| WO | WO 95/24923 | 9/1995 |
| WO | WO 96/10411 | 4/1996 |
| WO | WO 97/06821 | 2/1997 |
| WO | WO 97/10000 | 3/1997 |
| WO | WO 97/10001 | 3/1997 |
| WO | WO 97/10002 | 3/1997 |
| WO | WO 97/26910 | 7/1997 |
| WO | WO 98/23735 | 4/1998 |
| WO | WO 98/34641 | 8/1998 |
| WO | WO 98/35705 | 8/1998 |
| WO | WO 99/07860 | 2/1999 |
| WO | WO 00/44899 | 8/2000 |

OTHER PUBLICATIONS

Oh et al (Journal of Biological chemistry, 1997, vol. 272, pp. 31636-31640).*

Ikeda et al (BBRC, 1997, vol. 230, pp. 94-99).*

Lin et al (Molecular biology of the Cell, 1993, vol. 4, pp. 1109-1119).*

Santos et al (American Journal of Physiology, 1998, vol. 274, pp. F1054-F1061).*

Lee-Yoon et al (Journal of Biological Chemistry, 1995, vol. 270, pp. 15725-15733).*

Bachman et al., Journal of Immunology, 2005,vol. 175, pp. 4677-4685.

Bargmann, C.I. et al., "The neu oncogene encodes an epidermal growth factor receptor-related protein," 1986, Nature, 319(16):226-230. Bargmann, C.I. et al., "Multiple Independent Activations of the neu Oncogene by a Point Mutation Altering the Transmembrane Domain of p185," 1986, Cell, 45:649-657.

Blachere, N.E. et al., "Heat Shock Protein-Based Cancer Vaccines and Related Thoughts on Immunogenicity of Human Tumors," Cancer Biology, 1995, vol. 6: 349-355.

Blachere, N.E. et al., "Heat Shock Protein Vaccines Against Cancer," Jnl. of Immunology, 1993, 14(4): 352-356.

Boorstein, W.R. et al., "Molecular Evolution of the HSP70 Multigene Family," 1994, J Mol Evol, 38:1-17.

Chen, C-H. et al., "Enhancement of DNA Vaccine Potency by Linkage of Antigen Gene to an HSP70 Gene," Cancer Research, 2000, vol. 60: 1035-1042.

(Continued)

*Primary Examiner* — Karen Canella

(74) *Attorney, Agent, or Firm* — Karen S. Canady; canady + Lortz LLP

(57) ABSTRACT

Pharmaceutical compositions comprising a stress protein complex and related molecules encoding or cells presenting such a complex are provided. The stress protein complex comprises an hsp110 or grp170 polypeptide complexed with an immunogenic polypeptide. The immunogenic polypeptide of the stress protein complex can be associated with a cancer or an infectious disease. Preferred immunogenic polypeptides include gp100, her2/neu ECD-PD, ICD and *M. tuberculosis* antigens. The pharmaceutical compositions of the invention can be used for the treatment or prevention of cancer or infectious disease.

30 Claims, 45 Drawing Sheets

OTHER PUBLICATIONS

X. Chen et al., "The 170 kCa glucose regulated stress protein is a large HSP70-HSP110-like protein of the endoplasmic reticulum," XP-002060249, 1996, FEBS Letters, 380:68-72.
Coler, R.N., "Molecular Cloning and Immunologic Reactivity of a Novel Low Molecular Mass Antigen of *Mycobacterium tuberculosis*[1]," 1998, J Immun, 161(5):2356-2364.
Dillon, D.C. et al., "Molecular Characterization and Human T-Cell Responses to a Member of a Novel *Mycobacterium tuberculosis*," XP-002143391, 1999, Infection and Immunity, pp. 2941-2950.
Disis, M.L. et al., "Generation of Immunity to the HER-2/*neu* Oncogenic Protein in Patients with Breast and Ovarian Cancer Using a Peptide-based Vaccine," Clinical Cancer Research, 1999, vol. 5: 1289-1297.
Dong et al., Pharmaceutical Biotechnology, 1995, vol. 6, pp. 625-643.
Donnelly et al., "DNA Vaccines: Progress and Challenges", Journal & Immunology, 2005, 175(2):633-639.
Efferson et al., Anticancer Research, 2005, vol. 25, pp. 715-724.
Hatayama, T. et al., "Association of HSP105 with HSC70 in High Molecular Mass Complexes in Mouse FM3A Cells," 1998, Biochem and Biophys Res Comm, 248:395-401.
Heath, Pharmaceutical Biotechnology, 1995, vol. 6, pp. 645-658.
Janetzki, S. et al., "Immunization of Cancer Patients with Autologous Cancer-Derived Heat Shock Protein gp96 Preparations: A Pilot Study," International Jnl. of Cancer, 2000, vol. 88: 232-238.
Jindal, S., "Heat shock proteins: applications in health and disease,"1996, TB Tech, vol. 14, p. 5.
Li, Z., "Priming of T Cells by Heat Shock Protein-Peptide Complexes as the Basis of Tumor Vaccines," Seminars in Immunology, 1997, vol. 9: 315-322.
Manjili, M.H. et al., "Development of a Recombinant HSP110-HER-2/*neu* Vaccine Using the Chaperoning Properties of HSP110," Cancer Research, 2002, vol. 62: 1737-1742.
Manjili, M.H et al., "Immunotherapy of Cancer Using Heat Shock Proteins," Frontiers in Bioscience, 2002, vol. 7: d43-52.
Menoret, A. et al., "Heat-Shock Protein-Based Anticancer Immunotherapy: An Idea Whose Time Has Come," Seminars in Oncology, 1998, 25(6): 654-660.
Moroi, Y. et al., "Induction of Cellular Immunity by Immunization with Novel Hybrid Peptides Complexed to Heat Shock Protein 70," PNAS, 2000, 97(7): 3485-3490.
Mosley, P., "Stress proteins and the immune response", Immunopharmacology, vol. 48, Jul. 2000, pp. 299-302.
Oh, H. et al., "The Chaperoning Activity of hsp110," 1999, J of Biol Chem, 274(22):15712-15718.
Oh, H.J. et al., "hsp110 Protects Heat-denatured Proteins and Confers Cellular Thermoresistance," 1997, J Biol Chem, 272(5):31636-31640.
Palleros, D.R. et al., "hsp70-Protein Complexes," XP-002130137, 1994, 269(18):13107-13114.
Pzepiorka, D. et al., "Heat Shock Protein-Peptide Complexes as Immunotherapy for Human Cancer," Molecular Medicine Today, 1998, 4(11): 478-484.
Rakhmilevich, A.L. et al., "Effective Particle-mediated Vaccination Against Mouse Melanoma by Coadministration of Plasmid DNA Encoding Gp100 and Granulocyte-Macrophage Colony-Stimulating Factor," Cancer Research, 2001, 7: 952-961.
Shyy, T. et al., "Effect of Growth State and Heat Shock on Nucleolar Localization of the 110,000-Da Heat Shock Protein in Mouse Embryo Fibroblasts[1]," 1986, Cancer Research, 46:4738-4745.
Spee, P., "Identification of Novel Peptide Binding Proteins in the Endoplasmic Reticulum: ERp72, Calnexin, and grp 170", Biochemistry, 1999, V. 38, pp. 10559-10566.
Srivastava, P.K., "Purification of Heat Shock Protein-Peptide Complexes for Use in Vaccination Against Cancers and Intracellular Pathogens," Methods: A Companion to Methods in Enzymology, 1997, vol. 12: 165-171.
Subject, J., "The 110 kDa Heat-shock Protein and the 170 kDa Glucose Regulated Protein", 1992, vol. 2, pp. 986-991.
Suzue, K., et al., "Heat shock fusion proteins as vehicles for antigen delivery into the major histocompatibility complex class I presentation pathway," 1997, Proc Natl Acad Sci USA, 94:13146-13151.
Tamura, Y. et al., "Immunotherapy of Tumors with Autologous Tumor-Derived Heat Shock Protein Preparations," Science, 1997, vol. 278: 117-120.
Udono, H. et al., "Generation of Cytotoxic T Lymphocytes by MHC Class I Ligands Fused to Heat Shock Cognate Protein 70," International Immunology, 2001, 13(10): 1233-1242.
Vanaja, D.K. et al., "Tumor Prevention and Antitumor Immunity with Heat Shock Protein 70 Induced by 15-Deoxy-$\Delta^{12,14}$ -prostaglandin $J_2$ in Transgenic Adenocarcinoma of Mouse Prostate Cells," Cancer Research, 2000, vol. 60: 4714-4718.
Vanniaskinkam, et al., "Trichostatin-A enhances adaptive immune responses to DNA vaccination", J. of Clinical Virology, 2006, 36(4):292-297.
Wang, X-Y. et al., "Characterization of Heat Shock Protein 110 and Glucose-Regulated Protein 170 as Cancer Vaccines and the Effect of Fever-Range Hyperthermia on Vaccine Activity," Jnl. of Immunology, 2001, vol. 165, pp. 490-497.
The abstract of Wang et al., FEBS Letters, 1999, vol. 464, pp. 98-102.
Welch, W., et al., "Morphological Study of the Mammalian Stress Response: Characterization . . . Treatment", J. of Cell Biology, 1985, V101, pp. 1198-1211.
The abstract of Wheeler (Salud p'ublica de M'exico, Jul.-Aug. 1997) 39(4):283-7.
Yedavelli, S.P.K. et al., "Preventive and Therapeutic Effect of Tumor Derived Heat Shock Protein, gp96, in an Experimental Prostate Cancer Model," International Jnl. of Molecular Medicine, 1999, 4(3): 243-248.
USPTO Office Action dated Nov. 12, 2010 from U.S. Appl. No. 11/103,222, filed Apr. 11, 2005.

* cited by examiner

FIG. 38A-B

Control
gp100
hsp110
hsp110-gp100
2400
2100
1800
1500
1200
900
600
300
0
Relative tumor volume (mm3)
0 2 4 6 8 10 12 14 16 18 20 22 24
Days after tumor challenge

SEQUENCE LISTING

<160> NUMBER OF SEQ ID NOS: 185

<210> SEQ ID NO 1
<211> LENGTH: 33
<212> TYPE: DNA
<213> ORGANISM: Artificial Sequence
<220> FEATURE:
<223> OTHER INFORMATION: Primer

<400> SEQUENCE: 1
gctagaggat cctgtgcatt gcagtgtgca att 33

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
cagcgcaagc ttactagtcc aggtccatat tga 33

<210> SEQ ID NO 3
<211> LENGTH: 32
<212> TYPE: DNA
<213> ORGANISM: Artificial Sequence
<220> FEATURE:
<223> OTHER INFORMATION: Primer

<400> SEQUENCE: 3
gacgacggat cctctgtcga ggcagacatg ga 32

<210> SEQ ID NO 4
<211> LENGTH: 33
<212> TYPE: DNA
<213> ORGANISM: Artificial Sequence
<220> FEATURE:
<223> OTHER INFORMATION: Primer

<400> SEQUENCE: 4
cagcgcaagc ttactagtcc aggtccatat tga 33

<210> SEQ ID NO 5
<211> LENGTH: 10
<212> TYPE: PRT
<213> ORGANISM: Homo sapiens

<400> SEQUENCE: 5

Val Leu Gln Gly Leu Pro Arg Glu Tyr Val
1 5 10

<210> SEQ ID NO 6
<211> LENGTH: 9
<212> TYPE: PRT
<213> ORGANISM: Homo sapiens

<400> SEQUENCE: 6

Lys Ile Phe Gly Ser Leu Ala Phe Leu
1 5

<210> SEQ ID NO 7
<211> LENGTH: 26
<212> TYPE: DNA
<213> ORGANISM: Artificial Sequence
<220> FEATURE:
<223> OTHER INFORMATION: Primer

<400> SEQUENCE: 7
gcagctacag taaggaggca gaggcc 26

<210> SEQ ID NO 8
<211> LENGTH: 41
<212> TYPE: DNA
<213> ORGANISM: Artificial Sequence
<220> FEATURE:
<223> OTHER INFORMATION: Primer

<400> SEQUENCE: 8
cattgttagc ggccgctcat tacacgtgta gttcatcgtt c 41

<210> SEQ ID NO 9
<211> LENGTH: 27
<212> TYPE: DNA
<213> ORGANISM: Artificial Sequence
<220> FEATURE:

<223> OTHER INFORMATION: Primer

<400> SEQUENCE: 9
gatcccgtgg acgcggtcat taacacc 27

<210> SEQ ID NO 10
<211> LENGTH: 38
<212> TYPE: DNA
<213> ORGANISM: Artificial Sequence
<220> FEATURE:
<223> OTHER INFORMATION: Primer

<400> SEQUENCE: 10
cttacagagc ggccgctcat caatagttgt tgcaggag 38

<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11
gatcccgtgg acgcggtcat taacacc 27

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
ggaatagttg ttgcaggagc cggc 24

<210> SEQ ID NO 13
<211> LENGTH: 29
<212> TYPE: DNA
<213> ORGANISM: Artificial Sequence
<220> FEATURE:
<223> OTHER INFORMATION: Primer

<400> SEQUENCE: 13
cactcggtgg ttgggctaga cgtaggctc 29

<210> SEQ ID NO 14
<211> LENGTH: 37
<212> TYPE: DNA
<213> ORGANISM: Artificial Sequence
<220> FEATURE:
<223> OTHER INFORMATION: Primer

<400> SEQUENCE: 14
cagttgaatt catcacacgt gatccaggtc catgttg 37

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
gatcccgtgg acgcggtcat taacacc 27

<210> SEQ ID NO 16

-continued

<211> LENGTH: 30
<212> TYPE: DNA
<213> ORGANISM: Artificial Sequence
<220> FEATURE:
<223> OTHER INFORMATION: Primer

<400> SEQUENCE: 16
cctagaattc atcaatagtt gttgcaggag 30

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
gtggatttcg gggcgttacc accggag 27

<210> SEQ ID NO 18
<211> LENGTH: 36
<212> TYPE: DNA
<213> ORGANISM: Artificial Sequence
<220> FEATURE:
<223> OTHER INFORMATION: Primer

<400> SEQUENCE: 18
ccgaagaatt ctagaaggca cagcagatct ggatcc 36

<210> SEQ ID NO 19
<211> LENGTH: 3774
<212> TYPE: DNA
<213> ORGANISM: Mycobacterium tuberculosis

<400> SEQUENCE: 19
atgcagcatc accaccatca ccaccactcg gtggttgggc tagacgtagg ctcacagagc 60
tgctacattg cggtggcgcg ggccgggggc atcgagacca tcgccaacga gttcagcgac 120
cgctgcaccc cgtcagtcat atcatttgga tcaaaaaaca gaacaattgg agttgcagcc 180
aaaaaccagc aaatcactca tgcaaacaat acggtctcta gctttaagag atttcatggc 240
agagcattca atgacccctt cattcagaag gaaaaggaga acctgagcta tgatttggtc 300
ccaatgaaaa atggtggcgt gggaataaag gtcatgtaca tggatgaaga acatttcttc 360
agtgtggagc agataacagc catgctgctg actaagttaa aggaaactgc agaaaacaac 420
ctcaagaagc cagtgacaga ctgtgtcatc tcagtcccat ccttcttcac agatgctgag 480
cgaaggtctg tgctggatgc tgcgcagatt gtgggcttga actgcttgcg gctcatgaat 540
gacatgacgg ctgttgcttt gaattatggg atttataagc aagatctccc gaatgccgag 600
gagaagccac gggtggtggt gtttgttgac atgggacact catctttcca agtgtctgcc 660
tgtgctttta acaaaggaaa actgaaggtt ctaggcacag cttttgatcc cttcttagga 720
ggaaagaact ttgatgagaa gctagtagaa catttttgtg ctgaatttaa aaccaagtac 780
aaattggatg caaaatccaa aattcgagcc ctccttcgtc tccatcagga gtgtgaaaag 840
ttgaaaaagc tcatgagttc taacagcacg gacctgccgc tgaacatcga gtgctttatg 900
aatgacaagg atgtctctgg gaagatgaac aggtcacagt ttgaagaact gtgtgctgag 960
ctcctgcaaa aaatagaggt ccccccttcac tcgttgatgg cacagactca gctcaaggct 1020
gaagatgtga gtgccattga gatagtggga ggtgccacaa gaatcccagc tgtgaaagaa 1080
agaattgcca agttctttgg aaaagatgtc agcaccacgc tcaatgcaga cgaagctgtg 1140

-continued

```
gccagaggct gtgcactgca gtgtgcaatt ctttctccgg catttaaagt tagagagttc   1200
tctgtcaccg atgcagttcc ttttccaata tctctggtct ggaaccacga ctcggaagaa   1260
acggaaggtg tgcacgaggt gttcagtcgg aaccatgctg ctcctttctc caaagtgctc   1320
accttcctga gaaggggggcc ctttgagcta gaagctttct attctgaccc tcaaggagtt   1380
ccatatccag aagcaaaaat aggccgtttt gttgttcaga atgtttctgc acagaaagat   1440
ggagagaagt cgagagtgaa ggtcaaagtg cgtgtgaaca cacatggcat cttcaccatc   1500
tccacggctt ccatggtgga gaaggtcccg accgaggaag aggatggctc ctctctcgag   1560
gcagacatgg aatgtccaaa ccagaggcca acagaaagct cggatgtgga taaaaatatc   1620
cagcaagaca acagtgaagc tggaacacag ccccaggtac aaactgatgg tcaacaaacc   1680
tcacagtctc cccttcacc tgaacttacc tcagaagaaa gcaaaacccc agatgctgac   1740
aaagcaaatg aaaagaaagt tgatcagcct ccagaagcca agaaacctaa aataaaggtg   1800
gtaaatgttg agctgcctgt agaagccaac ttggtatggc agttagggag agaccttctt   1860
aacatgtata ttgagacaga gggcaagatg atcatgcaag acaagctgga gaaggagcgg   1920
aacgacgcca agaacgccgt ggaggagtgt gtatatgagt tcagggacaa gctatgtgga   1980
ccatatgaga aattcatatg tgagcaggaa catgagaagt tcttgaggct tctaacagag   2040
acggaagact ggctgtatga ggaaggggag gaccaggcta agcaggcata cattgacaag   2100
ttggaagagc tgatgaaaat gggcactcct gttaaagtca gatttcaaga agctgaggaa   2160
cgaccgaaag tgttggagga gctggggcag cgcctgcagc actatgccaa gattgcagcg   2220
gacttcagag gcaaggatga gaaatacaac cacattgatg aatcagaaat gaagaaggtt   2280
gagaagtctg ttaatgaggt gatggagtgg atgaataatg tcatgaatgc tcaggctaaa   2340
agaagtcttg atcaagaccc tgttgttcga actcatgaaa tcagagcgaa ggtcaaggaa   2400
ttgaacaatg tttgtgaacc tgttgtaact caacccaaac caaaaatcga gtcacctaaa   2460
ctggagagaa ctccaaatgg cccaaatatt gacaagaaag aagatttaga aggcaaaaat   2520
aatcttggtg ctgaagctcc gcatcagaat ggtgaatgcc accctaatga gaagggctct   2580
gtcaacatgg acctggatca cgtggatttc ggggcgttac caccggagat caactccgcg   2640
aggatgtacg ccggcccggg ttcggcctcg ctggtggccg cggctcagat gtgggacagc   2700
gtggcgagtg acctgttttc ggccgcgtcg gcgtttcagt cggtggtctg ggtctgacg   2760
gtggggtcgt ggataggttc gtcggcgggt ctgatggtgg cggcggcctc gccgtatgtg   2820
gcgtggatga gcgtcaccgc ggggcaggcc gagctgaccg ccgcccaggt ccgggttgct   2880
gcggcggcct acgagacggc gtatgggctg acggtgcccc cgccggtgat cgccgagaac   2940
cgtgctgaac tgatgattct gatagcgacc aacctcttgg ggcaaaacac cccggcgatc   3000
gcggtcaacg aggccgaata cggcgagatg tgggcccaag acgccgccgc gatgtttggc   3060
tacgccgcgg cgacggcgac ggcgacggcg acgttgctgc cgttcgagga ggcgccggag   3120
atgaccagcg cgggtgggct cctcgagcag gccgccgcgg tcgaggaggc ctccgacacc   3180
gccgcggcga accagttgat gaacaatgtg ccccaggcgc tgcaacagct ggcccagccc   3240
acgcagggca ccacgccttc ttccaagctg ggtggcctgt ggaagacggt ctcgccgcat   3300
cggtcgccga tcagcaacat ggtgtcgatg gccaacaacc acatgtcgat gaccaactcg   3360
ggtgtgtcga tgaccaacac cttgagctcg atgttgaagg gctttgctcc ggcggcggcc   3420
gcccaggccg tgcaaaccgc ggcgcaaaac ggggtccggg cgatgagctc gctgggcagc   3480
tcgctgggtt cttcgggtct gggcggtggg gtggccgcca acttgggtcg ggcggcctcg   3540
```

-continued gtcggttcgt tgtcggtgcc gcaggcctgg gccgcggcca accaggcagt caccccggcg 3600
gcgcgggcgc tgccgctgac cagcctgacc agcgccgcgg aaagagggcc cgggcagatg 3660
ctgggcgggc tgccggtggg gcagatgggc gccagggccg gtggtgggct cagtggtgtg 3720
ctgcgtgttc cgccgcgacc ctatgtgatg ccgcattctc cggcagccgg ctag 3774

<210> SEQ ID NO 20
<211> LENGTH: 2850
<212> TYPE: DNA
<213> ORGANISM: Mycobacterium tuberculosis

<400> SEQUENCE: 20
atgcagcatc accaccatca ccaccactcg gtggttgggc tagacgtagg ctcacagagc 60
tgctacattg cggtggcgcg ggccgggggc atcgagacca tcgccaacga gttcagcgac 120
cgctgcaccc cgtcagtcat atcatttgga tcaaaaaaca gaacaattgg agttgcagcc 180
aaaaaccagc aaatcactca tgcaaacaat acggtctcta gctttaagag atttcatggc 240
agagcattca atgacccctt cattcagaag gaaaaggaga acctgagcta tgatttggtc 300
ccaatgaaaa atggtggcgt gggaataaag gtcatgtaca tggatgaaga acatttcttc 360
agtgtggagc agataacagc catgctgctg actaagttaa aggaaactgc agaaaacaac 420
ctcaagaagc cagtgacaga ctgtgtcatc tcagtcccat ccttcttcac agatgctgag 480
cgaaggtctg tgctggatgc tgcgcagatt gtgggcttga actgcttgcg gctcatgaat 540
gacatgacgg ctgttgcttt gaattatggg atttataagc aagatctccc gaatgccgag 600
gagaagccac gggtggtggt gtttgttgac atgggacact catctttcca agtgtctgcc 660
tgtgctttta acaaaggaaa actgaaggtt ctaggcacag cttttgatcc cttcttagga 720
ggaaagaact ttgatgagaa gctagtagaa catttttgtg ctgaatttaa aaccaagtac 780
aaattggatg caaaatccaa aattcgagcc ctccttcgtc tccatcagga gtgtgaaaag 840
ttgaaaaagc tcatgagttc taacagcacg gacctgccgc tgaacatcga gtgctttatg 900
aatgacaagg atgtctctgg gaagatgaac aggtcacagt ttgaagaact gtgtgctgag 960
ctcctgcaaa aaatagaggt ccccccttcac tcgttgatgg cacagactca gctcaaggct 1020
gaagatgtga gtgccattga gatagtggga ggtgccacaa gaatcccagc tgtgaaagaa 1080
agaattgcca agttctttgg aaaagatgtc agcaccacgc tcaatgcaga cgaagctgtg 1140
gccagaggct gtgcactgca gtgtgcaatt ctttctccgg catttaaagt tagagagttc 1200
tctgtcaccg atgcagttcc ttttccaata tctctggtct ggaaccacga ctcggaagaa 1260
acggaaggtg tgcacgaggt gttcagtcgg aaccatgctg ctcctttctc caaagtgctc 1320
accttcctga gaagggggcc ctttgagcta gaagctttct attctgaccc tcaaggagtt 1380
ccatatccag aagcaaaaat aggccgtttt gttgttcaga atgtttctgc acagaaagat 1440
ggagagaagt cgagagtgaa ggtcaaagtg cgtgtgaaca cacatggcat cttcaccatc 1500
tccacggctt ccatggtgga gaaggtcccg accgaggaag aggatggctc ctctctcgag 1560
gcagacatgg aatgtccaaa ccagaggcca acagaaagct cggatgtgga taaaaatatc 1620
cagcaagaca acagtgaagc tggaacacag ccccaggtac aaactgatgg tcaacaaacc 1680
tcacagtctc ccccttcacc tgaacttacc tcagaagaaa gcaaaacccc agatgctgac 1740
aaagcaaatg aaaagaaagt tgatcagcct ccagaagcca agaaacctaa aataaaggtg 1800
gtaaatgttg agctgcctgt agaagccaac ttggtatggc agttagggag agaccttctt 1860
aacatgtata ttgagacaga gggcaagatg atcatgcaag acaagctgga gaaggagcgg 1920

-continued

```
aacgacgcca agaacgccgt ggaggagtgt gtatatgagt tcagggacaa gctatgtgga   1980

ccatatgaga aattcatatg tgagcaggaa catgagaagt tcttgaggct tctaacagag   2040

acggaagact ggctgtatga ggaaggggag gaccaggcta agcaggcata cattgacaag   2100

ttggaagagc tgatgaaaat gggcactcct gttaaagtca gatttcaaga agctgaggaa   2160

cgaccgaaag tgttggagga gctggggcag cgcctgcagc actatgccaa gattgcagcg   2220

gacttcagag gcaaggatga gaaatacaac cacattgatg aatcagaaat gaagaaggtt   2280

gagaagtctg ttaatgaggt gatggagtgg atgaataatg tcatgaatgc tcaggctaaa   2340

agaagtcttg atcaagaccc tgttgttcga actcatgaaa tcagagcgaa ggtcaaggaa   2400

ttgaacaatg tttgtgaacc tgttgtaact caacccaaac caaaaatcga gtcacctaaa   2460

ctggagagaa ctccaaatgg cccaaatatt gacaagaaag aagatttaga aggcaaaaat   2520

aatcttggtg ctgaagctcc gcatcagaat ggtgaatgcc accctaatga gaagggctct   2580

gtcaacatgg acctggatca cgatcccgtg gacgcggtca ttaacaccac ctgcaattac   2640

gggcaggtag tagctgcgct caacgcgacg gatccggggg ctgccgcaca gttcaacgcc   2700

tcaccggtgg cgcagtccta tttgcgcaat ttcctcgccg caccgccacc tcagcgcgct   2760

gccatggccg cgcaattgca agctgtgccg gggcggcac agtacatcgg ccttgtcgag   2820

tcggttgccg gctcctgcaa caactattga                                    2850
```

<210> SEQ ID NO 21
<211> LENGTH: 2871
<212> TYPE: DNA
<213> ORGANISM: Mycobacterium tuberculosis

<400> SEQUENCE: 21

```
atgcagcatc accaccatca ccacgatccc gtggacgcgg tcattaacac cacctgcaat     60

tacgggcagg tagtagctgc gctcaacgcg acggatccgg gggctgccgc acagttcaac    120

gcctcaccgg tggcgcagtc ctatttgcgc aatttcctcg ccgcaccgcc acctcagcgc    180

gctgccatgg ccgcgcaatt gcaagctgtg ccgggggcgg cacagtacat cggccttgtc    240

gagtcggttg ccggctcctg caacaactat tccgtgttac tgattggatc ctcggtggtt    300

gggctagacg taggctcaca gagctgctac attgcggtgg cgcgggccgg gggcatcgag    360

accatcgcca acgagttcag cgaccgctgc accccgtcag tcatatcatt tggatcaaaa    420

aacagaacaa ttggagttgc agccaaaaac cagcaaatca ctcatgcaaa caatacggtc    480

tctagcttta agagatttca tggcagagca ttcaatgacc ccttcattca gaaggaaaag    540

gagaacctga gctatgattt ggtcccaatg aaaaatggtg gcgtgggaat aaaggtcatg    600

tacatggatg aagaacattt cttcagtgtg gagcagataa cagccatgct gctgactaag    660

ttaaaggaaa ctgcagaaaa caacctcaag aagccagtga cagactgtgt catctcagtc    720

ccatccttct tcacagatgc tgagcgaagg tctgtgctgg atgctgcgca gattgtgggc    780

ttgaactgct tgcggctcat gaatgacatg acggctgttg ctttgaatta tgggatttat    840

aagcaagatc tcccgaatgc cgaggagaag ccacgggtgg tggtgtttgt tgacatggga    900

cactcatctt tccaagtgtc tgcctgtgct tttaacaaag gaaaactgaa ggttctaggc    960

acagcttttg atcccttctt aggaggaaag aactttgatg agaagctagt agaacatttt   1020

tgtgctgaat ttaaaaccaa gtacaaattg gatgcaaaat ccaaaattcg agccctcctt   1080

cgtctccatc aggagtgtga aaagttgaaa aagctcatga gttctaacag cacggacctg   1140

ccgctgaaca tcgagtgctt tatgaatgac aaggatgtct ctgggaagat gaacaggtca   1200
```

-continued

```
cagtttgaag aactgtgtgc tgagctcctg caaaaaatag aggtcccct tcactcgttg   1260

atggcacaga ctcagctcaa ggctgaagat gtgagtgcca ttgagatagt gggaggtgcc   1320

acaagaatcc cagctgtgaa agaaagaatt gccaagttct ttggaaaaga tgtcagcacc   1380

acgctcaatg cagacgaagc tgtggccaga ggctgtgcac tgcagtgtgc aattcttttct  1440

ccggcattta aagttagaga gttctctgtc accgatgcag ttcctttcc aatatctctg   1500

gtctggaacc acgactcgga agaaacggaa ggtgtgcacg aggtgttcag tcggaaccat   1560

gctgctcctt tctccaaagt gctcaccttc ctgagaaggg ggccctttga gctagaagct   1620

ttctattctg accctcaagg agttccatat ccagaagcaa aaataggccg ttttgttgtt   1680

cagaatgttt ctgcacagaa agatggagag aagtcgagag tgaaggtcaa agtgcgtgtg   1740

aacacacatg gcatcttcac catctccacg gcttccatgg tggagaaggt cccgaccgag   1800

gaagaggatg gctcctctct cgaggcagac atggaatgtc caaaccagag gccaacagaa   1860

agctcggatg tggataaaaa tatccagcaa gacaacagtg aagctggaac acagccccag   1920

gtacaaactg atggtcaaca aacctcacag tctcccctt cacctgaact tacctcagaa   1980

gaaagcaaaa ccccagatgc tgacaaagca aatgaaaaga aagttgatca gcctccagaa   2040

gccaagaaac ctaaaataaa ggtggtaaat gttgagctgc ctgtagaagc caacttggta   2100

tggcagttag ggagagacct tcttaacatg tatattgaga cagagggcaa gatgatcatg   2160

caagacaagc tggagaagga gcggaacgac gccaagaacg ccgtggagga gtgtgtatat   2220

gagttcaggg acaagctatg tggaccatat gagaaattca tatgtgagca ggaacatgag   2280

aagttcttga ggcttctaac agagacggaa gactggctgt atgaggaagg ggaggaccag   2340

gctaagcagg catacattga caagttggaa gagctgatga aaatgggcac tcctgttaaa   2400

gtcagatttc aagaagctga ggaacgaccg aaagtgttgg aggagctggg gcagcgcctg   2460

cagcactatg ccaagattgc agcggacttc agaggcaagg atgagaaata caaccacatt   2520

gatgaatcag aaatgaagaa ggttgagaag tctgttaatg aggtgatgga gtggatgaat   2580

aatgtcatga atgctcaggc taaaagaagt cttgatcaag accctgttgt tcgaactcat   2640

gaaatcagag cgaaggtcaa ggaattgaac aatgtttgtg aacctgttgt aactcaaccc   2700

aaaccaaaaa tcgagtcacc taaactggag agaactccaa atggcccaaa tattgacaag   2760

aaagaagatt tagaaggcaa aaataatctt ggtgctgaag ctccgcatca gaatggtgaa   2820

tgccacccta atgagaaggg ctctgtcaac atggacctgg atatctgatg a             2871
```

<210> SEQ ID NO 22
<211> LENGTH: 2607
<212> TYPE: DNA
<213> ORGANISM: Homo sapiens

<400> SEQUENCE: 22

```
atgcagcatc accaccatca ccaccactcg gtggttgggc tagacgtagg ctcacagagc     60

tgctacattg cggtggcgcg ggccgggggc atcgagacca tcgccaacga gttcagcgac    120

cgctgcaccc cgtcagtcat atcatttgga tcaaaaaaca gaacaattgg agttgcagcc    180

aaaaaccagc aaatcactca tgcaaacaat acggtctcta gctttaagag atttcatggc    240

agagcattca atgacccctt cattcagaag gaaaaggaga acctgagcta tgatttggtc    300

ccaatgaaaa atggtggcgt gggaataaag gtcatgtaca tggatgaaga acatttcttc    360

agtgtggagc agataacagc catgctgctg actaagttaa aggaaactgc agaaaacaac    420

ctcaagaagc cagtgacaga ctgtgtcatc tcagtcccat ccttcttcac agatgctgag    480
```

-continued

```
cgaaggtctg tgctggatgc tgcgcagatt gtgggcttga actgcttgcg gctcatgaat    540

gacatgacgg ctgttgcttt gaattatggg atttataagc aagatctccc gaatgccgag    600

gagaagccac gggtggtggt gtttgttgac atgggacact catctttcca agtgtctgcc    660

tgtgctttta acaaaggaaa actgaaggtt ctaggcacag cttttgatcc cttcttagga    720

ggaaagaact ttgatgagaa gctagtagaa catttttgtg ctgaatttaa aaccaagtac    780

aaattggatg caaaatccaa aattcgagcc ctccttcgtc tccatcagga gtgtgaaaag    840

ttgaaaaagc tcatgagttc taacagcacg gacctgccgc tgaacatcga gtgctttatg    900

aatgacaagg atgtctctgg gaagatgaac aggtcacagt ttgaagaact gtgtgctgag    960

ctcctgcaaa aaatagaggt ccccccttcac tcgttgatgg cacagactca gctcaaggct   1020

gaagatgtga gtgccattga gatagtggga ggtgccacaa gaatcccagc tgtgaaagaa   1080

agaattgcca agttctttgg aaaagatgtc agcaccacgc tcaatgcaga cgaagctgtg   1140

gccagaggct gtgcactgca gtgtgcaatt ctttctccgg catttaaagt tagagagttc   1200

tctgtcaccg atgcagttcc ttttccaata tctctggtct ggaaccacga ctcggaagaa   1260

acggaaggtg tgcacgaggt gttcagtcgg aaccatgctg ctcctttctc caaagtgctc   1320

accttcctga gaagggggcc ctttgagcta gaagctttct attctgaccc tcaaggagtt   1380

ccatatccag aagcaaaaat aggccgtttt gttgttcaga atgtttctgc acagaaagat   1440

ggagagaagt cgagagtgaa ggtcaaagtg cgtgtgaaca cacatggcat cttcaccatc   1500

tccacggctt ccatggtgga gaaggtcccg accgaggaag aggatggctc ctctctcgag   1560

gcagacatgg aatgtccaaa ccagaggcca acagaaagct cggatgtgga taaaaatatc   1620

cagcaagaca acagtgaagc tggaacacag ccccaggtac aaactgatgg tcaacaaacc   1680

tcacagtctc ccccttcacc tgaacttacc tcagaagaaa gcaaaacccc agatgctgac   1740

aaagcaaatg aaaagaaagt tgatcagcct ccagaagcca agaaacctaa aataaaggtg   1800

gtaaatgttg agctgcctgt agaagccaac ttggtatggc agttagggag agaccttctt   1860

aacatgtata ttgagacaga gggcaagatg atcatgcaag acaagctgga gaaggagcgg   1920

aacgacgcca agaacgccgt ggaggagtgt gtatatgagt tcagggacaa gctatgtgga   1980

ccatatgaga aattcatatg tgagcaggaa catgagaagt tcttgaggct tctaacagag   2040

acggaagact ggctgtatga ggaaggggag gaccaggcta agcaggcata cattgacaag   2100

ttggaagagc tgatgaaaat gggcactcct gttaaagtca gatttcaaga agctgaggaa   2160

cgaccgaaag tgttggagga gctggggcag cgcctgcagc actatgccaa gattgcagcg   2220

gacttcagag gcaaggatga gaaatacaac cacattgatg aatcagaaat gaagaaggtt   2280

gagaagtctg ttaatgaggt gatggagtgg atgaataatg tcatgaatgc tcaggctaaa   2340

agaagtcttg atcaagaccc tgttgttcga actcatgaaa tcagagcgaa ggtcaaggaa   2400

ttgaacaatg tttgtgaacc tgttgtaact caacccaaac caaaaatcga gtcacctaaa   2460

ctggagagaa ctccaaatgg cccaaatatt gacaagaaag aagatttaga aggcaaaaat   2520

aatcttggtg ctgaagctcc gcatcagaat ggtgaatgcc accctaatga gaagggctct   2580

gtcaacatgg acctggatat ctgatga                                         2607
```

<210> SEQ ID NO 23
<211> LENGTH: 3270
<212> TYPE: DNA
<213> ORGANISM: Homo sapiens

<400> SEQUENCE: 23

-continued

```
atgcagcatc accaccatca ccacgcagct acagtaagga ggcagaggcc aaggaggcta     60
ctctgttggg ccttggtggc tgtcctcttg gcagacctgt tggcactgag cgacacattg    120
gctgtgatgt ctgtagacct gggcagtgaa tccatgaagg tggccattgt caagcctgga    180
gtgcccatgg agattgtatt gaacaaggaa tctcggagga aaactccagt gactgtgacc    240
ttgaaagaaa atgaaaggtt tttaggtgat agtgcagccg gcatggccat caagaaccca    300
aaggctacgc tccgttattt ccagcacctc cttggaaaac aggcggataa ccctcatgtg    360
gccctttacc ggtcccgttt cccagaacat gagctaattg ttgacccaca gaggcagact    420
gtgcgcttcc agatcagtcc gcagctgcag ttctctcccg aggaggtact gggcatggtt    480
ctgaactact cccgttcctt ggctgaagat tttgctgaac aacccattaa ggatgcagtg    540
atcaccgtgc cagccttttt caaccaggct gagcgccgag ctgtgctgca ggctgctcgg    600
atggctggcc tcaaggtgct gcagctcatc aatgacaaca ctgccacagc cctcagctac    660
ggtgtcttcc gccggaaaga tatcaattcc actgcacaga acgtcatgtt ctatgacatg    720
ggctcgggca gcactgtgtg caccatcgtc acctaccaga cagtgaagac taaggaggct    780
gggatgcaac cacagctgca gatccggggc gtgggatttg accgcaccct gggtggcctg    840
gagatggagc ttcggcttcg agaacacctg gctaagctct tcaatgagca gcgcaagggc    900
cagaaagcca aggatgttcg ggaaaacccc cgggccatgg ccaaactgct tcgggaagcc    960
aaccggctta aaaccgtcct gagtgccaac gctgatcaca tggcacagat tgagggcttg   1020
atggatgatg tggacttcaa ggccaaagta actcgagtgg aattcgagga gctgtgtgca   1080
gatttgtttg accgtgtgcc tggacctgtg cagcaggcct tgcagagtgc agagatgagc   1140
ttggatcaaa ttgagcaggt gatcctggtg ggcggggcca ctcgtgttcc caaagttcaa   1200
gaagtgctgc tcaaggccgt gggcaaggag gaactaggaa agaacatcaa tgcggacgaa   1260
gctgctgcca tgggggctgt gtaccaggca gcggcgctca gcaaggcctt caaagtgaag   1320
ccatttgttg tgcgggatgc tgtcatttac ccaatcctgg tggagttcac aagggaggtg   1380
gaggaggagc ctgggctccg aagcctgaaa cacaataagc gtgtgctctt ctcccgaatg   1440
gggccctacc ctcagcgcaa agtcatcacc tttaaccgct acagccatga tttcaacttc   1500
cacatcaact acggtgacct gggcttcctg gggcctgagg atcttcgggt atttggctcc   1560
cagaatctga ccacagtaaa actaaaaggc gtgggagaga gcttcaagaa atatcccgac   1620
tatgagtcca aaggcatcaa ggcccacttt aacctggatg agagtggcgt gctcagttta   1680
gacagggtgg agtccgtatt tgagaccctg gtggaggata gcccagagga agaatctact   1740
cttaccaaac ttggcaacac catatccagc ctgtttggag gtggtacctc atcagatgcc   1800
aaagagaatg gtactgatgc tgtacaggag gaagaggaga gccccgctga ggggagcaag   1860
gatgagcctg cagagcaggg ggaactcaag gaagaagctg aacccccagc agaggagacc   1920
tctcagcctc caccctctga gcctaagggg gatgcagccc gtgagggaga gaaacctgat   1980
gaaaaagaga gtggggacaa gcctgaggcc cagaagccca atgagaaggg gcaagcaggg   2040
cctgagggtg ctgctccagc tcctgaggag gacaaaaagc cgaaacctgc ccggaagcag   2100
aaaatggtgg aggagatagg tgtggagctg gctgtcttgg acctgcctga cttgccagag   2160
gatgagctgg cccgttctgt gcagaaactt gaagaactga ccctgcgcga cctagagaag   2220
caggagaggg agaaagctgc caacagcttg gaggctttca tctttgagac ccaggacaag   2280
ctgtaccagc ctgagtacca ggaagtgtcc actgaggaac agcgggagga gatctcgggg   2340
aaactcagcg ccacttctac ctggctggag gatgagggat ttggagccac cactgtgatg   2400
```

ctgaaggaca agctggctga gctgagaaag ctgtgccaag ggctgttttt tcgggtggaa 2460
gaacgcagga aatggccaga gcggctttca gctctggata atctcctcaa ccattccagc 2520
attttcctca agggtgcccg gctcatcccg gagatggacc aggtcttcac tgaagtggag 2580
atgacgacat tagagaaagt tatcaatgac acctgggcct ggaagaatgc aactctggcc 2640
gaacaagcca agcttcctgc cacagagaag cctgtgctgc tttcaaaaga cattgaggcc 2700
aaaatgatgg ccctggaccg ggaggtacag tatctactca ataaggccaa gtttaccaag 2760
ccacggccac ggcccaaaga caagaatggc acccgggcag aacctcccct caatgccagt 2820
gctggtgacc aagaggagaa ggtcattcca cctgcaggcc agactgaaga ggcgaaaccc 2880
attttagaac ctgacaaaga agagactggt acggaaccag cagactcgga gcctctggaa 2940
ttaggaggtc ctggagctgg acctgaacag gaagagcagt cagcaggaca gaagcggcct 3000
tcaaagaacg atgaactaca cgatcccgtg gacgcggtca ttaacaccac ctgcaattac 3060
gggcaggtag tagctgcgct caacgcgacg gatccggggg ctgccgcaca gttcaacgcc 3120
tcaccggtgg cgcagtccta tttgcgcaat ttcctcgccg caccgccacc tcagcgcgct 3180
gccatggccg cgcaattgca agctgtgccg gggcgcgcac agtacatcgg ccttgtcgag 3240
tcggttgccg gctcctgcaa caactattga 3270

<210> SEQ ID NO 24
<211> LENGTH: 3027
<212> TYPE: DNA
<213> ORGANISM: Homo sapiens

<400> SEQUENCE: 24
atgcagcatc accaccatca ccacgcagct acagtaagga ggcagaggcc aaggaggcta 60
ctctgttggg ccttggtggc tgtcctcttg gcagacctgt tggcactgag cgacacattg 120
gctgtgatgt ctgtagacct gggcagtgaa tccatgaagg tggccattgt caagcctgga 180
gtgcccatgg agattgtatt gaacaaggaa tctcggagga aaactccagt gactgtgacc 240
ttgaaagaaa atgaaaggtt tttaggtgat agtgcagccg gcatggccat caagaaccca 300
aaggctacgc tccgttattt ccagcacctc cttggaaaac aggcggataa ccctcatgtg 360
gccctttacc ggtcccgttt cccagaacat gagctaattg ttgacccaca gaggcagact 420
gtgcgcttcc agatcagtcc gcagctgcag ttctctcccg aggaggtact gggcatggtt 480
ctgaactact cccgttcctt ggctgaagat tttgctgaac aacccattaa ggatgcagtg 540
atcaccgtgc cagccttttt caaccaggct gagcgccgag ctgtgctgca ggctgctcgg 600
atggctggcc tcaaggtgct gcagctcatc aatgacaaca ctgccacagc cctcagctac 660
ggtgtcttcc gccggaaaga tatcaattcc actgcacaga acgtcatgtt ctatgacatg 720
ggctcgggca gcactgtgtg caccatcgtc acctaccaga cagtgaagac taaggaggct 780
gggatgcaac cacagctgca gatccggggc gtgggatttg accgcaccct gggtggcctg 840
gagatggagc ttcggcttcg agaacacctg gctaagctct tcaatgagca gcgcaagggc 900
cagaaagcca aggatgttcg ggaaaacccc cgggccatgg ccaaactgct tcgggaagcc 960
aaccggctta aaaccgtcct gagtgccaac gctgatcaca tggcacagat tgagggcttg 1020
atggatgatg tggacttcaa ggccaaagta actcgagtgg aattcgagga gctgtgtgca 1080
gatttgtttg accgtgtgcc tggacctgtg cagcaggcct tgcagagtgc agagatgagc 1140
ttggatcaaa ttgagcaggt gatcctggtg ggcggggcca ctcgtgttcc caaagttcaa 1200
gaagtgctgc tcaaggccgt gggcaaggag gaactaggaa agaacatcaa tgcggacgaa 1260

-continued

```
gctgctgcca tgggggctgt gtaccaggca gcggcgctca gcaaggcctt caaagtgaag   1320

ccatttgttg tgcgggatgc tgtcatttac ccaatcctgg tggagttcac aagggaggtg   1380

gaggaggagc ctgggctccg aagcctgaaa cacaataagc gtgtgctctt ctcccgaatg   1440

gggccctacc ctcagcgcaa agtcatcacc tttaaccgct acagccatga tttcaacttc   1500

cacatcaact acggtgacct gggcttcctg gggcctgagg atcttcgggt atttggctcc   1560

cagaatctga ccacagtaaa actaaaaggc gtgggagaga gcttcaagaa atatcccgac   1620

tatgagtcca aaggcatcaa ggcccacttt aacctggatg agagtggcgt gctcagttta   1680

gacagggtgg agtccgtatt tgagaccctg gtggaggata gcccagagga agaatctact   1740

cttaccaaac ttggcaacac catatccagc ctgtttggag gtggtacctc atcagatgcc   1800

aaagagaatg gtactgatgc tgtacaggag gaagaggaga gccccgctga ggggagcaag   1860

gatgagcctg cagagcaggg ggaactcaag gaagaagctg aacccccagc agaggagacc   1920

tctcagcctc caccctctga gcctaagggg gatgcagccc gtgagggaga gaaacctgat   1980

gaaaaagaga gtggggacaa gcctgaggcc cagaagccca atgagaaggg gcaagcaggg   2040

cctgagggtg ctgctccagc tcctgaggag gacaaaaagc cgaaacctgc ccggaagcag   2100

aaaatggtgg aggagatagg tgtggagctg gctgtcttgg acctgcctga cttgccagag   2160

gatgagctgg cccgttctgt gcagaaactt gaagaactga ccctgcgcga cctagagaag   2220

caggagaggg agaaagctgc caacagcttg gaggctttca tctttgagac ccaggacaag   2280

ctgtaccagc ctgagtacca ggaagtgtcc actgaggaac agcgggagga gatctcgggg   2340

aaactcagcg ccacttctac ctggctggag gatgagggat ttggagccac cactgtgatg   2400

ctgaaggaca agctggctga gctgagaaag ctgtgccaag ggctgttttt tcgggtggaa   2460

gaacgcagga aatggccaga gcggctttca gctctggata atctcctcaa ccattccagc   2520

attttcctca agggtgcccg gctcatcccg gagatggacc aggtcttcac tgaagtggag   2580

atgacgacat tagagaaagt tatcaatgac acctgggcct ggaagaatgc aactctggcc   2640

gaacaagcca agcttcctgc cacagagaag cctgtgctgc tttcaaaaga cattgaggcc   2700

aaaatgatgg ccctggaccg ggaggtacag tatctactca ataaggccaa gtttaccaag   2760

ccacggccac ggcccaaaga caagaatggc acccgggcag aacctcccct caatgccagt   2820

gctggtgacc aagaggagaa ggtcattcca cctgcaggcc agactgaaga ggcgaaaccc   2880

attttagaac ctgacaaaga agagactggt acggaaccag cagactcgga gcctctggaa   2940

ttaggaggtc ctggagctgg acctgaacag gaagagcagt cagcaggaca gaagcggcct   3000

tcaaagaacg atgaactaca cgtgtaa                                       3027
```

<210> SEQ ID NO 25
<211> LENGTH: 1008
<212> TYPE: PRT
<213> ORGANISM: Homo sapiens

<400> SEQUENCE: 25

```
Met Gln His His His His His His Ala Ala Thr Val Arg Arg Gln Arg
 1               5                  10                  15

Pro Arg Arg Leu Leu Cys Trp Ala Leu Val Ala Val Leu Leu Ala Asp
            20                  25                  30

Leu Leu Ala Leu Ser Asp Thr Leu Ala Val Met Ser Val Asp Leu Gly
        35                  40                  45

Ser Glu Ser Met Lys Val Ala Ile Val Lys Pro Gly Val Pro Met Glu
    50                  55                  60
```

-continued

```
Ile Val Leu Asn Lys Glu Ser Arg Arg Lys Thr Pro Val Thr Val Thr
65                  70                  75                  80

Leu Lys Glu Asn Glu Arg Phe Leu Gly Asp Ser Ala Ala Gly Met Ala
                85                  90                  95

Ile Lys Asn Pro Lys Ala Thr Leu Arg Tyr Phe Gln His Leu Leu Gly
            100                 105                 110

Lys Gln Ala Asp Asn Pro His Val Ala Leu Tyr Arg Ser Arg Phe Pro
        115                 120                 125

Glu His Glu Leu Ile Val Asp Pro Gln Arg Gln Thr Val Arg Phe Gln
    130                 135                 140

Ile Ser Pro Gln Leu Gln Phe Ser Pro Glu Glu Val Leu Gly Met Val
145                 150                 155                 160

Leu Asn Tyr Ser Arg Ser Leu Ala Glu Asp Phe Ala Glu Gln Pro Ile
                165                 170                 175

Lys Asp Ala Val Ile Thr Val Pro Ala Phe Phe Asn Gln Ala Glu Arg
            180                 185                 190

Arg Ala Val Leu Gln Ala Ala Arg Met Ala Gly Leu Lys Val Leu Gln
        195                 200                 205

Leu Ile Asn Asp Asn Thr Ala Thr Ala Leu Ser Tyr Gly Val Phe Arg
    210                 215                 220

Arg Lys Asp Ile Asn Ser Thr Ala Gln Asn Val Met Phe Tyr Asp Met
225                 230                 235                 240

Gly Ser Gly Ser Thr Val Cys Thr Ile Val Thr Tyr Gln Thr Val Lys
                245                 250                 255

Thr Lys Glu Ala Gly Met Gln Pro Gln Leu Gln Ile Arg Gly Val Gly
            260                 265                 270

Phe Asp Arg Thr Leu Gly Gly Leu Glu Met Glu Leu Arg Leu Arg Glu
        275                 280                 285

His Leu Ala Lys Leu Phe Asn Glu Gln Arg Lys Gly Gln Lys Ala Lys
    290                 295                 300

Asp Val Arg Glu Asn Pro Arg Ala Met Ala Lys Leu Leu Arg Glu Ala
305                 310                 315                 320

Asn Arg Leu Lys Thr Val Leu Ser Ala Asn Ala Asp His Met Ala Gln
                325                 330                 335

Ile Glu Gly Leu Met Asp Asp Val Asp Phe Lys Ala Lys Val Thr Arg
            340                 345                 350

Val Glu Phe Glu Glu Leu Cys Ala Asp Leu Phe Asp Arg Val Pro Gly
        355                 360                 365

Pro Val Gln Gln Ala Leu Gln Ser Ala Glu Met Ser Leu Asp Gln Ile
    370                 375                 380

Glu Gln Val Ile Leu Val Gly Gly Ala Thr Arg Val Pro Lys Val Gln
385                 390                 395                 400

Glu Val Leu Leu Lys Ala Val Gly Lys Glu Glu Leu Gly Lys Asn Ile
                405                 410                 415

Asn Ala Asp Glu Ala Ala Ala Met Gly Ala Val Tyr Gln Ala Ala Ala
            420                 425                 430

Leu Ser Lys Ala Phe Lys Val Lys Pro Phe Val Val Arg Asp Ala Val
        435                 440                 445

Ile Tyr Pro Ile Leu Val Glu Phe Thr Arg Glu Val Glu Glu Glu Pro
    450                 455                 460

Gly Leu Arg Ser Leu Lys His Asn Lys Arg Val Leu Phe Ser Arg Met
465                 470                 475                 480

Gly Pro Tyr Pro Gln Arg Lys Val Ile Thr Phe Asn Arg Tyr Ser His
                485                 490                 495
```

```
Asp Phe Asn Phe His Ile Asn Tyr Gly Asp Leu Gly Phe Leu Gly Pro
            500                 505                 510

Glu Asp Leu Arg Val Phe Gly Ser Gln Asn Leu Thr Thr Val Lys Leu
        515                 520                 525

Lys Gly Val Gly Glu Ser Phe Lys Lys Tyr Pro Asp Tyr Glu Ser Lys
    530                 535                 540

Gly Ile Lys Ala His Phe Asn Leu Asp Glu Ser Gly Val Leu Ser Leu
545                 550                 555                 560

Asp Arg Val Glu Ser Val Phe Glu Thr Leu Val Glu Asp Ser Pro Glu
                565                 570                 575

Glu Glu Ser Thr Leu Thr Lys Leu Gly Asn Thr Ile Ser Ser Leu Phe
            580                 585                 590

Gly Gly Gly Thr Ser Ser Asp Ala Lys Glu Asn Gly Thr Asp Ala Val
        595                 600                 605

Gln Glu Glu Glu Glu Ser Pro Ala Glu Gly Ser Lys Asp Glu Pro Ala
    610                 615                 620

Glu Gln Gly Glu Leu Lys Glu Glu Ala Glu Pro Pro Ala Glu Glu Thr
625                 630                 635                 640

Ser Gln Pro Pro Pro Ser Glu Pro Lys Gly Asp Ala Ala Arg Glu Gly
                645                 650                 655

Glu Lys Pro Asp Glu Lys Glu Ser Gly Asp Lys Pro Glu Ala Gln Lys
            660                 665                 670

Pro Asn Glu Lys Gly Gln Ala Gly Pro Glu Gly Ala Ala Pro Ala Pro
        675                 680                 685

Glu Glu Asp Lys Lys Pro Lys Pro Ala Arg Lys Gln Lys Met Val Glu
    690                 695                 700

Glu Ile Gly Val Glu Leu Ala Val Leu Asp Leu Pro Asp Leu Pro Glu
705                 710                 715                 720

Asp Glu Leu Ala Arg Ser Val Gln Lys Leu Glu Glu Leu Thr Leu Arg
                725                 730                 735

Asp Leu Glu Lys Gln Glu Arg Glu Lys Ala Ala Asn Ser Leu Glu Ala
            740                 745                 750

Phe Ile Phe Glu Thr Gln Asp Lys Leu Tyr Gln Pro Glu Tyr Gln Glu
        755                 760                 765

Val Ser Thr Glu Glu Gln Arg Glu Glu Ile Ser Gly Lys Leu Ser Ala
    770                 775                 780

Thr Ser Thr Trp Leu Glu Asp Glu Gly Phe Gly Ala Thr Thr Val Met
785                 790                 795                 800

Leu Lys Asp Lys Leu Ala Glu Leu Arg Lys Leu Cys Gln Gly Leu Phe
                805                 810                 815

Phe Arg Val Glu Glu Arg Arg Lys Trp Pro Glu Arg Leu Ser Ala Leu
            820                 825                 830

Asp Asn Leu Leu Asn His Ser Ser Ile Phe Leu Lys Gly Ala Arg Leu
        835                 840                 845

Ile Pro Glu Met Asp Gln Val Phe Thr Glu Val Glu Met Thr Thr Leu
    850                 855                 860

Glu Lys Val Ile Asn Asp Thr Trp Ala Trp Lys Asn Ala Thr Leu Ala
865                 870                 875                 880

Glu Gln Ala Lys Leu Pro Ala Thr Glu Lys Pro Val Leu Leu Ser Lys
                885                 890                 895

Asp Ile Glu Ala Lys Met Met Ala Leu Asp Arg Glu Val Gln Tyr Leu
            900                 905                 910

Leu Asn Lys Ala Lys Phe Thr Lys Pro Arg Pro Arg Pro Lys Asp Lys
```

-continued

```
        915                 920                 925

Asn Gly Thr Arg Ala Glu Pro Pro Leu Asn Ala Ser Ala Gly Asp Gln
    930                 935                 940

Glu Glu Lys Val Ile Pro Pro Ala Gly Gln Thr Glu Glu Ala Lys Pro
945                 950                 955                 960

Ile Leu Glu Pro Asp Lys Glu Glu Thr Gly Thr Glu Pro Ala Asp Ser
                965                 970                 975

Glu Pro Leu Glu Leu Gly Gly Pro Gly Ala Gly Pro Glu Gln Glu Glu
            980                 985                 990

Gln Ser Ala Gly Gln Lys Arg Pro Ser Lys Asn Asp Glu Leu His Val
        995                 1000                1005


<210> SEQ ID NO 26
<211> LENGTH: 1089
<212> TYPE: PRT
<213> ORGANISM: Mycobacterium tuberculosis

<400> SEQUENCE: 26

Met Gln His His His His His His Ala Ala Thr Val Arg Arg Gln Arg
 1               5                  10                  15

Pro Arg Arg Leu Leu Cys Trp Ala Leu Val Ala Val Leu Leu Ala Asp
            20                  25                  30

Leu Leu Ala Leu Ser Asp Thr Leu Ala Val Met Ser Val Asp Leu Gly
        35                  40                  45

Ser Glu Ser Met Lys Val Ala Ile Val Lys Pro Gly Val Pro Met Glu
    50                  55                  60

Ile Val Leu Asn Lys Glu Ser Arg Arg Lys Thr Pro Val Thr Val Thr
65                  70                  75                  80

Leu Lys Glu Asn Glu Arg Phe Leu Gly Asp Ser Ala Ala Gly Met Ala
                85                  90                  95

Ile Lys Asn Pro Lys Ala Thr Leu Arg Tyr Phe Gln His Leu Leu Gly
            100                 105                 110

Lys Gln Ala Asp Asn Pro His Val Ala Leu Tyr Arg Ser Arg Phe Pro
        115                 120                 125

Glu His Glu Leu Ile Val Asp Pro Gln Arg Gln Thr Val Arg Phe Gln
    130                 135                 140

Ile Ser Pro Gln Leu Gln Phe Ser Pro Glu Glu Val Leu Gly Met Val
145                 150                 155                 160

Leu Asn Tyr Ser Arg Ser Leu Ala Glu Asp Phe Ala Glu Gln Pro Ile
                165                 170                 175

Lys Asp Ala Val Ile Thr Val Pro Ala Phe Phe Asn Gln Ala Glu Arg
            180                 185                 190

Arg Ala Val Leu Gln Ala Ala Arg Met Ala Gly Leu Lys Val Leu Gln
        195                 200                 205

Leu Ile Asn Asp Asn Thr Ala Thr Ala Leu Ser Tyr Gly Val Phe Arg
    210                 215                 220

Arg Lys Asp Ile Asn Ser Thr Ala Gln Asn Val Met Phe Tyr Asp Met
225                 230                 235                 240

Gly Ser Gly Ser Thr Val Cys Thr Ile Val Thr Tyr Gln Thr Val Lys
                245                 250                 255

Thr Lys Glu Ala Gly Met Gln Pro Gln Leu Gln Ile Arg Gly Val Gly
            260                 265                 270

Phe Asp Arg Thr Leu Gly Gly Leu Glu Met Glu Leu Arg Leu Arg Glu
        275                 280                 285

His Leu Ala Lys Leu Phe Asn Glu Gln Arg Lys Gly Gln Lys Ala Lys
```

-continued

```
    290                 295                 300

Asp Val Arg Glu Asn Pro Arg Ala Met Ala Lys Leu Leu Arg Glu Ala
305                 310                 315                 320

Asn Arg Leu Lys Thr Val Leu Ser Ala Asn Ala Asp His Met Ala Gln
                325                 330                 335

Ile Glu Gly Leu Met Asp Asp Val Asp Phe Lys Ala Lys Val Thr Arg
            340                 345                 350

Val Glu Phe Glu Glu Leu Cys Ala Asp Leu Phe Asp Arg Val Pro Gly
        355                 360                 365

Pro Val Gln Gln Ala Leu Gln Ser Ala Glu Met Ser Leu Asp Gln Ile
    370                 375                 380

Glu Gln Val Ile Leu Val Gly Gly Ala Thr Arg Val Pro Lys Val Gln
385                 390                 395                 400

Glu Val Leu Leu Lys Ala Val Gly Lys Glu Glu Leu Gly Lys Asn Ile
                405                 410                 415

Asn Ala Asp Glu Ala Ala Ala Met Gly Ala Val Tyr Gln Ala Ala Ala
            420                 425                 430

Leu Ser Lys Ala Phe Lys Val Lys Pro Phe Val Val Arg Asp Ala Val
        435                 440                 445

Ile Tyr Pro Ile Leu Val Glu Phe Thr Arg Glu Val Glu Glu Glu Pro
    450                 455                 460

Gly Leu Arg Ser Leu Lys His Asn Lys Arg Val Leu Phe Ser Arg Met
465                 470                 475                 480

Gly Pro Tyr Pro Gln Arg Lys Val Ile Thr Phe Asn Arg Tyr Ser His
                485                 490                 495

Asp Phe Asn Phe His Ile Asn Tyr Gly Asp Leu Gly Phe Leu Gly Pro
            500                 505                 510

Glu Asp Leu Arg Val Phe Gly Ser Gln Asn Leu Thr Thr Val Lys Leu
        515                 520                 525

Lys Gly Val Gly Glu Ser Phe Lys Lys Tyr Pro Asp Tyr Glu Ser Lys
    530                 535                 540

Gly Ile Lys Ala His Phe Asn Leu Asp Glu Ser Gly Val Leu Ser Leu
545                 550                 555                 560

Asp Arg Val Glu Ser Val Phe Glu Thr Leu Val Glu Asp Ser Pro Glu
                565                 570                 575

Glu Glu Ser Thr Leu Thr Lys Leu Gly Asn Thr Ile Ser Ser Leu Phe
            580                 585                 590

Gly Gly Gly Thr Ser Ser Asp Ala Lys Glu Asn Gly Thr Asp Ala Val
        595                 600                 605

Gln Glu Glu Glu Glu Ser Pro Ala Glu Gly Ser Lys Asp Glu Pro Ala
    610                 615                 620

Glu Gln Gly Glu Leu Lys Glu Glu Ala Glu Pro Pro Ala Glu Glu Thr
625                 630                 635                 640

Ser Gln Pro Pro Pro Ser Glu Pro Lys Gly Asp Ala Ala Arg Glu Gly
                645                 650                 655

Glu Lys Pro Asp Glu Lys Glu Ser Gly Asp Lys Pro Glu Ala Gln Lys
            660                 665                 670

Pro Asn Glu Lys Gly Gln Ala Gly Pro Glu Gly Ala Ala Pro Ala Pro
        675                 680                 685

Glu Glu Asp Lys Lys Pro Lys Pro Ala Arg Lys Gln Lys Met Val Glu
    690                 695                 700

Glu Ile Gly Val Glu Leu Ala Val Leu Asp Leu Pro Asp Leu Pro Glu
705                 710                 715                 720
```

Asp Glu Leu Ala Arg Ser Val Gln Lys Leu Glu Glu Leu Thr Leu Arg
725 730 735

Asp Leu Glu Lys Gln Glu Arg Glu Lys Ala Ala Asn Ser Leu Glu Ala
740 745 750

Phe Ile Phe Glu Thr Gln Asp Lys Leu Tyr Gln Pro Glu Tyr Gln Glu
755 760 765

Val Ser Thr Glu Glu Gln Arg Glu Glu Ile Ser Gly Lys Leu Ser Ala
770 775 780

Thr Ser Thr Trp Leu Glu Asp Glu Gly Phe Gly Ala Thr Thr Val Met
785 790 795 800

Leu Lys Asp Lys Leu Ala Glu Leu Arg Lys Leu Cys Gln Gly Leu Phe
805 810 815

Phe Arg Val Glu Glu Arg Arg Lys Trp Pro Glu Arg Leu Ser Ala Leu
820 825 830

Asp Asn Leu Leu Asn His Ser Ser Ile Phe Leu Lys Gly Ala Arg Leu
835 840 845

Ile Pro Glu Met Asp Gln Val Phe Thr Glu Val Glu Met Thr Thr Leu
850 855 860

Glu Lys Val Ile Asn Asp Thr Trp Ala Trp Lys Asn Ala Thr Leu Ala
865 870 875 880

Glu Gln Ala Lys Leu Pro Ala Thr Glu Lys Pro Val Leu Leu Ser Lys
885 890 895

Asp Ile Glu Ala Lys Met Met Ala Leu Asp Arg Glu Val Gln Tyr Leu
900 905 910

Leu Asn Lys Ala Lys Phe Thr Lys Pro Arg Pro Arg Pro Lys Asp Lys
915 920 925

Asn Gly Thr Arg Ala Glu Pro Pro Leu Asn Ala Ser Ala Gly Asp Gln
930 935 940

Glu Glu Lys Val Ile Pro Pro Ala Gly Gln Thr Glu Glu Ala Lys Pro
945 950 955 960

Ile Leu Glu Pro Asp Lys Glu Glu Thr Gly Thr Glu Pro Ala Asp Ser
965 970 975

Glu Pro Leu Glu Leu Gly Gly Pro Gly Ala Gly Pro Glu Gln Glu Glu
980 985 990

Gln Ser Ala Gly Gln Lys Arg Pro Ser Lys Asn Asp Glu Leu His Asp
995 1000 1005

Pro Val Asp Ala Val Ile Asn Thr Thr Cys Asn Tyr Gly Gln Val Val
1010 1015 1020

Ala Ala Leu Asn Ala Thr Asp Pro Gly Ala Ala Ala Gln Phe Asn Ala
1025 1030 1035 1040

Ser Pro Val Ala Gln Ser Tyr Leu Arg Asn Phe Leu Ala Ala Pro Pro
1045 1050 1055

Pro Gln Arg Ala Ala Met Ala Ala Gln Leu Gln Ala Val Pro Gly Ala
1060 1065 1070

Ala Gln Tyr Ile Gly Leu Val Glu Ser Val Ala Gly Ser Cys Asn Asn
1075 1080 1085

Tyr

<210> SEQ ID NO 27
<211> LENGTH: 1257
<212> TYPE: PRT
<213> ORGANISM: Mycobacterium tuberculosis

<400> SEQUENCE: 27

Met Gln His His His His His His His Ser Val Val Gly Leu Asp Val

-continued

```
1               5                   10                  15

Gly Ser Gln Ser Cys Tyr Ile Ala Val Ala Arg Ala Gly Gly Ile Glu
            20                  25                  30

Thr Ile Ala Asn Glu Phe Ser Asp Arg Cys Thr Pro Ser Val Ile Ser
        35                  40                  45

Phe Gly Ser Lys Asn Arg Thr Ile Gly Val Ala Ala Lys Asn Gln Gln
    50                  55                  60

Ile Thr His Ala Asn Asn Thr Val Ser Ser Phe Lys Arg Phe His Gly
65                  70                  75                  80

Arg Ala Phe Asn Asp Pro Phe Ile Gln Lys Glu Lys Glu Asn Leu Ser
                85                  90                  95

Tyr Asp Leu Val Pro Met Lys Asn Gly Gly Val Gly Ile Lys Val Met
            100                 105                 110

Tyr Met Asp Glu Glu His Phe Phe Ser Val Glu Gln Ile Thr Ala Met
        115                 120                 125

Leu Leu Thr Lys Leu Lys Glu Thr Ala Glu Asn Asn Leu Lys Lys Pro
    130                 135                 140

Val Thr Asp Cys Val Ile Ser Val Pro Ser Phe Phe Thr Asp Ala Glu
145                 150                 155                 160

Arg Arg Ser Val Leu Asp Ala Ala Gln Ile Val Gly Leu Asn Cys Leu
                165                 170                 175

Arg Leu Met Asn Asp Met Thr Ala Val Ala Leu Asn Tyr Gly Ile Tyr
            180                 185                 190

Lys Gln Asp Leu Pro Asn Ala Glu Glu Lys Pro Arg Val Val Val Phe
        195                 200                 205

Val Asp Met Gly His Ser Ser Phe Gln Val Ser Ala Cys Ala Phe Asn
    210                 215                 220

Lys Gly Lys Leu Lys Val Leu Gly Thr Ala Phe Asp Pro Phe Leu Gly
225                 230                 235                 240

Gly Lys Asn Phe Asp Glu Lys Leu Val Glu His Phe Cys Ala Glu Phe
                245                 250                 255

Lys Thr Lys Tyr Lys Leu Asp Ala Lys Ser Lys Ile Arg Ala Leu Leu
            260                 265                 270

Arg Leu His Gln Glu Cys Glu Lys Leu Lys Lys Leu Met Ser Ser Asn
        275                 280                 285

Ser Thr Asp Leu Pro Leu Asn Ile Glu Cys Phe Met Asn Asp Lys Asp
    290                 295                 300

Val Ser Gly Lys Met Asn Arg Ser Gln Phe Glu Glu Leu Cys Ala Glu
305                 310                 315                 320

Leu Leu Gln Lys Ile Glu Val Pro Leu His Ser Leu Met Ala Gln Thr
                325                 330                 335

Gln Leu Lys Ala Glu Asp Val Ser Ala Ile Glu Ile Val Gly Gly Ala
            340                 345                 350

Thr Arg Ile Pro Ala Val Lys Glu Arg Ile Ala Lys Phe Phe Gly Lys
        355                 360                 365

Asp Val Ser Thr Thr Leu Asn Ala Asp Glu Ala Val Ala Arg Gly Cys
    370                 375                 380

Ala Leu Gln Cys Ala Ile Leu Ser Pro Ala Phe Lys Val Arg Glu Phe
385                 390                 395                 400

Ser Val Thr Asp Ala Val Pro Phe Pro Ile Ser Leu Val Trp Asn His
                405                 410                 415

Asp Ser Glu Glu Thr Glu Gly Val His Glu Val Phe Ser Arg Asn His
            420                 425                 430
```

```
Ala Ala Pro Phe Ser Lys Val Leu Thr Phe Leu Arg Arg Gly Pro Phe
        435                 440                 445

Glu Leu Glu Ala Phe Tyr Ser Asp Pro Gln Gly Val Pro Tyr Pro Glu
    450                 455                 460

Ala Lys Ile Gly Arg Phe Val Val Gln Asn Val Ser Ala Gln Lys Asp
465                 470                 475                 480

Gly Glu Lys Ser Arg Val Lys Val Lys Val Arg Val Asn Thr His Gly
                485                 490                 495

Ile Phe Thr Ile Ser Thr Ala Ser Met Val Glu Lys Val Pro Thr Glu
            500                 505                 510

Glu Glu Asp Gly Ser Ser Leu Glu Ala Asp Met Glu Cys Pro Asn Gln
        515                 520                 525

Arg Pro Thr Glu Ser Ser Asp Val Asp Lys Asn Ile Gln Gln Asp Asn
    530                 535                 540

Ser Glu Ala Gly Thr Gln Pro Gln Val Gln Thr Asp Gly Gln Gln Thr
545                 550                 555                 560

Ser Gln Ser Pro Pro Ser Pro Glu Leu Thr Ser Glu Glu Ser Lys Thr
                565                 570                 575

Pro Asp Ala Asp Lys Ala Asn Glu Lys Lys Val Asp Gln Pro Pro Glu
            580                 585                 590

Ala Lys Lys Pro Lys Ile Lys Val Val Asn Val Glu Leu Pro Val Glu
        595                 600                 605

Ala Asn Leu Val Trp Gln Leu Gly Arg Asp Leu Leu Asn Met Tyr Ile
    610                 615                 620

Glu Thr Glu Gly Lys Met Ile Met Gln Asp Lys Leu Glu Lys Glu Arg
625                 630                 635                 640

Asn Asp Ala Lys Asn Ala Val Glu Glu Cys Val Tyr Glu Phe Arg Asp
                645                 650                 655

Lys Leu Cys Gly Pro Tyr Glu Lys Phe Ile Cys Glu Gln Glu His Glu
            660                 665                 670

Lys Phe Leu Arg Leu Leu Thr Glu Thr Glu Asp Trp Leu Tyr Glu Glu
        675                 680                 685

Gly Glu Asp Gln Ala Lys Gln Ala Tyr Ile Asp Lys Leu Glu Glu Leu
    690                 695                 700

Met Lys Met Gly Thr Pro Val Lys Val Arg Phe Gln Glu Ala Glu Glu
705                 710                 715                 720

Arg Pro Lys Val Leu Glu Glu Leu Gly Gln Arg Leu Gln His Tyr Ala
                725                 730                 735

Lys Ile Ala Ala Asp Phe Arg Gly Lys Asp Glu Lys Tyr Asn His Ile
            740                 745                 750

Asp Glu Ser Glu Met Lys Lys Val Glu Lys Ser Val Asn Glu Val Met
        755                 760                 765

Glu Trp Met Asn Asn Val Met Asn Ala Gln Ala Lys Arg Ser Leu Asp
    770                 775                 780

Gln Asp Pro Val Val Arg Thr His Glu Ile Arg Ala Lys Val Lys Glu
785                 790                 795                 800

Leu Asn Asn Val Cys Glu Pro Val Val Thr Gln Pro Lys Pro Lys Ile
                805                 810                 815

Glu Ser Pro Lys Leu Glu Arg Thr Pro Asn Gly Pro Asn Ile Asp Lys
            820                 825                 830

Lys Glu Asp Leu Glu Gly Lys Asn Asn Leu Gly Ala Glu Ala Pro His
        835                 840                 845

Gln Asn Gly Glu Cys His Pro Asn Glu Lys Gly Ser Val Asn Met Asp
    850                 855                 860
```

```
Leu Asp His Val Asp Phe Gly Ala Leu Pro Pro Glu Ile Asn Ser Ala
865                 870                 875                 880

Arg Met Tyr Ala Gly Pro Gly Ser Ala Ser Leu Val Ala Ala Ala Gln
                885                 890                 895

Met Trp Asp Ser Val Ala Ser Asp Leu Phe Ser Ala Ala Ser Ala Phe
            900                 905                 910

Gln Ser Val Val Trp Gly Leu Thr Val Gly Ser Trp Ile Gly Ser Ser
        915                 920                 925

Ala Gly Leu Met Val Ala Ala Ala Ser Pro Tyr Val Ala Trp Met Ser
    930                 935                 940

Val Thr Ala Gly Gln Ala Glu Leu Thr Ala Ala Gln Val Arg Val Ala
945                 950                 955                 960

Ala Ala Ala Tyr Glu Thr Ala Tyr Gly Leu Thr Val Pro Pro Pro Val
                965                 970                 975

Ile Ala Glu Asn Arg Ala Glu Leu Met Ile Leu Ile Ala Thr Asn Leu
            980                 985                 990

Leu Gly Gln Asn Thr Pro Ala Ile Ala Val Asn Glu Ala Glu Tyr Gly
        995                 1000                1005

Glu Met Trp Ala Gln Asp Ala Ala Ala Met Phe Gly Tyr Ala Ala Ala
    1010                1015                1020

Thr Ala Thr Ala Thr Ala Thr Leu Leu Pro Phe Glu Glu Ala Pro Glu
1025                1030                1035                1040

Met Thr Ser Ala Gly Gly Leu Leu Glu Gln Ala Ala Ala Val Glu Glu
                1045                1050                1055

Ala Ser Asp Thr Ala Ala Ala Asn Gln Leu Met Asn Asn Val Pro Gln
            1060                1065                1070

Ala Leu Gln Gln Leu Ala Gln Pro Thr Gln Gly Thr Thr Pro Ser Ser
        1075                1080                1085

Lys Leu Gly Gly Leu Trp Lys Thr Val Ser Pro His Arg Ser Pro Ile
    1090                1095                1100

Ser Asn Met Val Ser Met Ala Asn Asn His Met Ser Met Thr Asn Ser
1105                1110                1115                1120

Gly Val Ser Met Thr Asn Thr Leu Ser Ser Met Leu Lys Gly Phe Ala
                1125                1130                1135

Pro Ala Ala Ala Ala Gln Ala Val Gln Thr Ala Ala Gln Asn Gly Val
            1140                1145                1150

Arg Ala Met Ser Ser Leu Gly Ser Ser Leu Gly Ser Ser Gly Leu Gly
        1155                1160                1165

Gly Gly Val Ala Ala Asn Leu Gly Arg Ala Ala Ser Val Gly Ser Leu
    1170                1175                1180

Ser Val Pro Gln Ala Trp Ala Ala Ala Asn Gln Ala Val Thr Pro Ala
1185                1190                1195                1200

Ala Arg Ala Leu Pro Leu Thr Ser Leu Thr Ser Ala Ala Glu Arg Gly
                1205                1210                1215

Pro Gly Gln Met Leu Gly Gly Leu Pro Val Gly Gln Met Gly Ala Arg
            1220                1225                1230

Ala Gly Gly Gly Leu Ser Gly Val Leu Arg Val Pro Pro Arg Pro Tyr
        1235                1240                1245

Val Met Pro His Ser Pro Ala Ala Gly
    1250                1255
```

<210> SEQ ID NO 28
<211> LENGTH: 949
<212> TYPE: PRT

<213> ORGANISM: Mycobacterium tuberculosis

<400> SEQUENCE: 28

```
Met Gln His His His His His His His Ser Val Val Gly Leu Asp Val
 1               5                  10                  15

Gly Ser Gln Ser Cys Tyr Ile Ala Val Ala Arg Ala Gly Gly Ile Glu
            20                  25                  30

Thr Ile Ala Asn Glu Phe Ser Asp Arg Cys Thr Pro Ser Val Ile Ser
        35                  40                  45

Phe Gly Ser Lys Asn Arg Thr Ile Gly Val Ala Ala Lys Asn Gln Gln
    50                  55                  60

Ile Thr His Ala Asn Asn Thr Val Ser Ser Phe Lys Arg Phe His Gly
65                  70                  75                  80

Arg Ala Phe Asn Asp Pro Phe Ile Gln Lys Glu Lys Glu Asn Leu Ser
                85                  90                  95

Tyr Asp Leu Val Pro Met Lys Asn Gly Gly Val Gly Ile Lys Val Met
            100                 105                 110

Tyr Met Asp Glu Glu His Phe Phe Ser Val Glu Gln Ile Thr Ala Met
        115                 120                 125

Leu Leu Thr Lys Leu Lys Glu Thr Ala Glu Asn Asn Leu Lys Lys Pro
    130                 135                 140

Val Thr Asp Cys Val Ile Ser Val Pro Ser Phe Phe Thr Asp Ala Glu
145                 150                 155                 160

Arg Arg Ser Val Leu Asp Ala Ala Gln Ile Val Gly Leu Asn Cys Leu
                165                 170                 175

Arg Leu Met Asn Asp Met Thr Ala Val Ala Leu Asn Tyr Gly Ile Tyr
            180                 185                 190

Lys Gln Asp Leu Pro Asn Ala Glu Glu Lys Pro Arg Val Val Val Phe
        195                 200                 205

Val Asp Met Gly His Ser Ser Phe Gln Val Ser Ala Cys Ala Phe Asn
    210                 215                 220

Lys Gly Lys Leu Lys Val Leu Gly Thr Ala Phe Asp Pro Phe Leu Gly
225                 230                 235                 240

Gly Lys Asn Phe Asp Glu Lys Leu Val Glu His Phe Cys Ala Glu Phe
                245                 250                 255

Lys Thr Lys Tyr Lys Leu Asp Ala Lys Ser Lys Ile Arg Ala Leu Leu
            260                 265                 270

Arg Leu His Gln Glu Cys Glu Lys Leu Lys Lys Leu Met Ser Ser Asn
        275                 280                 285

Ser Thr Asp Leu Pro Leu Asn Ile Glu Cys Phe Met Asn Asp Lys Asp
    290                 295                 300

Val Ser Gly Lys Met Asn Arg Ser Gln Phe Glu Glu Leu Cys Ala Glu
305                 310                 315                 320

Leu Leu Gln Lys Ile Glu Val Pro Leu His Ser Leu Met Ala Gln Thr
                325                 330                 335

Gln Leu Lys Ala Glu Asp Val Ser Ala Ile Glu Ile Val Gly Gly Ala
            340                 345                 350

Thr Arg Ile Pro Ala Val Lys Glu Arg Ile Ala Lys Phe Phe Gly Lys
        355                 360                 365

Asp Val Ser Thr Thr Leu Asn Ala Asp Glu Ala Val Ala Arg Gly Cys
    370                 375                 380

Ala Leu Gln Cys Ala Ile Leu Ser Pro Ala Phe Lys Val Arg Glu Phe
385                 390                 395                 400

Ser Val Thr Asp Ala Val Pro Phe Pro Ile Ser Leu Val Trp Asn His
```

```
                405                 410                 415

Asp Ser Glu Glu Thr Glu Gly Val His Glu Val Phe Ser Arg Asn His
            420                 425                 430

Ala Ala Pro Phe Ser Lys Val Leu Thr Phe Leu Arg Arg Gly Pro Phe
        435                 440                 445

Glu Leu Glu Ala Phe Tyr Ser Asp Pro Gln Gly Val Pro Tyr Pro Glu
    450                 455                 460

Ala Lys Ile Gly Arg Phe Val Val Gln Asn Val Ser Ala Gln Lys Asp
465                 470                 475                 480

Gly Glu Lys Ser Arg Val Lys Val Lys Val Arg Val Asn Thr His Gly
                485                 490                 495

Ile Phe Thr Ile Ser Thr Ala Ser Met Val Glu Lys Val Pro Thr Glu
            500                 505                 510

Glu Glu Asp Gly Ser Ser Leu Glu Ala Asp Met Glu Cys Pro Asn Gln
        515                 520                 525

Arg Pro Thr Glu Ser Ser Asp Val Asp Lys Asn Ile Gln Gln Asp Asn
    530                 535                 540

Ser Glu Ala Gly Thr Gln Pro Gln Val Gln Thr Asp Gly Gln Gln Thr
545                 550                 555                 560

Ser Gln Ser Pro Pro Ser Pro Glu Leu Thr Ser Glu Glu Ser Lys Thr
                565                 570                 575

Pro Asp Ala Asp Lys Ala Asn Glu Lys Lys Val Asp Gln Pro Pro Glu
            580                 585                 590

Ala Lys Lys Pro Lys Ile Lys Val Val Asn Val Glu Leu Pro Val Glu
        595                 600                 605

Ala Asn Leu Val Trp Gln Leu Gly Arg Asp Leu Leu Asn Met Tyr Ile
    610                 615                 620

Glu Thr Glu Gly Lys Met Ile Met Gln Asp Lys Leu Glu Lys Glu Arg
625                 630                 635                 640

Asn Asp Ala Lys Asn Ala Val Glu Glu Cys Val Tyr Glu Phe Arg Asp
                645                 650                 655

Lys Leu Cys Gly Pro Tyr Glu Lys Phe Ile Cys Glu Gln Glu His Glu
            660                 665                 670

Lys Phe Leu Arg Leu Leu Thr Glu Thr Glu Asp Trp Leu Tyr Glu Glu
        675                 680                 685

Gly Glu Asp Gln Ala Lys Gln Ala Tyr Ile Asp Lys Leu Glu Glu Leu
    690                 695                 700

Met Lys Met Gly Thr Pro Val Lys Val Arg Phe Gln Glu Ala Glu Glu
705                 710                 715                 720

Arg Pro Lys Val Leu Glu Glu Leu Gly Gln Arg Leu Gln His Tyr Ala
                725                 730                 735

Lys Ile Ala Ala Asp Phe Arg Gly Lys Asp Glu Lys Tyr Asn His Ile
            740                 745                 750

Asp Glu Ser Glu Met Lys Lys Val Glu Lys Ser Val Asn Glu Val Met
        755                 760                 765

Glu Trp Met Asn Asn Val Met Asn Ala Gln Ala Lys Arg Ser Leu Asp
    770                 775                 780

Gln Asp Pro Val Val Arg Thr His Glu Ile Arg Ala Lys Val Lys Glu
785                 790                 795                 800

Leu Asn Asn Val Cys Glu Pro Val Val Thr Gln Pro Lys Pro Lys Ile
                805                 810                 815

Glu Ser Pro Lys Leu Glu Arg Thr Pro Asn Gly Pro Asn Ile Asp Lys
            820                 825                 830
```

```
Lys Glu Asp Leu Glu Gly Lys Asn Asn Leu Gly Ala Glu Ala Pro His
        835                 840                 845

Gln Asn Gly Glu Cys His Pro Asn Glu Lys Gly Ser Val Asn Met Asp
    850                 855                 860

Leu Asp His Asp Pro Val Asp Ala Val Ile Asn Thr Thr Cys Asn Tyr
865                 870                 875                 880

Gly Gln Val Val Ala Ala Leu Asn Ala Thr Asp Pro Gly Ala Ala Ala
                885                 890                 895

Gln Phe Asn Ala Ser Pro Val Ala Gln Ser Tyr Leu Arg Asn Phe Leu
            900                 905                 910

Ala Ala Pro Pro Pro Gln Arg Ala Ala Met Ala Ala Gln Leu Gln Ala
        915                 920                 925

Val Pro Gly Ala Ala Gln Tyr Ile Gly Leu Val Glu Ser Val Ala Gly
    930                 935                 940

Ser Cys Asn Asn Tyr
945


<210> SEQ ID NO 29
<211> LENGTH: 955
<212> TYPE: PRT
<213> ORGANISM: Mycobacterium tuberculosis

<400> SEQUENCE: 29

Met Gln His His His His His His Asp Pro Val Asp Ala Val Ile Asn
 1               5                  10                  15

Thr Thr Cys Asn Tyr Gly Gln Val Val Ala Ala Leu Asn Ala Thr Asp
            20                  25                  30

Pro Gly Ala Ala Ala Gln Phe Asn Ala Ser Pro Val Ala Gln Ser Tyr
        35                  40                  45

Leu Arg Asn Phe Leu Ala Ala Pro Pro Pro Gln Arg Ala Ala Met Ala
    50                  55                  60

Ala Gln Leu Gln Ala Val Pro Gly Ala Ala Gln Tyr Ile Gly Leu Val
65                  70                  75                  80

Glu Ser Val Ala Gly Ser Cys Asn Asn Tyr Ser Val Leu Leu Ile Gly
                85                  90                  95

Ser Ser Val Val Gly Leu Asp Val Gly Ser Gln Ser Cys Tyr Ile Ala
            100                 105                 110

Val Ala Arg Ala Gly Gly Ile Glu Thr Ile Ala Asn Glu Phe Ser Asp
        115                 120                 125

Arg Cys Thr Pro Ser Val Ile Ser Phe Gly Ser Lys Asn Arg Thr Ile
    130                 135                 140

Gly Val Ala Ala Lys Asn Gln Gln Ile Thr His Ala Asn Asn Thr Val
145                 150                 155                 160

Ser Ser Phe Lys Arg Phe His Gly Arg Ala Phe Asn Asp Pro Phe Ile
                165                 170                 175

Gln Lys Glu Lys Glu Asn Leu Ser Tyr Asp Leu Val Pro Met Lys Asn
            180                 185                 190

Gly Gly Val Gly Ile Lys Val Met Tyr Met Asp Glu Glu His Phe Phe
        195                 200                 205

Ser Val Glu Gln Ile Thr Ala Met Leu Leu Thr Lys Leu Lys Glu Thr
    210                 215                 220

Ala Glu Asn Asn Leu Lys Lys Pro Val Thr Asp Cys Val Ile Ser Val
225                 230                 235                 240

Pro Ser Phe Phe Thr Asp Ala Glu Arg Arg Ser Val Leu Asp Ala Ala
                245                 250                 255
```

```
Gln Ile Val Gly Leu Asn Cys Leu Arg Leu Met Asn Asp Met Thr Ala
            260                 265                 270

Val Ala Leu Asn Tyr Gly Ile Tyr Lys Gln Asp Leu Pro Asn Ala Glu
        275                 280                 285

Glu Lys Pro Arg Val Val Val Phe Val Asp Met Gly His Ser Ser Phe
    290                 295                 300

Gln Val Ser Ala Cys Ala Phe Asn Lys Gly Lys Leu Lys Val Leu Gly
305                 310                 315                 320

Thr Ala Phe Asp Pro Phe Leu Gly Gly Lys Asn Phe Asp Glu Lys Leu
                325                 330                 335

Val Glu His Phe Cys Ala Glu Phe Lys Thr Lys Tyr Lys Leu Asp Ala
            340                 345                 350

Lys Ser Lys Ile Arg Ala Leu Leu Arg Leu His Gln Glu Cys Glu Lys
        355                 360                 365

Leu Lys Lys Leu Met Ser Ser Asn Ser Thr Asp Leu Pro Leu Asn Ile
    370                 375                 380

Glu Cys Phe Met Asn Asp Lys Asp Val Ser Gly Lys Met Asn Arg Ser
385                 390                 395                 400

Gln Phe Glu Glu Leu Cys Ala Glu Leu Leu Gln Lys Ile Glu Val Pro
                405                 410                 415

Leu His Ser Leu Met Ala Gln Thr Gln Leu Lys Ala Glu Asp Val Ser
            420                 425                 430

Ala Ile Glu Ile Val Gly Gly Ala Thr Arg Ile Pro Ala Val Lys Glu
        435                 440                 445

Arg Ile Ala Lys Phe Phe Gly Lys Asp Val Ser Thr Thr Leu Asn Ala
    450                 455                 460

Asp Glu Ala Val Ala Arg Gly Cys Ala Leu Gln Cys Ala Ile Leu Ser
465                 470                 475                 480

Pro Ala Phe Lys Val Arg Glu Phe Ser Val Thr Asp Ala Val Pro Phe
                485                 490                 495

Pro Ile Ser Leu Val Trp Asn His Asp Ser Glu Glu Thr Glu Gly Val
            500                 505                 510

His Glu Val Phe Ser Arg Asn His Ala Ala Pro Phe Ser Lys Val Leu
        515                 520                 525

Thr Phe Leu Arg Arg Gly Pro Phe Glu Leu Glu Ala Phe Tyr Ser Asp
    530                 535                 540

Pro Gln Gly Val Pro Tyr Pro Glu Ala Lys Ile Gly Arg Phe Val Val
545                 550                 555                 560

Gln Asn Val Ser Ala Gln Lys Asp Gly Glu Lys Ser Arg Val Lys Val
                565                 570                 575

Lys Val Arg Val Asn Thr His Gly Ile Phe Thr Ile Ser Thr Ala Ser
            580                 585                 590

Met Val Glu Lys Val Pro Thr Glu Glu Glu Asp Gly Ser Ser Leu Glu
        595                 600                 605

Ala Asp Met Glu Cys Pro Asn Gln Arg Pro Thr Glu Ser Ser Asp Val
    610                 615                 620

Asp Lys Asn Ile Gln Gln Asp Asn Ser Glu Ala Gly Thr Gln Pro Gln
625                 630                 635                 640

Val Gln Thr Asp Gly Gln Gln Thr Ser Gln Ser Pro Pro Ser Pro Glu
                645                 650                 655

Leu Thr Ser Glu Glu Ser Lys Thr Pro Asp Ala Asp Lys Ala Asn Glu
            660                 665                 670

Lys Lys Val Asp Gln Pro Pro Glu Ala Lys Lys Pro Lys Ile Lys Val
        675                 680                 685
```

Val Asn Val Glu Leu Pro Val Glu Ala Asn Leu Val Trp Gln Leu Gly
690 695 700

Arg Asp Leu Leu Asn Met Tyr Ile Glu Thr Glu Gly Lys Met Ile Met
705 710 715 720

Gln Asp Lys Leu Glu Lys Glu Arg Asn Asp Ala Lys Asn Ala Val Glu
725 730 735

Glu Cys Val Tyr Glu Phe Arg Asp Lys Leu Cys Gly Pro Tyr Glu Lys
740 745 750

Phe Ile Cys Glu Gln Glu His Glu Lys Phe Leu Arg Leu Leu Thr Glu
755 760 765

Thr Glu Asp Trp Leu Tyr Glu Glu Gly Glu Asp Gln Ala Lys Gln Ala
770 775 780

Tyr Ile Asp Lys Leu Glu Glu Leu Met Lys Met Gly Thr Pro Val Lys
785 790 795 800

Val Arg Phe Gln Glu Ala Glu Glu Arg Pro Lys Val Leu Glu Glu Leu
805 810 815

Gly Gln Arg Leu Gln His Tyr Ala Lys Ile Ala Ala Asp Phe Arg Gly
820 825 830

Lys Asp Glu Lys Tyr Asn His Ile Asp Glu Ser Glu Met Lys Lys Val
835 840 845

Glu Lys Ser Val Asn Glu Val Met Glu Trp Met Asn Asn Val Met Asn
850 855 860

Ala Gln Ala Lys Arg Ser Leu Asp Gln Asp Pro Val Val Arg Thr His
865 870 875 880

Glu Ile Arg Ala Lys Val Lys Glu Leu Asn Asn Val Cys Glu Pro Val
885 890 895

Val Thr Gln Pro Lys Pro Lys Ile Glu Ser Pro Lys Leu Glu Arg Thr
900 905 910

Pro Asn Gly Pro Asn Ile Asp Lys Lys Glu Asp Leu Glu Gly Lys Asn
915 920 925

Asn Leu Gly Ala Glu Ala Pro His Gln Asn Gly Glu Cys His Pro Asn
930 935 940

Glu Lys Gly Ser Val Asn Met Asp Leu Asp Ile
945 950 955

<210> SEQ ID NO 30
<211> LENGTH: 1257
<212> TYPE: PRT
<213> ORGANISM: Homo sapiens

<400> SEQUENCE: 30

Met Gln His His His His His His His Ser Val Val Gly Leu Asp Val
1 5 10 15

Gly Ser Gln Ser Cys Tyr Ile Ala Val Ala Arg Ala Gly Gly Ile Glu
20 25 30

Thr Ile Ala Asn Glu Phe Ser Asp Arg Cys Thr Pro Ser Val Ile Ser
35 40 45

Phe Gly Ser Lys Asn Arg Thr Ile Gly Val Ala Ala Lys Asn Gln Gln
50 55 60

Ile Thr His Ala Asn Asn Thr Val Ser Ser Phe Lys Arg Phe His Gly
65 70 75 80

Arg Ala Phe Asn Asp Pro Phe Ile Gln Lys Glu Lys Glu Asn Leu Ser
85 90 95

Tyr Asp Leu Val Pro Met Lys Asn Gly Gly Val Gly Ile Lys Val Met
100 105 110

```
Tyr Met Asp Glu Glu His Phe Phe Ser Val Glu Gln Ile Thr Ala Met
        115                 120                 125

Leu Leu Thr Lys Leu Lys Glu Thr Ala Glu Asn Asn Leu Lys Lys Pro
    130                 135                 140

Val Thr Asp Cys Val Ile Ser Val Pro Ser Phe Phe Thr Asp Ala Glu
145                 150                 155                 160

Arg Arg Ser Val Leu Asp Ala Ala Gln Ile Val Gly Leu Asn Cys Leu
                165                 170                 175

Arg Leu Met Asn Asp Met Thr Ala Val Ala Leu Asn Tyr Gly Ile Tyr
            180                 185                 190

Lys Gln Asp Leu Pro Asn Ala Glu Glu Lys Pro Arg Val Val Val Phe
        195                 200                 205

Val Asp Met Gly His Ser Ser Phe Gln Val Ser Ala Cys Ala Phe Asn
    210                 215                 220

Lys Gly Lys Leu Lys Val Leu Gly Thr Ala Phe Asp Pro Phe Leu Gly
225                 230                 235                 240

Gly Lys Asn Phe Asp Glu Lys Leu Val Glu His Phe Cys Ala Glu Phe
                245                 250                 255

Lys Thr Lys Tyr Lys Leu Asp Ala Lys Ser Lys Ile Arg Ala Leu Leu
            260                 265                 270

Arg Leu His Gln Glu Cys Glu Lys Leu Lys Lys Leu Met Ser Ser Asn
        275                 280                 285

Ser Thr Asp Leu Pro Leu Asn Ile Glu Cys Phe Met Asn Asp Lys Asp
    290                 295                 300

Val Ser Gly Lys Met Asn Arg Ser Gln Phe Glu Glu Leu Cys Ala Glu
305                 310                 315                 320

Leu Leu Gln Lys Ile Glu Val Pro Leu His Ser Leu Met Ala Gln Thr
                325                 330                 335

Gln Leu Lys Ala Glu Asp Val Ser Ala Ile Glu Ile Val Gly Gly Ala
            340                 345                 350

Thr Arg Ile Pro Ala Val Lys Glu Arg Ile Ala Lys Phe Phe Gly Lys
        355                 360                 365

Asp Val Ser Thr Thr Leu Asn Ala Asp Glu Ala Val Ala Arg Gly Cys
    370                 375                 380

Ala Leu Gln Cys Ala Ile Leu Ser Pro Ala Phe Lys Val Arg Glu Phe
385                 390                 395                 400

Ser Val Thr Asp Ala Val Pro Phe Pro Ile Ser Leu Val Trp Asn His
                405                 410                 415

Asp Ser Glu Glu Thr Glu Gly Val His Glu Val Phe Ser Arg Asn His
            420                 425                 430

Ala Ala Pro Phe Ser Lys Val Leu Thr Phe Leu Arg Arg Gly Pro Phe
        435                 440                 445

Glu Leu Glu Ala Phe Tyr Ser Asp Pro Gln Gly Val Pro Tyr Pro Glu
    450                 455                 460

Ala Lys Ile Gly Arg Phe Val Val Gln Asn Val Ser Ala Gln Lys Asp
465                 470                 475                 480

Gly Glu Lys Ser Arg Val Lys Val Lys Val Arg Val Asn Thr His Gly
                485                 490                 495

Ile Phe Thr Ile Ser Thr Ala Ser Met Val Glu Lys Val Pro Thr Glu
            500                 505                 510

Glu Glu Asp Gly Ser Ser Leu Glu Ala Asp Met Glu Cys Pro Asn Gln
        515                 520                 525

Arg Pro Thr Glu Ser Ser Asp Val Asp Lys Asn Ile Gln Gln Asp Asn
```

-continued

```
    530                 535                 540

Ser Glu Ala Gly Thr Gln Pro Gln Val Gln Thr Asp Gly Gln Gln Thr
545                 550                 555                 560

Ser Gln Ser Pro Pro Ser Pro Glu Leu Thr Ser Glu Glu Ser Lys Thr
                565                 570                 575

Pro Asp Ala Asp Lys Ala Asn Glu Lys Lys Val Asp Gln Pro Pro Glu
            580                 585                 590

Ala Lys Lys Pro Lys Ile Lys Val Val Asn Val Glu Leu Pro Val Glu
        595                 600                 605

Ala Asn Leu Val Trp Gln Leu Gly Arg Asp Leu Leu Asn Met Tyr Ile
    610                 615                 620

Glu Thr Glu Gly Lys Met Ile Met Gln Asp Lys Leu Glu Lys Glu Arg
625                 630                 635                 640

Asn Asp Ala Lys Asn Ala Val Glu Glu Cys Val Tyr Glu Phe Arg Asp
                645                 650                 655

Lys Leu Cys Gly Pro Tyr Glu Lys Phe Ile Cys Glu Gln Glu His Glu
            660                 665                 670

Lys Phe Leu Arg Leu Leu Thr Glu Thr Glu Asp Trp Leu Tyr Glu Glu
        675                 680                 685

Gly Glu Asp Gln Ala Lys Gln Ala Tyr Ile Asp Lys Leu Glu Glu Leu
    690                 695                 700

Met Lys Met Gly Thr Pro Val Lys Val Arg Phe Gln Glu Ala Glu Glu
705                 710                 715                 720

Arg Pro Lys Val Leu Glu Glu Leu Gly Gln Arg Leu Gln His Tyr Ala
                725                 730                 735

Lys Ile Ala Ala Asp Phe Arg Gly Lys Asp Glu Lys Tyr Asn His Ile
            740                 745                 750

Asp Glu Ser Glu Met Lys Lys Val Glu Lys Ser Val Asn Glu Val Met
        755                 760                 765

Glu Trp Met Asn Asn Val Met Asn Ala Gln Ala Lys Arg Ser Leu Asp
    770                 775                 780

Gln Asp Pro Val Val Arg Thr His Glu Ile Arg Ala Lys Val Lys Glu
785                 790                 795                 800

Leu Asn Asn Val Cys Glu Pro Val Val Thr Gln Pro Lys Pro Lys Ile
                805                 810                 815

Glu Ser Pro Lys Leu Glu Arg Thr Pro Asn Gly Pro Asn Ile Asp Lys
            820                 825                 830

Lys Glu Asp Leu Glu Gly Lys Asn Asn Leu Gly Ala Glu Ala Pro His
        835                 840                 845

Gln Asn Gly Glu Cys His Pro Asn Glu Lys Gly Ser Val Asn Met Asp
    850                 855                 860

Leu Asp His Val Asp Phe Gly Ala Leu Pro Pro Glu Ile Asn Ser Ala
865                 870                 875                 880

Arg Met Tyr Ala Gly Pro Gly Ser Ala Ser Leu Val Ala Ala Ala Gln
                885                 890                 895

Met Trp Asp Ser Val Ala Ser Asp Leu Phe Ser Ala Ala Ser Ala Phe
            900                 905                 910

Gln Ser Val Val Trp Gly Leu Thr Val Gly Ser Trp Ile Gly Ser Ser
        915                 920                 925

Ala Gly Leu Met Val Ala Ala Ala Ser Pro Tyr Val Ala Trp Met Ser
    930                 935                 940

Val Thr Ala Gly Gln Ala Glu Leu Thr Ala Ala Gln Val Arg Val Ala
945                 950                 955                 960
```

-continued

```
Ala Ala Ala Tyr Glu Thr Ala Tyr Gly Leu Thr Val Pro Pro Pro Val
                965                 970                 975

Ile Ala Glu Asn Arg Ala Glu Leu Met Ile Leu Ile Ala Thr Asn Leu
            980                 985                 990

Leu Gly Gln Asn Thr Pro Ala Ile Ala Val Asn Glu Ala Glu Tyr Gly
        995                 1000                1005

Glu Met Trp Ala Gln Asp Ala Ala Ala Met Phe Gly Tyr Ala Ala Ala
    1010                1015                1020

Thr Ala Thr Ala Thr Ala Thr Leu Leu Pro Phe Glu Glu Ala Pro Glu
1025                1030                1035                1040

Met Thr Ser Ala Gly Gly Leu Leu Glu Gln Ala Ala Ala Val Glu Glu
                1045                1050                1055

Ala Ser Asp Thr Ala Ala Ala Asn Gln Leu Met Asn Asn Val Pro Gln
            1060                1065                1070

Ala Leu Gln Gln Leu Ala Gln Pro Thr Gln Gly Thr Thr Pro Ser Ser
        1075                1080                1085

Lys Leu Gly Gly Leu Trp Lys Thr Val Ser Pro His Arg Ser Pro Ile
    1090                1095                1100

Ser Asn Met Val Ser Met Ala Asn Asn His Met Ser Met Thr Asn Ser
1105                1110                1115                1120

Gly Val Ser Met Thr Asn Thr Leu Ser Ser Met Leu Lys Gly Phe Ala
                1125                1130                1135

Pro Ala Ala Ala Ala Gln Ala Val Gln Thr Ala Ala Gln Asn Gly Val
            1140                1145                1150

Arg Ala Met Ser Ser Leu Gly Ser Ser Leu Gly Ser Ser Gly Leu Gly
        1155                1160                1165

Gly Gly Val Ala Ala Asn Leu Gly Arg Ala Ala Ser Val Gly Ser Leu
    1170                1175                1180

Ser Val Pro Gln Ala Trp Ala Ala Ala Asn Gln Ala Val Thr Pro Ala
1185                1190                1195                1200

Ala Arg Ala Leu Pro Leu Thr Ser Leu Thr Ser Ala Ala Glu Arg Gly
                1205                1210                1215

Pro Gly Gln Met Leu Gly Gly Leu Pro Val Gly Gln Met Gly Ala Arg
            1220                1225                1230

Ala Gly Gly Gly Leu Ser Gly Val Leu Arg Val Pro Pro Arg Pro Tyr
        1235                1240                1245

Val Met Pro His Ser Pro Ala Ala Gly
    1250                1255
```

```
<210> SEQ ID NO 31
<211> LENGTH: 1257
<212> TYPE: PRT
<213> ORGANISM: Mycobacterium tuberculosis

<400> SEQUENCE: 31

Met Gln His His His His His His His Ser Val Val Gly Leu Asp Val
 1               5                  10                  15

Gly Ser Gln Ser Cys Tyr Ile Ala Val Ala Arg Ala Gly Gly Ile Glu
            20                  25                  30

Thr Ile Ala Asn Glu Phe Ser Asp Arg Cys Thr Pro Ser Val Ile Ser
        35                  40                  45

Phe Gly Ser Lys Asn Arg Thr Ile Gly Val Ala Ala Lys Asn Gln Gln
    50                  55                  60

Ile Thr His Ala Asn Asn Thr Val Ser Ser Phe Lys Arg Phe His Gly
65                  70                  75                  80
```

-continued

```
Arg Ala Phe Asn Asp Pro Phe Ile Gln Lys Glu Lys Glu Asn Leu Ser
                 85                  90                  95

Tyr Asp Leu Val Pro Met Lys Asn Gly Gly Val Gly Ile Lys Val Met
            100                 105                 110

Tyr Met Asp Glu Glu His Phe Phe Ser Val Glu Gln Ile Thr Ala Met
        115                 120                 125

Leu Leu Thr Lys Leu Lys Glu Thr Ala Glu Asn Asn Leu Lys Lys Pro
    130                 135                 140

Val Thr Asp Cys Val Ile Ser Val Pro Ser Phe Phe Thr Asp Ala Glu
145                 150                 155                 160

Arg Arg Ser Val Leu Asp Ala Ala Gln Ile Val Gly Leu Asn Cys Leu
                165                 170                 175

Arg Leu Met Asn Asp Met Thr Ala Val Ala Leu Asn Tyr Gly Ile Tyr
            180                 185                 190

Lys Gln Asp Leu Pro Asn Ala Glu Glu Lys Pro Arg Val Val Val Phe
        195                 200                 205

Val Asp Met Gly His Ser Ser Phe Gln Val Ser Ala Cys Ala Phe Asn
    210                 215                 220

Lys Gly Lys Leu Lys Val Leu Gly Thr Ala Phe Asp Pro Phe Leu Gly
225                 230                 235                 240

Gly Lys Asn Phe Asp Glu Lys Leu Val Glu His Phe Cys Ala Glu Phe
                245                 250                 255

Lys Thr Lys Tyr Lys Leu Asp Ala Lys Ser Lys Ile Arg Ala Leu Leu
            260                 265                 270

Arg Leu His Gln Glu Cys Glu Lys Leu Lys Lys Leu Met Ser Ser Asn
        275                 280                 285

Ser Thr Asp Leu Pro Leu Asn Ile Glu Cys Phe Met Asn Asp Lys Asp
    290                 295                 300

Val Ser Gly Lys Met Asn Arg Ser Gln Phe Glu Glu Leu Cys Ala Glu
305                 310                 315                 320

Leu Leu Gln Lys Ile Glu Val Pro Leu His Ser Leu Met Ala Gln Thr
                325                 330                 335

Gln Leu Lys Ala Glu Asp Val Ser Ala Ile Glu Ile Val Gly Gly Ala
            340                 345                 350

Thr Arg Ile Pro Ala Val Lys Glu Arg Ile Ala Lys Phe Phe Gly Lys
        355                 360                 365

Asp Val Ser Thr Thr Leu Asn Ala Asp Glu Ala Val Ala Arg Gly Cys
    370                 375                 380

Ala Leu Gln Cys Ala Ile Leu Ser Pro Ala Phe Lys Val Arg Glu Phe
385                 390                 395                 400

Ser Val Thr Asp Ala Val Pro Phe Pro Ile Ser Leu Val Trp Asn His
                405                 410                 415

Asp Ser Glu Glu Thr Glu Gly Val His Glu Val Phe Ser Arg Asn His
            420                 425                 430

Ala Ala Pro Phe Ser Lys Val Leu Thr Phe Leu Arg Arg Gly Pro Phe
        435                 440                 445

Glu Leu Glu Ala Phe Tyr Ser Asp Pro Gln Gly Val Pro Tyr Pro Glu
    450                 455                 460

Ala Lys Ile Gly Arg Phe Val Val Gln Asn Val Ser Ala Gln Lys Asp
465                 470                 475                 480

Gly Glu Lys Ser Arg Val Lys Val Lys Val Arg Val Asn Thr His Gly
                485                 490                 495

Ile Phe Thr Ile Ser Thr Ala Ser Met Val Glu Lys Val Pro Thr Glu
            500                 505                 510
```

-continued

```
Glu Glu Asp Gly Ser Ser Leu Glu Ala Asp Met Glu Cys Pro Asn Gln
        515                 520                 525

Arg Pro Thr Glu Ser Ser Asp Val Asp Lys Asn Ile Gln Gln Asp Asn
    530                 535                 540

Ser Glu Ala Gly Thr Gln Pro Gln Val Gln Thr Asp Gly Gln Gln Thr
545                 550                 555                 560

Ser Gln Ser Pro Pro Ser Pro Glu Leu Thr Ser Glu Glu Ser Lys Thr
                565                 570                 575

Pro Asp Ala Asp Lys Ala Asn Glu Lys Lys Val Asp Gln Pro Pro Glu
            580                 585                 590

Ala Lys Lys Pro Lys Ile Lys Val Val Asn Val Glu Leu Pro Val Glu
        595                 600                 605

Ala Asn Leu Val Trp Gln Leu Gly Arg Asp Leu Leu Asn Met Tyr Ile
    610                 615                 620

Glu Thr Glu Gly Lys Met Ile Met Gln Asp Lys Leu Glu Lys Glu Arg
625                 630                 635                 640

Asn Asp Ala Lys Asn Ala Val Glu Glu Cys Val Tyr Glu Phe Arg Asp
                645                 650                 655

Lys Leu Cys Gly Pro Tyr Glu Lys Phe Ile Cys Glu Gln Glu His Glu
            660                 665                 670

Lys Phe Leu Arg Leu Leu Thr Glu Thr Glu Asp Trp Leu Tyr Glu Glu
        675                 680                 685

Gly Glu Asp Gln Ala Lys Gln Ala Tyr Ile Asp Lys Leu Glu Glu Leu
    690                 695                 700

Met Lys Met Gly Thr Pro Val Lys Val Arg Phe Gln Glu Ala Glu Glu
705                 710                 715                 720

Arg Pro Lys Val Leu Glu Glu Leu Gly Gln Arg Leu Gln His Tyr Ala
                725                 730                 735

Lys Ile Ala Ala Asp Phe Arg Gly Lys Asp Glu Lys Tyr Asn His Ile
            740                 745                 750

Asp Glu Ser Glu Met Lys Lys Val Glu Lys Ser Val Asn Glu Val Met
        755                 760                 765

Glu Trp Met Asn Asn Val Met Asn Ala Gln Ala Lys Arg Ser Leu Asp
    770                 775                 780

Gln Asp Pro Val Val Arg Thr His Glu Ile Arg Ala Lys Val Lys Glu
785                 790                 795                 800

Leu Asn Asn Val Cys Glu Pro Val Val Thr Gln Pro Lys Pro Lys Ile
                805                 810                 815

Glu Ser Pro Lys Leu Glu Arg Thr Pro Asn Gly Pro Asn Ile Asp Lys
            820                 825                 830

Lys Glu Asp Leu Glu Gly Lys Asn Asn Leu Gly Ala Glu Ala Pro His
        835                 840                 845

Gln Asn Gly Glu Cys His Pro Asn Glu Lys Gly Ser Val Asn Met Asp
    850                 855                 860

Leu Asp His Val Asp Phe Gly Ala Leu Pro Pro Glu Ile Asn Ser Ala
865                 870                 875                 880

Arg Met Tyr Ala Gly Pro Gly Ser Ala Ser Leu Val Ala Ala Ala Gln
                885                 890                 895

Met Trp Asp Ser Val Ala Ser Asp Leu Phe Ser Ala Ala Ser Ala Phe
            900                 905                 910

Gln Ser Val Val Trp Gly Leu Thr Val Gly Ser Trp Ile Gly Ser Ser
        915                 920                 925

Ala Gly Leu Met Val Ala Ala Ala Ser Pro Tyr Val Ala Trp Met Ser
```

-continued

```
    930                 935                 940

Val Thr Ala Gly Gln Ala Glu Leu Thr Ala Ala Gln Val Arg Val Ala
945                 950                 955                 960

Ala Ala Ala Tyr Glu Thr Ala Tyr Gly Leu Thr Val Pro Pro Pro Val
                965                 970                 975

Ile Ala Glu Asn Arg Ala Glu Leu Met Ile Leu Ile Ala Thr Asn Leu
            980                 985                 990

Leu Gly Gln Asn Thr Pro Ala Ile Ala Val Asn Glu Ala Glu Tyr Gly
        995                 1000                1005

Glu Met Trp Ala Gln Asp Ala Ala Ala Met Phe Gly Tyr Ala Ala Ala
    1010                1015                1020

Thr Ala Thr Ala Thr Ala Thr Leu Leu Pro Phe Glu Glu Ala Pro Glu
1025                1030                1035                1040

Met Thr Ser Ala Gly Gly Leu Leu Glu Gln Ala Ala Ala Val Glu Glu
                1045                1050                1055

Ala Ser Asp Thr Ala Ala Ala Asn Gln Leu Met Asn Asn Val Pro Gln
            1060                1065                1070

Ala Leu Gln Gln Leu Ala Gln Pro Thr Gln Gly Thr Thr Pro Ser Ser
        1075                1080                1085

Lys Leu Gly Gly Leu Trp Lys Thr Val Ser Pro His Arg Ser Pro Ile
    1090                1095                1100

Ser Asn Met Val Ser Met Ala Asn Asn His Met Ser Met Thr Asn Ser
1105                1110                1115                1120

Gly Val Ser Met Thr Asn Thr Leu Ser Ser Met Leu Lys Gly Phe Ala
                1125                1130                1135

Pro Ala Ala Ala Ala Gln Ala Val Gln Thr Ala Ala Gln Asn Gly Val
            1140                1145                1150

Arg Ala Met Ser Ser Leu Gly Ser Ser Leu Gly Ser Ser Gly Leu Gly
        1155                1160                1165

Gly Gly Val Ala Ala Asn Leu Gly Arg Ala Ala Ser Val Gly Ser Leu
    1170                1175                1180

Ser Val Pro Gln Ala Trp Ala Ala Ala Asn Gln Ala Val Thr Pro Ala
1185                1190                1195                1200

Ala Arg Ala Leu Pro Leu Thr Ser Leu Thr Ser Ala Ala Glu Arg Gly
                1205                1210                1215

Pro Gly Gln Met Leu Gly Gly Leu Pro Val Gly Gln Met Gly Ala Arg
            1220                1225                1230

Ala Gly Gly Gly Leu Ser Gly Val Leu Arg Val Pro Pro Arg Pro Tyr
        1235                1240                1245

Val Met Pro His Ser Pro Ala Ala Gly
    1250                1255


<210> SEQ ID NO 32
<211> LENGTH: 78
<212> TYPE: PRT
<213> ORGANISM: Mycobacterium tuberculosis

<400> SEQUENCE: 32

Ala His Arg Ala Ala Thr Leu Arg Trp Arg Gly Pro Gly Ala Ser Arg
 1               5                  10                  15

Pro Ser Pro Thr Ser Ser Ala Thr Ala Ala Pro Arg Gln Ser Tyr His
            20                  25                  30

Leu Asp Gln Lys Thr Glu Gln Leu Glu Leu Gln Pro Lys Thr Ser Lys
        35                  40                  45

Ser Leu Met Gln Thr Ile Arg Ser Leu Ala Leu Arg Asp Phe Met Ala
```

```
    50                  55                  60

Glu His Ser Met Thr Pro Ser Phe Arg Arg Lys Arg Arg Thr
65                  70                  75


<210> SEQ ID NO 33
<211> LENGTH: 84
<212> TYPE: PRT
<213> ORGANISM: Mycobacterium tuberculosis

<400> SEQUENCE: 33

Lys Lys Glu Leu Pro Ser Ser Leu Glu Lys Met Ser Ala Pro Arg Ser
 1               5                  10                  15

Met Gln Thr Lys Leu Trp Pro Glu Ala Val His Cys Ser Val Gln Phe
            20                  25                  30

Phe Leu Arg His Leu Lys Leu Glu Ser Ser Leu Ser Pro Met Gln Phe
        35                  40                  45

Leu Phe Gln Tyr Leu Trp Ser Gly Thr Thr Thr Arg Lys Lys Arg Lys
    50                  55                  60

Val Cys Thr Arg Cys Ser Val Gly Thr Met Leu Leu Leu Ser Pro Lys
65                  70                  75                  80

Cys Ser Pro Ser


<210> SEQ ID NO 34
<211> LENGTH: 105
<212> TYPE: PRT
<213> ORGANISM: Mycobacterium tuberculosis

<400> SEQUENCE: 34

Thr His Met Ala Ser Ser Pro Ser Pro Arg Leu Pro Trp Trp Arg Arg
 1               5                  10                  15

Ser Arg Pro Arg Lys Arg Met Ala Pro Leu Ser Arg Gln Thr Trp Asn
            20                  25                  30

Val Gln Thr Arg Gly Gln Gln Lys Ala Arg Met Trp Ile Lys Ile Ser
        35                  40                  45

Ser Lys Thr Thr Val Lys Leu Glu His Ser Pro Arg Tyr Lys Leu Met
    50                  55                  60

Val Asn Lys Pro His Ser Leu Pro Leu His Leu Asn Leu Pro Gln Lys
65                  70                  75                  80

Lys Ala Lys Pro Gln Met Leu Thr Lys Gln Met Lys Arg Lys Leu Ile
                85                  90                  95

Ser Leu Gln Lys Pro Arg Asn Leu Lys
            100                 105


<210> SEQ ID NO 35
<211> LENGTH: 51
<212> TYPE: PRT
<213> ORGANISM: Mycobacterium tuberculosis

<400> SEQUENCE: 35

Lys Trp Ala Leu Leu Leu Lys Ser Asp Phe Lys Lys Leu Arg Asn Asp
 1               5                  10                  15

Arg Lys Cys Trp Arg Ser Trp Gly Ser Ala Cys Ser Thr Met Pro Arg
            20                  25                  30

Leu Gln Arg Thr Ser Glu Ala Arg Met Arg Asn Thr Thr Thr Leu Met
        35                  40                  45

Asn Gln Lys
    50
```

<210> SEQ ID NO 36
<211> LENGTH: 82
<212> TYPE: PRT
<213> ORGANISM: Mycobacterium tuberculosis

<400> SEQUENCE: 36

```
Lys Ala Lys Ile Ile Leu Val Leu Lys Leu Arg Ile Arg Met Val Asn
 1               5                  10                  15

Ala Thr Leu Met Arg Arg Ala Leu Ser Thr Trp Thr Trp Ile Thr Trp
            20                  25                  30

Ile Ser Gly Arg Tyr His Arg Arg Ser Thr Pro Arg Gly Cys Thr Pro
        35                  40                  45

Ala Arg Val Arg Pro Arg Trp Trp Pro Arg Leu Arg Cys Gly Thr Ala
    50                  55                  60

Trp Arg Val Thr Cys Phe Arg Pro Arg Arg Arg Phe Ser Arg Trp Ser
65                  70                  75                  80

Gly Val
```

<210> SEQ ID NO 37
<211> LENGTH: 52
<212> TYPE: PRT
<213> ORGANISM: Mycobacterium tuberculosis

<400> SEQUENCE: 37

```
Arg Pro Thr Ser Trp Gly Lys Thr Pro Arg Arg Ser Arg Ser Thr Arg
 1               5                  10                  15

Pro Asn Thr Ala Arg Cys Gly Pro Lys Thr Pro Pro Arg Cys Leu Ala
            20                  25                  30

Thr Pro Arg Arg Arg Arg Arg Arg Arg Arg Arg Cys Cys Arg Ser Arg
        35                  40                  45

Arg Arg Arg Arg
    50
```

<210> SEQ ID NO 38
<211> LENGTH: 50
<212> TYPE: PRT
<213> ORGANISM: Mycobacterium tuberculosis

<400> SEQUENCE: 38

```
Ala Arg Trp Ala Ala Arg Trp Val Leu Arg Val Trp Ala Val Gly Trp
 1               5                  10                  15

Pro Pro Thr Trp Val Gly Arg Pro Arg Ser Val Arg Cys Arg Cys Arg
            20                  25                  30

Arg Pro Gly Pro Arg Pro Thr Arg Gln Ser Pro Arg Arg Arg Gly Arg
        35                  40                  45

Cys Arg
    50
```

<210> SEQ ID NO 39
<211> LENGTH: 72
<212> TYPE: PRT
<213> ORGANISM: Mycobacterium tuberculosis

<400> SEQUENCE: 39

```
Ala Ala Ser Pro Pro Ser Pro Pro Leu Gly Gly Trp Ala Arg Arg Arg
 1               5                  10                  15

Leu Thr Glu Leu Leu His Cys Gly Gly Ala Gly Arg Gly His Arg Asp
            20                  25                  30

His Arg Gln Arg Val Gln Arg Pro Leu His Pro Val Ser His Ile Ile
        35                  40                  45
```

```
Trp Ile Lys Lys Gln Asn Asn Trp Ser Cys Ser Gln Lys Pro Ala Asn
    50                  55                  60

His Ser Cys Lys Gln Tyr Gly Leu
65                  70
```

<210> SEQ ID NO 40
<211> LENGTH: 50
<212> TYPE: PRT
<213> ORGANISM: Mycobacterium tuberculosis

<400> SEQUENCE: 40

```
Arg Val Leu Cys His Arg Cys Ser Ser Phe Ser Asn Ile Ser Gly Leu
 1               5                  10                  15

Glu Pro Arg Leu Gly Arg Asn Gly Arg Cys Ala Arg Gly Val Gln Ser
            20                  25                  30

Glu Pro Cys Cys Ser Phe Leu Gln Ser Ala His Leu Pro Glu Lys Gly
        35                  40                  45

Ala Leu
    50
```

<210> SEQ ID NO 41
<211> LENGTH: 81
<212> TYPE: PRT
<213> ORGANISM: Mycobacterium tuberculosis

<400> SEQUENCE: 41

```
Pro Ser Arg Ser Ser Ile Ser Arg Ser Lys Asn Arg Pro Phe Cys Cys
 1               5                  10                  15

Ser Glu Cys Phe Cys Thr Glu Arg Trp Arg Glu Val Glu Ser Glu Gly
            20                  25                  30

Gln Ser Ala Cys Glu His Thr Trp His Leu His His Leu His Gly Phe
        35                  40                  45

His Gly Gly Glu Gly Pro Asp Arg Gly Arg Gly Trp Leu Leu Ser Arg
    50                  55                  60

Gly Arg His Gly Met Ser Lys Pro Glu Ala Asn Arg Lys Leu Gly Cys
65                  70                  75                  80

Gly
```

<210> SEQ ID NO 42
<211> LENGTH: 78
<212> TYPE: PRT
<213> ORGANISM: Mycobacterium tuberculosis

<400> SEQUENCE: 42

```
Pro Val Phe Gly Arg Val Gly Val Ser Val Gly Gly Leu Gly Ser Asp
 1               5                  10                  15

Gly Gly Val Val Asp Arg Phe Val Gly Gly Ser Asp Gly Gly Gly Gly
            20                  25                  30

Leu Ala Val Cys Gly Val Asp Glu Arg His Arg Gly Ala Gly Arg Ala
        35                  40                  45

Asp Arg Arg Pro Gly Pro Gly Cys Cys Gly Gly Leu Arg Asp Gly Val
    50                  55                  60

Trp Ala Asp Gly Ala Pro Ala Gly Asp Arg Arg Glu Pro Cys
65                  70                  75
```

<210> SEQ ID NO 43
<211> LENGTH: 275
<212> TYPE: PRT
<213> ORGANISM: Mycobacterium tuberculosis

<400> SEQUENCE: 43

Thr Asp Asp Ser Asp Ser Asp Gln Pro Leu Gly Ala Lys His Pro Gly
1 5 10 15

Asp Arg Gly Gln Arg Gly Arg Ile Arg Arg Asp Val Gly Pro Arg Arg
20 25 30

Arg Arg Asp Val Trp Leu Arg Arg Gly Asp Gly Asp Gly Asp Gly Asp
35 40 45

Val Ala Ala Val Arg Gly Gly Ala Gly Asp Asp Gln Arg Gly Trp Ala
50 55 60

Pro Arg Ala Gly Arg Arg Gly Arg Gly Gly Leu Arg His Arg Arg Gly
65 70 75 80

Glu Pro Val Asp Glu Gln Cys Ala Pro Gly Ala Ala Thr Ala Gly Pro
85 90 95

Ala His Ala Gly His His Ala Phe Phe Gln Ala Gly Trp Pro Val Glu
100 105 110

Asp Gly Leu Ala Ala Ser Val Ala Asp Gln Gln His Gly Val Asp Gly
115 120 125

Gln Gln Pro His Val Asp Asp Gln Leu Gly Cys Val Asp Asp Gln His
130 135 140

Leu Glu Leu Asp Val Glu Gly Leu Cys Ser Gly Gly Gly Arg Pro Gly
145 150 155 160

Arg Ala Asn Arg Gly Ala Lys Arg Gly Pro Gly Asp Glu Leu Ala Gly
165 170 175

Gln Leu Ala Gly Phe Phe Gly Ser Gly Arg Trp Gly Gly Arg Gln Leu
180 185 190

Gly Ser Gly Gly Leu Gly Arg Phe Val Val Gly Ala Ala Gly Leu Gly
195 200 205

Arg Gly Gln Pro Gly Ser His Pro Gly Gly Ala Gly Ala Ala Ala Asp
210 215 220

Gln Pro Asp Gln Arg Arg Gly Lys Arg Ala Arg Ala Asp Ala Gly Arg
225 230 235 240

Ala Ala Gly Gly Ala Asp Gly Arg Gln Gly Arg Trp Trp Ala Gln Trp
245 250 255

Cys Ala Ala Cys Ser Ala Ala Thr Leu Cys Asp Ala Ala Phe Ser Gly
260 265 270

Ser Arg Leu
275

<210> SEQ ID NO 44
<211> LENGTH: 385
<212> TYPE: PRT
<213> ORGANISM: Mycobacterium tuberculosis

<400> SEQUENCE: 44

Leu Ala Gly Cys Arg Arg Met Arg His His Ile Gly Ser Arg Arg Asn
1 5 10 15

Thr Gln His Thr Thr Glu Pro Thr Thr Gly Pro Gly Ala His Leu Pro
20 25 30

His Arg Gln Pro Ala Gln His Leu Pro Gly Pro Ser Phe Arg Gly Ala
35 40 45

Gly Gln Ala Gly Gln Arg Gln Arg Pro Arg Arg Arg Gly Asp Cys Leu
50 55 60

Val Gly Arg Gly Pro Gly Leu Arg His Arg Gln Arg Thr Asp Arg Gly
65 70 75 80

-continued

Arg Pro Thr Gln Val Gly Gly His Pro Thr Ala Gln Thr Arg Arg Thr
85 90 95

Gln Arg Ala Ala Gln Arg Ala His Arg Pro Asp Pro Val Leu Arg Arg
100 105 110

Gly Leu His Gly Leu Gly Gly Arg Arg Arg Ser Lys Ala Leu Gln His
115 120 125

Arg Ala Gln Gly Val Gly His Arg His Thr Arg Val Gly His Arg His
130 135 140

Val Val Val Gly His Arg His His Val Ala Asp Arg Arg Pro Met Arg
145 150 155 160

Arg Asp Arg Leu Pro Gln Ala Thr Gln Leu Gly Arg Arg Arg Gly Ala
165 170 175

Leu Arg Gly Leu Gly Gln Leu Leu Gln Arg Leu Gly His Ile Val His
180 185 190

Gln Leu Val Arg Arg Gly Gly Val Gly Gly Leu Leu Asp Arg Gly Gly
195 200 205

Leu Leu Glu Glu Pro Thr Arg Ala Gly His Leu Arg Arg Leu Leu Glu
210 215 220

Arg Gln Gln Arg Arg Arg Arg Arg Arg Arg Arg Arg Gly Val Ala Lys
225 230 235 240

His Arg Gly Gly Val Leu Gly Pro His Leu Ala Val Phe Gly Leu Val
245 250 255

Asp Arg Asp Arg Arg Gly Val Leu Pro Gln Glu Val Gly Arg Tyr Gln
260 265 270

Asn His Gln Phe Ser Thr Val Leu Gly Asp His Arg Arg Gly His Arg
275 280 285

Gln Pro Ile Arg Arg Leu Val Gly Arg Arg Ser Asn Pro Asp Leu Gly
290 295 300

Gly Gly Gln Leu Gly Leu Pro Arg Gly Asp Ala His Pro Arg His Ile
305 310 315 320

Arg Arg Gly Arg Arg His His Gln Thr Arg Arg Arg Thr Tyr Pro Arg
325 330 335

Pro His Arg Gln Thr Pro Asp His Arg Leu Lys Arg Arg Arg Gly Arg
340 345 350

Lys Gln Val Thr Arg His Ala Val Pro His Leu Ser Arg Gly His Gln
355 360 365

Arg Gly Arg Thr Arg Ala Gly Val His Pro Arg Gly Val Asp Leu Arg
370 375 380

Trp
385

<210> SEQ ID NO 45
<211> LENGTH: 62
<212> TYPE: PRT
<213> ORGANISM: Mycobacterium tuberculosis

<400> SEQUENCE: 45

Leu Asp Phe Trp Phe Gly Leu Ser Tyr Asn Arg Phe Thr Asn Ile Val
1 5 10 15

Gln Phe Leu Asp Leu Arg Ser Asp Phe Met Ser Ser Asn Asn Arg Val
20 25 30

Leu Ile Lys Thr Ser Phe Ser Leu Ser Ile His Asp Ile Ile His Pro
35 40 45

Leu His His Leu Ile Asn Arg Leu Leu Asn Leu Leu His Phe
50 55 60

<210> SEQ ID NO 46
<211> LENGTH: 76
<212> TYPE: PRT
<213> ORGANISM: Mycobacterium tuberculosis

<400> SEQUENCE: 46

```
Phe Ile Asn Val Val Val Phe Leu Ile Leu Ala Ser Glu Val Arg Cys
 1               5                  10                  15

Asn Leu Gly Ile Val Leu Gln Ala Leu Pro Gln Leu Leu Gln His Phe
            20                  25                  30

Arg Ser Phe Leu Ser Phe Leu Lys Ser Asp Phe Asn Arg Ser Ala His
        35                  40                  45

Phe His Gln Leu Phe Gln Leu Val Asn Val Cys Leu Leu Ser Leu Val
    50                  55                  60

Leu Pro Phe Leu Ile Gln Pro Val Phe Arg Leu Cys
65                  70                  75
```

<210> SEQ ID NO 47
<211> LENGTH: 110
<212> TYPE: PRT
<213> ORGANISM: Mycobacterium tuberculosis

<400> SEQUENCE: 47

```
Gly Leu Leu Thr Ile Ser Leu Tyr Leu Gly Leu Cys Ser Ser Phe Thr
 1               5                  10                  15

Val Val Leu Leu Asp Ile Phe Ile His Ile Arg Ala Phe Cys Trp Pro
            20                  25                  30

Leu Val Trp Thr Phe His Val Cys Leu Glu Arg Gly Ala Ile Leu Phe
        35                  40                  45

Leu Gly Arg Asp Leu Leu His His Gly Ser Arg Gly Asp Gly Glu Asp
    50                  55                  60

Ala Met Cys Val His Thr His Phe Asp Leu His Ser Arg Leu Leu Ser
65                  70                  75                  80

Ile Phe Leu Cys Arg Asn Ile Leu Asn Asn Lys Thr Ala Tyr Phe Cys
                85                  90                  95

Phe Trp Ile Trp Asn Ser Leu Arg Val Arg Ile Glu Ser Phe
            100                 105                 110
```

<210> SEQ ID NO 48
<211> LENGTH: 137
<212> TYPE: PRT
<213> ORGANISM: Mycobacterium tuberculosis

<400> SEQUENCE: 48

```
Leu Lys Gly Pro Pro Ser Gln Glu Gly Glu His Phe Gly Glu Arg Ser
 1               5                  10                  15

Ser Met Val Pro Thr Glu His Leu Val His Thr Phe Arg Phe Phe Arg
            20                  25                  30

Val Val Val Pro Asp Gln Arg Tyr Trp Lys Arg Asn Cys Ile Gly Asp
        35                  40                  45

Arg Glu Leu Ser Asn Phe Lys Cys Arg Arg Lys Asn Cys Thr Leu Gln
    50                  55                  60

Cys Thr Ala Ser Gly His Ser Phe Val Cys Ile Glu Arg Gly Ala Asp
65                  70                  75                  80

Ile Phe Ser Lys Glu Leu Gly Asn Ser Phe Phe His Ser Trp Asp Ser
                85                  90                  95

Cys Gly Thr Ser His Tyr Leu Asn Gly Thr His Ile Phe Ser Leu Glu
            100                 105                 110
```

```
Leu Ser Leu Cys His Gln Arg Val Lys Gly Asp Leu Tyr Phe Leu Gln
        115                 120                 125

Glu Leu Ser Thr Gln Phe Phe Lys Leu
    130                 135


<210> SEQ ID NO 49
<211> LENGTH: 63
<212> TYPE: PRT
<213> ORGANISM: Mycobacterium tuberculosis

<400> SEQUENCE: 49

Pro Val His Leu Pro Arg Asp Ile Leu Val Ile His Lys Ala Leu Asp
 1               5                  10                  15

Val Gln Arg Gln Val Arg Ala Val Arg Thr His Glu Leu Phe Gln Leu
            20                  25                  30

Phe Thr Leu Leu Met Glu Thr Lys Glu Gly Ser Asn Phe Gly Phe Cys
        35                  40                  45

Ile Gln Phe Val Leu Gly Phe Lys Phe Ser Thr Lys Met Phe Tyr
    50                  55                  60


<210> SEQ ID NO 50
<211> LENGTH: 62
<212> TYPE: PRT
<213> ORGANISM: Mycobacterium tuberculosis

<400> SEQUENCE: 50

Val Ser His Val Asn Lys His His His Pro Trp Leu Leu Leu Gly Ile
 1               5                  10                  15

Arg Glu Ile Leu Leu Ile Asn Pro Ile Ile Gln Ser Asn Ser Arg His
            20                  25                  30

Val Ile His Glu Pro Gln Ala Val Gln Ala His Asn Leu Arg Ser Ile
        35                  40                  45

Gln His Arg Pro Ser Leu Ser Ile Cys Glu Glu Gly Trp Asp
    50                  55                  60


<210> SEQ ID NO 51
<211> LENGTH: 81
<212> TYPE: PRT
<213> ORGANISM: Mycobacterium tuberculosis

<400> SEQUENCE: 51

Leu Ser Gln Gln His Gly Cys Tyr Leu Leu His Thr Glu Glu Met Phe
 1               5                  10                  15

Phe Ile His Val His Asp Leu Tyr Ser His Ala Thr Ile Phe His Trp
            20                  25                  30

Asp Gln Ile Ile Ala Gln Val Leu Leu Phe Leu Leu Asn Glu Gly Val
        35                  40                  45

Ile Glu Cys Ser Ala Met Lys Ser Leu Lys Ala Arg Asp Arg Ile Val
    50                  55                  60

Cys Met Ser Asp Leu Leu Val Phe Gly Cys Asn Ser Asn Cys Ser Val
65                  70                  75                  80

Phe


<210> SEQ ID NO 52
<211> LENGTH: 226
<212> TYPE: PRT
<213> ORGANISM: Mycobacterium tuberculosis

<400> SEQUENCE: 52
```

-continued

Gly Arg Gly Gly Thr Arg Ser Thr Pro Leu Ser Pro Pro Pro Ala Leu
1 5 10 15

Ala Pro Ile Cys Pro Thr Gly Ser Pro Pro Ser Ile Cys Pro Gly Pro
20 25 30

Leu Ser Ala Ala Leu Val Arg Leu Val Ser Gly Ser Ala Arg Ala Ala
35 40 45

Gly Val Thr Ala Trp Leu Ala Ala Ala Gln Ala Cys Gly Thr Asp Asn
50 55 60

Glu Pro Thr Glu Ala Ala Arg Pro Lys Leu Ala Ala Thr Pro Pro Pro
65 70 75 80

Arg Pro Glu Glu Pro Ser Glu Leu Pro Ser Glu Leu Ile Ala Arg Thr
85 90 95

Pro Phe Cys Ala Ala Val Cys Thr Ala Trp Ala Ala Ala Ala Gly Ala
100 105 110

Lys Pro Phe Asn Ile Glu Leu Lys Val Leu Val Ile Asp Thr Pro Glu
115 120 125

Leu Val Ile Asp Met Trp Leu Leu Ala Ile Asp Thr Met Leu Leu Ile
130 135 140

Gly Asp Arg Cys Gly Glu Thr Val Phe His Arg Pro Pro Ser Leu Glu
145 150 155 160

Glu Gly Val Val Pro Cys Val Gly Trp Ala Ser Cys Cys Ser Ala Trp
165 170 175

Gly Thr Leu Phe Ile Asn Trp Phe Ala Ala Ala Val Ser Glu Ala Ser
180 185 190

Ser Thr Ala Ala Ala Cys Ser Arg Ser Pro Pro Ala Leu Val Ile Ser
195 200 205

Gly Ala Ser Ser Asn Gly Ser Asn Val Ala Val Ala Val Ala Val Ala
210 215 220

Ala Ala
225

<210> SEQ ID NO 53
<211> LENGTH: 56
<212> TYPE: PRT
<213> ORGANISM: Mycobacterium tuberculosis

<400> SEQUENCE: 53

Pro Asn Ile Ala Ala Ala Ser Trp Ala His Ile Ser Pro Tyr Ser Ala
1 5 10 15

Ser Leu Thr Ala Ile Ala Gly Val Phe Cys Pro Lys Arg Leu Val Ala
20 25 30

Ile Arg Ile Ile Ser Ser Ala Arg Phe Ser Ala Ile Thr Gly Gly Gly
35 40 45

Thr Val Ser Pro Tyr Ala Val Ser
50 55

<210> SEQ ID NO 54
<211> LENGTH: 50
<212> TYPE: PRT
<213> ORGANISM: Mycobacterium tuberculosis

<400> SEQUENCE: 54

Ala Ala Ala Ala Thr Arg Thr Trp Ala Ala Val Ser Ser Ala Cys Pro
1 5 10 15

Ala Val Thr Leu Ile His Ala Thr Tyr Gly Glu Ala Ala Ala Thr Ile
20 25 30

Arg Pro Ala Asp Glu Pro Ile His Asp Pro Thr Val Arg Pro Gln Thr

```
        35                  40                  45

Thr Asp
    50


<210> SEQ ID NO 55
<211> LENGTH: 126
<212> TYPE: PRT
<213> ORGANISM: Mycobacterium tuberculosis

<400> SEQUENCE: 55

Asn Leu Thr Leu Thr Gly Val Pro Ile Phe Ile Ser Ser Ser Asn Leu
 1               5                  10                  15

Ser Met Tyr Ala Cys Leu Ala Trp Ser Ser Pro Ser Ser Tyr Ser Gln
            20                  25                  30

Ser Ser Val Ser Val Arg Ser Leu Lys Asn Phe Ser Cys Ser Cys Ser
        35                  40                  45

His Met Asn Phe Ser Tyr Gly Pro His Ser Leu Ser Leu Asn Ser Tyr
    50                  55                  60

Thr His Ser Ser Thr Ala Phe Leu Ala Ser Phe Arg Ser Phe Ser Ser
65                  70                  75                  80

Leu Ser Cys Met Ile Ile Leu Pro Ser Val Ser Ile Tyr Met Leu Arg
                85                  90                  95

Arg Ser Leu Pro Asn Cys His Thr Lys Leu Ala Ser Thr Gly Ser Ser
            100                 105                 110

Thr Phe Thr Thr Phe Ile Leu Gly Phe Leu Ala Ser Gly Gly
        115                 120                 125


<210> SEQ ID NO 56
<211> LENGTH: 84
<212> TYPE: PRT
<213> ORGANISM: Mycobacterium tuberculosis

<400> SEQUENCE: 56

Pro Ser Val Cys Thr Trp Gly Cys Val Pro Ala Ser Leu Leu Ser Cys
 1               5                  10                  15

Trp Ile Phe Leu Ser Thr Ser Glu Leu Ser Val Gly Leu Trp Phe Gly
            20                  25                  30

His Ser Met Ser Ala Ser Arg Glu Glu Pro Ser Ser Ser Ser Val Gly
        35                  40                  45

Thr Phe Ser Thr Met Glu Ala Val Glu Met Val Lys Met Pro Cys Val
    50                  55                  60

Phe Thr Arg Thr Leu Thr Phe Thr Leu Asp Phe Ser Pro Ser Phe Cys
65                  70                  75                  80

Ala Glu Thr Phe


<210> SEQ ID NO 57
<211> LENGTH: 116
<212> TYPE: PRT
<213> ORGANISM: Mycobacterium tuberculosis

<400> SEQUENCE: 57

Lys Ala Ser Ser Ser Lys Gly Pro Leu Leu Arg Lys Val Ser Thr Leu
 1               5                  10                  15

Glu Lys Gly Ala Ala Trp Phe Arg Leu Asn Thr Ser Cys Thr Pro Ser
            20                  25                  30

Val Ser Ser Glu Ser Trp Phe Gln Thr Arg Asp Ile Gly Lys Gly Thr
        35                  40                  45

Ala Ser Val Thr Glu Asn Ser Leu Thr Leu Asn Ala Gly Glu Arg Ile
```

```
    50                  55                  60

Ala His Cys Ser Ala Gln Pro Leu Ala Thr Ala Ser Ser Ala Leu Ser
65                  70                  75                  80

Val Val Leu Thr Ser Phe Pro Lys Asn Leu Ala Ile Leu Ser Phe Thr
                85                  90                  95

Ala Gly Ile Leu Val Ala Pro Pro Thr Ile Ser Met Ala Leu Thr Ser
            100                 105                 110

Ser Ala Leu Ser
        115


<210> SEQ ID NO 58
<211> LENGTH: 53
<212> TYPE: PRT
<213> ORGANISM: Mycobacterium tuberculosis

<400> SEQUENCE: 58

Arg Gly Thr Ser Ile Phe Cys Arg Ser Ser Ala His Ser Ser Ser Asn
 1               5                  10                  15

Cys Asp Leu Phe Ile Phe Pro Glu Thr Ser Leu Ser Phe Ile Lys His
            20                  25                  30

Ser Met Phe Ser Gly Arg Ser Val Leu Leu Glu Leu Met Ser Phe Phe
        35                  40                  45

Asn Phe Ser His Ser
    50


<210> SEQ ID NO 59
<211> LENGTH: 83
<212> TYPE: PRT
<213> ORGANISM: Mycobacterium tuberculosis

<400> SEQUENCE: 59

Trp Arg Arg Arg Arg Ala Arg Ile Leu Asp Phe Ala Ser Asn Leu Tyr
 1               5                  10                  15

Leu Val Leu Asn Ser Ala Gln Lys Cys Ser Thr Ser Phe Ser Ser Lys
            20                  25                  30

Phe Phe Pro Pro Lys Lys Gly Ser Lys Ala Val Pro Arg Thr Phe Ser
        35                  40                  45

Phe Pro Leu Leu Lys Ala Gln Ala Asp Thr Trp Lys Asp Glu Cys Pro
    50                  55                  60

Met Ser Thr Asn Thr Thr Thr Arg Gly Phe Ser Ser Ala Phe Gly Arg
65                  70                  75                  80

Ser Cys Leu


<210> SEQ ID NO 60
<211> LENGTH: 91
<212> TYPE: PRT
<213> ORGANISM: Mycobacterium tuberculosis

<400> SEQUENCE: 60

Phe Lys Ala Thr Ala Val Met Ser Phe Met Ser Arg Lys Gln Phe Lys
 1               5                  10                  15

Pro Thr Ile Cys Ala Ala Ser Ser Thr Asp Leu Arg Ser Ala Ser Val
            20                  25                  30

Lys Lys Asp Gly Thr Glu Met Thr Gln Ser Val Thr Gly Phe Leu Arg
        35                  40                  45

Leu Phe Ser Ala Val Ser Phe Asn Leu Val Ser Ser Met Ala Val Ile
    50                  55                  60

Cys Ser Thr Leu Lys Lys Cys Ser Ser Ser Met Tyr Met Thr Phe Ile
```

```
65                  70                  75                  80

Pro Thr Pro Pro Phe Phe Ile Gly Thr Lys Ser
                85                  90


<210> SEQ ID NO 61
<211> LENGTH: 92
<212> TYPE: PRT
<213> ORGANISM: Mycobacterium tuberculosis

<400> SEQUENCE: 61

Leu Pro Gly Trp Pro Arg Pro Arg Pro Ala Ala Pro Thr Thr Asn Arg
 1               5                  10                  15

Pro Arg Pro Pro Asp Pro Ser Trp Arg Pro Pro His Arg Pro Asp Pro
            20                  25                  30

Lys Asn Pro Ala Ser Cys Pro Ala Ser Ser Ser Pro Gly Pro Arg Phe
        35                  40                  45

Ala Pro Arg Phe Ala Arg Pro Gly Arg Pro Pro Pro Glu Gln Ser Pro
    50                  55                  60

Ser Thr Ser Ser Ser Arg Cys Trp Ser Ser Thr His Pro Ser Trp Ser
65                  70                  75                  80

Ser Thr Cys Gly Cys Trp Pro Ser Thr Pro Cys Cys
                85                  90


<210> SEQ ID NO 62
<211> LENGTH: 101
<212> TYPE: PRT
<213> ORGANISM: Mycobacterium tuberculosis

<400> SEQUENCE: 62

Ser Ala Thr Asp Ala Ala Arg Pro Ser Ser Thr Gly His Pro Ala Trp
 1               5                  10                  15

Lys Lys Ala Trp Cys Pro Ala Trp Ala Gly Pro Ala Val Ala Ala Pro
            20                  25                  30

Gly Ala His Cys Ser Ser Thr Gly Ser Pro Arg Arg Cys Arg Arg Pro
        35                  40                  45

Pro Arg Pro Arg Arg Pro Ala Arg Gly Ala His Pro Arg Trp Ser Ser
    50                  55                  60

Pro Ala Pro Pro Arg Thr Ala Ala Thr Ser Pro Ser Pro Ser Pro Ser
65                  70                  75                  80

Pro Arg Arg Ser Gln Thr Ser Arg Arg Arg Leu Gly Pro Thr Ser Arg
                85                  90                  95

Arg Ile Arg Pro Arg
            100


<210> SEQ ID NO 63
<211> LENGTH: 56
<212> TYPE: PRT
<213> ORGANISM: Mycobacterium tuberculosis

<400> SEQUENCE: 63

Pro Arg Ser Pro Gly Cys Phe Ala Pro Arg Gly Trp Ser Leu Ser Glu
 1               5                  10                  15

Ser Ser Val Gln His Gly Ser Arg Arg Ser Pro Ala Gly Ala Pro Ser
            20                  25                  30

Ala His Thr Pro Ser Arg Arg Pro Pro Gln Gln Pro Gly Pro Gly Arg
        35                  40                  45

Arg Ser Ala Arg Pro Ala Pro Arg
    50                  55
```

<210> SEQ ID NO 64
<211> LENGTH: 67
<212> TYPE: PRT
<213> ORGANISM: Mycobacterium tuberculosis

<400> SEQUENCE: 64

```
Arg Ser Ser Thr Pro His Thr Ala Arg Pro Pro Pro Pro Ser Asp Pro
 1               5                  10                  15

Pro Thr Asn Leu Ser Thr Thr Pro Pro Ser Asp Pro Arg Pro Pro Thr
            20                  25                  30

Glu Thr Pro Thr Arg Pro Lys Thr Gly His Ser Pro Arg Cys Pro Thr
        35                  40                  45

Ser Glu Pro Arg Pro Pro Ala Arg Pro Asn Pro Gly Arg Arg Thr Ser
    50                  55                  60

Ser Arg Ser
65
```

<210> SEQ ID NO 65
<211> LENGTH: 70
<212> TYPE: PRT
<213> ORGANISM: Mycobacterium tuberculosis

<400> SEQUENCE: 65

```
Val Gln Val Lys Gly Glu Thr Val Arg Phe Val Asp His Gln Phe Val
 1               5                  10                  15

Pro Gly Ala Val Phe Gln Leu His Cys Cys Leu Ala Gly Tyr Phe Tyr
            20                  25                  30

Pro His Pro Ser Phe Leu Leu Ala Ser Gly Leu Asp Ile Pro Cys Leu
        35                  40                  45

Pro Arg Glu Arg Ser His Pro Leu Pro Arg Ser Gly Pro Ser Pro Pro
    50                  55                  60

Trp Lys Pro Trp Arg Trp
65                  70
```

<210> SEQ ID NO 66
<211> LENGTH: 949
<212> TYPE: PRT
<213> ORGANISM: Mycobacterium tuberculosis

<400> SEQUENCE: 66

```
Met Gln His His His His His His His Ser Val Val Gly Leu Asp Val
 1               5                  10                  15

Gly Ser Gln Ser Cys Tyr Ile Ala Val Ala Arg Ala Gly Gly Ile Glu
            20                  25                  30

Thr Ile Ala Asn Glu Phe Ser Asp Arg Cys Thr Pro Ser Val Ile Ser
        35                  40                  45

Phe Gly Ser Lys Asn Arg Thr Ile Gly Val Ala Ala Lys Asn Gln Gln
    50                  55                  60

Ile Thr His Ala Asn Asn Thr Val Ser Ser Phe Lys Arg Phe His Gly
65                  70                  75                  80

Arg Ala Phe Asn Asp Pro Phe Ile Gln Lys Glu Lys Glu Asn Leu Ser
                85                  90                  95

Tyr Asp Leu Val Pro Met Lys Asn Gly Gly Val Gly Ile Lys Val Met
            100                 105                 110

Tyr Met Asp Glu Glu His Phe Phe Ser Val Glu Gln Ile Thr Ala Met
        115                 120                 125

Leu Leu Thr Lys Leu Lys Glu Thr Ala Glu Asn Asn Leu Lys Lys Pro
    130                 135                 140
```

-continued

Val Thr Asp Cys Val Ile Ser Val Pro Ser Phe Phe Thr Asp Ala Glu
145 150 155 160

Arg Arg Ser Val Leu Asp Ala Ala Gln Ile Val Gly Leu Asn Cys Leu
165 170 175

Arg Leu Met Asn Asp Met Thr Ala Val Ala Leu Asn Tyr Gly Ile Tyr
180 185 190

Lys Gln Asp Leu Pro Asn Ala Glu Glu Lys Pro Arg Val Val Val Phe
195 200 205

Val Asp Met Gly His Ser Ser Phe Gln Val Ser Ala Cys Ala Phe Asn
210 215 220

Lys Gly Lys Leu Lys Val Leu Gly Thr Ala Phe Asp Pro Phe Leu Gly
225 230 235 240

Gly Lys Asn Phe Asp Glu Lys Leu Val Glu His Phe Cys Ala Glu Phe
245 250 255

Lys Thr Lys Tyr Lys Leu Asp Ala Lys Ser Lys Ile Arg Ala Leu Leu
260 265 270

Arg Leu His Gln Glu Cys Glu Lys Leu Lys Lys Leu Met Ser Ser Asn
275 280 285

Ser Thr Asp Leu Pro Leu Asn Ile Glu Cys Phe Met Asn Asp Lys Asp
290 295 300

Val Ser Gly Lys Met Asn Arg Ser Gln Phe Glu Glu Leu Cys Ala Glu
305 310 315 320

Leu Leu Gln Lys Ile Glu Val Pro Leu His Ser Leu Met Ala Gln Thr
325 330 335

Gln Leu Lys Ala Glu Asp Val Ser Ala Ile Glu Ile Val Gly Gly Ala
340 345 350

Thr Arg Ile Pro Ala Val Lys Glu Arg Ile Ala Lys Phe Phe Gly Lys
355 360 365

Asp Val Ser Thr Thr Leu Asn Ala Asp Glu Ala Val Ala Arg Gly Cys
370 375 380

Ala Leu Gln Cys Ala Ile Leu Ser Pro Ala Phe Lys Val Arg Glu Phe
385 390 395 400

Ser Val Thr Asp Ala Val Pro Phe Pro Ile Ser Leu Val Trp Asn His
405 410 415

Asp Ser Glu Glu Thr Glu Gly Val His Glu Val Phe Ser Arg Asn His
420 425 430

Ala Ala Pro Phe Ser Lys Val Leu Thr Phe Leu Arg Arg Gly Pro Phe
435 440 445

Glu Leu Glu Ala Phe Tyr Ser Asp Pro Gln Gly Val Pro Tyr Pro Glu
450 455 460

Ala Lys Ile Gly Arg Phe Val Val Gln Asn Val Ser Ala Gln Lys Asp
465 470 475 480

Gly Glu Lys Ser Arg Val Lys Val Lys Val Arg Val Asn Thr His Gly
485 490 495

Ile Phe Thr Ile Ser Thr Ala Ser Met Val Glu Lys Val Pro Thr Glu
500 505 510

Glu Glu Asp Gly Ser Ser Leu Glu Ala Asp Met Glu Cys Pro Asn Gln
515 520 525

Arg Pro Thr Glu Ser Ser Asp Val Asp Lys Asn Ile Gln Gln Asp Asn
530 535 540

Ser Glu Ala Gly Thr Gln Pro Gln Val Gln Thr Asp Gly Gln Gln Thr
545 550 555 560

Ser Gln Ser Pro Pro Ser Pro Glu Leu Thr Ser Glu Glu Ser Lys Thr

```
                565                 570                 575

Pro Asp Ala Asp Lys Ala Asn Glu Lys Lys Val Asp Gln Pro Pro Glu
            580                 585                 590

Ala Lys Lys Pro Lys Ile Lys Val Val Asn Val Glu Leu Pro Val Glu
        595                 600                 605

Ala Asn Leu Val Trp Gln Leu Gly Arg Asp Leu Leu Asn Met Tyr Ile
    610                 615                 620

Glu Thr Glu Gly Lys Met Ile Met Gln Asp Lys Leu Glu Lys Glu Arg
625                 630                 635                 640

Asn Asp Ala Lys Asn Ala Val Glu Glu Cys Val Tyr Glu Phe Arg Asp
                645                 650                 655

Lys Leu Cys Gly Pro Tyr Glu Lys Phe Ile Cys Glu Gln Glu His Glu
            660                 665                 670

Lys Phe Leu Arg Leu Leu Thr Glu Thr Glu Asp Trp Leu Tyr Glu Glu
        675                 680                 685

Gly Glu Asp Gln Ala Lys Gln Ala Tyr Ile Asp Lys Leu Glu Glu Leu
    690                 695                 700

Met Lys Met Gly Thr Pro Val Lys Val Arg Phe Gln Glu Ala Glu Glu
705                 710                 715                 720

Arg Pro Lys Val Leu Glu Glu Leu Gly Gln Arg Leu Gln His Tyr Ala
                725                 730                 735

Lys Ile Ala Ala Asp Phe Arg Gly Lys Asp Glu Lys Tyr Asn His Ile
            740                 745                 750

Asp Glu Ser Glu Met Lys Lys Val Glu Lys Ser Val Asn Glu Val Met
        755                 760                 765

Glu Trp Met Asn Asn Val Met Asn Ala Gln Ala Lys Arg Ser Leu Asp
    770                 775                 780

Gln Asp Pro Val Val Arg Thr His Glu Ile Arg Ala Lys Val Lys Glu
785                 790                 795                 800

Leu Asn Asn Val Cys Glu Pro Val Val Thr Gln Pro Lys Pro Lys Ile
                805                 810                 815

Glu Ser Pro Lys Leu Glu Arg Thr Pro Asn Gly Pro Asn Ile Asp Lys
            820                 825                 830

Lys Glu Asp Leu Glu Gly Lys Asn Asn Leu Gly Ala Glu Ala Pro His
        835                 840                 845

Gln Asn Gly Glu Cys His Pro Asn Glu Lys Gly Ser Val Asn Met Asp
    850                 855                 860

Leu Asp His Asp Pro Val Asp Ala Val Ile Asn Thr Thr Cys Asn Tyr
865                 870                 875                 880

Gly Gln Val Val Ala Ala Leu Asn Ala Thr Asp Pro Gly Ala Ala Ala
                885                 890                 895

Gln Phe Asn Ala Ser Pro Val Ala Gln Ser Tyr Leu Arg Asn Phe Leu
            900                 905                 910

Ala Ala Pro Pro Pro Gln Arg Ala Ala Met Ala Ala Gln Leu Gln Ala
        915                 920                 925

Val Pro Gly Ala Ala Gln Tyr Ile Gly Leu Val Glu Ser Val Ala Gly
    930                 935                 940

Ser Cys Asn Asn Tyr
945
```

<210> SEQ ID NO 67
<211> LENGTH: 78
<212> TYPE: PRT
<213> ORGANISM: Mycobacterium tuberculosis

<400> SEQUENCE: 67

Ala His Arg Ala Ala Thr Leu Arg Trp Arg Gly Pro Gly Ala Ser Arg
1 5 10 15

Pro Ser Pro Thr Ser Ser Ala Thr Ala Ala Pro Arg Gln Ser Tyr His
20 25 30

Leu Asp Gln Lys Thr Glu Gln Leu Glu Leu Gln Pro Lys Thr Ser Lys
35 40 45

Ser Leu Met Gln Thr Ile Arg Ser Leu Ala Leu Arg Asp Phe Met Ala
50 55 60

Glu His Ser Met Thr Pro Ser Phe Arg Arg Lys Arg Arg Thr
65 70 75

<210> SEQ ID NO 68
<211> LENGTH: 84
<212> TYPE: PRT
<213> ORGANISM: Mycobacterium tuberculosis

<400> SEQUENCE: 68

Lys Lys Glu Leu Pro Ser Ser Leu Glu Lys Met Ser Ala Pro Arg Ser
1 5 10 15

Met Gln Thr Lys Leu Trp Pro Glu Ala Val His Cys Ser Val Gln Phe
20 25 30

Phe Leu Arg His Leu Lys Leu Glu Ser Ser Leu Ser Pro Met Gln Phe
35 40 45

Leu Phe Gln Tyr Leu Trp Ser Gly Thr Thr Thr Arg Lys Lys Arg Lys
50 55 60

Val Cys Thr Arg Cys Ser Val Gly Thr Met Leu Leu Leu Ser Pro Lys
65 70 75 80

Cys Ser Pro Ser

<210> SEQ ID NO 69
<211> LENGTH: 105
<212> TYPE: PRT
<213> ORGANISM: Mycobacterium tuberculosis

<400> SEQUENCE: 69

Thr His Met Ala Ser Ser Pro Ser Pro Arg Leu Pro Trp Trp Arg Arg
1 5 10 15

Ser Arg Pro Arg Lys Arg Met Ala Pro Leu Ser Arg Gln Thr Trp Asn
20 25 30

Val Gln Thr Arg Gly Gln Gln Lys Ala Arg Met Trp Ile Lys Ile Ser
35 40 45

Ser Lys Thr Thr Val Lys Leu Glu His Ser Pro Arg Tyr Lys Leu Met
50 55 60

Val Asn Lys Pro His Ser Leu Pro Leu His Leu Asn Leu Pro Gln Lys
65 70 75 80

Lys Ala Lys Pro Gln Met Leu Thr Lys Gln Met Lys Arg Lys Leu Ile
85 90 95

Ser Leu Gln Lys Pro Arg Asn Leu Lys
100 105

<210> SEQ ID NO 70
<211> LENGTH: 51
<212> TYPE: PRT
<213> ORGANISM: Mycobacterium tuberculosis

<400> SEQUENCE: 70

Lys Trp Ala Leu Leu Leu Lys Ser Asp Phe Lys Lys Leu Arg Asn Asp

-continued

```
 1               5                   10                  15

Arg Lys Cys Trp Arg Ser Trp Gly Ser Ala Cys Ser Thr Met Pro Arg
            20                  25                  30

Leu Gln Arg Thr Ser Glu Ala Arg Met Arg Asn Thr Thr Thr Leu Met
        35                  40                  45

Asn Gln Lys
    50
```

<210> SEQ ID NO 71
<211> LENGTH: 65
<212> TYPE: PRT
<213> ORGANISM: Mycobacterium tuberculosis

<400> SEQUENCE: 71

```
Leu Arg Ser Thr Arg Arg Ile Arg Gly Leu Pro His Ser Ser Thr Pro
 1               5                   10                  15

His Arg Trp Arg Ser Pro Ile Cys Ala Ile Ser Ser Pro His Arg His
            20                  25                  30

Leu Ser Ala Leu Pro Trp Pro Arg Asn Cys Lys Leu Cys Arg Gly Arg
        35                  40                  45

His Ser Thr Ser Ala Leu Ser Ser Arg Leu Pro Ala Pro Ala Thr Thr
    50                  55                  60

Ile
65
```

<210> SEQ ID NO 72
<211> LENGTH: 72
<212> TYPE: PRT
<213> ORGANISM: Mycobacterium tuberculosis

<400> SEQUENCE: 72

```
Ala Ala Ser Pro Pro Ser Pro Pro Leu Gly Gly Trp Ala Arg Arg Arg
 1               5                   10                  15

Leu Thr Glu Leu Leu His Cys Gly Gly Ala Gly Arg Gly His Arg Asp
            20                  25                  30

His Arg Gln Arg Val Gln Arg Pro Leu His Pro Val Ser His Ile Ile
        35                  40                  45

Trp Ile Lys Lys Gln Asn Asn Trp Ser Cys Ser Gln Lys Pro Ala Asn
    50                  55                  60

His Ser Cys Lys Gln Tyr Gly Leu
65                  70
```

<210> SEQ ID NO 73
<211> LENGTH: 50
<212> TYPE: PRT
<213> ORGANISM: Mycobacterium tuberculosis

<400> SEQUENCE: 73

```
Arg Val Leu Cys His Arg Cys Ser Ser Phe Ser Asn Ile Ser Gly Leu
 1               5                   10                  15

Glu Pro Arg Leu Gly Arg Asn Gly Arg Cys Ala Arg Gly Val Gln Ser
            20                  25                  30

Glu Pro Cys Cys Ser Phe Leu Gln Ser Ala His Leu Pro Glu Lys Gly
        35                  40                  45

Ala Leu
    50
```

<210> SEQ ID NO 74
<211> LENGTH: 81

<212> TYPE: PRT
<213> ORGANISM: Mycobacterium tuberculosis

<400> SEQUENCE: 74

Pro Ser Arg Ser Ser Ile Ser Arg Ser Lys Asn Arg Pro Phe Cys Cys
1 5 10 15

Ser Glu Cys Phe Cys Thr Glu Arg Trp Arg Glu Val Glu Ser Glu Gly
20 25 30

Gln Ser Ala Cys Glu His Thr Trp His Leu His His Leu His Gly Phe
35 40 45

His Gly Gly Glu Gly Pro Asp Arg Gly Arg Gly Trp Leu Leu Ser Arg
50 55 60

Gly Arg His Gly Met Ser Lys Pro Glu Ala Asn Arg Lys Leu Gly Cys
65 70 75 80

Gly

<210> SEQ ID NO 75
<211> LENGTH: 75
<212> TYPE: PRT
<213> ORGANISM: Mycobacterium tuberculosis

<400> SEQUENCE: 75

His His Leu Gln Leu Arg Ala Gly Ser Ser Cys Ala Gln Arg Asp Gly
1 5 10 15

Ser Gly Gly Cys Arg Thr Val Gln Arg Leu Thr Gly Gly Ala Val Leu
20 25 30

Phe Ala Gln Phe Pro Arg Arg Thr Ala Thr Ser Ala Arg Cys His Gly
35 40 45

Arg Ala Ile Ala Ser Cys Ala Gly Gly Gly Thr Val His Arg Pro Cys
50 55 60

Arg Val Gly Cys Arg Leu Leu Gln Gln Leu Leu
65 70 75

<210> SEQ ID NO 76
<211> LENGTH: 64
<212> TYPE: PRT
<213> ORGANISM: Mycobacterium tuberculosis

<400> SEQUENCE: 76

Gly Val Glu Leu Cys Gly Ser Pro Arg Ile Arg Arg Val Glu Arg Ser
1 5 10 15

Tyr Tyr Leu Pro Val Ile Ala Gly Gly Val Asn Asp Arg Val His Gly
20 25 30

Ile Val Ile Gln Val His Val Asp Arg Ala Leu Leu Ile Arg Val Ala
35 40 45

Phe Thr Ile Leu Met Arg Ser Phe Ser Thr Lys Ile Ile Phe Ala Phe
50 55 60

<210> SEQ ID NO 77
<211> LENGTH: 62
<212> TYPE: PRT
<213> ORGANISM: Mycobacterium tuberculosis

<400> SEQUENCE: 77

Leu Asp Phe Trp Phe Gly Leu Ser Tyr Asn Arg Phe Thr Asn Ile Val
1 5 10 15

Gln Phe Leu Asp Leu Arg Ser Asp Phe Met Ser Ser Asn Asn Arg Val
20 25 30

Leu Ile Lys Thr Ser Phe Ser Leu Ser Ile His Asp Ile Ile His Pro

```
        35                  40                  45

Leu His His Leu Ile Asn Arg Leu Leu Asn Leu Leu His Phe
    50                  55                  60


<210> SEQ ID NO 78
<211> LENGTH: 76
<212> TYPE: PRT
<213> ORGANISM: Mycobacterium tuberculosis

<400> SEQUENCE: 78

Phe Ile Asn Val Val Val Phe Leu Ile Leu Ala Ser Glu Val Arg Cys
 1               5                  10                  15

Asn Leu Gly Ile Val Leu Gln Ala Leu Pro Gln Leu Leu Gln His Phe
            20                  25                  30

Arg Ser Phe Leu Ser Phe Leu Lys Ser Asp Phe Asn Arg Ser Ala His
        35                  40                  45

Phe His Gln Leu Phe Gln Leu Val Asn Val Cys Leu Leu Ser Leu Val
    50                  55                  60

Leu Pro Phe Leu Ile Gln Pro Val Phe Arg Leu Cys
65                  70                  75


<210> SEQ ID NO 79
<211> LENGTH: 110
<212> TYPE: PRT
<213> ORGANISM: Mycobacterium tuberculosis

<400> SEQUENCE: 79

Gly Leu Leu Thr Ile Ser Leu Tyr Leu Gly Leu Cys Ser Ser Phe Thr
 1               5                  10                  15

Val Val Leu Leu Asp Ile Phe Ile His Ile Arg Ala Phe Cys Trp Pro
            20                  25                  30

Leu Val Trp Thr Phe His Val Cys Leu Glu Arg Gly Ala Ile Leu Phe
        35                  40                  45

Leu Gly Arg Asp Leu Leu His His Gly Ser Arg Gly Asp Gly Glu Asp
    50                  55                  60

Ala Met Cys Val His Thr His Phe Asp Leu His Ser Arg Leu Leu Ser
65                  70                  75                  80

Ile Phe Leu Cys Arg Asn Ile Leu Asn Asn Lys Thr Ala Tyr Phe Cys
                85                  90                  95

Phe Trp Ile Trp Asn Ser Leu Arg Val Arg Ile Glu Ser Phe
            100                 105                 110


<210> SEQ ID NO 80
<211> LENGTH: 137
<212> TYPE: PRT
<213> ORGANISM: Mycobacterium tuberculosis

<400> SEQUENCE: 80

Leu Lys Gly Pro Pro Ser Gln Glu Gly Glu His Phe Gly Glu Arg Ser
 1               5                  10                  15

Ser Met Val Pro Thr Glu His Leu Val His Thr Phe Arg Phe Phe Arg
            20                  25                  30

Val Val Val Pro Asp Gln Arg Tyr Trp Lys Arg Asn Cys Ile Gly Asp
        35                  40                  45

Arg Glu Leu Ser Asn Phe Lys Cys Arg Arg Lys Asn Cys Thr Leu Gln
    50                  55                  60

Cys Thr Ala Ser Gly His Ser Phe Val Cys Ile Glu Arg Gly Ala Asp
65                  70                  75                  80
```

```
Ile Phe Ser Lys Glu Leu Gly Asn Ser Phe Phe His Ser Trp Asp Ser
                85                  90                  95

Cys Gly Thr Ser His Tyr Leu Asn Gly Thr His Ile Phe Ser Leu Glu
            100                 105                 110

Leu Ser Leu Cys His Gln Arg Val Lys Gly Asp Leu Tyr Phe Leu Gln
        115                 120                 125

Glu Leu Ser Thr Gln Phe Phe Lys Leu
    130                 135


<210> SEQ ID NO 81
<211> LENGTH: 63
<212> TYPE: PRT
<213> ORGANISM: Mycobacterium tuberculosis

<400> SEQUENCE: 81

Pro Val His Leu Pro Arg Asp Ile Leu Val Ile His Lys Ala Leu Asp
 1               5                  10                  15

Val Gln Arg Gln Val Arg Ala Val Arg Thr His Glu Leu Phe Gln Leu
            20                  25                  30

Phe Thr Leu Leu Met Glu Thr Lys Glu Gly Ser Asn Phe Gly Phe Cys
        35                  40                  45

Ile Gln Phe Val Leu Gly Phe Lys Phe Ser Thr Lys Met Phe Tyr
    50                  55                  60


<210> SEQ ID NO 82
<211> LENGTH: 62
<212> TYPE: PRT
<213> ORGANISM: Mycobacterium tuberculosis

<400> SEQUENCE: 82

Val Ser His Val Asn Lys His His His Pro Trp Leu Leu Leu Gly Ile
 1               5                  10                  15

Arg Glu Ile Leu Leu Ile Asn Pro Ile Ile Gln Ser Asn Ser Arg His
            20                  25                  30

Val Ile His Glu Pro Gln Ala Val Gln Ala His Asn Leu Arg Ser Ile
        35                  40                  45

Gln His Arg Pro Ser Leu Ser Ile Cys Glu Glu Gly Trp Asp
    50                  55                  60


<210> SEQ ID NO 83
<211> LENGTH: 81
<212> TYPE: PRT
<213> ORGANISM: Mycobacterium tuberculosis

<400> SEQUENCE: 83

Leu Ser Gln Gln His Gly Cys Tyr Leu Leu His Thr Glu Glu Met Phe
 1               5                  10                  15

Phe Ile His Val His Asp Leu Tyr Ser His Ala Thr Ile Phe His Trp
            20                  25                  30

Asp Gln Ile Ile Ala Gln Val Leu Leu Phe Leu Leu Asn Glu Gly Val
        35                  40                  45

Ile Glu Cys Ser Ala Met Lys Ser Leu Lys Ala Arg Asp Arg Ile Val
    50                  55                  60

Cys Met Ser Asp Leu Leu Val Phe Gly Cys Asn Ser Asn Cys Ser Val
65                  70                  75                  80

Phe


<210> SEQ ID NO 84
<211> LENGTH: 126
```

<212> TYPE: PRT
<213> ORGANISM: Mycobacterium tuberculosis

<400> SEQUENCE: 84

Asn Leu Thr Leu Thr Gly Val Pro Ile Phe Ile Ser Ser Ser Asn Leu
1 5 10 15

Ser Met Tyr Ala Cys Leu Ala Trp Ser Ser Pro Ser Ser Tyr Ser Gln
20 25 30

Ser Ser Val Ser Val Arg Ser Leu Lys Asn Phe Ser Cys Ser Cys Ser
35 40 45

His Met Asn Phe Ser Tyr Gly Pro His Ser Leu Ser Leu Asn Ser Tyr
50 55 60

Thr His Ser Ser Thr Ala Phe Leu Ala Ser Phe Arg Ser Phe Ser Ser
65 70 75 80

Leu Ser Cys Met Ile Ile Leu Pro Ser Val Ser Ile Tyr Met Leu Arg
85 90 95

Arg Ser Leu Pro Asn Cys His Thr Lys Leu Ala Ser Thr Gly Ser Ser
100 105 110

Thr Phe Thr Thr Phe Ile Leu Gly Phe Leu Ala Ser Gly Gly
115 120 125

<210> SEQ ID NO 85
<211> LENGTH: 84
<212> TYPE: PRT
<213> ORGANISM: Mycobacterium tuberculosis

<400> SEQUENCE: 85

Pro Ser Val Cys Thr Trp Gly Cys Val Pro Ala Ser Leu Leu Ser Cys
1 5 10 15

Trp Ile Phe Leu Ser Thr Ser Glu Leu Ser Val Gly Leu Trp Phe Gly
20 25 30

His Ser Met Ser Ala Ser Arg Glu Glu Pro Ser Ser Ser Ser Val Gly
35 40 45

Thr Phe Ser Thr Met Glu Ala Val Glu Met Val Lys Met Pro Cys Val
50 55 60

Phe Thr Arg Thr Leu Thr Phe Thr Leu Asp Phe Ser Pro Ser Phe Cys
65 70 75 80

Ala Glu Thr Phe

<210> SEQ ID NO 86
<211> LENGTH: 116
<212> TYPE: PRT
<213> ORGANISM: Mycobacterium tuberculosis

<400> SEQUENCE: 86

Lys Ala Ser Ser Ser Lys Gly Pro Leu Leu Arg Lys Val Ser Thr Leu
1 5 10 15

Glu Lys Gly Ala Ala Trp Phe Arg Leu Asn Thr Ser Cys Thr Pro Ser
20 25 30

Val Ser Ser Glu Ser Trp Phe Gln Thr Arg Asp Ile Gly Lys Gly Thr
35 40 45

Ala Ser Val Thr Glu Asn Ser Leu Thr Leu Asn Ala Gly Glu Arg Ile
50 55 60

Ala His Cys Ser Ala Gln Pro Leu Ala Thr Ala Ser Ser Ala Leu Ser
65 70 75 80

Val Val Leu Thr Ser Phe Pro Lys Asn Leu Ala Ile Leu Ser Phe Thr
85 90 95

```
Ala Gly Ile Leu Val Ala Pro Pro Thr Ile Ser Met Ala Leu Thr Ser
            100                 105                 110

Ser Ala Leu Ser
        115


<210> SEQ ID NO 87
<211> LENGTH: 53
<212> TYPE: PRT
<213> ORGANISM: Mycobacterium tuberculosis

<400> SEQUENCE: 87

Arg Gly Thr Ser Ile Phe Cys Arg Ser Ser Ala His Ser Ser Ser Asn
 1               5                  10                  15

Cys Asp Leu Phe Ile Phe Pro Glu Thr Ser Leu Ser Phe Ile Lys His
            20                  25                  30

Ser Met Phe Ser Gly Arg Ser Val Leu Leu Glu Leu Met Ser Phe Phe
        35                  40                  45

Asn Phe Ser His Ser
    50


<210> SEQ ID NO 88
<211> LENGTH: 83
<212> TYPE: PRT
<213> ORGANISM: Mycobacterium tuberculosis

<400> SEQUENCE: 88

Trp Arg Arg Arg Arg Ala Arg Ile Leu Asp Phe Ala Ser Asn Leu Tyr
 1               5                  10                  15

Leu Val Leu Asn Ser Ala Gln Lys Cys Ser Thr Ser Phe Ser Ser Lys
            20                  25                  30

Phe Phe Pro Pro Lys Lys Gly Ser Lys Ala Val Pro Arg Thr Phe Ser
        35                  40                  45

Phe Pro Leu Leu Lys Ala Gln Ala Asp Thr Trp Lys Asp Glu Cys Pro
    50                  55                  60

Met Ser Thr Asn Thr Thr Thr Arg Gly Phe Ser Ser Ala Phe Gly Arg
65                  70                  75                  80

Ser Cys Leu


<210> SEQ ID NO 89
<211> LENGTH: 91
<212> TYPE: PRT
<213> ORGANISM: Mycobacterium tuberculosis

<400> SEQUENCE: 89

Phe Lys Ala Thr Ala Val Met Ser Phe Met Ser Arg Lys Gln Phe Lys
 1               5                  10                  15

Pro Thr Ile Cys Ala Ala Ser Ser Thr Asp Leu Arg Ser Ala Ser Val
            20                  25                  30

Lys Lys Asp Gly Thr Glu Met Thr Gln Ser Val Thr Gly Phe Leu Arg
        35                  40                  45

Leu Phe Ser Ala Val Ser Phe Asn Leu Val Ser Ser Met Ala Val Ile
    50                  55                  60

Cys Ser Thr Leu Lys Lys Cys Ser Ser Ser Met Tyr Met Thr Phe Ile
65                  70                  75                  80

Pro Thr Pro Pro Phe Phe Ile Gly Thr Lys Ser
                85                  90


<210> SEQ ID NO 90
<211> LENGTH: 51
```

<212> TYPE: PRT
<213> ORGANISM: Mycobacterium tuberculosis

<400> SEQUENCE: 90

Asn Ser Cys Cys Arg Ser Arg Gln Pro Thr Arg Gln Gly Arg Cys Thr
1 5 10 15

Val Pro Pro Pro Ala Gln Leu Ala Ile Ala Arg Pro Trp Gln Arg Ala
20 25 30

Glu Val Ala Val Arg Arg Gly Asn Cys Ala Asn Arg Thr Ala Pro Pro
35 40 45

Val Arg Arg
50

<210> SEQ ID NO 91
<211> LENGTH: 70
<212> TYPE: PRT
<213> ORGANISM: Mycobacterium tuberculosis

<400> SEQUENCE: 91

Val Gln Val Lys Gly Glu Thr Val Arg Phe Val Asp His Gln Phe Val
1 5 10 15

Pro Gly Ala Val Phe Gln Leu His Cys Cys Leu Ala Gly Tyr Phe Tyr
20 25 30

Pro His Pro Ser Phe Leu Leu Ala Ser Gly Leu Asp Ile Pro Cys Leu
35 40 45

Pro Arg Glu Arg Ser His Pro Leu Pro Arg Ser Gly Pro Ser Pro Pro
50 55 60

Trp Lys Pro Trp Arg Trp
65 70

<210> SEQ ID NO 92
<211> LENGTH: 955
<212> TYPE: PRT
<213> ORGANISM: Mycobacterium tuberculosis

<400> SEQUENCE: 92

Met Gln His His His His His His Asp Pro Val Asp Ala Val Ile Asn
1 5 10 15

Thr Thr Cys Asn Tyr Gly Gln Val Val Ala Ala Leu Asn Ala Thr Asp
20 25 30

Pro Gly Ala Ala Ala Gln Phe Asn Ala Ser Pro Val Ala Gln Ser Tyr
35 40 45

Leu Arg Asn Phe Leu Ala Ala Pro Pro Pro Gln Arg Ala Ala Met Ala
50 55 60

Ala Gln Leu Gln Ala Val Pro Gly Ala Ala Gln Tyr Ile Gly Leu Val
65 70 75 80

Glu Ser Val Ala Gly Ser Cys Asn Asn Tyr Ser Val Leu Leu Ile Gly
85 90 95

Ser Ser Val Val Gly Leu Asp Val Gly Ser Gln Ser Cys Tyr Ile Ala
100 105 110

Val Ala Arg Ala Gly Gly Ile Glu Thr Ile Ala Asn Glu Phe Ser Asp
115 120 125

Arg Cys Thr Pro Ser Val Ile Ser Phe Gly Ser Lys Asn Arg Thr Ile
130 135 140

Gly Val Ala Ala Lys Asn Gln Gln Ile Thr His Ala Asn Asn Thr Val
145 150 155 160

Ser Ser Phe Lys Arg Phe His Gly Arg Ala Phe Asn Asp Pro Phe Ile
165 170 175

```
Gln Lys Glu Lys Glu Asn Leu Ser Tyr Asp Leu Val Pro Met Lys Asn
            180                 185                 190

Gly Gly Val Gly Ile Lys Val Met Tyr Met Asp Glu Glu His Phe Phe
        195                 200                 205

Ser Val Glu Gln Ile Thr Ala Met Leu Leu Thr Lys Leu Lys Glu Thr
    210                 215                 220

Ala Glu Asn Asn Leu Lys Lys Pro Val Thr Asp Cys Val Ile Ser Val
225                 230                 235                 240

Pro Ser Phe Phe Thr Asp Ala Glu Arg Arg Ser Val Leu Asp Ala Ala
                245                 250                 255

Gln Ile Val Gly Leu Asn Cys Leu Arg Leu Met Asn Asp Met Thr Ala
            260                 265                 270

Val Ala Leu Asn Tyr Gly Ile Tyr Lys Gln Asp Leu Pro Asn Ala Glu
        275                 280                 285

Glu Lys Pro Arg Val Val Val Phe Val Asp Met Gly His Ser Ser Phe
    290                 295                 300

Gln Val Ser Ala Cys Ala Phe Asn Lys Gly Lys Leu Lys Val Leu Gly
305                 310                 315                 320

Thr Ala Phe Asp Pro Phe Leu Gly Gly Lys Asn Phe Asp Glu Lys Leu
                325                 330                 335

Val Glu His Phe Cys Ala Glu Phe Lys Thr Lys Tyr Lys Leu Asp Ala
            340                 345                 350

Lys Ser Lys Ile Arg Ala Leu Leu Arg Leu His Gln Glu Cys Glu Lys
        355                 360                 365

Leu Lys Lys Leu Met Ser Ser Asn Ser Thr Asp Leu Pro Leu Asn Ile
    370                 375                 380

Glu Cys Phe Met Asn Asp Lys Asp Val Ser Gly Lys Met Asn Arg Ser
385                 390                 395                 400

Gln Phe Glu Glu Leu Cys Ala Glu Leu Leu Gln Lys Ile Glu Val Pro
                405                 410                 415

Leu His Ser Leu Met Ala Gln Thr Gln Leu Lys Ala Glu Asp Val Ser
            420                 425                 430

Ala Ile Glu Ile Val Gly Gly Ala Thr Arg Ile Pro Ala Val Lys Glu
        435                 440                 445

Arg Ile Ala Lys Phe Phe Gly Lys Asp Val Ser Thr Thr Leu Asn Ala
    450                 455                 460

Asp Glu Ala Val Ala Arg Gly Cys Ala Leu Gln Cys Ala Ile Leu Ser
465                 470                 475                 480

Pro Ala Phe Lys Val Arg Glu Phe Ser Val Thr Asp Ala Val Pro Phe
                485                 490                 495

Pro Ile Ser Leu Val Trp Asn His Asp Ser Glu Glu Thr Glu Gly Val
            500                 505                 510

His Glu Val Phe Ser Arg Asn His Ala Ala Pro Phe Ser Lys Val Leu
        515                 520                 525

Thr Phe Leu Arg Arg Gly Pro Phe Glu Leu Glu Ala Phe Tyr Ser Asp
    530                 535                 540

Pro Gln Gly Val Pro Tyr Pro Glu Ala Lys Ile Gly Arg Phe Val Val
545                 550                 555                 560

Gln Asn Val Ser Ala Gln Lys Asp Gly Glu Lys Ser Arg Val Lys Val
                565                 570                 575

Lys Val Arg Val Asn Thr His Gly Ile Phe Thr Ile Ser Thr Ala Ser
            580                 585                 590

Met Val Glu Lys Val Pro Thr Glu Glu Glu Asp Gly Ser Ser Leu Glu
```

595 600 605

Ala Asp Met Glu Cys Pro Asn Gln Arg Pro Thr Glu Ser Ser Asp Val
610 615 620

Asp Lys Asn Ile Gln Gln Asp Asn Ser Glu Ala Gly Thr Gln Pro Gln
625 630 635 640

Val Gln Thr Asp Gly Gln Gln Thr Ser Gln Ser Pro Pro Ser Pro Glu
645 650 655

Leu Thr Ser Glu Glu Ser Lys Thr Pro Asp Ala Asp Lys Ala Asn Glu
660 665 670

Lys Lys Val Asp Gln Pro Pro Glu Ala Lys Lys Pro Lys Ile Lys Val
675 680 685

Val Asn Val Glu Leu Pro Val Glu Ala Asn Leu Val Trp Gln Leu Gly
690 695 700

Arg Asp Leu Leu Asn Met Tyr Ile Glu Thr Glu Gly Lys Met Ile Met
705 710 715 720

Gln Asp Lys Leu Glu Lys Glu Arg Asn Asp Ala Lys Asn Ala Val Glu
725 730 735

Glu Cys Val Tyr Glu Phe Arg Asp Lys Leu Cys Gly Pro Tyr Glu Lys
740 745 750

Phe Ile Cys Glu Gln Glu His Glu Lys Phe Leu Arg Leu Leu Thr Glu
755 760 765

Thr Glu Asp Trp Leu Tyr Glu Glu Gly Glu Asp Gln Ala Lys Gln Ala
770 775 780

Tyr Ile Asp Lys Leu Glu Glu Leu Met Lys Met Gly Thr Pro Val Lys
785 790 795 800

Val Arg Phe Gln Glu Ala Glu Glu Arg Pro Lys Val Leu Glu Glu Leu
805 810 815

Gly Gln Arg Leu Gln His Tyr Ala Lys Ile Ala Ala Asp Phe Arg Gly
820 825 830

Lys Asp Glu Lys Tyr Asn His Ile Asp Glu Ser Glu Met Lys Lys Val
835 840 845

Glu Lys Ser Val Asn Glu Val Met Glu Trp Met Asn Asn Val Met Asn
850 855 860

Ala Gln Ala Lys Arg Ser Leu Asp Gln Asp Pro Val Val Arg Thr His
865 870 875 880

Glu Ile Arg Ala Lys Val Lys Glu Leu Asn Asn Val Cys Glu Pro Val
885 890 895

Val Thr Gln Pro Lys Pro Lys Ile Glu Ser Pro Lys Leu Glu Arg Thr
900 905 910

Pro Asn Gly Pro Asn Ile Asp Lys Lys Glu Asp Leu Glu Gly Lys Asn
915 920 925

Asn Leu Gly Ala Glu Ala Pro His Gln Asn Gly Glu Cys His Pro Asn
930 935 940

Glu Lys Gly Ser Val Asn Met Asp Leu Asp Ile
945 950 955

<210> SEQ ID NO 93
<211> LENGTH: 68
<212> TYPE: PRT
<213> ORGANISM: Mycobacterium tuberculosis

<400> SEQUENCE: 93

Leu Arg Ser Thr Arg Arg Ile Arg Gly Leu Pro His Ser Ser Thr Pro
1 5 10 15

His Arg Trp Arg Ser Pro Ile Cys Ala Ile Ser Ser Pro His Arg His

-continued

```
            20                  25                  30

Leu Ser Ala Leu Pro Trp Pro Arg Asn Cys Lys Leu Cys Arg Gly Arg
        35                  40                  45

His Ser Thr Ser Ala Leu Ser Ser Arg Leu Pro Ala Pro Ala Thr Thr
    50                  55                  60

Ile Pro Cys Tyr
65


<210> SEQ ID NO 94
<211> LENGTH: 78
<212> TYPE: PRT
<213> ORGANISM: Mycobacterium tuberculosis

<400> SEQUENCE: 94

Ala His Arg Ala Ala Thr Leu Arg Trp Arg Gly Pro Gly Ala Ser Arg
 1               5                  10                  15

Pro Ser Pro Thr Ser Ser Ala Thr Ala Ala Pro Arg Gln Ser Tyr His
            20                  25                  30

Leu Asp Gln Lys Thr Glu Gln Leu Glu Leu Gln Pro Lys Thr Ser Lys
        35                  40                  45

Ser Leu Met Gln Thr Ile Arg Ser Leu Ala Leu Arg Asp Phe Met Ala
    50                  55                  60

Glu His Ser Met Thr Pro Ser Phe Arg Arg Lys Arg Arg Thr
65                  70                  75


<210> SEQ ID NO 95
<211> LENGTH: 84
<212> TYPE: PRT
<213> ORGANISM: Mycobacterium tuberculosis

<400> SEQUENCE: 95

Lys Lys Glu Leu Pro Ser Ser Leu Glu Lys Met Ser Ala Pro Arg Ser
 1               5                  10                  15

Met Gln Thr Lys Leu Trp Pro Glu Ala Val His Cys Ser Val Gln Phe
            20                  25                  30

Phe Leu Arg His Leu Lys Leu Glu Ser Ser Leu Ser Pro Met Gln Phe
        35                  40                  45

Leu Phe Gln Tyr Leu Trp Ser Gly Thr Thr Thr Arg Lys Lys Arg Lys
    50                  55                  60

Val Cys Thr Arg Cys Ser Val Gly Thr Met Leu Leu Leu Ser Pro Lys
65                  70                  75                  80

Cys Ser Pro Ser


<210> SEQ ID NO 96
<211> LENGTH: 105
<212> TYPE: PRT
<213> ORGANISM: Mycobacterium tuberculosis

<400> SEQUENCE: 96

Thr His Met Ala Ser Ser Pro Ser Pro Arg Leu Pro Trp Trp Arg Arg
 1               5                  10                  15

Ser Arg Pro Arg Lys Arg Met Ala Pro Leu Ser Arg Gln Thr Trp Asn
            20                  25                  30

Val Gln Thr Arg Gly Gln Gln Lys Ala Arg Met Trp Ile Lys Ile Ser
        35                  40                  45

Ser Lys Thr Thr Val Lys Leu Glu His Ser Pro Arg Tyr Lys Leu Met
    50                  55                  60

Val Asn Lys Pro His Ser Leu Pro Leu His Leu Asn Leu Pro Gln Lys
```

```
65                  70                  75                  80

Lys Ala Lys Pro Gln Met Leu Thr Lys Gln Met Lys Arg Lys Leu Ile
                85                  90                  95

Ser Leu Gln Lys Pro Arg Asn Leu Lys
            100                 105


<210> SEQ ID NO 97
<211> LENGTH: 51
<212> TYPE: PRT
<213> ORGANISM: Mycobacterium tuberculosis

<400> SEQUENCE: 97

Lys Trp Ala Leu Leu Leu Lys Ser Asp Phe Lys Lys Leu Arg Asn Asp
 1               5                  10                  15

Arg Lys Cys Trp Arg Ser Trp Gly Ser Ala Cys Ser Thr Met Pro Arg
            20                  25                  30

Leu Gln Arg Thr Ser Glu Ala Arg Met Arg Asn Thr Thr Thr Leu Met
        35                  40                  45

Asn Gln Lys
    50


<210> SEQ ID NO 98
<211> LENGTH: 145
<212> TYPE: PRT
<213> ORGANISM: Mycobacterium tuberculosis

<400> SEQUENCE: 98

His His Leu Gln Leu Arg Ala Gly Ser Ser Cys Ala Gln Arg Asp Gly
 1               5                  10                  15

Ser Gly Gly Cys Arg Thr Val Gln Arg Leu Thr Gly Gly Ala Val Leu
            20                  25                  30

Phe Ala Gln Phe Pro Arg Arg Thr Ala Thr Ser Ala Arg Cys His Gly
        35                  40                  45

Arg Ala Ile Ala Ser Cys Ala Gly Gly Gly Thr Val His Arg Pro Cys
    50                  55                  60

Arg Val Gly Cys Arg Leu Leu Gln Gln Leu Phe Arg Val Thr Asp Trp
65                  70                  75                  80

Ile Leu Gly Gly Trp Ala Arg Arg Arg Leu Thr Glu Leu Leu His Cys
                85                  90                  95

Gly Gly Ala Gly Arg Gly His Arg Asp His Arg Gln Arg Val Gln Arg
            100                 105                 110

Pro Leu His Pro Val Ser His Ile Ile Trp Ile Lys Lys Gln Asn Asn
        115                 120                 125

Trp Ser Cys Ser Gln Lys Pro Ala Asn His Ser Cys Lys Gln Tyr Gly
    130                 135                 140

Leu
145


<210> SEQ ID NO 99
<211> LENGTH: 50
<212> TYPE: PRT
<213> ORGANISM: Mycobacterium tuberculosis

<400> SEQUENCE: 99

Arg Val Leu Cys His Arg Cys Ser Ser Phe Ser Asn Ile Ser Gly Leu
 1               5                  10                  15

Glu Pro Arg Leu Gly Arg Asn Gly Arg Cys Ala Arg Gly Val Gln Ser
            20                  25                  30
```

```
Glu Pro Cys Cys Ser Phe Leu Gln Ser Ala His Leu Pro Glu Lys Gly
        35                  40                  45

Ala Leu
    50


<210> SEQ ID NO 100
<211> LENGTH: 81
<212> TYPE: PRT
<213> ORGANISM: Mycobacterium tuberculosis

<400> SEQUENCE: 100

Pro Ser Arg Ser Ser Ile Ser Arg Ser Lys Asn Arg Pro Phe Cys Cys
 1               5                  10                  15

Ser Glu Cys Phe Cys Thr Glu Arg Trp Arg Glu Val Glu Ser Glu Gly
            20                  25                  30

Gln Ser Ala Cys Glu His Thr Trp His Leu His His Leu His Gly Phe
        35                  40                  45

His Gly Gly Glu Gly Pro Asp Arg Gly Arg Gly Trp Leu Leu Ser Arg
    50                  55                  60

Gly Arg His Gly Met Ser Lys Pro Glu Ala Asn Arg Lys Leu Gly Cys
65                  70                  75                  80

Gly


<210> SEQ ID NO 101
<211> LENGTH: 62
<212> TYPE: PRT
<213> ORGANISM: Mycobacterium tuberculosis

<400> SEQUENCE: 101

Leu Asp Phe Trp Phe Gly Leu Ser Tyr Asn Arg Phe Thr Asn Ile Val
 1               5                  10                  15

Gln Phe Leu Asp Leu Arg Ser Asp Phe Met Ser Ser Asn Asn Arg Val
            20                  25                  30

Leu Ile Lys Thr Ser Phe Ser Leu Ser Ile His Asp Ile Ile His Pro
        35                  40                  45

Leu His His Leu Ile Asn Arg Leu Leu Asn Leu Leu His Phe
    50                  55                  60


<210> SEQ ID NO 102
<211> LENGTH: 76
<212> TYPE: PRT
<213> ORGANISM: Mycobacterium tuberculosis

<400> SEQUENCE: 102

Phe Ile Asn Val Val Val Phe Leu Ile Leu Ala Ser Glu Val Arg Cys
 1               5                  10                  15

Asn Leu Gly Ile Val Leu Gln Ala Leu Pro Gln Leu Leu Gln His Phe
            20                  25                  30

Arg Ser Phe Leu Ser Phe Leu Lys Ser Asp Phe Asn Arg Ser Ala His
        35                  40                  45

Phe His Gln Leu Phe Gln Leu Val Asn Val Cys Leu Leu Ser Leu Val
    50                  55                  60

Leu Pro Phe Leu Ile Gln Pro Val Phe Arg Leu Cys
65                  70                  75


<210> SEQ ID NO 103
<211> LENGTH: 110
<212> TYPE: PRT
<213> ORGANISM: Mycobacterium tuberculosis
```

<400> SEQUENCE: 103

```
Gly Leu Leu Thr Ile Ser Leu Tyr Leu Gly Leu Cys Ser Ser Phe Thr
 1               5                  10                  15

Val Val Leu Leu Asp Ile Phe Ile His Ile Arg Ala Phe Cys Trp Pro
            20                  25                  30

Leu Val Trp Thr Phe His Val Cys Leu Glu Arg Gly Ala Ile Leu Phe
        35                  40                  45

Leu Gly Arg Asp Leu Leu His His Gly Ser Arg Gly Asp Gly Glu Asp
    50                  55                  60

Ala Met Cys Val His Thr His Phe Asp Leu His Ser Arg Leu Leu Ser
65                  70                  75                  80

Ile Phe Leu Cys Arg Asn Ile Leu Asn Asn Lys Thr Ala Tyr Phe Cys
                85                  90                  95

Phe Trp Ile Trp Asn Ser Leu Arg Val Arg Ile Glu Ser Phe
            100                 105                 110
```

<210> SEQ ID NO 104
<211> LENGTH: 137
<212> TYPE: PRT
<213> ORGANISM: Mycobacterium tuberculosis

<400> SEQUENCE: 104

```
Leu Lys Gly Pro Pro Ser Gln Glu Gly Glu His Phe Gly Glu Arg Ser
 1               5                  10                  15

Ser Met Val Pro Thr Glu His Leu Val His Thr Phe Arg Phe Phe Arg
            20                  25                  30

Val Val Val Pro Asp Gln Arg Tyr Trp Lys Arg Asn Cys Ile Gly Asp
        35                  40                  45

Arg Glu Leu Ser Asn Phe Lys Cys Arg Arg Lys Asn Cys Thr Leu Gln
    50                  55                  60

Cys Thr Ala Ser Gly His Ser Phe Val Cys Ile Glu Arg Gly Ala Asp
65                  70                  75                  80

Ile Phe Ser Lys Glu Leu Gly Asn Ser Phe Phe His Ser Trp Asp Ser
                85                  90                  95

Cys Gly Thr Ser His Tyr Leu Asn Gly Thr His Ile Phe Ser Leu Glu
            100                 105                 110

Leu Ser Leu Cys His Gln Arg Val Lys Gly Asp Leu Tyr Phe Leu Gln
        115                 120                 125

Glu Leu Ser Thr Gln Phe Phe Lys Leu
    130                 135
```

<210> SEQ ID NO 105
<211> LENGTH: 63
<212> TYPE: PRT
<213> ORGANISM: Mycobacterium tuberculosis

<400> SEQUENCE: 105

```
Pro Val His Leu Pro Arg Asp Ile Leu Val Ile His Lys Ala Leu Asp
 1               5                  10                  15

Val Gln Arg Gln Val Arg Ala Val Arg Thr His Glu Leu Phe Gln Leu
            20                  25                  30

Phe Thr Leu Leu Met Glu Thr Lys Glu Gly Ser Asn Phe Gly Phe Cys
        35                  40                  45

Ile Gln Phe Val Leu Gly Phe Lys Phe Ser Thr Lys Met Phe Tyr
    50                  55                  60
```

<210> SEQ ID NO 106

<211> LENGTH: 62
<212> TYPE: PRT
<213> ORGANISM: Mycobacterium tuberculosis

<400> SEQUENCE: 106

```
Val Ser His Val Asn Lys His His His Pro Trp Leu Leu Leu Gly Ile
 1               5                  10                  15

Arg Glu Ile Leu Leu Ile Asn Pro Ile Ile Gln Ser Asn Ser Arg His
            20                  25                  30

Val Ile His Glu Pro Gln Ala Val Gln Ala His Asn Leu Arg Ser Ile
        35                  40                  45

Gln His Arg Pro Ser Leu Ser Ile Cys Glu Glu Gly Trp Asp
    50                  55                  60
```

<210> SEQ ID NO 107
<211> LENGTH: 81
<212> TYPE: PRT
<213> ORGANISM: Mycobacterium tuberculosis

<400> SEQUENCE: 107

```
Leu Ser Gln Gln His Gly Cys Tyr Leu Leu His Thr Glu Glu Met Phe
 1               5                  10                  15

Phe Ile His Val His Asp Leu Tyr Ser His Ala Thr Ile Phe His Trp
            20                  25                  30

Asp Gln Ile Ile Ala Gln Val Leu Leu Phe Leu Leu Asn Glu Gly Val
        35                  40                  45

Ile Glu Cys Ser Ala Met Lys Ser Leu Lys Ala Arg Asp Arg Ile Val
    50                  55                  60

Cys Met Ser Asp Leu Leu Val Phe Gly Cys Asn Ser Asn Cys Ser Val
65                  70                  75                  80

Phe
```

<210> SEQ ID NO 108
<211> LENGTH: 50
<212> TYPE: PRT
<213> ORGANISM: Mycobacterium tuberculosis

<400> SEQUENCE: 108

```
His Gly Ile Val Val Ala Gly Ala Gly Asn Arg Leu Asp Lys Ala Asp
 1               5                  10                  15

Val Leu Cys Arg Pro Arg His Ser Leu Gln Leu Arg Gly His Gly Ser
            20                  25                  30

Ala Leu Arg Trp Arg Cys Gly Glu Glu Ile Ala Gln Ile Gly Leu Arg
        35                  40                  45

His Arg
    50
```

<210> SEQ ID NO 109
<211> LENGTH: 126
<212> TYPE: PRT
<213> ORGANISM: Mycobacterium tuberculosis

<400> SEQUENCE: 109

```
Asn Leu Thr Leu Thr Gly Val Pro Ile Phe Ile Ser Ser Ser Asn Leu
 1               5                  10                  15

Ser Met Tyr Ala Cys Leu Ala Trp Ser Ser Pro Ser Ser Tyr Ser Gln
            20                  25                  30

Ser Ser Val Ser Val Arg Ser Leu Lys Asn Phe Ser Cys Ser Cys Ser
        35                  40                  45
```

```
His Met Asn Phe Ser Tyr Gly Pro His Ser Leu Ser Leu Asn Ser Tyr
    50                  55                  60

Thr His Ser Ser Thr Ala Phe Leu Ala Ser Phe Arg Ser Phe Ser Ser
65                  70                  75                  80

Leu Ser Cys Met Ile Ile Leu Pro Ser Val Ser Ile Tyr Met Leu Arg
                85                  90                  95

Arg Ser Leu Pro Asn Cys His Thr Lys Leu Ala Ser Thr Gly Ser Ser
            100                 105                 110

Thr Phe Thr Thr Phe Ile Leu Gly Phe Leu Ala Ser Gly Gly
        115                 120                 125


<210> SEQ ID NO 110
<211> LENGTH: 84
<212> TYPE: PRT
<213> ORGANISM: Mycobacterium tuberculosis

<400> SEQUENCE: 110

Pro Ser Val Cys Thr Trp Gly Cys Val Pro Ala Ser Leu Leu Ser Cys
 1               5                  10                  15

Trp Ile Phe Leu Ser Thr Ser Glu Leu Ser Val Gly Leu Trp Phe Gly
            20                  25                  30

His Ser Met Ser Ala Ser Arg Glu Glu Pro Ser Ser Ser Ser Val Gly
        35                  40                  45

Thr Phe Ser Thr Met Glu Ala Val Glu Met Val Lys Met Pro Cys Val
    50                  55                  60

Phe Thr Arg Thr Leu Thr Phe Thr Leu Asp Phe Ser Pro Ser Phe Cys
65                  70                  75                  80

Ala Glu Thr Phe


<210> SEQ ID NO 111
<211> LENGTH: 116
<212> TYPE: PRT
<213> ORGANISM: Mycobacterium tuberculosis

<400> SEQUENCE: 111

Lys Ala Ser Ser Ser Lys Gly Pro Leu Leu Arg Lys Val Ser Thr Leu
 1               5                  10                  15

Glu Lys Gly Ala Ala Trp Phe Arg Leu Asn Thr Ser Cys Thr Pro Ser
            20                  25                  30

Val Ser Ser Glu Ser Trp Phe Gln Thr Arg Asp Ile Gly Lys Gly Thr
        35                  40                  45

Ala Ser Val Thr Glu Asn Ser Leu Thr Leu Asn Ala Gly Glu Arg Ile
    50                  55                  60

Ala His Cys Ser Ala Gln Pro Leu Ala Thr Ala Ser Ser Ala Leu Ser
65                  70                  75                  80

Val Val Leu Thr Ser Phe Pro Lys Asn Leu Ala Ile Leu Ser Phe Thr
                85                  90                  95

Ala Gly Ile Leu Val Ala Pro Pro Thr Ile Ser Met Ala Leu Thr Ser
            100                 105                 110

Ser Ala Leu Ser
        115


<210> SEQ ID NO 112
<211> LENGTH: 53
<212> TYPE: PRT
<213> ORGANISM: Mycobacterium tuberculosis

<400> SEQUENCE: 112
```

```
Arg Gly Thr Ser Ile Phe Cys Arg Ser Ser Ala His Ser Ser Ser Asn
 1               5                  10                  15

Cys Asp Leu Phe Ile Phe Pro Glu Thr Ser Leu Ser Phe Ile Lys His
            20                  25                  30

Ser Met Phe Ser Gly Arg Ser Val Leu Leu Glu Leu Met Ser Phe Phe
        35                  40                  45

Asn Phe Ser His Ser
    50
```

<210> SEQ ID NO 113
<211> LENGTH: 83
<212> TYPE: PRT
<213> ORGANISM: Mycobacterium tuberculosis

<400> SEQUENCE: 113

```
Trp Arg Arg Arg Arg Ala Arg Ile Leu Asp Phe Ala Ser Asn Leu Tyr
 1               5                  10                  15

Leu Val Leu Asn Ser Ala Gln Lys Cys Ser Thr Ser Phe Ser Ser Lys
            20                  25                  30

Phe Phe Pro Pro Lys Lys Gly Ser Lys Ala Val Pro Arg Thr Phe Ser
        35                  40                  45

Phe Pro Leu Leu Lys Ala Gln Ala Asp Thr Trp Lys Asp Glu Cys Pro
    50                  55                  60

Met Ser Thr Asn Thr Thr Thr Arg Gly Phe Ser Ser Ala Phe Gly Arg
65                  70                  75                  80

Ser Cys Leu
```

<210> SEQ ID NO 114
<211> LENGTH: 91
<212> TYPE: PRT
<213> ORGANISM: Mycobacterium tuberculosis

<400> SEQUENCE: 114

```
Phe Lys Ala Thr Ala Val Met Ser Phe Met Ser Arg Lys Gln Phe Lys
 1               5                  10                  15

Pro Thr Ile Cys Ala Ala Ser Ser Thr Asp Leu Arg Ser Ala Ser Val
            20                  25                  30

Lys Lys Asp Gly Thr Glu Met Thr Gln Ser Val Thr Gly Phe Leu Arg
        35                  40                  45

Leu Phe Ser Ala Val Ser Phe Asn Leu Val Ser Ser Met Ala Val Ile
    50                  55                  60

Cys Ser Thr Leu Lys Lys Cys Ser Ser Ser Met Tyr Met Thr Phe Ile
65                  70                  75                  80

Pro Thr Pro Pro Phe Phe Ile Gly Thr Lys Ser
                85                  90
```

<210> SEQ ID NO 115
<211> LENGTH: 70
<212> TYPE: PRT
<213> ORGANISM: Mycobacterium tuberculosis

<400> SEQUENCE: 115

```
Val Gln Val Lys Gly Glu Thr Val Arg Phe Val Asp His Gln Phe Val
 1               5                  10                  15

Pro Gly Ala Val Phe Gln Leu His Cys Cys Leu Ala Gly Tyr Phe Tyr
            20                  25                  30

Pro His Pro Ser Phe Leu Leu Ala Ser Gly Leu Asp Ile Pro Cys Leu
        35                  40                  45
```

```
Pro Arg Glu Arg Ser His Pro Leu Pro Arg Ser Gly Pro Ser Pro Pro
    50                  55                  60

Trp Lys Pro Trp Arg Trp
65                  70


<210> SEQ ID NO 116
<211> LENGTH: 86
<212> TYPE: PRT
<213> ORGANISM: Mycobacterium tuberculosis

<400> SEQUENCE: 116

Thr Arg Trp Arg Trp Ser Arg Cys Pro Arg Pro Ala Pro Pro Gln Cys
 1               5                  10                  15

Ser Ser Ser Val Ser Leu Arg Leu Ala Gln Pro Pro Arg Ile Gln Ser
            20                  25                  30

Val Thr Arg Asn Ser Cys Cys Arg Ser Arg Gln Pro Thr Arg Gln Gly
        35                  40                  45

Arg Cys Thr Val Pro Pro Pro Ala Gln Leu Ala Ile Ala Arg Pro Trp
    50                  55                  60

Gln Arg Ala Glu Val Ala Val Arg Arg Gly Asn Cys Ala Asn Arg Thr
65                  70                  75                  80

Ala Pro Pro Val Arg Arg
                85


<210> SEQ ID NO 117
<211> LENGTH: 867
<212> TYPE: PRT
<213> ORGANISM: Homo sapiens

<400> SEQUENCE: 117

Met Gln His His His His His His His Ser Val Val Gly Leu Asp Val
 1               5                  10                  15

Gly Ser Gln Ser Cys Tyr Ile Ala Val Ala Arg Ala Gly Gly Ile Glu
            20                  25                  30

Thr Ile Ala Asn Glu Phe Ser Asp Arg Cys Thr Pro Ser Val Ile Ser
        35                  40                  45

Phe Gly Ser Lys Asn Arg Thr Ile Gly Val Ala Ala Lys Asn Gln Gln
    50                  55                  60

Ile Thr His Ala Asn Asn Thr Val Ser Ser Phe Lys Arg Phe His Gly
65                  70                  75                  80

Arg Ala Phe Asn Asp Pro Phe Ile Gln Lys Glu Lys Glu Asn Leu Ser
                85                  90                  95

Tyr Asp Leu Val Pro Met Lys Asn Gly Gly Val Gly Ile Lys Val Met
            100                 105                 110

Tyr Met Asp Glu Glu His Phe Phe Ser Val Glu Gln Ile Thr Ala Met
        115                 120                 125

Leu Leu Thr Lys Leu Lys Glu Thr Ala Glu Asn Asn Leu Lys Lys Pro
    130                 135                 140

Val Thr Asp Cys Val Ile Ser Val Pro Ser Phe Phe Thr Asp Ala Glu
145                 150                 155                 160

Arg Arg Ser Val Leu Asp Ala Ala Gln Ile Val Gly Leu Asn Cys Leu
                165                 170                 175

Arg Leu Met Asn Asp Met Thr Ala Val Ala Leu Asn Tyr Gly Ile Tyr
            180                 185                 190

Lys Gln Asp Leu Pro Asn Ala Glu Glu Lys Pro Arg Val Val Val Phe
        195                 200                 205

Val Asp Met Gly His Ser Ser Phe Gln Val Ser Ala Cys Ala Phe Asn
```

-continued

```
    210                 215                 220

Lys Gly Lys Leu Lys Val Leu Gly Thr Ala Phe Asp Pro Phe Leu Gly
225                 230                 235                 240

Gly Lys Asn Phe Asp Glu Lys Leu Val Glu His Phe Cys Ala Glu Phe
                245                 250                 255

Lys Thr Lys Tyr Lys Leu Asp Ala Lys Ser Lys Ile Arg Ala Leu Leu
            260                 265                 270

Arg Leu His Gln Glu Cys Glu Lys Leu Lys Lys Leu Met Ser Ser Asn
        275                 280                 285

Ser Thr Asp Leu Pro Leu Asn Ile Glu Cys Phe Met Asn Asp Lys Asp
    290                 295                 300

Val Ser Gly Lys Met Asn Arg Ser Gln Phe Glu Glu Leu Cys Ala Glu
305                 310                 315                 320

Leu Leu Gln Lys Ile Glu Val Pro Leu His Ser Leu Met Ala Gln Thr
                325                 330                 335

Gln Leu Lys Ala Glu Asp Val Ser Ala Ile Glu Ile Val Gly Gly Ala
            340                 345                 350

Thr Arg Ile Pro Ala Val Lys Glu Arg Ile Ala Lys Phe Phe Gly Lys
        355                 360                 365

Asp Val Ser Thr Thr Leu Asn Ala Asp Glu Ala Val Ala Arg Gly Cys
    370                 375                 380

Ala Leu Gln Cys Ala Ile Leu Ser Pro Ala Phe Lys Val Arg Glu Phe
385                 390                 395                 400

Ser Val Thr Asp Ala Val Pro Phe Pro Ile Ser Leu Val Trp Asn His
                405                 410                 415

Asp Ser Glu Glu Thr Glu Gly Val His Glu Val Phe Ser Arg Asn His
            420                 425                 430

Ala Ala Pro Phe Ser Lys Val Leu Thr Phe Leu Arg Arg Gly Pro Phe
        435                 440                 445

Glu Leu Glu Ala Phe Tyr Ser Asp Pro Gln Gly Val Pro Tyr Pro Glu
    450                 455                 460

Ala Lys Ile Gly Arg Phe Val Val Gln Asn Val Ser Ala Gln Lys Asp
465                 470                 475                 480

Gly Glu Lys Ser Arg Val Lys Val Lys Val Arg Val Asn Thr His Gly
                485                 490                 495

Ile Phe Thr Ile Ser Thr Ala Ser Met Val Glu Lys Val Pro Thr Glu
            500                 505                 510

Glu Glu Asp Gly Ser Ser Leu Glu Ala Asp Met Glu Cys Pro Asn Gln
        515                 520                 525

Arg Pro Thr Glu Ser Ser Asp Val Asp Lys Asn Ile Gln Gln Asp Asn
    530                 535                 540

Ser Glu Ala Gly Thr Gln Pro Gln Val Gln Thr Asp Gly Gln Gln Thr
545                 550                 555                 560

Ser Gln Ser Pro Pro Ser Pro Glu Leu Thr Ser Glu Glu Ser Lys Thr
                565                 570                 575

Pro Asp Ala Asp Lys Ala Asn Glu Lys Lys Val Asp Gln Pro Pro Glu
            580                 585                 590

Ala Lys Lys Pro Lys Ile Lys Val Val Asn Val Glu Leu Pro Val Glu
        595                 600                 605

Ala Asn Leu Val Trp Gln Leu Gly Arg Asp Leu Leu Asn Met Tyr Ile
    610                 615                 620

Glu Thr Glu Gly Lys Met Ile Met Gln Asp Lys Leu Glu Lys Glu Arg
625                 630                 635                 640
```

Asn Asp Ala Lys Asn Ala Val Glu Glu Cys Val Tyr Glu Phe Arg Asp
645 650 655

Lys Leu Cys Gly Pro Tyr Glu Lys Phe Ile Cys Glu Gln Glu His Glu
660 665 670

Lys Phe Leu Arg Leu Leu Thr Glu Thr Glu Asp Trp Leu Tyr Glu Glu
675 680 685

Gly Glu Asp Gln Ala Lys Gln Ala Tyr Ile Asp Lys Leu Glu Glu Leu
690 695 700

Met Lys Met Gly Thr Pro Val Lys Val Arg Phe Gln Glu Ala Glu Glu
705 710 715 720

Arg Pro Lys Val Leu Glu Glu Leu Gly Gln Arg Leu Gln His Tyr Ala
725 730 735

Lys Ile Ala Ala Asp Phe Arg Gly Lys Asp Glu Lys Tyr Asn His Ile
740 745 750

Asp Glu Ser Glu Met Lys Lys Val Glu Lys Ser Val Asn Glu Val Met
755 760 765

Glu Trp Met Asn Asn Val Met Asn Ala Gln Ala Lys Arg Ser Leu Asp
770 775 780

Gln Asp Pro Val Val Arg Thr His Glu Ile Arg Ala Lys Val Lys Glu
785 790 795 800

Leu Asn Asn Val Cys Glu Pro Val Val Thr Gln Pro Lys Pro Lys Ile
805 810 815

Glu Ser Pro Lys Leu Glu Arg Thr Pro Asn Gly Pro Asn Ile Asp Lys
820 825 830

Lys Glu Asp Leu Glu Gly Lys Asn Asn Leu Gly Ala Glu Ala Pro His
835 840 845

Gln Asn Gly Glu Cys His Pro Asn Glu Lys Gly Ser Val Asn Met Asp
850 855 860

Leu Asp Ile
865

<210> SEQ ID NO 118
<211> LENGTH: 78
<212> TYPE: PRT
<213> ORGANISM: Homo sapiens

<400> SEQUENCE: 118

Ala His Arg Ala Ala Thr Leu Arg Trp Arg Gly Pro Gly Ala Ser Arg
1 5 10 15

Pro Ser Pro Thr Ser Ser Ala Thr Ala Ala Pro Arg Gln Ser Tyr His
20 25 30

Leu Asp Gln Lys Thr Glu Gln Leu Glu Leu Gln Pro Lys Thr Ser Lys
35 40 45

Ser Leu Met Gln Thr Ile Arg Ser Leu Ala Leu Arg Asp Phe Met Ala
50 55 60

Glu His Ser Met Thr Pro Ser Phe Arg Arg Lys Arg Arg Thr
65 70 75

<210> SEQ ID NO 119
<211> LENGTH: 84
<212> TYPE: PRT
<213> ORGANISM: Homo sapiens

<400> SEQUENCE: 119

Lys Lys Glu Leu Pro Ser Ser Leu Glu Lys Met Ser Ala Pro Arg Ser
1 5 10 15

Met Gln Thr Lys Leu Trp Pro Glu Ala Val His Cys Ser Val Gln Phe

```
            20                  25                  30

Phe Leu Arg His Leu Lys Leu Glu Ser Ser Leu Ser Pro Met Gln Phe
        35                  40                  45

Leu Phe Gln Tyr Leu Trp Ser Gly Thr Thr Thr Arg Lys Lys Arg Lys
    50                  55                  60

Val Cys Thr Arg Cys Ser Val Gly Thr Met Leu Leu Leu Ser Pro Lys
65                  70                  75                  80

Cys Ser Pro Ser


<210> SEQ ID NO 120
<211> LENGTH: 105
<212> TYPE: PRT
<213> ORGANISM: Homo sapiens

<400> SEQUENCE: 120

Thr His Met Ala Ser Ser Pro Ser Pro Arg Leu Pro Trp Trp Arg Arg
 1               5                  10                  15

Ser Arg Pro Arg Lys Arg Met Ala Pro Leu Ser Arg Gln Thr Trp Asn
            20                  25                  30

Val Gln Thr Arg Gly Gln Gln Lys Ala Arg Met Trp Ile Lys Ile Ser
        35                  40                  45

Ser Lys Thr Thr Val Lys Leu Glu His Ser Pro Arg Tyr Lys Leu Met
    50                  55                  60

Val Asn Lys Pro His Ser Leu Pro Leu His Leu Asn Leu Pro Gln Lys
65                  70                  75                  80

Lys Ala Lys Pro Gln Met Leu Thr Lys Gln Met Lys Arg Lys Leu Ile
                85                  90                  95

Ser Leu Gln Lys Pro Arg Asn Leu Lys
            100                 105


<210> SEQ ID NO 121
<211> LENGTH: 51
<212> TYPE: PRT
<213> ORGANISM: Homo sapiens

<400> SEQUENCE: 121

Lys Trp Ala Leu Leu Leu Lys Ser Asp Phe Lys Lys Leu Arg Asn Asp
 1               5                  10                  15

Arg Lys Cys Trp Arg Ser Trp Gly Ser Ala Cys Ser Thr Met Pro Arg
            20                  25                  30

Leu Gln Arg Thr Ser Glu Ala Arg Met Arg Asn Thr Thr Thr Leu Met
        35                  40                  45

Asn Gln Lys
    50


<210> SEQ ID NO 122
<211> LENGTH: 72
<212> TYPE: PRT
<213> ORGANISM: Homo sapiens

<400> SEQUENCE: 122

Ala Ala Ser Pro Pro Ser Pro Pro Leu Gly Gly Trp Ala Arg Arg Arg
 1               5                  10                  15

Leu Thr Glu Leu Leu His Cys Gly Gly Ala Gly Arg Gly His Arg Asp
            20                  25                  30

His Arg Gln Arg Val Gln Arg Pro Leu His Pro Val Ser His Ile Ile
        35                  40                  45

Trp Ile Lys Lys Gln Asn Asn Trp Ser Cys Ser Gln Lys Pro Ala Asn
```

50 55 60

His Ser Cys Lys Gln Tyr Gly Leu
65 70

<210> SEQ ID NO 123
<211> LENGTH: 50
<212> TYPE: PRT
<213> ORGANISM: Homo sapiens

<400> SEQUENCE: 123

Arg Val Leu Cys His Arg Cys Ser Ser Phe Ser Asn Ile Ser Gly Leu
1 5 10 15

Glu Pro Arg Leu Gly Arg Asn Gly Arg Cys Ala Arg Gly Val Gln Ser
20 25 30

Glu Pro Cys Cys Ser Phe Leu Gln Ser Ala His Leu Pro Glu Lys Gly
35 40 45

Ala Leu
50

<210> SEQ ID NO 124
<211> LENGTH: 81
<212> TYPE: PRT
<213> ORGANISM: Homo sapiens

<400> SEQUENCE: 124

Pro Ser Arg Ser Ser Ile Ser Arg Ser Lys Asn Arg Pro Phe Cys Cys
1 5 10 15

Ser Glu Cys Phe Cys Thr Glu Arg Trp Arg Glu Val Glu Ser Glu Gly
20 25 30

Gln Ser Ala Cys Glu His Thr Trp His Leu His His Leu His Gly Phe
35 40 45

His Gly Gly Glu Gly Pro Asp Arg Gly Arg Gly Trp Leu Leu Ser Arg
50 55 60

Gly Arg His Gly Met Ser Lys Pro Glu Ala Asn Arg Lys Leu Gly Cys
65 70 75 80

Gly

<210> SEQ ID NO 125
<211> LENGTH: 62
<212> TYPE: PRT
<213> ORGANISM: Homo sapiens

<400> SEQUENCE: 125

Leu Asp Phe Trp Phe Gly Leu Ser Tyr Asn Arg Phe Thr Asn Ile Val
1 5 10 15

Gln Phe Leu Asp Leu Arg Ser Asp Phe Met Ser Ser Asn Asn Arg Val
20 25 30

Leu Ile Lys Thr Ser Phe Ser Leu Ser Ile His Asp Ile Ile His Pro
35 40 45

Leu His His Leu Ile Asn Arg Leu Leu Asn Leu Leu His Phe
50 55 60

<210> SEQ ID NO 126
<211> LENGTH: 76
<212> TYPE: PRT
<213> ORGANISM: Homo sapiens

<400> SEQUENCE: 126

Phe Ile Asn Val Val Val Phe Leu Ile Leu Ala Ser Glu Val Arg Cys
1 5 10 15

```
Asn Leu Gly Ile Val Leu Gln Ala Leu Pro Gln Leu Leu Gln His Phe
            20                  25                  30

Arg Ser Phe Leu Ser Phe Leu Lys Ser Asp Phe Asn Arg Ser Ala His
        35                  40                  45

Phe His Gln Leu Phe Gln Leu Val Asn Val Cys Leu Leu Ser Leu Val
    50                  55                  60

Leu Pro Phe Leu Ile Gln Pro Val Phe Arg Leu Cys
65                  70                  75


<210> SEQ ID NO 127
<211> LENGTH: 110
<212> TYPE: PRT
<213> ORGANISM: Homo sapiens

<400> SEQUENCE: 127

Gly Leu Leu Thr Ile Ser Leu Tyr Leu Gly Leu Cys Ser Ser Phe Thr
 1               5                  10                  15

Val Val Leu Leu Asp Ile Phe Ile His Ile Arg Ala Phe Cys Trp Pro
            20                  25                  30

Leu Val Trp Thr Phe His Val Cys Leu Glu Arg Gly Ala Ile Leu Phe
        35                  40                  45

Leu Gly Arg Asp Leu Leu His His Gly Ser Arg Gly Asp Gly Glu Asp
    50                  55                  60

Ala Met Cys Val His Thr His Phe Asp Leu His Ser Arg Leu Leu Ser
65                  70                  75                  80

Ile Phe Leu Cys Arg Asn Ile Leu Asn Asn Lys Thr Ala Tyr Phe Cys
                85                  90                  95

Phe Trp Ile Trp Asn Ser Leu Arg Val Arg Ile Glu Ser Phe
            100                 105                 110


<210> SEQ ID NO 128
<211> LENGTH: 137
<212> TYPE: PRT
<213> ORGANISM: Homo sapiens

<400> SEQUENCE: 128

Leu Lys Gly Pro Pro Ser Gln Glu Gly Glu His Phe Gly Glu Arg Ser
 1               5                  10                  15

Ser Met Val Pro Thr Glu His Leu Val His Thr Phe Arg Phe Phe Arg
            20                  25                  30

Val Val Val Pro Asp Gln Arg Tyr Trp Lys Arg Asn Cys Ile Gly Asp
        35                  40                  45

Arg Glu Leu Ser Asn Phe Lys Cys Arg Arg Lys Asn Cys Thr Leu Gln
    50                  55                  60

Cys Thr Ala Ser Gly His Ser Phe Val Cys Ile Glu Arg Gly Ala Asp
65                  70                  75                  80

Ile Phe Ser Lys Glu Leu Gly Asn Ser Phe Phe His Ser Trp Asp Ser
                85                  90                  95

Cys Gly Thr Ser His Tyr Leu Asn Gly Thr His Ile Phe Ser Leu Glu
            100                 105                 110

Leu Ser Leu Cys His Gln Arg Val Lys Gly Asp Leu Tyr Phe Leu Gln
        115                 120                 125

Glu Leu Ser Thr Gln Phe Phe Lys Leu
    130                 135


<210> SEQ ID NO 129
<211> LENGTH: 63
```

<212> TYPE: PRT
<213> ORGANISM: Homo sapiens

<400> SEQUENCE: 129

Pro Val His Leu Pro Arg Asp Ile Leu Val Ile His Lys Ala Leu Asp
1 5 10 15

Val Gln Arg Gln Val Arg Ala Val Arg Thr His Glu Leu Phe Gln Leu
20 25 30

Phe Thr Leu Leu Met Glu Thr Lys Glu Gly Ser Asn Phe Gly Phe Cys
35 40 45

Ile Gln Phe Val Leu Gly Phe Lys Phe Ser Thr Lys Met Phe Tyr
50 55 60

<210> SEQ ID NO 130
<211> LENGTH: 62
<212> TYPE: PRT
<213> ORGANISM: Homo sapiens

<400> SEQUENCE: 130

Val Ser His Val Asn Lys His His His Pro Trp Leu Leu Leu Gly Ile
1 5 10 15

Arg Glu Ile Leu Leu Ile Asn Pro Ile Ile Gln Ser Asn Ser Arg His
20 25 30

Val Ile His Glu Pro Gln Ala Val Gln Ala His Asn Leu Arg Ser Ile
35 40 45

Gln His Arg Pro Ser Leu Ser Ile Cys Glu Glu Gly Trp Asp
50 55 60

<210> SEQ ID NO 131
<211> LENGTH: 81
<212> TYPE: PRT
<213> ORGANISM: Homo sapiens

<400> SEQUENCE: 131

Leu Ser Gln Gln His Gly Cys Tyr Leu Leu His Thr Glu Glu Met Phe
1 5 10 15

Phe Ile His Val His Asp Leu Tyr Ser His Ala Thr Ile Phe His Trp
20 25 30

Asp Gln Ile Ile Ala Gln Val Leu Leu Phe Leu Leu Asn Glu Gly Val
35 40 45

Ile Glu Cys Ser Ala Met Lys Ser Leu Lys Ala Arg Asp Arg Ile Val
50 55 60

Cys Met Ser Asp Leu Leu Val Phe Gly Cys Asn Ser Asn Cys Ser Val
65 70 75 80

Phe

<210> SEQ ID NO 132
<211> LENGTH: 126
<212> TYPE: PRT
<213> ORGANISM: Homo sapiens

<400> SEQUENCE: 132

Asn Leu Thr Leu Thr Gly Val Pro Ile Phe Ile Ser Ser Ser Asn Leu
1 5 10 15

Ser Met Tyr Ala Cys Leu Ala Trp Ser Ser Pro Ser Ser Tyr Ser Gln
20 25 30

Ser Ser Val Ser Val Arg Ser Leu Lys Asn Phe Ser Cys Ser Cys Ser
35 40 45

His Met Asn Phe Ser Tyr Gly Pro His Ser Leu Ser Leu Asn Ser Tyr

```
    50                  55                  60

Thr His Ser Ser Thr Ala Phe Leu Ala Ser Phe Arg Ser Phe Ser Ser
65                  70                  75                  80

Leu Ser Cys Met Ile Ile Leu Pro Ser Val Ser Ile Tyr Met Leu Arg
                85                  90                  95

Arg Ser Leu Pro Asn Cys His Thr Lys Leu Ala Ser Thr Gly Ser Ser
            100                 105                 110

Thr Phe Thr Thr Phe Ile Leu Gly Phe Leu Ala Ser Gly Gly
        115                 120                 125


<210> SEQ ID NO 133
<211> LENGTH: 84
<212> TYPE: PRT
<213> ORGANISM: Homo sapiens

<400> SEQUENCE: 133

Pro Ser Val Cys Thr Trp Gly Cys Val Pro Ala Ser Leu Leu Ser Cys
 1               5                  10                  15

Trp Ile Phe Leu Ser Thr Ser Glu Leu Ser Val Gly Leu Trp Phe Gly
            20                  25                  30

His Ser Met Ser Ala Ser Arg Glu Glu Pro Ser Ser Ser Ser Val Gly
        35                  40                  45

Thr Phe Ser Thr Met Glu Ala Val Glu Met Val Lys Met Pro Cys Val
    50                  55                  60

Phe Thr Arg Thr Leu Thr Phe Thr Leu Asp Phe Ser Pro Ser Phe Cys
65                  70                  75                  80

Ala Glu Thr Phe


<210> SEQ ID NO 134
<211> LENGTH: 116
<212> TYPE: PRT
<213> ORGANISM: Homo sapiens

<400> SEQUENCE: 134

Lys Ala Ser Ser Ser Lys Gly Pro Leu Leu Arg Lys Val Ser Thr Leu
 1               5                  10                  15

Glu Lys Gly Ala Ala Trp Phe Arg Leu Asn Thr Ser Cys Thr Pro Ser
            20                  25                  30

Val Ser Ser Glu Ser Trp Phe Gln Thr Arg Asp Ile Gly Lys Gly Thr
        35                  40                  45

Ala Ser Val Thr Glu Asn Ser Leu Thr Leu Asn Ala Gly Glu Arg Ile
    50                  55                  60

Ala His Cys Ser Ala Gln Pro Leu Ala Thr Ala Ser Ser Ala Leu Ser
65                  70                  75                  80

Val Val Leu Thr Ser Phe Pro Lys Asn Leu Ala Ile Leu Ser Phe Thr
                85                  90                  95

Ala Gly Ile Leu Val Ala Pro Pro Thr Ile Ser Met Ala Leu Thr Ser
            100                 105                 110

Ser Ala Leu Ser
        115


<210> SEQ ID NO 135
<211> LENGTH: 53
<212> TYPE: PRT
<213> ORGANISM: Homo sapiens

<400> SEQUENCE: 135

Arg Gly Thr Ser Ile Phe Cys Arg Ser Ser Ala His Ser Ser Ser Asn
```

-continued

```
 1               5                   10                  15

Cys Asp Leu Phe Ile Phe Pro Glu Thr Ser Leu Ser Phe Ile Lys His
            20                  25                  30

Ser Met Phe Ser Gly Arg Ser Val Leu Leu Glu Leu Met Ser Phe Phe
        35                  40                  45

Asn Phe Ser His Ser
    50


<210> SEQ ID NO 136
<211> LENGTH: 83
<212> TYPE: PRT
<213> ORGANISM: Homo sapiens

<400> SEQUENCE: 136

Trp Arg Arg Arg Arg Ala Arg Ile Leu Asp Phe Ala Ser Asn Leu Tyr
 1               5                   10                  15

Leu Val Leu Asn Ser Ala Gln Lys Cys Ser Thr Ser Phe Ser Ser Lys
            20                  25                  30

Phe Phe Pro Pro Lys Lys Gly Ser Lys Ala Val Pro Arg Thr Phe Ser
        35                  40                  45

Phe Pro Leu Leu Lys Ala Gln Ala Asp Thr Trp Lys Asp Glu Cys Pro
    50                  55                  60

Met Ser Thr Asn Thr Thr Thr Arg Gly Phe Ser Ser Ala Phe Gly Arg
65                  70                  75                  80

Ser Cys Leu


<210> SEQ ID NO 137
<211> LENGTH: 91
<212> TYPE: PRT
<213> ORGANISM: Homo sapiens

<400> SEQUENCE: 137

Phe Lys Ala Thr Ala Val Met Ser Phe Met Ser Arg Lys Gln Phe Lys
 1               5                   10                  15

Pro Thr Ile Cys Ala Ala Ser Ser Thr Asp Leu Arg Ser Ala Ser Val
            20                  25                  30

Lys Lys Asp Gly Thr Glu Met Thr Gln Ser Val Thr Gly Phe Leu Arg
        35                  40                  45

Leu Phe Ser Ala Val Ser Phe Asn Leu Val Ser Ser Met Ala Val Ile
    50                  55                  60

Cys Ser Thr Leu Lys Lys Cys Ser Ser Ser Met Tyr Met Thr Phe Ile
65                  70                  75                  80

Pro Thr Pro Pro Phe Phe Ile Gly Thr Lys Ser
                85                  90


<210> SEQ ID NO 138
<211> LENGTH: 70
<212> TYPE: PRT
<213> ORGANISM: Homo sapiens

<400> SEQUENCE: 138

Val Gln Val Lys Gly Glu Thr Val Arg Phe Val Asp His Gln Phe Val
 1               5                   10                  15

Pro Gly Ala Val Phe Gln Leu His Cys Cys Leu Ala Gly Tyr Phe Tyr
            20                  25                  30

Pro His Pro Ser Phe Leu Leu Ala Ser Gly Leu Asp Ile Pro Cys Leu
        35                  40                  45

Pro Arg Glu Arg Ser His Pro Leu Pro Arg Ser Gly Pro Ser Pro Pro
```

50 55 60

Trp Lys Pro Trp Arg Trp
65 70

<210> SEQ ID NO 139
<211> LENGTH: 1089
<212> TYPE: PRT
<213> ORGANISM: Mycobacterium tuberculosis

<400> SEQUENCE: 139

Met Gln His His His His His His Ala Ala Thr Val Arg Arg Gln Arg
1 5 10 15

Pro Arg Arg Leu Leu Cys Trp Ala Leu Val Ala Val Leu Leu Ala Asp
20 25 30

Leu Leu Ala Leu Ser Asp Thr Leu Ala Val Met Ser Val Asp Leu Gly
35 40 45

Ser Glu Ser Met Lys Val Ala Ile Val Lys Pro Gly Val Pro Met Glu
50 55 60

Ile Val Leu Asn Lys Glu Ser Arg Arg Lys Thr Pro Val Thr Val Thr
65 70 75 80

Leu Lys Glu Asn Glu Arg Phe Leu Gly Asp Ser Ala Ala Gly Met Ala
85 90 95

Ile Lys Asn Pro Lys Ala Thr Leu Arg Tyr Phe Gln His Leu Leu Gly
100 105 110

Lys Gln Ala Asp Asn Pro His Val Ala Leu Tyr Arg Ser Arg Phe Pro
115 120 125

Glu His Glu Leu Ile Val Asp Pro Gln Arg Gln Thr Val Arg Phe Gln
130 135 140

Ile Ser Pro Gln Leu Gln Phe Ser Pro Glu Glu Val Leu Gly Met Val
145 150 155 160

Leu Asn Tyr Ser Arg Ser Leu Ala Glu Asp Phe Ala Glu Gln Pro Ile
165 170 175

Lys Asp Ala Val Ile Thr Val Pro Ala Phe Phe Asn Gln Ala Glu Arg
180 185 190

Arg Ala Val Leu Gln Ala Ala Arg Met Ala Gly Leu Lys Val Leu Gln
195 200 205

Leu Ile Asn Asp Asn Thr Ala Thr Ala Leu Ser Tyr Gly Val Phe Arg
210 215 220

Arg Lys Asp Ile Asn Ser Thr Ala Gln Asn Val Met Phe Tyr Asp Met
225 230 235 240

Gly Ser Gly Ser Thr Val Cys Thr Ile Val Thr Tyr Gln Thr Val Lys
245 250 255

Thr Lys Glu Ala Gly Met Gln Pro Gln Leu Gln Ile Arg Gly Val Gly
260 265 270

Phe Asp Arg Thr Leu Gly Gly Leu Glu Met Glu Leu Arg Leu Arg Glu
275 280 285

His Leu Ala Lys Leu Phe Asn Glu Gln Arg Lys Gly Gln Lys Ala Lys
290 295 300

Asp Val Arg Glu Asn Pro Arg Ala Met Ala Lys Leu Leu Arg Glu Ala
305 310 315 320

Asn Arg Leu Lys Thr Val Leu Ser Ala Asn Ala Asp His Met Ala Gln
325 330 335

Ile Glu Gly Leu Met Asp Asp Val Asp Phe Lys Ala Lys Val Thr Arg
340 345 350

Val Glu Phe Glu Glu Leu Cys Ala Asp Leu Phe Asp Arg Val Pro Gly

-continued

```
        355                 360                 365

Pro Val Gln Gln Ala Leu Gln Ser Ala Glu Met Ser Leu Asp Gln Ile
    370                 375                 380

Glu Gln Val Ile Leu Val Gly Gly Ala Thr Arg Val Pro Lys Val Gln
385                 390                 395                 400

Glu Val Leu Leu Lys Ala Val Gly Lys Glu Glu Leu Gly Lys Asn Ile
                405                 410                 415

Asn Ala Asp Glu Ala Ala Ala Met Gly Ala Val Tyr Gln Ala Ala Ala
            420                 425                 430

Leu Ser Lys Ala Phe Lys Val Lys Pro Phe Val Val Arg Asp Ala Val
        435                 440                 445

Ile Tyr Pro Ile Leu Val Glu Phe Thr Arg Glu Val Glu Glu Glu Pro
    450                 455                 460

Gly Leu Arg Ser Leu Lys His Asn Lys Arg Val Leu Phe Ser Arg Met
465                 470                 475                 480

Gly Pro Tyr Pro Gln Arg Lys Val Ile Thr Phe Asn Arg Tyr Ser His
                485                 490                 495

Asp Phe Asn Phe His Ile Asn Tyr Gly Asp Leu Gly Phe Leu Gly Pro
            500                 505                 510

Glu Asp Leu Arg Val Phe Gly Ser Gln Asn Leu Thr Thr Val Lys Leu
        515                 520                 525

Lys Gly Val Gly Glu Ser Phe Lys Lys Tyr Pro Asp Tyr Glu Ser Lys
    530                 535                 540

Gly Ile Lys Ala His Phe Asn Leu Asp Glu Ser Gly Val Leu Ser Leu
545                 550                 555                 560

Asp Arg Val Glu Ser Val Phe Glu Thr Leu Val Glu Asp Ser Pro Glu
                565                 570                 575

Glu Glu Ser Thr Leu Thr Lys Leu Gly Asn Thr Ile Ser Ser Leu Phe
            580                 585                 590

Gly Gly Gly Thr Ser Ser Asp Ala Lys Glu Asn Gly Thr Asp Ala Val
        595                 600                 605

Gln Glu Glu Glu Glu Ser Pro Ala Glu Gly Ser Lys Asp Glu Pro Ala
    610                 615                 620

Glu Gln Gly Glu Leu Lys Glu Glu Ala Glu Pro Pro Ala Glu Glu Thr
625                 630                 635                 640

Ser Gln Pro Pro Pro Ser Glu Pro Lys Gly Asp Ala Ala Arg Glu Gly
                645                 650                 655

Glu Lys Pro Asp Glu Lys Glu Ser Gly Asp Lys Pro Glu Ala Gln Lys
            660                 665                 670

Pro Asn Glu Lys Gly Gln Ala Gly Pro Glu Gly Ala Ala Pro Ala Pro
        675                 680                 685

Glu Glu Asp Lys Lys Pro Lys Pro Ala Arg Lys Gln Lys Met Val Glu
    690                 695                 700

Glu Ile Gly Val Glu Leu Ala Val Leu Asp Leu Pro Asp Leu Pro Glu
705                 710                 715                 720

Asp Glu Leu Ala Arg Ser Val Gln Lys Leu Glu Glu Leu Thr Leu Arg
                725                 730                 735

Asp Leu Glu Lys Gln Glu Arg Glu Lys Ala Ala Asn Ser Leu Glu Ala
            740                 745                 750

Phe Ile Phe Glu Thr Gln Asp Lys Leu Tyr Gln Pro Glu Tyr Gln Glu
        755                 760                 765

Val Ser Thr Glu Glu Gln Arg Glu Glu Ile Ser Gly Lys Leu Ser Ala
    770                 775                 780
```

```
Thr Ser Thr Trp Leu Glu Asp Glu Gly Phe Gly Ala Thr Thr Val Met
785                 790                 795                 800

Leu Lys Asp Lys Leu Ala Glu Leu Arg Lys Leu Cys Gln Gly Leu Phe
                805                 810                 815

Phe Arg Val Glu Glu Arg Arg Lys Trp Pro Glu Arg Leu Ser Ala Leu
            820                 825                 830

Asp Asn Leu Leu Asn His Ser Ser Ile Phe Leu Lys Gly Ala Arg Leu
        835                 840                 845

Ile Pro Glu Met Asp Gln Val Phe Thr Glu Val Glu Met Thr Thr Leu
    850                 855                 860

Glu Lys Val Ile Asn Asp Thr Trp Ala Trp Lys Asn Ala Thr Leu Ala
865                 870                 875                 880

Glu Gln Ala Lys Leu Pro Ala Thr Glu Lys Pro Val Leu Leu Ser Lys
                885                 890                 895

Asp Ile Glu Ala Lys Met Met Ala Leu Asp Arg Glu Val Gln Tyr Leu
            900                 905                 910

Leu Asn Lys Ala Lys Phe Thr Lys Pro Arg Pro Arg Pro Lys Asp Lys
        915                 920                 925

Asn Gly Thr Arg Ala Glu Pro Pro Leu Asn Ala Ser Ala Gly Asp Gln
    930                 935                 940

Glu Glu Lys Val Ile Pro Pro Ala Gly Gln Thr Glu Glu Ala Lys Pro
945                 950                 955                 960

Ile Leu Glu Pro Asp Lys Glu Glu Thr Gly Thr Glu Pro Ala Asp Ser
                965                 970                 975

Glu Pro Leu Glu Leu Gly Gly Pro Gly Ala Gly Pro Glu Gln Glu Glu
            980                 985                 990

Gln Ser Ala Gly Gln Lys Arg Pro Ser Lys Asn Asp Glu Leu His Asp
        995                 1000                1005

Pro Val Asp Ala Val Ile Asn Thr Thr Cys Asn Tyr Gly Gln Val Val
    1010                1015                1020

Ala Ala Leu Asn Ala Thr Asp Pro Gly Ala Ala Ala Gln Phe Asn Ala
1025                1030                1035                1040

Ser Pro Val Ala Gln Ser Tyr Leu Arg Asn Phe Leu Ala Ala Pro Pro
                1045                1050                1055

Pro Gln Arg Ala Ala Met Ala Ala Gln Leu Gln Ala Val Pro Gly Ala
            1060                1065                1070

Ala Gln Tyr Ile Gly Leu Val Glu Ser Val Ala Gly Ser Cys Asn Asn
        1075                1080                1085

Tyr


<210> SEQ ID NO 140
<211> LENGTH: 74
<212> TYPE: PRT
<213> ORGANISM: Mycobacterium tuberculosis

<400> SEQUENCE: 140

Ser Pro Cys Gln Pro Phe Ser Thr Arg Leu Ser Ala Glu Leu Cys Cys
 1               5                  10                  15

Arg Leu Leu Gly Trp Leu Ala Ser Arg Cys Cys Ser Ser Ser Met Thr
            20                  25                  30

Thr Leu Pro Gln Pro Ser Ala Thr Val Ser Ser Ala Gly Lys Ile Ser
        35                  40                  45

Ile Pro Leu His Arg Thr Ser Cys Ser Met Thr Trp Ala Arg Ala Ala
    50                  55                  60

Leu Cys Ala Pro Ser Ser Pro Thr Arg Gln
```

65 70

<210> SEQ ID NO 141
<211> LENGTH: 71
<212> TYPE: PRT
<213> ORGANISM: Mycobacterium tuberculosis

<400> SEQUENCE: 141

```
Arg Leu Arg Arg Leu Gly Cys Asn His Ser Cys Arg Ser Gly Ala Trp
 1               5                  10                  15

Asp Leu Thr Ala Pro Trp Val Ala Trp Arg Trp Ser Phe Gly Phe Glu
            20                  25                  30

Asn Thr Trp Leu Ser Ser Ser Met Ser Ser Ala Arg Ala Arg Lys Pro
        35                  40                  45

Arg Met Phe Gly Lys Thr Pro Gly Pro Trp Pro Asn Cys Phe Gly Lys
    50                  55                  60

Pro Thr Gly Leu Lys Pro Ser
65                  70
```

<210> SEQ ID NO 142
<211> LENGTH: 53
<212> TYPE: PRT
<213> ORGANISM: Mycobacterium tuberculosis

<400> SEQUENCE: 142

```
Asn Thr Ile Ser Val Cys Ser Ser Pro Glu Trp Gly Pro Thr Leu Ser
 1               5                  10                  15

Ala Lys Ser Ser Pro Leu Thr Ala Thr Ala Met Ile Ser Thr Ser Thr
            20                  25                  30

Ser Thr Thr Val Thr Trp Ala Ser Trp Gly Leu Arg Ile Phe Gly Tyr
        35                  40                  45

Leu Ala Pro Arg Ile
    50
```

<210> SEQ ID NO 143
<211> LENGTH: 145
<212> TYPE: PRT
<213> ORGANISM: Mycobacterium tuberculosis

<400> SEQUENCE: 143

```
Thr Gly Trp Ser Pro Tyr Leu Arg Pro Trp Trp Arg Ile Ala Gln Arg
 1               5                  10                  15

Lys Asn Leu Leu Leu Pro Asn Leu Ala Thr Pro Tyr Pro Ala Cys Leu
            20                  25                  30

Glu Val Val Pro His Gln Met Pro Lys Arg Met Val Leu Met Leu Tyr
        35                  40                  45

Arg Arg Lys Arg Arg Ala Pro Leu Arg Gly Ala Arg Met Ser Leu Gln
    50                  55                  60

Ser Arg Gly Asn Ser Arg Lys Lys Leu Asn Pro Gln Gln Arg Arg Pro
65                  70                  75                  80

Leu Ser Leu His Pro Leu Ser Leu Arg Gly Met Gln Pro Val Arg Glu
                85                  90                  95

Arg Asn Leu Met Lys Lys Arg Val Gly Thr Ser Leu Arg Pro Arg Ser
            100                 105                 110

Pro Met Arg Arg Gly Lys Gln Gly Leu Arg Val Leu Leu Gln Leu Leu
        115                 120                 125

Arg Arg Thr Lys Ser Arg Asn Leu Pro Gly Ser Arg Lys Trp Trp Arg
    130                 135                 140
```

Arg
145

<210> SEQ ID NO 144
<211> LENGTH: 60
<212> TYPE: PRT
<213> ORGANISM: Mycobacterium tuberculosis

<400> SEQUENCE: 144

Arg Ser Arg Arg Gly Arg Lys Leu Pro Thr Ala Trp Arg Leu Ser Ser
1 5 10 15

Leu Arg Pro Arg Thr Ser Cys Thr Ser Leu Ser Thr Arg Lys Cys Pro
20 25 30

Leu Arg Asn Ser Gly Arg Arg Ser Arg Gly Asn Ser Ala Pro Leu Leu
35 40 45

Pro Gly Trp Arg Met Arg Asp Leu Glu Pro Pro Leu
50 55 60

<210> SEQ ID NO 145
<211> LENGTH: 52
<212> TYPE: PRT
<213> ORGANISM: Mycobacterium tuberculosis

<400> SEQUENCE: 145

Glu Ser Cys Ala Lys Gly Cys Phe Phe Gly Trp Lys Asn Ala Gly Asn
1 5 10 15

Gly Gln Ser Gly Phe Gln Leu Trp Ile Ile Ser Ser Thr Ile Pro Ala
20 25 30

Phe Ser Ser Arg Val Pro Gly Ser Ser Arg Arg Trp Thr Arg Ser Ser
35 40 45

Leu Lys Trp Arg
50

<210> SEQ ID NO 146
<211> LENGTH: 59
<212> TYPE: PRT
<213> ORGANISM: Mycobacterium tuberculosis

<400> SEQUENCE: 146

Trp Pro Trp Thr Gly Arg Tyr Ser Ile Tyr Ser Ile Arg Pro Ser Leu
1 5 10 15

Pro Ser His Gly His Gly Pro Lys Thr Arg Met Ala Pro Gly Gln Asn
20 25 30

Leu Pro Ser Met Pro Val Leu Val Thr Lys Arg Arg Arg Ser Phe His
35 40 45

Leu Gln Ala Arg Leu Lys Arg Arg Asn Pro Phe
50 55

<210> SEQ ID NO 147
<211> LENGTH: 65
<212> TYPE: PRT
<213> ORGANISM: Mycobacterium tuberculosis

<400> SEQUENCE: 147

Leu Arg Ser Thr Arg Arg Ile Arg Gly Leu Pro His Ser Ser Thr Pro
1 5 10 15

His Arg Trp Arg Ser Pro Ile Cys Ala Ile Ser Ser Pro His Arg His
20 25 30

Leu Ser Ala Leu Pro Trp Pro Arg Asn Cys Lys Leu Cys Arg Gly Arg
35 40 45

```
His Ser Thr Ser Ala Leu Ser Ser Arg Leu Pro Ala Pro Ala Thr Thr
    50                  55                  60

Ile
65
```

<210> SEQ ID NO 148
<211> LENGTH: 87
<212> TYPE: PRT
<213> ORGANISM: Mycobacterium tuberculosis

<400> SEQUENCE: 148

```
Ala Gly Asp Pro Gly Gly Arg Gly His Ser Cys Ser Gln Ser Ser Arg
 1               5                  10                  15

Ser Ala Ala Gln Gly Arg Gly Gln Gly Gly Thr Arg Lys Glu His Gln
            20                  25                  30

Cys Gly Arg Ser Cys Cys His Gly Gly Cys Val Pro Gly Ser Gly Ala
        35                  40                  45

Gln Gln Gly Leu Gln Ser Glu Ala Ile Cys Cys Ala Gly Cys Cys His
    50                  55                  60

Leu Pro Asn Pro Gly Gly Val His Lys Gly Gly Gly Gly Gly Ala Trp
65                  70                  75                  80

Ala Pro Lys Pro Glu Thr Gln
                85
```

<210> SEQ ID NO 149
<211> LENGTH: 75
<212> TYPE: PRT
<213> ORGANISM: Mycobacterium tuberculosis

<400> SEQUENCE: 149

```
His His Leu Gln Leu Arg Ala Gly Ser Ser Cys Ala Gln Arg Asp Gly
 1               5                  10                  15

Ser Gly Gly Cys Arg Thr Val Gln Arg Leu Thr Gly Gly Ala Val Leu
            20                  25                  30

Phe Ala Gln Phe Pro Arg Arg Thr Ala Thr Ser Ala Arg Cys His Gly
        35                  40                  45

Arg Ala Ile Ala Ser Cys Ala Gly Gly Gly Thr Val His Arg Pro Cys
    50                  55                  60

Arg Val Gly Cys Arg Leu Leu Gln Gln Leu Leu
65                  70                  75
```

<210> SEQ ID NO 150
<211> LENGTH: 91
<212> TYPE: PRT
<213> ORGANISM: Mycobacterium tuberculosis

<400> SEQUENCE: 150

```
Lys Pro Leu Trp Pro Phe Pro Ala Phe Phe His Pro Lys Lys Gln Pro
 1               5                  10                  15

Leu Ala Gln Leu Ser Gln Leu Ser Gln Leu Val Leu Gln His His Ser
            20                  25                  30

Gly Gly Ser Lys Ser Leu Ile Leu Gln Pro Gly Arg Ser Gly Ala Glu
        35                  40                  45

Phe Pro Arg Asp Leu Leu Pro Leu Phe Leu Ser Gly His Phe Leu Val
    50                  55                  60

Leu Arg Leu Val Gln Leu Val Leu Gly Leu Lys Asp Glu Ser Leu Gln
65                  70                  75                  80

Ala Val Gly Ser Phe Leu Pro Leu Leu Leu Leu
                85                  90
```

<210> SEQ ID NO 151
<211> LENGTH: 139
<212> TYPE: PRT
<213> ORGANISM: Mycobacterium tuberculosis

<400> SEQUENCE: 151

```
Val Ala Gln Gly Gln Phe Phe Lys Phe Leu His Arg Thr Gly Gln Leu
 1               5                  10                  15

Ile Leu Trp Gln Val Arg Gln Val Gln Asp Ser Gln Leu His Thr Tyr
            20                  25                  30

Leu Leu His His Phe Leu Leu Pro Gly Arg Phe Arg Leu Phe Val Leu
        35                  40                  45

Leu Arg Ser Trp Ser Ser Thr Leu Arg Pro Cys Leu Pro Leu Leu Ile
    50                  55                  60

Gly Leu Leu Gly Leu Arg Leu Val Pro Thr Leu Phe Phe Ile Arg Phe
65                  70                  75                  80

Leu Ser Leu Thr Gly Cys Ile Pro Leu Arg Leu Arg Gly Trp Arg Leu
                85                  90                  95

Arg Gly Leu Leu Cys Trp Gly Phe Ser Phe Phe Leu Glu Phe Pro Leu
            100                 105                 110

Leu Cys Arg Leu Ile Leu Ala Pro Leu Ser Gly Ala Leu Leu Phe Leu
        115                 120                 125

Leu Tyr Ser Ile Ser Thr Ile Leu Phe Gly Ile
    130                 135
```

<210> SEQ ID NO 152
<211> LENGTH: 115
<212> TYPE: PRT
<213> ORGANISM: Mycobacterium tuberculosis

<400> SEQUENCE: 152

```
Phe Tyr Cys Gly Gln Ile Leu Gly Ala Lys Tyr Pro Lys Ile Leu Arg
 1               5                  10                  15

Pro Gln Glu Ala Gln Val Thr Val Val Asp Val Glu Val Glu Ile Met
            20                  25                  30

Ala Val Ala Val Lys Gly Asp Asp Phe Ala Leu Arg Val Gly Pro His
        35                  40                  45

Ser Gly Glu Glu His Thr Leu Ile Val Phe Gln Ala Ser Glu Pro Arg
    50                  55                  60

Leu Leu Leu His Leu Pro Cys Glu Leu His Gln Asp Trp Val Asn Asp
65                  70                  75                  80

Ser Ile Pro His Asn Lys Trp Leu His Phe Glu Gly Leu Ala Glu Arg
                85                  90                  95

Arg Cys Leu Val His Ser Pro His Gly Ser Ser Phe Val Arg Ile Asp
            100                 105                 110

Val Leu Ser
        115
```

<210> SEQ ID NO 153
<211> LENGTH: 279
<212> TYPE: PRT
<213> ORGANISM: Mycobacterium tuberculosis

<400> SEQUENCE: 153

```
Phe Leu Leu Ala His Gly Leu Glu Gln His Phe Leu Asn Phe Gly Asn
 1               5                  10                  15

Thr Ser Gly Pro Ala His Gln Asp His Leu Leu Asn Leu Ile Gln Ala
```

```
            20                  25                  30

His Leu Cys Thr Leu Gln Gly Leu Leu His Arg Ser Arg His Thr Val
        35                  40                  45

Lys Gln Ile Cys Thr Gln Leu Leu Glu Phe His Ser Ser Tyr Phe Gly
    50                  55                  60

Leu Glu Val His Ile Ile His Gln Ala Leu Asn Leu Cys His Val Ile
65                  70                  75                  80

Ser Val Gly Thr Gln Asp Gly Phe Lys Pro Val Gly Phe Pro Lys Gln
                85                  90                  95

Phe Gly His Gly Pro Gly Val Phe Pro Asn Ile Leu Gly Phe Leu Ala
            100                 105                 110

Leu Ala Leu Leu Ile Glu Glu Leu Ser Gln Val Phe Ser Lys Pro Lys
        115                 120                 125

Leu His Leu Gln Ala Thr Gln Gly Ala Val Lys Ser His Ala Pro Asp
    130                 135                 140

Leu Gln Leu Trp Leu His Pro Ser Leu Leu Ser Leu His Cys Leu Val
145                 150                 155                 160

Gly Asp Asp Gly Ala His Ser Ala Ala Arg Ala His Val Ile Glu His
                165                 170                 175

Asp Val Leu Cys Ser Gly Ile Asp Ile Phe Pro Ala Glu Asp Thr Val
            180                 185                 190

Ala Glu Gly Cys Gly Ser Val Val Ile Asp Glu Leu Gln His Leu Glu
        195                 200                 205

Ala Ser His Pro Ser Ser Leu Gln His Ser Ser Ala Leu Ser Leu Val
    210                 215                 220

Glu Lys Gly Trp His Gly Asp His Cys Ile Leu Asn Gly Leu Phe Ser
225                 230                 235                 240

Lys Ile Phe Ser Gln Gly Thr Gly Val Val Gln Asn His Ala Gln Tyr
                245                 250                 255

Leu Leu Gly Arg Glu Leu Gln Leu Arg Thr Asp Leu Glu Ala His Ser
            260                 265                 270

Leu Pro Leu Trp Val Asn Asn
        275
```

<210> SEQ ID NO 154
<211> LENGTH: 67
<212> TYPE: PRT
<213> ORGANISM: Mycobacterium tuberculosis

<400> SEQUENCE: 154

```
Lys Pro Phe Ile Phe Phe Gln Gly His Ser His Trp Ser Phe Pro Pro
 1               5                  10                  15

Arg Phe Leu Val Gln Tyr Asn Leu His Gly His Ser Arg Leu Asp Asn
            20                  25                  30

Gly His Leu His Gly Phe Thr Ala Gln Val Tyr Arg His His Ser Gln
        35                  40                  45

Cys Val Ala Gln Cys Gln Gln Val Cys Gln Glu Asp Ser His Gln Gly
    50                  55                  60

Pro Thr Glu
65
```

<210> SEQ ID NO 155
<211> LENGTH: 377
<212> TYPE: PRT
<213> ORGANISM: Mycobacterium tuberculosis

<400> SEQUENCE: 155

-continued

Leu Gln Val Val Leu Met Thr Ala Ser Thr Gly Ser Cys Ser Ser Ser
1 5 10 15

Phe Phe Glu Gly Arg Phe Cys Pro Ala Asp Cys Ser Ser Cys Ser Gly
20 25 30

Pro Ala Pro Gly Pro Pro Asn Ser Arg Gly Ser Glu Ser Ala Gly Ser
35 40 45

Val Pro Val Ser Ser Leu Ser Gly Ser Lys Met Gly Phe Ala Ser Ser
50 55 60

Val Trp Pro Ala Gly Gly Met Thr Phe Ser Ser Trp Ser Pro Ala Leu
65 70 75 80

Ala Leu Arg Gly Gly Ser Ala Arg Val Pro Phe Leu Ser Leu Gly Arg
85 90 95

Gly Arg Gly Leu Val Asn Leu Ala Leu Leu Ser Arg Tyr Cys Thr Ser
100 105 110

Arg Ser Arg Ala Ile Ile Leu Ala Ser Met Ser Phe Glu Ser Ser Thr
115 120 125

Gly Phe Ser Val Ala Gly Ser Leu Ala Cys Ser Ala Arg Val Ala Phe
130 135 140

Phe Gln Ala Gln Val Ser Leu Ile Thr Phe Ser Asn Val Val Ile Ser
145 150 155 160

Thr Ser Val Lys Thr Trp Ser Ile Ser Gly Met Ser Arg Ala Pro Leu
165 170 175

Arg Lys Met Leu Glu Trp Leu Arg Arg Leu Ser Arg Ala Glu Ser Arg
180 185 190

Ser Gly His Phe Leu Arg Ser Ser Thr Arg Lys Asn Ser Pro Trp His
195 200 205

Ser Phe Leu Ser Ser Ala Ser Leu Ser Phe Ser Ile Thr Val Val Ala
210 215 220

Pro Asn Pro Ser Ser Ser Ser Gln Val Glu Val Ala Leu Ser Phe Pro
225 230 235 240

Glu Ile Ser Ser Arg Cys Ser Ser Val Asp Thr Ser Trp Tyr Ser Gly
245 250 255

Trp Tyr Ser Leu Ser Trp Val Ser Lys Met Lys Ala Ser Lys Leu Leu
260 265 270

Ala Ala Phe Ser Leu Ser Cys Phe Ser Arg Ser Arg Arg Val Ser Ser
275 280 285

Ser Ser Phe Cys Thr Glu Arg Ala Ser Ser Ser Ser Gly Lys Ser Gly
290 295 300

Arg Ser Lys Thr Ala Ser Ser Thr Pro Ile Ser Ser Thr Ile Phe Cys
305 310 315 320

Phe Arg Ala Gly Phe Gly Phe Leu Ser Ser Ser Gly Ala Gly Ala Ala
325 330 335

Pro Ser Gly Pro Ala Cys Pro Phe Ser Leu Gly Phe Trp Ala Ser Gly
340 345 350

Leu Ser Pro Leu Ser Phe Ser Ser Gly Phe Ser Pro Ser Arg Ala Ala
355 360 365

Ser Pro Leu Gly Ser Glu Gly Gly Gly
370 375

<210> SEQ ID NO 156
<211> LENGTH: 100
<212> TYPE: PRT
<213> ORGANISM: Mycobacterium tuberculosis

<400> SEQUENCE: 156

```
Glu Val Ser Ser Ala Gly Gly Ser Ala Ser Ser Leu Ser Ser Pro Cys
 1               5                  10                  15

Ser Ala Gly Ser Ser Leu Leu Pro Ser Ala Gly Leu Ser Ser Ser Ser
            20                  25                  30

Cys Thr Ala Ser Val Pro Phe Ser Leu Ala Ser Asp Glu Val Pro Pro
        35                  40                  45

Pro Asn Arg Leu Asp Met Val Leu Pro Ser Leu Val Arg Val Asp Ser
    50                  55                  60

Ser Ser Gly Leu Ser Ser Thr Arg Val Ser Asn Thr Asp Ser Thr Leu
65                  70                  75                  80

Ser Lys Leu Ser Thr Pro Leu Ser Ser Arg Leu Lys Trp Ala Leu Met
                85                  90                  95

Pro Leu Asp Ser
            100


<210> SEQ ID NO 157
<211> LENGTH: 80
<212> TYPE: PRT
<213> ORGANISM: Mycobacterium tuberculosis

<400> SEQUENCE: 157

Ser Ala Leu Ala Leu Arg Thr Val Leu Ser Arg Leu Ala Ser Arg Ser
 1               5                  10                  15

Ser Leu Ala Met Ala Arg Gly Phe Ser Arg Thr Ser Leu Ala Phe Trp
            20                  25                  30

Pro Leu Arg Cys Ser Leu Lys Ser Leu Ala Arg Cys Ser Arg Ser Arg
        35                  40                  45

Ser Ser Ile Ser Arg Pro Pro Arg Val Arg Ser Asn Pro Thr Pro Arg
    50                  55                  60

Ile Cys Ser Cys Gly Cys Ile Pro Ala Ser Leu Val Phe Thr Val Trp
65                  70                  75                  80


<210> SEQ ID NO 158
<211> LENGTH: 56
<212> TYPE: PRT
<213> ORGANISM: Mycobacterium tuberculosis

<400> SEQUENCE: 158

Leu Arg Ala Val Ala Val Leu Ser Leu Met Ser Cys Ser Thr Leu Arg
 1               5                  10                  15

Pro Ala Ile Arg Ala Ala Cys Ser Thr Ala Arg Arg Ser Ala Trp Leu
            20                  25                  30

Lys Lys Ala Gly Thr Val Ile Thr Ala Ser Leu Met Gly Cys Ser Ala
        35                  40                  45

Lys Ser Ser Ala Lys Glu Arg Glu
    50                  55


<210> SEQ ID NO 159
<211> LENGTH: 98
<212> TYPE: PRT
<213> ORGANISM: Mycobacterium tuberculosis

<400> SEQUENCE: 159

Arg Ser Val Ala Phe Gly Phe Leu Met Ala Met Pro Ala Ala Leu Ser
 1               5                  10                  15

Pro Lys Asn Leu Ser Phe Ser Phe Lys Val Thr Val Thr Gly Val Phe
            20                  25                  30

Leu Arg Asp Ser Leu Phe Asn Thr Ile Ser Met Gly Thr Pro Gly Leu
```

35 40 45

Thr Met Ala Thr Phe Met Asp Ser Leu Pro Arg Ser Thr Asp Ile Thr
50 55 60

Ala Asn Val Ser Leu Ser Ala Asn Arg Ser Ala Lys Arg Thr Ala Thr
65 70 75 80

Lys Ala Gln Gln Ser Ser Leu Leu Gly Leu Cys Leu Leu Thr Val Ala
85 90 95

Ala Trp

<210> SEQ ID NO 160
<211> LENGTH: 51
<212> TYPE: PRT
<213> ORGANISM: Mycobacterium tuberculosis

<400> SEQUENCE: 160

Asn Ser Cys Cys Arg Ser Arg Gln Pro Thr Arg Gln Gly Arg Cys Thr
1 5 10 15

Val Pro Pro Pro Ala Gln Leu Ala Ile Ala Arg Pro Trp Gln Arg Ala
20 25 30

Glu Val Ala Val Arg Arg Gly Asn Cys Ala Asn Arg Thr Ala Pro Pro
35 40 45

Val Arg Arg
50

<210> SEQ ID NO 161
<211> LENGTH: 64
<212> TYPE: PRT
<213> ORGANISM: Mycobacterium tuberculosis

<400> SEQUENCE: 161

Pro Arg Pro Arg Asp Arg Val Val His Arg Ser Leu Lys Ala Ala Ser
1 5 10 15

Val Leu Leu Thr Ala Leu Pro Val Gln Val Gln Leu Gln Asp Leu Leu
20 25 30

Ile Pro Glu Ala Pro Ser Leu Leu Val Pro Tyr Gln Ser Leu Leu Cys
35 40 45

Gln Val Leu Lys Trp Val Ser Pro Leu Gln Ser Gly Leu Gln Val Glu
50 55 60

<210> SEQ ID NO 162
<211> LENGTH: 104
<212> TYPE: PRT
<213> ORGANISM: Mycobacterium tuberculosis

<400> SEQUENCE: 162

Lys Pro Pro Ser Cys Trp Gln Leu Ser Pro Ser Pro Ala Ser Leu Gly
1 5 10 15

Arg Ala Gly Ser Val Leu Gln Val Ser Ala Gln Asn Gly Pro Ala His
20 25 30

Pro Leu Ala Ser Gln Ala Gly Pro Arg Gln Pro Ala Pro His Leu Ser
35 40 45

Pro Pro Pro Phe Ser Ala Ser Gly Gln Val Ser Ala Phe Cys Pro Pro
50 55 60

Gln Glu Leu Glu Gln His Pro Gln Ala Leu Leu Ala Pro Ser His Trp
65 70 75 80

Ala Ser Gly Pro Gln Ala Cys Pro His Ser Leu Phe His Gln Val Ser
85 90 95

Leu Pro His Gly Leu His Pro Pro

100

<210> SEQ ID NO 163
<211> LENGTH: 57
<212> TYPE: PRT
<213> ORGANISM: Mycobacterium tuberculosis

<400> SEQUENCE: 163

```
Ala Ala Leu Leu Glu Leu Trp Glu His Glu Trp Pro Arg Pro Pro Gly
 1               5                  10                  15

Ser Pro Ala Gln Phe Asp Pro Ser Ser Ser Leu His Ser Ala Arg Pro
            20                  25                  30

Ala Ala Gln Val Gln Ala His Gly Gln Thr Asn Leu His Thr Ala Pro
        35                  40                  45

Arg Ile Pro Leu Glu Leu Leu Trp Pro
    50                  55
```

<210> SEQ ID NO 164
<211> LENGTH: 1008
<212> TYPE: PRT
<213> ORGANISM: Homo sapiens

<400> SEQUENCE: 164

```
Met Gln His His His His His His Ala Ala Thr Val Arg Arg Gln Arg
 1               5                  10                  15

Pro Arg Arg Leu Leu Cys Trp Ala Leu Val Ala Val Leu Leu Ala Asp
            20                  25                  30

Leu Leu Ala Leu Ser Asp Thr Leu Ala Val Met Ser Val Asp Leu Gly
        35                  40                  45

Ser Glu Ser Met Lys Val Ala Ile Val Lys Pro Gly Val Pro Met Glu
    50                  55                  60

Ile Val Leu Asn Lys Glu Ser Arg Arg Lys Thr Pro Val Thr Val Thr
65                  70                  75                  80

Leu Lys Glu Asn Glu Arg Phe Leu Gly Asp Ser Ala Ala Gly Met Ala
                85                  90                  95

Ile Lys Asn Pro Lys Ala Thr Leu Arg Tyr Phe Gln His Leu Leu Gly
            100                 105                 110

Lys Gln Ala Asp Asn Pro His Val Ala Leu Tyr Arg Ser Arg Phe Pro
        115                 120                 125

Glu His Glu Leu Ile Val Asp Pro Gln Arg Gln Thr Val Arg Phe Gln
    130                 135                 140

Ile Ser Pro Gln Leu Gln Phe Ser Pro Glu Glu Val Leu Gly Met Val
145                 150                 155                 160

Leu Asn Tyr Ser Arg Ser Leu Ala Glu Asp Phe Ala Glu Gln Pro Ile
                165                 170                 175

Lys Asp Ala Val Ile Thr Val Pro Ala Phe Phe Asn Gln Ala Glu Arg
            180                 185                 190

Arg Ala Val Leu Gln Ala Ala Arg Met Ala Gly Leu Lys Val Leu Gln
        195                 200                 205

Leu Ile Asn Asp Asn Thr Ala Thr Ala Leu Ser Tyr Gly Val Phe Arg
    210                 215                 220

Arg Lys Asp Ile Asn Ser Thr Ala Gln Asn Val Met Phe Tyr Asp Met
225                 230                 235                 240

Gly Ser Gly Ser Thr Val Cys Thr Ile Val Thr Tyr Gln Thr Val Lys
                245                 250                 255

Thr Lys Glu Ala Gly Met Gln Pro Gln Leu Gln Ile Arg Gly Val Gly
            260                 265                 270
```

```
Phe Asp Arg Thr Leu Gly Gly Leu Glu Met Glu Leu Arg Leu Arg Glu
        275                 280                 285

His Leu Ala Lys Leu Phe Asn Glu Gln Arg Lys Gly Gln Lys Ala Lys
    290                 295                 300

Asp Val Arg Glu Asn Pro Arg Ala Met Ala Lys Leu Leu Arg Glu Ala
305                 310                 315                 320

Asn Arg Leu Lys Thr Val Leu Ser Ala Asn Ala Asp His Met Ala Gln
                325                 330                 335

Ile Glu Gly Leu Met Asp Asp Val Asp Phe Lys Ala Lys Val Thr Arg
            340                 345                 350

Val Glu Phe Glu Glu Leu Cys Ala Asp Leu Phe Asp Arg Val Pro Gly
        355                 360                 365

Pro Val Gln Gln Ala Leu Gln Ser Ala Glu Met Ser Leu Asp Gln Ile
    370                 375                 380

Glu Gln Val Ile Leu Val Gly Gly Ala Thr Arg Val Pro Lys Val Gln
385                 390                 395                 400

Glu Val Leu Leu Lys Ala Val Gly Lys Glu Glu Leu Gly Lys Asn Ile
                405                 410                 415

Asn Ala Asp Glu Ala Ala Ala Met Gly Ala Val Tyr Gln Ala Ala Ala
            420                 425                 430

Leu Ser Lys Ala Phe Lys Val Lys Pro Phe Val Val Arg Asp Ala Val
        435                 440                 445

Ile Tyr Pro Ile Leu Val Glu Phe Thr Arg Glu Val Glu Glu Glu Pro
    450                 455                 460

Gly Leu Arg Ser Leu Lys His Asn Lys Arg Val Leu Phe Ser Arg Met
465                 470                 475                 480

Gly Pro Tyr Pro Gln Arg Lys Val Ile Thr Phe Asn Arg Tyr Ser His
                485                 490                 495

Asp Phe Asn Phe His Ile Asn Tyr Gly Asp Leu Gly Phe Leu Gly Pro
            500                 505                 510

Glu Asp Leu Arg Val Phe Gly Ser Gln Asn Leu Thr Thr Val Lys Leu
        515                 520                 525

Lys Gly Val Gly Glu Ser Phe Lys Lys Tyr Pro Asp Tyr Glu Ser Lys
    530                 535                 540

Gly Ile Lys Ala His Phe Asn Leu Asp Glu Ser Gly Val Leu Ser Leu
545                 550                 555                 560

Asp Arg Val Glu Ser Val Phe Glu Thr Leu Val Glu Asp Ser Pro Glu
                565                 570                 575

Glu Glu Ser Thr Leu Thr Lys Leu Gly Asn Thr Ile Ser Ser Leu Phe
            580                 585                 590

Gly Gly Gly Thr Ser Ser Asp Ala Lys Glu Asn Gly Thr Asp Ala Val
        595                 600                 605

Gln Glu Glu Glu Glu Ser Pro Ala Glu Gly Ser Lys Asp Glu Pro Ala
    610                 615                 620

Glu Gln Gly Glu Leu Lys Glu Glu Ala Glu Pro Pro Ala Glu Glu Thr
625                 630                 635                 640

Ser Gln Pro Pro Pro Ser Glu Pro Lys Gly Asp Ala Ala Arg Glu Gly
                645                 650                 655

Glu Lys Pro Asp Glu Lys Glu Ser Gly Asp Lys Pro Glu Ala Gln Lys
            660                 665                 670

Pro Asn Glu Lys Gly Gln Ala Gly Pro Glu Gly Ala Ala Pro Ala Pro
        675                 680                 685

Glu Glu Asp Lys Lys Pro Lys Pro Ala Arg Lys Gln Lys Met Val Glu
```

```
    690                 695                 700

Glu Ile Gly Val Glu Leu Ala Val Leu Asp Leu Pro Asp Leu Pro Glu
705                 710                 715                 720

Asp Glu Leu Ala Arg Ser Val Gln Lys Leu Glu Glu Leu Thr Leu Arg
                725                 730                 735

Asp Leu Glu Lys Gln Glu Arg Glu Lys Ala Ala Asn Ser Leu Glu Ala
            740                 745                 750

Phe Ile Phe Glu Thr Gln Asp Lys Leu Tyr Gln Pro Glu Tyr Gln Glu
        755                 760                 765

Val Ser Thr Glu Glu Gln Arg Glu Glu Ile Ser Gly Lys Leu Ser Ala
    770                 775                 780

Thr Ser Thr Trp Leu Glu Asp Glu Gly Phe Gly Ala Thr Thr Val Met
785                 790                 795                 800

Leu Lys Asp Lys Leu Ala Glu Leu Arg Lys Leu Cys Gln Gly Leu Phe
                805                 810                 815

Phe Arg Val Glu Glu Arg Arg Lys Trp Pro Glu Arg Leu Ser Ala Leu
            820                 825                 830

Asp Asn Leu Leu Asn His Ser Ser Ile Phe Leu Lys Gly Ala Arg Leu
        835                 840                 845

Ile Pro Glu Met Asp Gln Val Phe Thr Glu Val Glu Met Thr Thr Leu
    850                 855                 860

Glu Lys Val Ile Asn Asp Thr Trp Ala Trp Lys Asn Ala Thr Leu Ala
865                 870                 875                 880

Glu Gln Ala Lys Leu Pro Ala Thr Glu Lys Pro Val Leu Leu Ser Lys
                885                 890                 895

Asp Ile Glu Ala Lys Met Met Ala Leu Asp Arg Glu Val Gln Tyr Leu
            900                 905                 910

Leu Asn Lys Ala Lys Phe Thr Lys Pro Arg Pro Arg Pro Lys Asp Lys
        915                 920                 925

Asn Gly Thr Arg Ala Glu Pro Pro Leu Asn Ala Ser Ala Gly Asp Gln
    930                 935                 940

Glu Glu Lys Val Ile Pro Pro Ala Gly Gln Thr Glu Glu Ala Lys Pro
945                 950                 955                 960

Ile Leu Glu Pro Asp Lys Glu Glu Thr Gly Thr Glu Pro Ala Asp Ser
                965                 970                 975

Glu Pro Leu Glu Leu Gly Gly Pro Gly Ala Gly Pro Glu Gln Glu Glu
            980                 985                 990

Gln Ser Ala Gly Gln Lys Arg Pro Ser Lys Asn Asp Glu Leu His Val
        995                 1000                1005


<210> SEQ ID NO 165
<211> LENGTH: 74
<212> TYPE: PRT
<213> ORGANISM: Homo sapiens

<400> SEQUENCE: 165

Ser Pro Cys Gln Pro Phe Ser Thr Arg Leu Ser Ala Glu Leu Cys Cys
 1               5                  10                  15

Arg Leu Leu Gly Trp Leu Ala Ser Arg Cys Cys Ser Ser Ser Met Thr
            20                  25                  30

Thr Leu Pro Gln Pro Ser Ala Thr Val Ser Ser Ala Gly Lys Ile Ser
        35                  40                  45

Ile Pro Leu His Arg Thr Ser Cys Ser Met Thr Trp Ala Arg Ala Ala
    50                  55                  60

Leu Cys Ala Pro Ser Ser Pro Thr Arg Gln
```

65 70

<210> SEQ ID NO 166
<211> LENGTH: 71
<212> TYPE: PRT
<213> ORGANISM: Homo sapiens

<400> SEQUENCE: 166

Arg Leu Arg Arg Leu Gly Cys Asn His Ser Cys Arg Ser Gly Ala Trp
1 5 10 15

Asp Leu Thr Ala Pro Trp Val Ala Trp Arg Trp Ser Phe Gly Phe Glu
20 25 30

Asn Thr Trp Leu Ser Ser Ser Met Ser Ser Ala Arg Ala Arg Lys Pro
35 40 45

Arg Met Phe Gly Lys Thr Pro Gly Pro Trp Pro Asn Cys Phe Gly Lys
50 55 60

Pro Thr Gly Leu Lys Pro Ser
65 70

<210> SEQ ID NO 167
<211> LENGTH: 53
<212> TYPE: PRT
<213> ORGANISM: Homo sapiens

<400> SEQUENCE: 167

Asn Thr Ile Ser Val Cys Ser Ser Pro Glu Trp Gly Pro Thr Leu Ser
1 5 10 15

Ala Lys Ser Ser Pro Leu Thr Ala Thr Ala Met Ile Ser Thr Ser Thr
20 25 30

Ser Thr Thr Val Thr Trp Ala Ser Trp Gly Leu Arg Ile Phe Gly Tyr
35 40 45

Leu Ala Pro Arg Ile
50

<210> SEQ ID NO 168
<211> LENGTH: 145
<212> TYPE: PRT
<213> ORGANISM: Homo sapiens

<400> SEQUENCE: 168

Thr Gly Trp Ser Pro Tyr Leu Arg Pro Trp Trp Arg Ile Ala Gln Arg
1 5 10 15

Lys Asn Leu Leu Leu Pro Asn Leu Ala Thr Pro Tyr Pro Ala Cys Leu
20 25 30

Glu Val Val Pro His Gln Met Pro Lys Arg Met Val Leu Met Leu Tyr
35 40 45

Arg Arg Lys Arg Arg Ala Pro Leu Arg Gly Ala Arg Met Ser Leu Gln
50 55 60

Ser Arg Gly Asn Ser Arg Lys Lys Leu Asn Pro Gln Gln Arg Arg Pro
65 70 75 80

Leu Ser Leu His Pro Leu Ser Leu Arg Gly Met Gln Pro Val Arg Glu
85 90 95

Arg Asn Leu Met Lys Lys Arg Val Gly Thr Ser Leu Arg Pro Arg Ser
100 105 110

Pro Met Arg Arg Gly Lys Gln Gly Leu Arg Val Leu Leu Gln Leu Leu
115 120 125

Arg Arg Thr Lys Ser Arg Asn Leu Pro Gly Ser Arg Lys Trp Trp Arg
130 135 140

Arg
145

<210> SEQ ID NO 169
<211> LENGTH: 60
<212> TYPE: PRT
<213> ORGANISM: Homo sapiens

<400> SEQUENCE: 169

Arg Ser Arg Arg Gly Arg Lys Leu Pro Thr Ala Trp Arg Leu Ser Ser
1 5 10 15

Leu Arg Pro Arg Thr Ser Cys Thr Ser Leu Ser Thr Arg Lys Cys Pro
20 25 30

Leu Arg Asn Ser Gly Arg Arg Ser Arg Gly Asn Ser Ala Pro Leu Leu
35 40 45

Pro Gly Trp Arg Met Arg Asp Leu Glu Pro Pro Leu
50 55 60

<210> SEQ ID NO 170
<211> LENGTH: 52
<212> TYPE: PRT
<213> ORGANISM: Homo sapiens

<400> SEQUENCE: 170

Glu Ser Cys Ala Lys Gly Cys Phe Phe Gly Trp Lys Asn Ala Gly Asn
1 5 10 15

Gly Gln Ser Gly Phe Gln Leu Trp Ile Ile Ser Ser Thr Ile Pro Ala
20 25 30

Phe Ser Ser Arg Val Pro Gly Ser Ser Arg Arg Trp Thr Arg Ser Ser
35 40 45

Leu Lys Trp Arg
50

<210> SEQ ID NO 171
<211> LENGTH: 59
<212> TYPE: PRT
<213> ORGANISM: Homo sapiens

<400> SEQUENCE: 171

Trp Pro Trp Thr Gly Arg Tyr Ser Ile Tyr Ser Ile Arg Pro Ser Leu
1 5 10 15

Pro Ser His Gly His Gly Pro Lys Thr Arg Met Ala Pro Gly Gln Asn
20 25 30

Leu Pro Ser Met Pro Val Leu Val Thr Lys Arg Arg Arg Ser Phe His
35 40 45

Leu Gln Ala Arg Leu Lys Arg Arg Asn Pro Phe
50 55

<210> SEQ ID NO 172
<211> LENGTH: 87
<212> TYPE: PRT
<213> ORGANISM: Homo sapiens

<400> SEQUENCE: 172

Ala Gly Asp Pro Gly Gly Arg Gly His Ser Cys Ser Gln Ser Ser Arg
1 5 10 15

Ser Ala Ala Gln Gly Arg Gly Gln Gly Gly Thr Arg Lys Glu His Gln
20 25 30

Cys Gly Arg Ser Cys Cys His Gly Gly Cys Val Pro Gly Ser Gly Ala
35 40 45

```
Gln Gln Gly Leu Gln Ser Glu Ala Ile Cys Cys Ala Gly Cys Cys His
    50                  55                  60

Leu Pro Asn Pro Gly Gly Val His Lys Gly Gly Gly Gly Gly Ala Trp
65                  70                  75                  80

Ala Pro Lys Pro Glu Thr Gln
                85
```

<210> SEQ ID NO 173
<211> LENGTH: 91
<212> TYPE: PRT
<213> ORGANISM: Homo sapiens

<400> SEQUENCE: 173

```
Lys Pro Leu Trp Pro Phe Pro Ala Phe Phe His Pro Lys Lys Gln Pro
 1               5                  10                  15

Leu Ala Gln Leu Ser Gln Leu Ser Gln Leu Val Leu Gln His His Ser
            20                  25                  30

Gly Gly Ser Lys Ser Leu Ile Leu Gln Pro Gly Arg Ser Gly Ala Glu
        35                  40                  45

Phe Pro Arg Asp Leu Leu Pro Leu Phe Leu Ser Gly His Phe Leu Val
    50                  55                  60

Leu Arg Leu Val Gln Leu Val Leu Gly Leu Lys Asp Glu Ser Leu Gln
65                  70                  75                  80

Ala Val Gly Ser Phe Leu Pro Leu Leu Leu Leu
                85                  90
```

<210> SEQ ID NO 174
<211> LENGTH: 139
<212> TYPE: PRT
<213> ORGANISM: Homo sapiens

<400> SEQUENCE: 174

```
Val Ala Gln Gly Gln Phe Phe Lys Phe Leu His Arg Thr Gly Gln Leu
 1               5                  10                  15

Ile Leu Trp Gln Val Arg Gln Val Gln Asp Ser Gln Leu His Thr Tyr
            20                  25                  30

Leu Leu His His Phe Leu Leu Pro Gly Arg Phe Arg Leu Phe Val Leu
        35                  40                  45

Leu Arg Ser Trp Ser Ser Thr Leu Arg Pro Cys Leu Pro Leu Leu Ile
    50                  55                  60

Gly Leu Leu Gly Leu Arg Leu Val Pro Thr Leu Phe Phe Ile Arg Phe
65                  70                  75                  80

Leu Ser Leu Thr Gly Cys Ile Pro Leu Arg Leu Arg Gly Trp Arg Leu
                85                  90                  95

Arg Gly Leu Leu Cys Trp Gly Phe Ser Phe Phe Leu Glu Phe Pro Leu
            100                 105                 110

Leu Cys Arg Leu Ile Leu Ala Pro Leu Ser Gly Ala Leu Leu Phe Leu
        115                 120                 125

Leu Tyr Ser Ile Ser Thr Ile Leu Phe Gly Ile
    130                 135
```

<210> SEQ ID NO 175
<211> LENGTH: 115
<212> TYPE: PRT
<213> ORGANISM: Homo sapiens

<400> SEQUENCE: 175

```
Phe Tyr Cys Gly Gln Ile Leu Gly Ala Lys Tyr Pro Lys Ile Leu Arg
 1               5                  10                  15
```

```
Pro Gln Glu Ala Gln Val Thr Val Val Asp Val Glu Val Glu Ile Met
            20                  25                  30

Ala Val Ala Val Lys Gly Asp Asp Phe Ala Leu Arg Val Gly Pro His
        35                  40                  45

Ser Gly Glu Glu His Thr Leu Ile Val Phe Gln Ala Ser Glu Pro Arg
    50                  55                  60

Leu Leu Leu His Leu Pro Cys Glu Leu His Gln Asp Trp Val Asn Asp
65                  70                  75                  80

Ser Ile Pro His Asn Lys Trp Leu His Phe Glu Gly Leu Ala Glu Arg
                85                  90                  95

Arg Cys Leu Val His Ser Pro His Gly Ser Ser Phe Val Arg Ile Asp
            100                 105                 110

Val Leu Ser
        115


<210> SEQ ID NO 176
<211> LENGTH: 279
<212> TYPE: PRT
<213> ORGANISM: Homo sapiens

<400> SEQUENCE: 176

Phe Leu Leu Ala His Gly Leu Glu Gln His Phe Leu Asn Phe Gly Asn
 1               5                  10                  15

Thr Ser Gly Pro Ala His Gln Asp His Leu Leu Asn Leu Ile Gln Ala
            20                  25                  30

His Leu Cys Thr Leu Gln Gly Leu Leu His Arg Ser Arg His Thr Val
        35                  40                  45

Lys Gln Ile Cys Thr Gln Leu Leu Glu Phe His Ser Ser Tyr Phe Gly
    50                  55                  60

Leu Glu Val His Ile Ile His Gln Ala Leu Asn Leu Cys His Val Ile
65                  70                  75                  80

Ser Val Gly Thr Gln Asp Gly Phe Lys Pro Val Gly Phe Pro Lys Gln
                85                  90                  95

Phe Gly His Gly Pro Gly Val Phe Pro Asn Ile Leu Gly Phe Leu Ala
            100                 105                 110

Leu Ala Leu Leu Ile Glu Glu Leu Ser Gln Val Phe Ser Lys Pro Lys
        115                 120                 125

Leu His Leu Gln Ala Thr Gln Gly Ala Val Lys Ser His Ala Pro Asp
    130                 135                 140

Leu Gln Leu Trp Leu His Pro Ser Leu Leu Ser Leu His Cys Leu Val
145                 150                 155                 160

Gly Asp Asp Gly Ala His Ser Ala Ala Arg Ala His Val Ile Glu His
                165                 170                 175

Asp Val Leu Cys Ser Gly Ile Asp Ile Phe Pro Ala Glu Asp Thr Val
            180                 185                 190

Ala Glu Gly Cys Gly Ser Val Val Ile Asp Glu Leu Gln His Leu Glu
        195                 200                 205

Ala Ser His Pro Ser Ser Leu Gln His Ser Ser Ala Leu Ser Leu Val
    210                 215                 220

Glu Lys Gly Trp His Gly Asp His Cys Ile Leu Asn Gly Leu Phe Ser
225                 230                 235                 240

Lys Ile Phe Ser Gln Gly Thr Gly Val Val Gln Asn His Ala Gln Tyr
                245                 250                 255

Leu Leu Gly Arg Glu Leu Gln Leu Arg Thr Asp Leu Glu Ala His Ser
            260                 265                 270
```

Leu Pro Leu Trp Val Asn Asn
        275

<210> SEQ ID NO 177
<211> LENGTH: 67
<212> TYPE: PRT
<213> ORGANISM: Homo sapiens

<400> SEQUENCE: 177

Lys Pro Phe Ile Phe Phe Gln Gly His Ser His Trp Ser Phe Pro Pro
1               5                   10                  15

Arg Phe Leu Val Gln Tyr Asn Leu His Gly His Ser Arg Leu Asp Asn
            20                  25                  30

Gly His Leu His Gly Phe Thr Ala Gln Val Tyr Arg His His Ser Gln
        35                  40                  45

Cys Val Ala Gln Cys Gln Gln Val Cys Gln Glu Asp Ser His Gln Gly
    50                  55                  60

Pro Thr Glu
65

<210> SEQ ID NO 178
<211> LENGTH: 367
<212> TYPE: PRT
<213> ORGANISM: Homo sapiens

<400> SEQUENCE: 178

Tyr Thr Cys Ser Ser Ser Phe Phe Glu Gly Arg Phe Cys Pro Ala Asp
1               5                   10                  15

Cys Ser Ser Cys Ser Gly Pro Ala Pro Gly Pro Pro Asn Ser Arg Gly
            20                  25                  30

Ser Glu Ser Ala Gly Ser Val Pro Val Ser Ser Leu Ser Gly Ser Lys
        35                  40                  45

Met Gly Phe Ala Ser Ser Val Trp Pro Ala Gly Gly Met Thr Phe Ser
    50                  55                  60

Ser Trp Ser Pro Ala Leu Ala Leu Arg Gly Gly Ser Ala Arg Val Pro
65                  70                  75                  80

Phe Leu Ser Leu Gly Arg Gly Arg Gly Leu Val Asn Leu Ala Leu Leu
                85                  90                  95

Ser Arg Tyr Cys Thr Ser Arg Ser Arg Ala Ile Ile Leu Ala Ser Met
            100                 105                 110

Ser Phe Glu Ser Ser Thr Gly Phe Ser Val Ala Gly Ser Leu Ala Cys
        115                 120                 125

Ser Ala Arg Val Ala Phe Phe Gln Ala Gln Val Ser Leu Ile Thr Phe
    130                 135                 140

Ser Asn Val Val Ile Ser Thr Ser Val Lys Thr Trp Ser Ile Ser Gly
145                 150                 155                 160

Met Ser Arg Ala Pro Leu Arg Lys Met Leu Glu Trp Leu Arg Arg Leu
                165                 170                 175

Ser Arg Ala Glu Ser Arg Ser Gly His Phe Leu Arg Ser Ser Thr Arg
            180                 185                 190

Lys Asn Ser Pro Trp His Ser Phe Leu Ser Ser Ala Ser Leu Ser Phe
        195                 200                 205

Ser Ile Thr Val Val Ala Pro Asn Pro Ser Ser Ser Ser Gln Val Glu
    210                 215                 220

Val Ala Leu Ser Phe Pro Glu Ile Ser Ser Arg Cys Ser Ser Val Asp
225                 230                 235                 240

```
Thr Ser Trp Tyr Ser Gly Trp Tyr Ser Leu Ser Trp Val Ser Lys Met
                245                 250                 255

Lys Ala Ser Lys Leu Leu Ala Ala Phe Ser Leu Ser Cys Phe Ser Arg
            260                 265                 270

Ser Arg Arg Val Ser Ser Ser Ser Phe Cys Thr Glu Arg Ala Ser Ser
        275                 280                 285

Ser Ser Gly Lys Ser Gly Arg Ser Lys Thr Ala Ser Ser Thr Pro Ile
    290                 295                 300

Ser Ser Thr Ile Phe Cys Phe Arg Ala Gly Phe Gly Phe Leu Ser Ser
305                 310                 315                 320

Ser Gly Ala Gly Ala Ala Pro Ser Gly Pro Ala Cys Pro Phe Ser Leu
                325                 330                 335

Gly Phe Trp Ala Ser Gly Leu Ser Pro Leu Ser Phe Ser Ser Gly Phe
            340                 345                 350

Ser Pro Ser Arg Ala Ala Ser Pro Leu Gly Ser Glu Gly Gly Gly
        355                 360                 365
```

<210> SEQ ID NO 179
<211> LENGTH: 100
<212> TYPE: PRT
<213> ORGANISM: Homo sapiens

<400> SEQUENCE: 179

```
Glu Val Ser Ser Ala Gly Gly Ser Ala Ser Ser Leu Ser Ser Pro Cys
 1               5                  10                  15

Ser Ala Gly Ser Ser Leu Leu Pro Ser Ala Gly Leu Ser Ser Ser Ser
            20                  25                  30

Cys Thr Ala Ser Val Pro Phe Ser Leu Ala Ser Asp Glu Val Pro Pro
        35                  40                  45

Pro Asn Arg Leu Asp Met Val Leu Pro Ser Leu Val Arg Val Asp Ser
    50                  55                  60

Ser Ser Gly Leu Ser Ser Thr Arg Val Ser Asn Thr Asp Ser Thr Leu
65                  70                  75                  80

Ser Lys Leu Ser Thr Pro Leu Ser Ser Arg Leu Lys Trp Ala Leu Met
                85                  90                  95

Pro Leu Asp Ser
            100
```

<210> SEQ ID NO 180
<211> LENGTH: 80
<212> TYPE: PRT
<213> ORGANISM: Homo sapiens

<400> SEQUENCE: 180

```
Ser Ala Leu Ala Leu Arg Thr Val Leu Ser Arg Leu Ala Ser Arg Ser
 1               5                  10                  15

Ser Leu Ala Met Ala Arg Gly Phe Ser Arg Thr Ser Leu Ala Phe Trp
            20                  25                  30

Pro Leu Arg Cys Ser Leu Lys Ser Leu Ala Arg Cys Ser Arg Ser Arg
        35                  40                  45

Ser Ser Ile Ser Arg Pro Pro Arg Val Arg Ser Asn Pro Thr Pro Arg
    50                  55                  60

Ile Cys Ser Cys Gly Cys Ile Pro Ala Ser Leu Val Phe Thr Val Trp
65                  70                  75                  80
```

<210> SEQ ID NO 181
<211> LENGTH: 56
<212> TYPE: PRT

<213> ORGANISM: Homo sapiens

<400> SEQUENCE: 181

```
Leu Arg Ala Val Ala Val Leu Ser Leu Met Ser Cys Ser Thr Leu Arg
 1               5                  10                  15

Pro Ala Ile Arg Ala Ala Cys Ser Thr Ala Arg Arg Ser Ala Trp Leu
            20                  25                  30

Lys Lys Ala Gly Thr Val Ile Thr Ala Ser Leu Met Gly Cys Ser Ala
        35                  40                  45

Lys Ser Ser Ala Lys Glu Arg Glu
    50                  55
```

<210> SEQ ID NO 182
<211> LENGTH: 98
<212> TYPE: PRT
<213> ORGANISM: Homo sapiens

<400> SEQUENCE: 182

```
Arg Ser Val Ala Phe Gly Phe Leu Met Ala Met Pro Ala Ala Leu Ser
 1               5                  10                  15

Pro Lys Asn Leu Ser Phe Ser Phe Lys Val Thr Val Thr Gly Val Phe
            20                  25                  30

Leu Arg Asp Ser Leu Phe Asn Thr Ile Ser Met Gly Thr Pro Gly Leu
        35                  40                  45

Thr Met Ala Thr Phe Met Asp Ser Leu Pro Arg Ser Thr Asp Ile Thr
    50                  55                  60

Ala Asn Val Ser Leu Ser Ala Asn Arg Ser Ala Lys Arg Thr Ala Thr
65                  70                  75                  80

Lys Ala Gln Gln Ser Ser Leu Leu Gly Leu Cys Leu Leu Thr Val Ala
                85                  90                  95

Ala Trp
```

<210> SEQ ID NO 183
<211> LENGTH: 60
<212> TYPE: PRT
<213> ORGANISM: Homo sapiens

<400> SEQUENCE: 183

```
Thr Arg Val Val His Arg Ser Leu Lys Ala Ala Ser Val Leu Leu Thr
 1               5                  10                  15

Ala Leu Pro Val Gln Val Gln Leu Gln Asp Leu Leu Ile Pro Glu Ala
            20                  25                  30

Pro Ser Leu Leu Val Pro Tyr Gln Ser Leu Leu Cys Gln Val Leu Lys
        35                  40                  45

Trp Val Ser Pro Leu Gln Ser Gly Leu Gln Val Glu
    50                  55                  60
```

<210> SEQ ID NO 184
<211> LENGTH: 104
<212> TYPE: PRT
<213> ORGANISM: Homo sapiens

<400> SEQUENCE: 184

```
Lys Pro Pro Ser Cys Trp Gln Leu Ser Pro Ser Pro Ala Ser Leu Gly
 1               5                  10                  15

Arg Ala Gly Ser Val Leu Gln Val Ser Ala Gln Asn Gly Pro Ala His
            20                  25                  30

Pro Leu Ala Ser Gln Ala Gly Pro Arg Gln Pro Ala Pro His Leu Ser
        35                  40                  45
```

-continued

```
Pro Pro Pro Phe Ser Ala Ser Gly Gln Val Ser Ala Phe Cys Pro Pro
    50                  55                  60

Gln Glu Leu Glu Gln His Pro Gln Ala Leu Leu Ala Pro Ser His Trp
65                  70                  75                  80

Ala Ser Gly Pro Gln Ala Cys Pro His Ser Leu Phe His Gln Val Ser
                85                  90                  95

Leu Pro His Gly Leu His Pro Pro
            100


<210> SEQ ID NO 185
<211> LENGTH: 57
<212> TYPE: PRT
<213> ORGANISM: Homo sapiens

<400> SEQUENCE: 185

Ala Ala Leu Leu Glu Leu Trp Glu His Glu Trp Pro Arg Pro Pro Gly
 1               5                  10                  15

Ser Pro Ala Gln Phe Asp Pro Ser Ser Ser Leu His Ser Ala Arg Pro
            20                  25                  30

Ala Ala Gln Val Gln Ala His Gly Gln Thr Asn Leu His Thr Ala Pro
        35                  40                  45

Arg Ile Pro Leu Glu Leu Leu Trp Pro
    50                  55
```

STRESS PROTEIN COMPOSITIONS AND METHODS FOR PREVENTION AND TREATMENT OF CANCER AND INFECTIOUS DISEASE

This application is a continuation of U.S. patent application Ser. No. 10/161,028, filed Jun. 3, 2002, now U.S. Pat. No. 7,378,096, issued May 27, 2008, which is a continuation-in-part of U.S. patent application Ser. No. 09/872,186, filed Jun. 1, 2001, now abandoned, which application is a continuation-in-part of U.S. patent application Ser. No. 09/676,340, filed Sep. 29, 2000, now U.S. Pat. No. 6,984,384, issued Jan. 10, 2006, which application claims benefit of U.S. provisional patent application Ser. Nos. 60/156,821, filed Sep. 30, 1999, 60/163,138, filed Nov. 2, 1999, and 60/215,497, filed Jun. 30, 2000, the entire contents of each of which are hereby incorporated herein by reference. Throughout this application various publications are referenced. The disclosures of these publications in their entireties are hereby incorporated by reference into this application in order to describe more fully the state of the art to which this invention pertains.

The invention disclosed herein was made in the course of work done under the support of Grant No. GM 45994, awarded by the National Institutes of Health, and by National Cancer Institute Grant No. CA71599. The government may have certain rights in this invention.

TECHNICAL FIELD

The present invention relates generally to prevention and therapy of cancer and infectious disease. The invention is more specifically related to polypeptides comprising at least a portion of a stress protein, such as heat shock protein 110 (hsp110) or glucose-regulated protein 170 (grp170), complexed with an immunogenic polypeptide, and to polynucleotides encoding such stress proteins and immunogenic polypeptides, as well as antigen presenting cells that present the stress proteins and the immunogenic polypeptides. Such polypeptides, polynucleotides and antigen presenting cells may be used in vaccines and pharmaceutical compositions for the prevention and treatment of cancers and infectious diseases. The invention further relates to increasing the efficacy of stress protein complexes, such as by heating.

BACKGROUND OF THE INVENTION

Cancer and infectious disease are significant health problems throughout the world. Although advances have been made in detection and therapy of these diseases, no vaccine or other universally successful method for prevention or treatment is currently available. Current therapies, which are generally based on a combination of chemotherapy or surgery and radiation, continue to prove inadequate in many patients.

For example, primary breast carcinomas can often be treated effectively by surgical excision. If further disease recurs, however, additional treatment options are limited, and there are no effective means of treating systemic disease. While immune responses to autologous tumors have been observed, they have been ineffective in controlling the disease. One effort to stimulate a further anti-tumor response is directed at the identification of tumor antigens useful for vaccines. A related approach takes advantage of the promiscuous peptide binding properties of heat shock proteins, such as hsp70. These molecular chaperones bind peptides and are involved in numerous protein folding, transport and assembly processes, and could be involved in the antigen presentation pathway of MHC complexes.

The heat shock proteins of mammalian cells can be classified into several families of sequence related proteins. The principal mammalian hsps, based on protein expression levels, are cytoplasmic/nuclear proteins with masses of (approximately) 25 kDa (hsp25), 70 kDa (hsp70), 90 kDa (hsp90), and 110 kDa (hsp110). However, in addition to hsps, a second set of stress proteins is localized in the endoplasmic reticulum (ER). The induction of these stress proteins is not readily responsive to hyperthermic stress, as are the hsps, but are regulated by stresses that disrupt the function of the ER (e.g. glucose starvation and inhibitors of glycosylation, anoxia and reducing conditions, or certain agents that disrupt calcium homeostasis). These stress proteins are referred to as glucose regulated proteins (grps). The principal grps, on the basis of expression, have approximate sizes of 78 kDa (grp78), 94 kDa (grp94), and 170 kDa (grp170). Grp78 is homologous to cytoplasmic hsp70, while grp94 is homologous to hsp90.

While individual stress proteins have been studied for several years (in some cases intensively studied, e.g. hsp70), the largest of the above hsp and grp groups, hsp110 and grp170, have received little attention. Both have been found by sequence analysis to represent large and highly diverged relatives of the hsp70 family. It is recognized that the hsp70 family, the hsp110 family, and the grp170 family comprise three distinguishable stress protein groups of eukaryotic cells that share a common evolutionary ancestor. The existence of hsp110 in parallel with hsp70 in the cytoplasm and of grp170 in parallel with grp78 in the ER of (apparently) all eukaryotic cells argues for important differential functions for these distantly related protein families. Not all stress proteins function as vaccines, however, and it can be expected that different ones may exhibit different activities.

In spite of considerable research into therapies for infectious disease and cancer, these diseases remain difficult to diagnose and treat effectively. Accordingly, there is a need in the art for improved methods for treating cancer and infectious disease. The present invention fulfills these needs and further provides other related advantages.

SUMMARY OF THE INVENTION

The invention provides a pharmaceutical composition comprising a stress protein complex. The stress protein complex comprises an hsp110 or grp170 polypeptide and an immunogenic polypeptide. In some embodiments, the hsp110 or grp170 polypeptide is complexed with the immunogenic polypeptide, for example, by non-covalent interaction or by covalent interaction, including a fusion protein. In some embodiments, the complex is derived from a tumor. In other embodiments, the complex is derived from cells infected with an infectious agent. The immunogenic polypeptide of the stress protein complex can be associated with a cancer or an infectious disease. The stress protein complex of the invention can further include additional stress polypeptides, including members of the hsp70, hsp90, grp78 and grp94 stress protein families. In one embodiment, the stress protein complex comprises hsp110 complexed with hsp70 and/or hsp25.

The invention additionally provides a pharmaceutical composition comprising a first polynucleotide encoding an hsp110 or a grp170 polypeptide and a second polynucleotide encoding an immunogenic polypeptide. In some embodiments involving first and second polynucleotides, the first polynucleotide is linked to the second polynucleotide. The pharmaceutical compositions of the invention can further comprise a physiologically acceptable carrier and/or an adjuvant. The efficacy of a pharmaceutical composition can further comprise GM-CSF-secreting cells. Alternatively, GM-CSF-secreting cells can be co-administered with a pharmaceutical composition of the invention, by administration before, during or after administration of the pharmaceutical composition. The use of GM-CSF-secreting cells enhances the efficacy of the pharmaceutical composition.

In some embodiments, the complex is purified from a tumor or from cells infected with an infectious agent. In such embodiments, the stress polypeptide, as purified, is complexed with one or more immunogenic polypeptides. The binding of the stress polypeptide to the immunogenic polypeptide can be altered and/or enhanced by stress, such as by exposure to heat, anoxic and/or ischemic conditions, or proteotoxic stress. In particular, a stress protein complex of the invention can comprise a stress polypeptide complexed with an immunogenic polypeptide, wherein the complex has been heated. Such heating, particularly wherein the stress polypeptide comprises a heat-inducible stress protein, can increase the efficacy of the stress protein complex as a vaccine. Examples of heat-inducible stress proteins include, but are not limited to, hsp70 and hsp110.

In some embodiments, the immunogenic polypeptide is known. Where the immunogenic polypeptide is a known molecule, the immunogenic polypeptide can be provided in admixture with the stress polypeptide, or as a complex with the stress polypeptide. The hsp110 or grp170 polypeptide can be complexed with the immunogenic polypeptide by non-covalent binding. Alternatively, the complex can comprise a fusion protein, wherein the stress polypeptide is linked to the immunogenic polypeptide. Examples of immunogenic polypeptides include, but are not limited to, antigens associated with cancer or infectious disease, such as the melanoma-associated antigen gp100, the breast cancer antigen her2/neu or the *Mycobacterium tuberculosis* antigens Mtb8.4, TbH9 and Mtb39. Where the immunogenic polypeptide is unknown, it can be obtained incidentally to the purification of the stress polypeptide from tissue of a subject having cancer or an infectious disease.

Also provided is a pharmaceutical composition comprising an antigen-presenting cell (APC) modified to present an hsp110 or grp170 polypeptide and an immunogenic polypeptide. Alternatively, the APC can be modified to present an immunogenic polypeptide obtained by purification of hsp110 or grp170 from disease cells, including cancer cells and cells infected with an infectious agent. Preferably, the APC is a dendritic cell or a macrophage. The APC can be modified by various means including, but not limited to, peptide loading and transfection with a polynucleotide encoding an immunogenic polypeptide.

The pharmaceutical compositions of the invention can be administered to a subject, thereby providing methods for inhibiting *M. tuberculosis*-infection, for inhibiting tumor growth, for inhibiting the development of a cancer, and for the treatment or prevention of cancer or infectious disease.

The invention further provides a method for producing T cells directed against a tumor cell. The method comprises contacting a T cell with an antigen presenting cell (APC), wherein the APC is modified to present an hsp110 or grp170 polypeptide and an immunogenic polypeptide associated with the tumor cell. Such T cells can be used in a method for killing a tumor cell, wherein the tumor cell is contacted with the T cell. Likewise, the invention provides a method for producing T cells directed against a *M. tuberculosis*-infected cell, wherein a T cell is contacted with an APC that is modified to present an hsp110 or grp170 polypeptide and an immunogenic polypeptide associated with the *M. tuberculosis*-infected cell. Included in the invention are T cells produced by this method and a pharmaceutical composition comprising such T cells. The T cells can be contacted with a *M. tuberculosis*-infected cell in a method for killing a *M. tuberculosis*-infected cell. The T cells can be CD4+ or CD8+.

The invention also provides a method for removing tumor cells from a biological sample. The method comprises contacting a biological sample with a T cell of the invention. In a preferred embodiment, the biological sample is blood or a fraction thereof. Also provided is a method for inhibiting tumor growth in a subject. The method comprises incubating CD4+ and/or CD8+ T cells isolated from the subject with an antigen presenting cell (APC), wherein the APC is modified to present an hsp110 or grp170 polypeptide and an immunogenic polypeptide associated with the tumor cell such that T cells proliferate. The method further comprises administering to the subject an effective amount of the proliferated T cells, and thereby inhibiting tumor growth in the subject. In an alternative embodiment, the method for inhibiting tumor growth in a subject comprises incubating CD4+ and/or CD8+ T cells isolated from the subject with an antigen presenting cell (APC), wherein the APC is modified to present an hsp110 or grp170 polypeptide and an immunogenic polypeptide associated with the tumor cell such that T cells proliferate, cloning at least one proliferated cell, and administering to the patient an effective amount of the cloned T cells, thereby inhibiting tumor growth in the subject.

In a preferred embodiment, the immunogenic polypeptide comprises the extracellular domain (ECD; ECD-PD) or the intracellular domain (ICD) of the breast cancer antigen, her2/neu. In another preferred embodiment, the immunogenic polypeptide comprises gp100, a melanoma-associated antigen. Preferably, the ECD, ICD or gp100 is non-covalently complexed with HSP110.

BRIEF DESCRIPTION OF THE FIGURES

FIG. 10A shows results observed when cell lysates (lane 2) were incubated with antibodies for hsp110 (1:100).

FIG. 10B shows results observed when cell lysates (lane 2) were incubated with antibodies for hsp70 (1:200).

FIG. 10C shows results observed when cell lysates (lane 2) were incubated with antibodies for hsp25 (1:100).

Figure 17:
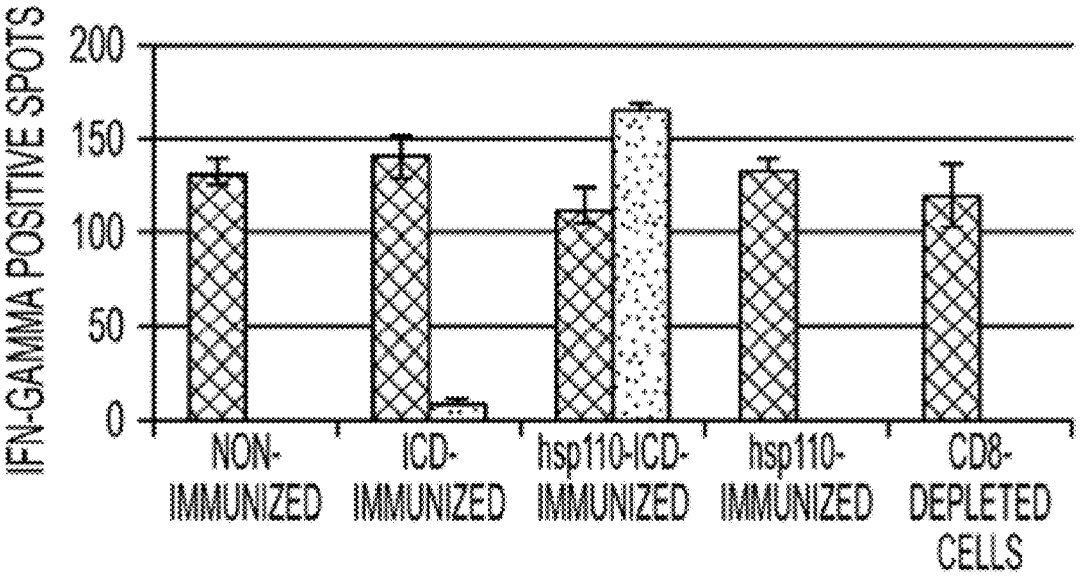

FIG. 17 is a bar graph showing gamma interferon (IFN-gamma) production (determined by number of spots in an ELISPOT assay) by T cells of A2/Kb transgenic mice (5 animals per group) after i.p. immunization with 25 μg of recombinant mouse hsp110-ICD complex. Total splenocytes or depleted cells ($5\times10^6$ cells/ml) were cultured in vitro with 25 μg/ml PHA (checkered bars) or 20 μg/ml ICD (dark stippled bars) overnight and IFN-gamma secretion was detected using the ELISPOT assay.

Figure 18:
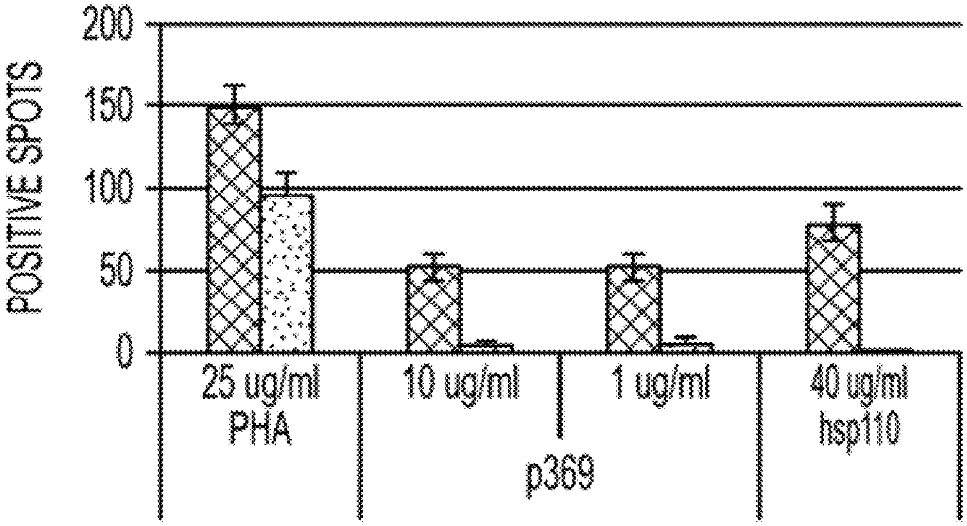

FIG. 18 is a bar graph showing immunogenicity of hsp110-peptide complexes reconstituted in vitro, as determined by number of positive spots in an ELISPOT assay for IFN-gamma secretion. Recombinant hamster hsp110 (100 μg) was incubated with 100 μg of the 9-mer her-2/neu peptide p369, an HLA-A2 binder. Eight-week old HLA-A2 transgenic mice (n=4) were immunized i.p. with either hsp110+peptide complex (group A, cross-hatched bars) or peptide alone (group B, dark stippled bars). Counts for the non-stimulated cells (negative controls) were <40 and were subtracted from the counts for stimulated cells.

Figure 19:
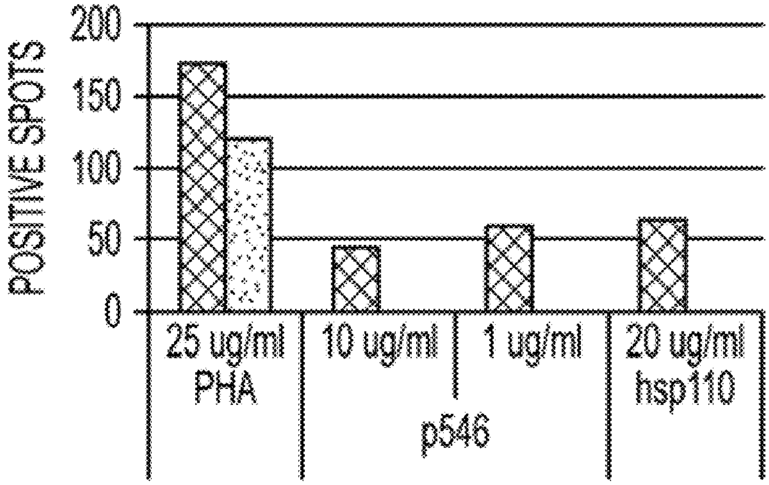

FIG. 19 is a bar graph showing immunogenicity of hsp110-peptide complexes reconstituted in vitro, as determined by number of positive spots in an ELISPOT assay for IFN-gamma secretion. Recombinant hamster hsp110 (100 μg) was incubated with 100 μg of the 10-mer her-2/neu peptide p546, an HLA-A2 binder. Eight-week old HLA-A2 transgenic mice (n=2) were immunized i.p. with either hsp110+peptide complex (group A, cross-hatched bars) or peptide alone (group B, dark stippled bars). Counts for the non-stimulated cells (negative controls) were <40 and were subtracted from the counts for stimulated cells.

Figure 20:
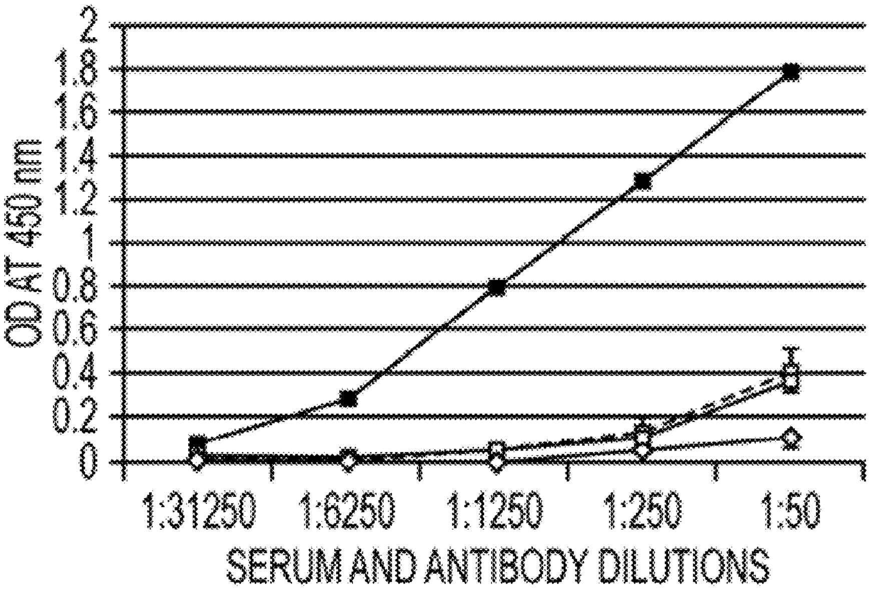

FIG. 20 is a graph showing specific anti-hsp110 antibody response in A2/Kb transgenic mice following i.p. immunization with the hsp110-ICD (her2/neu) complex. ELISA results are plotted as optical density (OD) at 450 nm as a function of serum and antibody dilutions. Results are shown for the positive control of anti-hsp110 (solid squares), the negative control of unrelated antibody (open circles), and serum at day 0 (closed circles), day 14 (open squares, dashed line), and day 28 (open squares, solid line). These results confirm that the mice did not develop an autoimmune response to hsp110.

Figure 21:
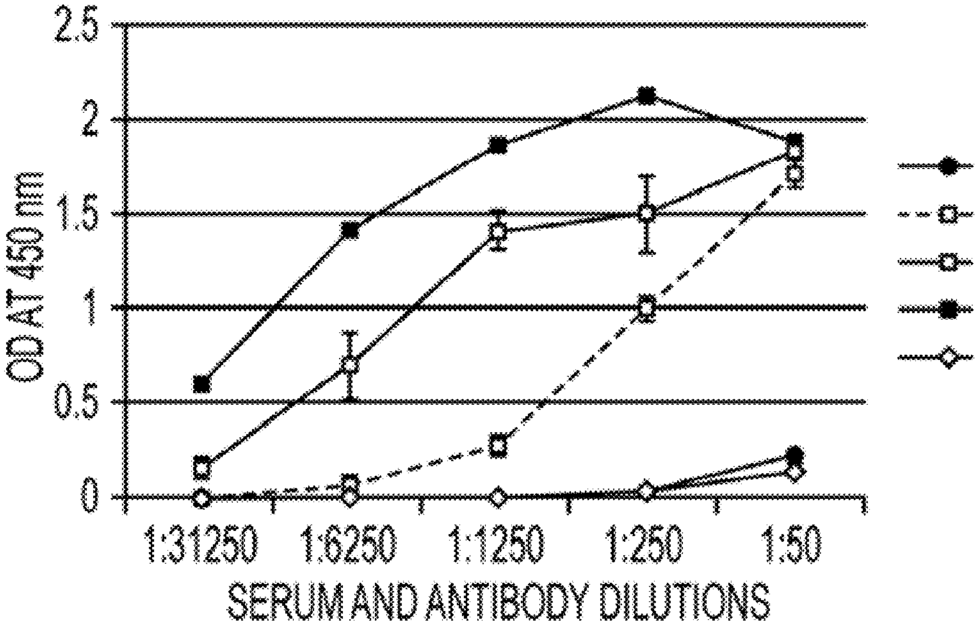

FIG. 21 is a graph showing specific anti-ICD antibody response in A2/Kb transgenic mice following i.p. immunization with the hsp110-ICD complex. ELISA results are plotted as optical density (OD) at 450 nm as a function of serum and antibody dilutions. Results are shown for the positive control of anti-ICD (solid squares), the negative control of unrelated antibody (open diamonds), and serum at day 0 (closed circles), day 14 (open squares, dashed line), and day 28 (open squares, solid line). These results confirm that the mice developed a specific antibody response to ICD of her2/neu after immunization with the stress protein complex.

Figure 22:
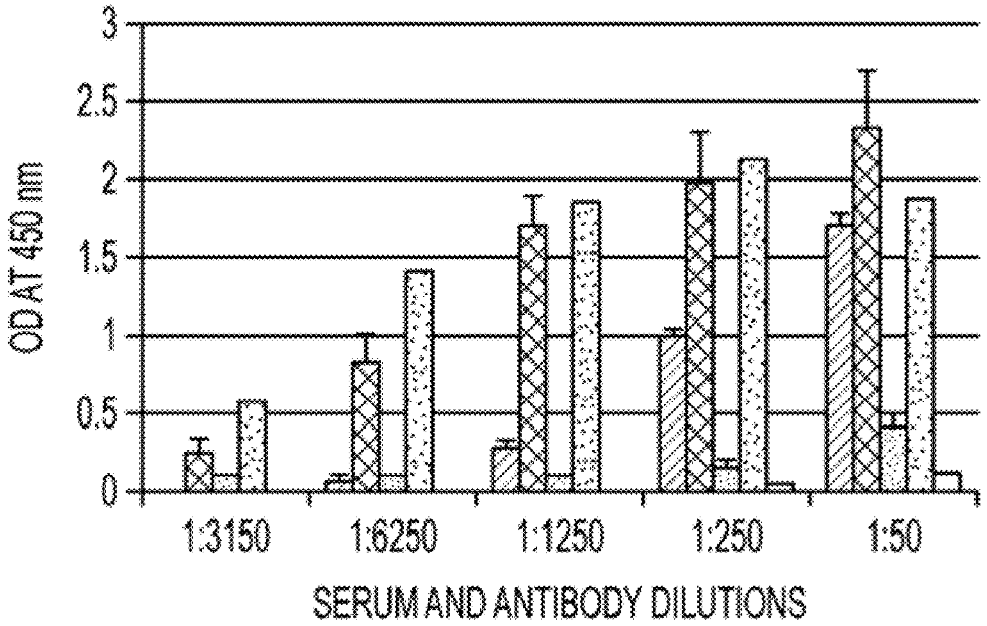

FIG. 22 is a bar graph comparing specific anti-ICD antibody responses in A2/Kb transgenic animals 2 weeks after priming with different vaccine formulas. Results are plotted as OD at 450 nm for the various serum and antibody dilutions and bars represent data for animals primed with hsp110-ICD (stippled bars), the positive control of ICD in complete Freund's adjuvant (checkered bars), ICD alone (cross-hatched bars), anti-ICD antibody (dark stippled bars), and the negative control of unrelated antibody (open bars).

Figure 23:
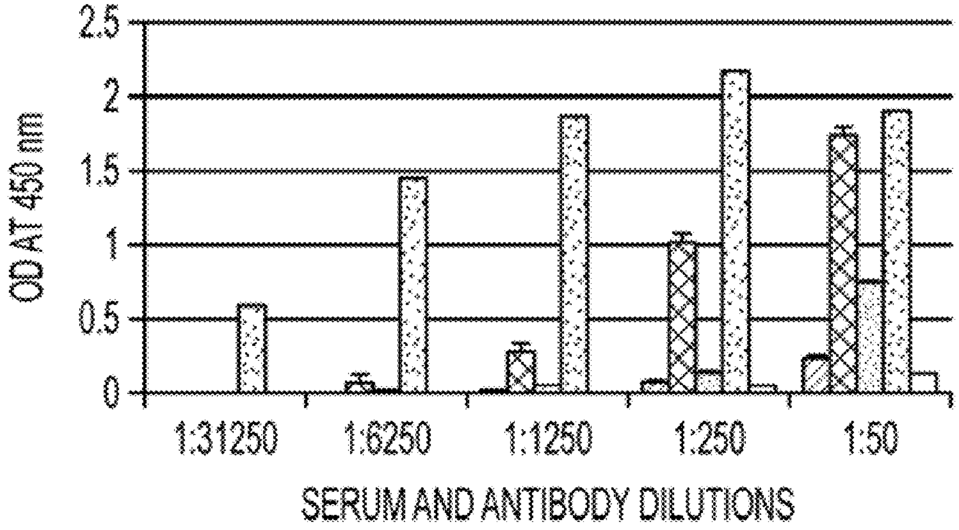

FIG. 23 is a bar graph comparing specific anti-ICD antibody generation 2 weeks after s.c. or i.p. priming of A2/Kb transgenic with hsp110-ICD complex. Results are plotted as OD at 450 nm for the various serum and antibody dilutions and bars represent serum at day 0 (stippled bars), serum i.p. at day 14 (checkered bars), serum s.c. at day 14 (cross-hatched bars), anti-ICD antibody (dark stippled bars), and the negative control of unrelated antibody (open bars).

Figure 24A:
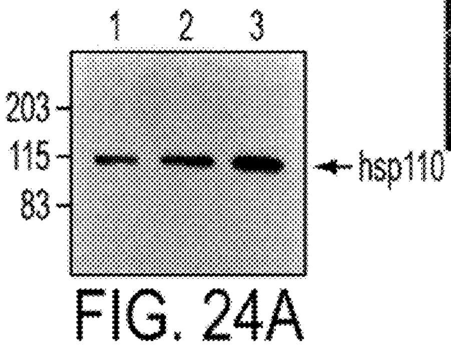

FIG. 24A is an immunoblot showing that colon 26 cells (CT26) transfected with a vector encoding hsp110 exhibit increased hsp110 expression relative to untransfected CT26 cells and CT26 cells transfected with an empty vector. Equivalent protein samples from CT26 (lane 1), CT26-vector (lane 2), and CT26-hsp110 (lane 3) were subjected to 10% SDS PAGE and transferred onto immobilon-P membrane. Membranes were probed with antibodies for hsp110. After washing, membranes were incubated with horseradish peroxidase-conjugated goat anti-rabbit IgG or goat anti-mouse IgG diluted 1:2,000 in TBST. Immunoreactivity was detected using the Enhanced Chemiluminescence detection system.

Figure 24B:
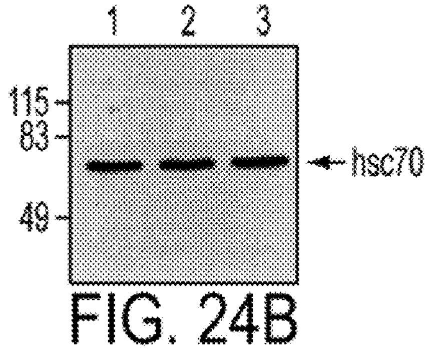

FIG. 24B shows that CT26-hsp110 cells do not exhibit enhanced hsc70 expression relative to untransfected CT26 cells or CT26 cells transfected with an empty vector. Equivalent protein samples from CT26 (lane 1), CT26-vector (lane 2), and CT26-hsp110 (lane 3) were prepared as for FIG. 24A, except that membranes were probed with antibodies for hsc/hsp70.

Figure 25A:
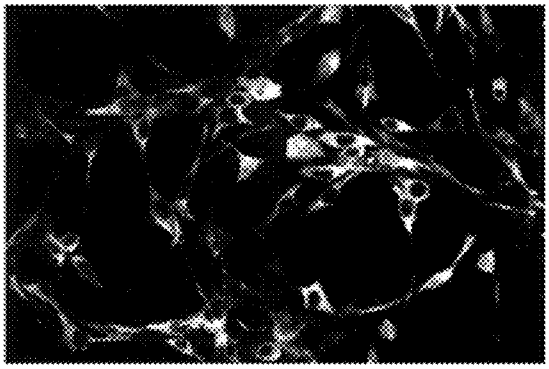

FIG. 25A is a photomicrograph showing immunofluorescence staining of hsp110 in CT26 cells. Cells were seeded on the cover slips one day before the staining. Cover slips were then incubated with rabbit anti-hsp110 antibody (1:500 dilution) followed by FITC-labeled dog anti-rabbit IgG staining. Normal rabbit IgG was used as negative control.

Figure 25B:
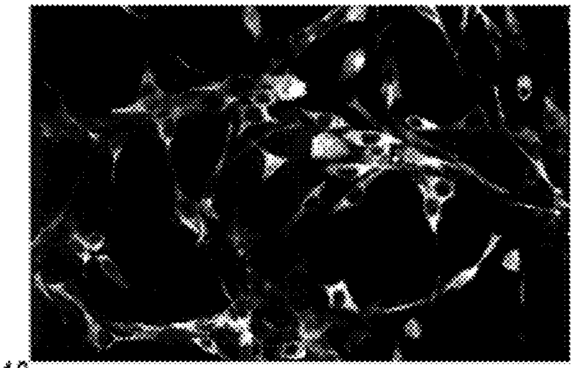

FIG. 25B is a photomicrograph showing immunofluorescence staining of hsp 110 in empty vector transfected CT26 cells. Cells were prepared and immunostained as in FIG. 25A.

Figure 25C:
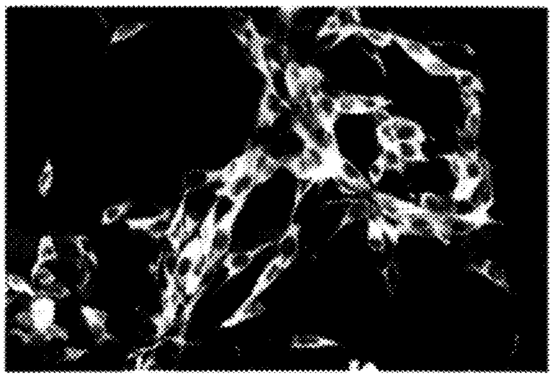

FIG. 25C is a photomicrograph showing immunofluorescence staining of hsp110 in hsp110 over-expressing cells. Cells were prepared and immunostained as in FIG. 25A.

Figure 26:
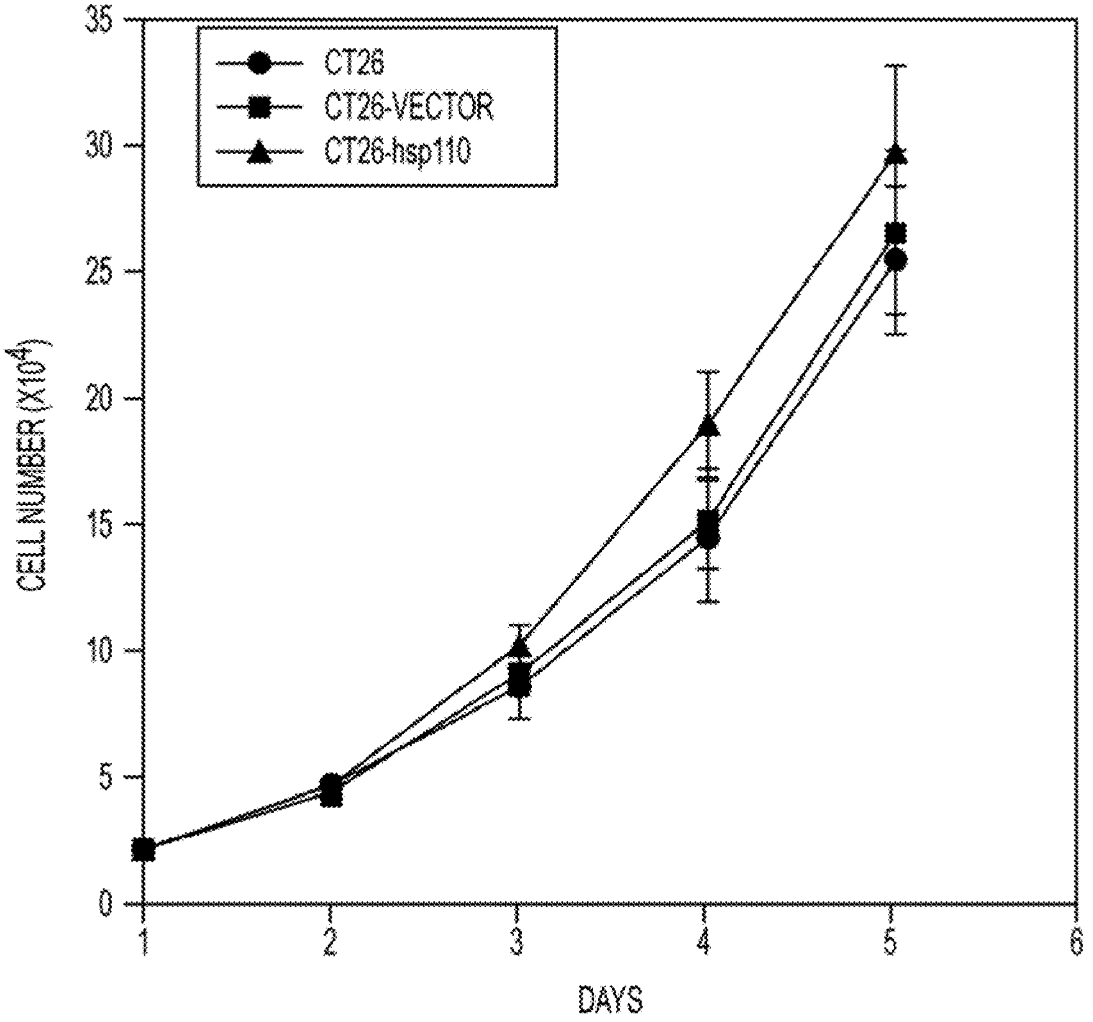

FIG. 26 is a graph demonstrating in vitro growth properties of wild type and hsp110-transfected cell lines, plotted as cell number at 1-5 days after seeding. Cells were seeded at a density of $2\times10^4$ cells per well. 24 hours later cells were counted (assigned as day 0). Cells from triplicate wells were counted on the indicated days. The results are means±SD of three independent experiments using wild type CT26 cells (circles), CT26 cells transfected with empty vector (squares), and hsp110-transfected CT26 cells (triangles).

Figure 27:
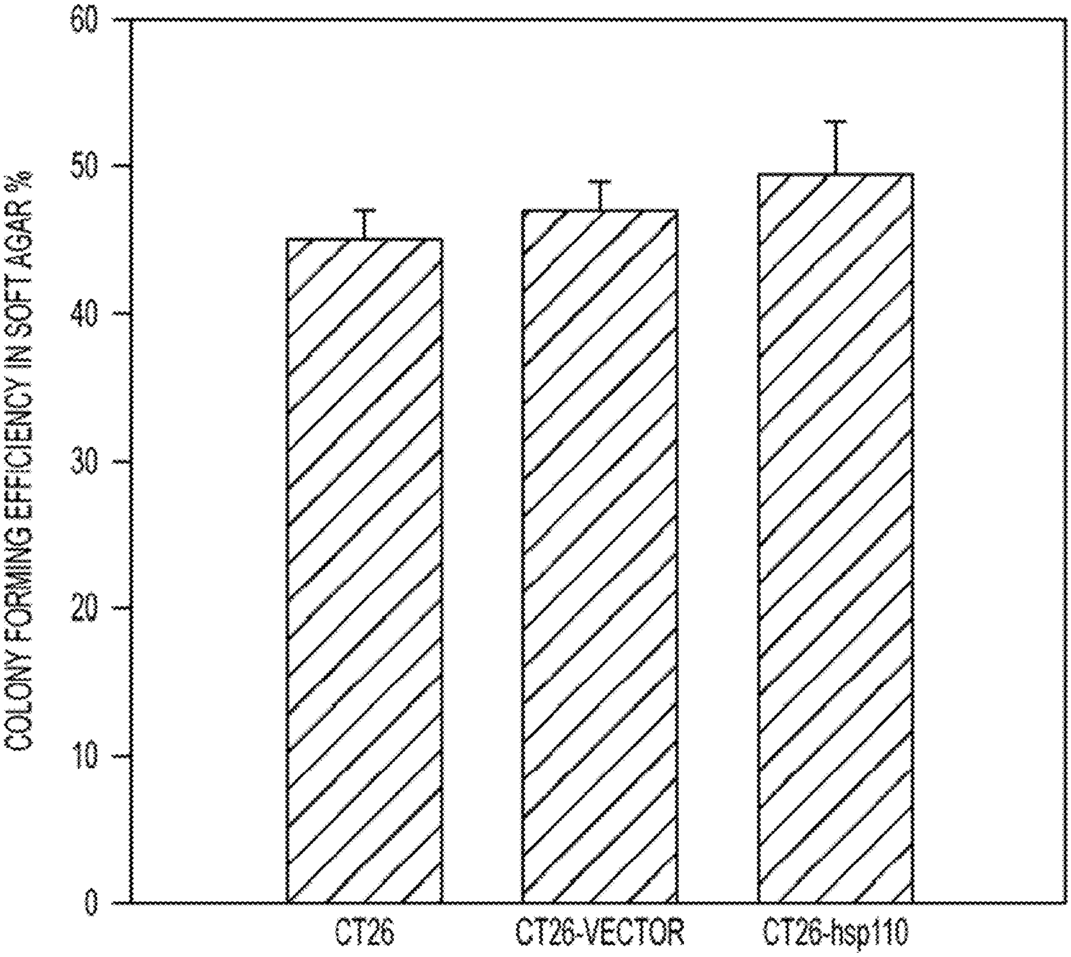

FIG. 27 is a bar graph showing the effect of hsp110 over-expression on colony forming ability in soft agar. Wild-type CT26 cells, empty vector transfected CT26-vector cells and hsp110 over-expressing CT26-hsp110 cells were plated in 0.3% agar and analyzed for their ability to form colonies (≧0.2) in soft agar. $P<0.05$, compared with CT26-vector, as assessed by student's t test.

Figure 28:
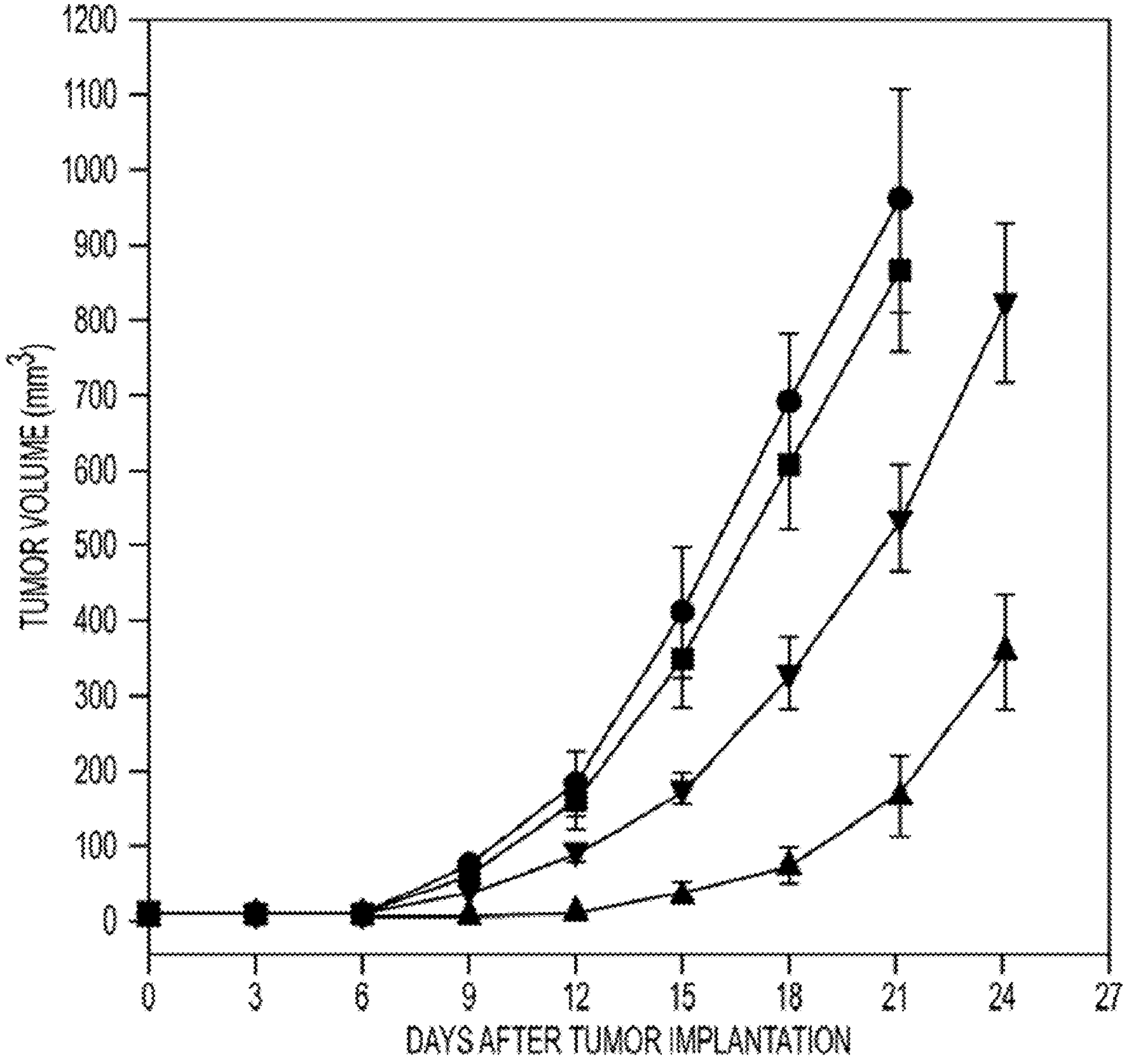

FIG. 28 is a graph showing in vivo growth properties of wild-type and hsp110 transfected CT26 cell line. $5\times10^4$ cells were inoculated s.c. into flank area of balb/c mice. Tumor growth was recorded twice a week measuring both the longitudinal and transverse diameter with a caliper. Tumor volume, in cubic mm, is plotted as a function of days after tumor implantation for CT26 wild type cells (circles), CT26 cells transfected with empty vector (squares), CT26 cells transfected with hsp110, $5\times10^4$ (upward triangles), and CT26 cells transfected with hsp110, $5\times10^5$ (downward triangles).

Figure 29:
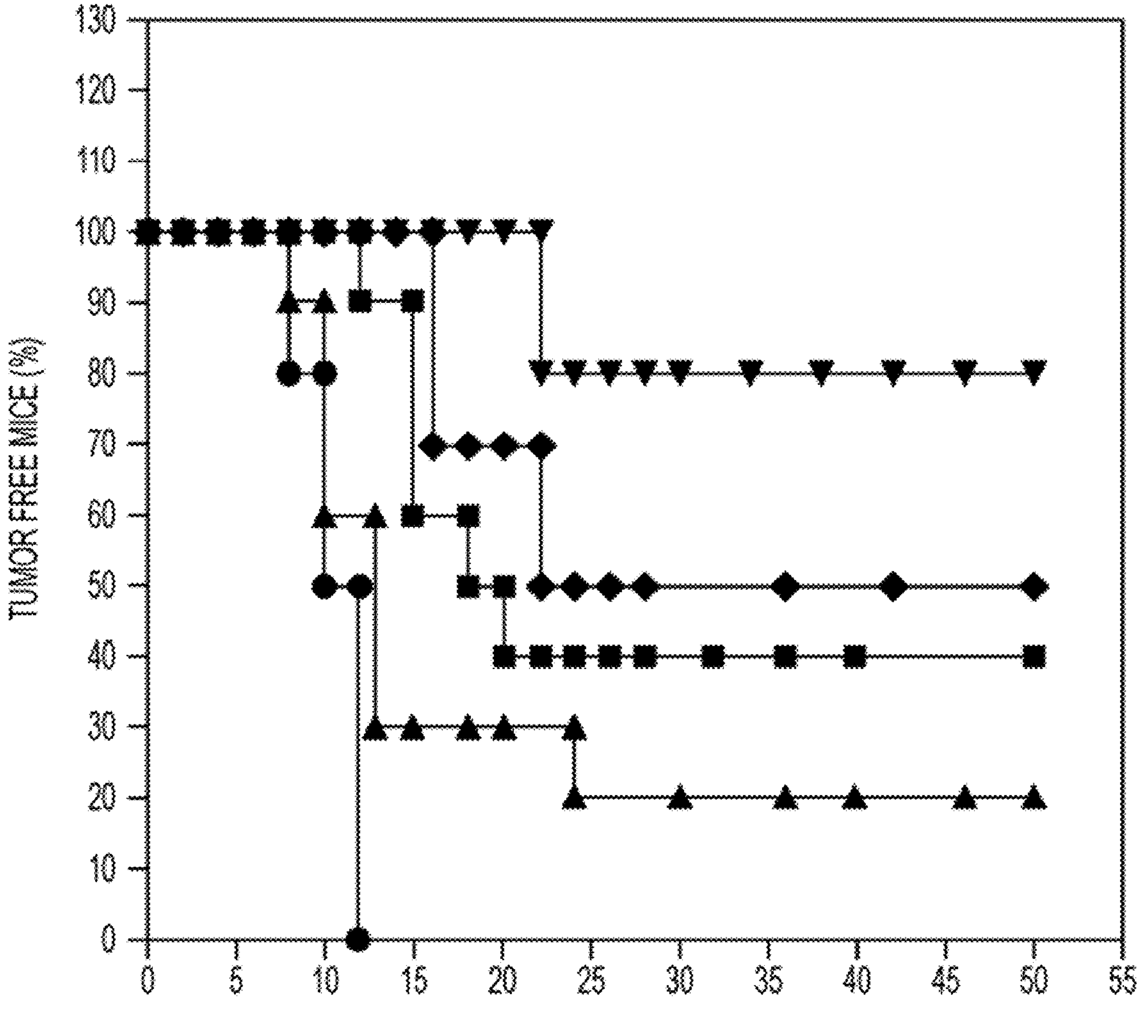

FIG. 29 is a plot showing the effect of injection with irradiated hsp110-overexpressing cells on the response to challenge with live CT26 cells. Mice were injected with $5\times10^5$ irradiated (9,000 rad) CT26-hsp110 cells subcutaneously in the left flank. Two weeks later, mice were challenged on the right flank with live CT26 cells. Growth of tumor in mice without preimmunization was also shown. Results are plotted as percent tumor free mice as a function of days after tumor challenge for mice immunized with PBS and challenged with $5\times10^4$ CT26 cells (circles); irradiated CT26 cells with empty vector/$5\times10^5$ CT26 cells (squares); irradiated CT26 cells with empty vector/$5\times10^6$ CT26 cells (upward triangles); irradiated CT26-hsp110 cells/$5\times10^5$CT26 cells (downward triangles); and irradiated CT26-hsp110 cells/$5\times10^6$ CT26 cells (diamonds).

Figure 30:
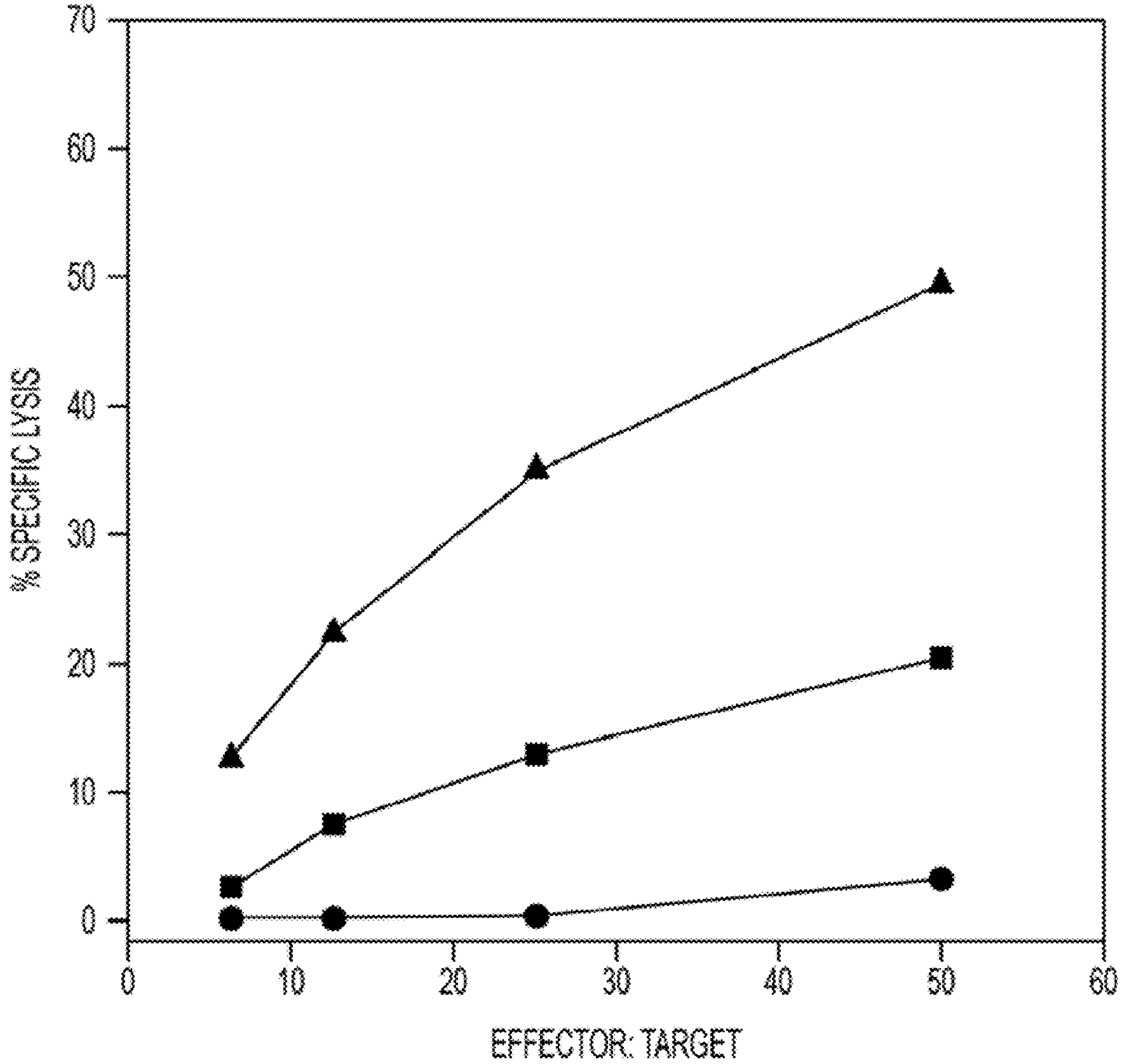

FIG. 30 is a graph showing tumor specific CTL response elicited by immunization with tumor derived hsp110. Mice were injected with $5\times10^5$ irradiated (9,000 rad) CT26-empty vector and CT26-hsp 110 cells subcutaneously. Two weeks later, splenocytes were isolated as effector cells and re-stimulated with irradiated Colon 26 in vitro for 5 days. The lymphocytes were analyzed for cytotoxic activity using $^{51}$Cr-labeled Colon 26 as target cells. Meth A tumor cells were also used as target in the experiment, and no cell lysis was observed. Results are plotted as percent specific lysis as a function of effector:target ratio for control (circles), irradiated CT26 cells (squares), and irradiated CT26-hsp110 cells (triangles).

Figure 31:
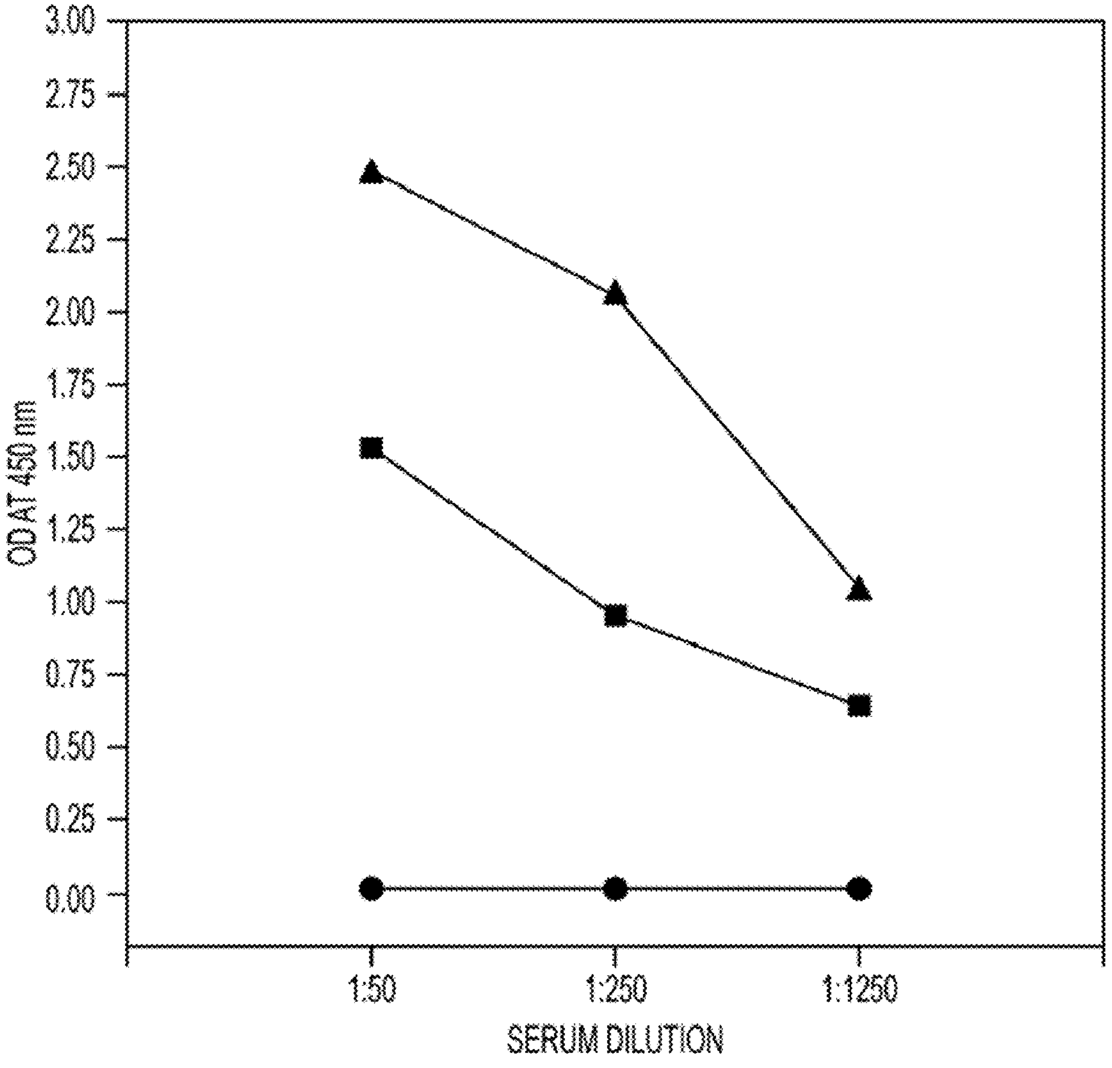

FIG. 31 is a graph showing antibody response against CT26 cells following immunization with irradiated hsp110-overexpressing cells. Mice were injected with $5\times10^5$ irradiated (9,000 rad) CT26 empty vector and CT26-hsp110 cells subcutaneously. Two weeks later, serum was collected and assayed for antibody response using ELISA. Results are plotted as OD at 450 nm as a function of serum dilution for control (circles), CT26-empty vector (squares), and CT26-hsp110 (triangles).

Figure 32:
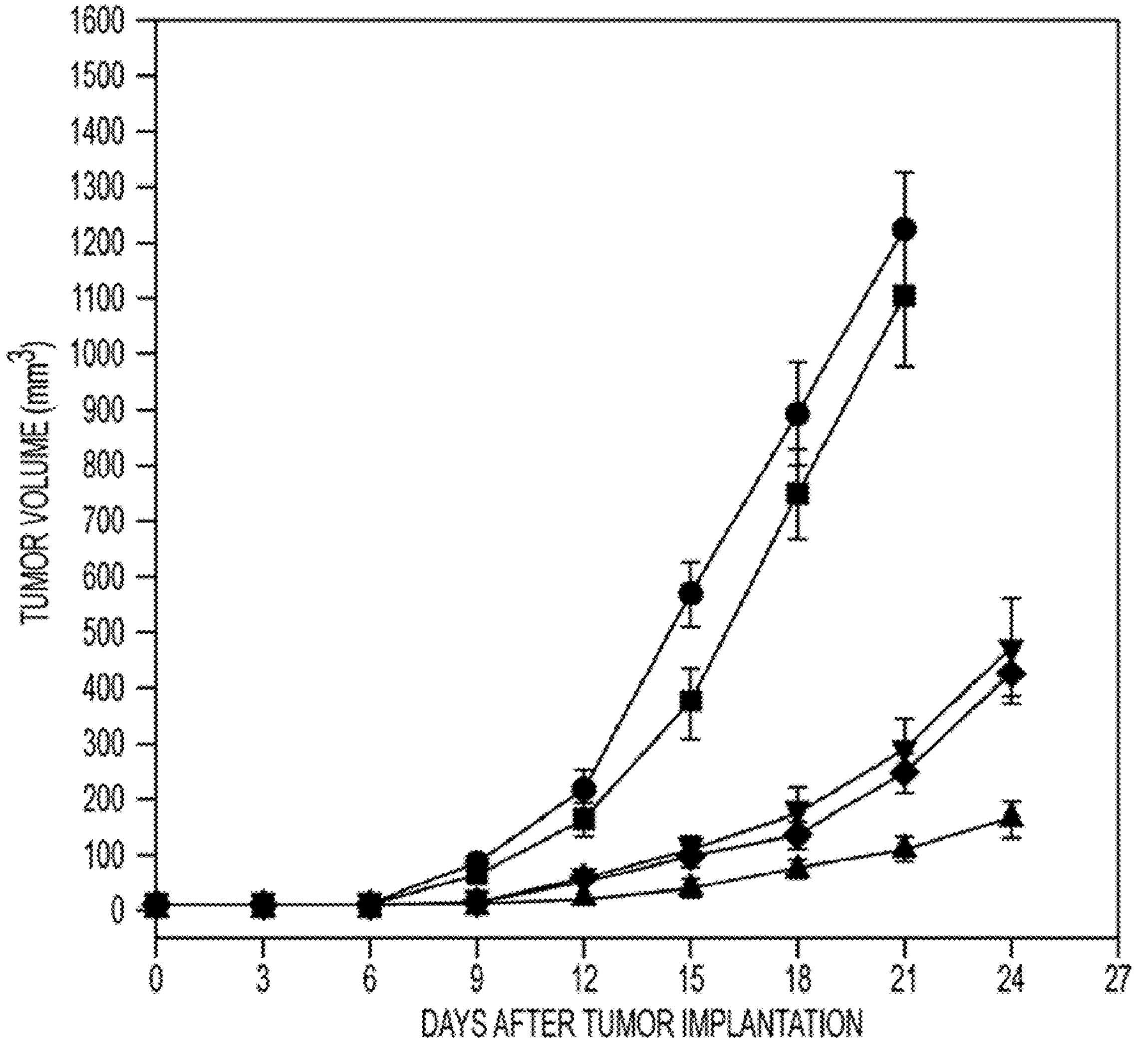

FIG. 32 is a graph showing the effect of GM-CSF from bystander cells on the growth of hsp110 overexpressing cells. Mice were injected subcutaneously with $5\times10^4$ live tumor cells as follows: CT26-empty vector cells (circles), CT26-vector cells plus irradiated B78H1GM-CSF cells (2:1 ratio; squares), CT26-hsp110 cells plus irradiated B78H1GM CSF cells (2:1 ratio; upward triangles), CT26-hsp110 cells (downward triangles), CT26-hsp110 plus irradiated B78H1 cells (2:1 ratio; diamonds). The B78H1GM-CSF are B16 cells transfected with CM-CSF gene, while B78H1 are wild type cells. Tumor growth was recorded by measuring the size of tumor, and is plotted as tumor volume in cubic mm as a function of days after implantation.

Figure 33:
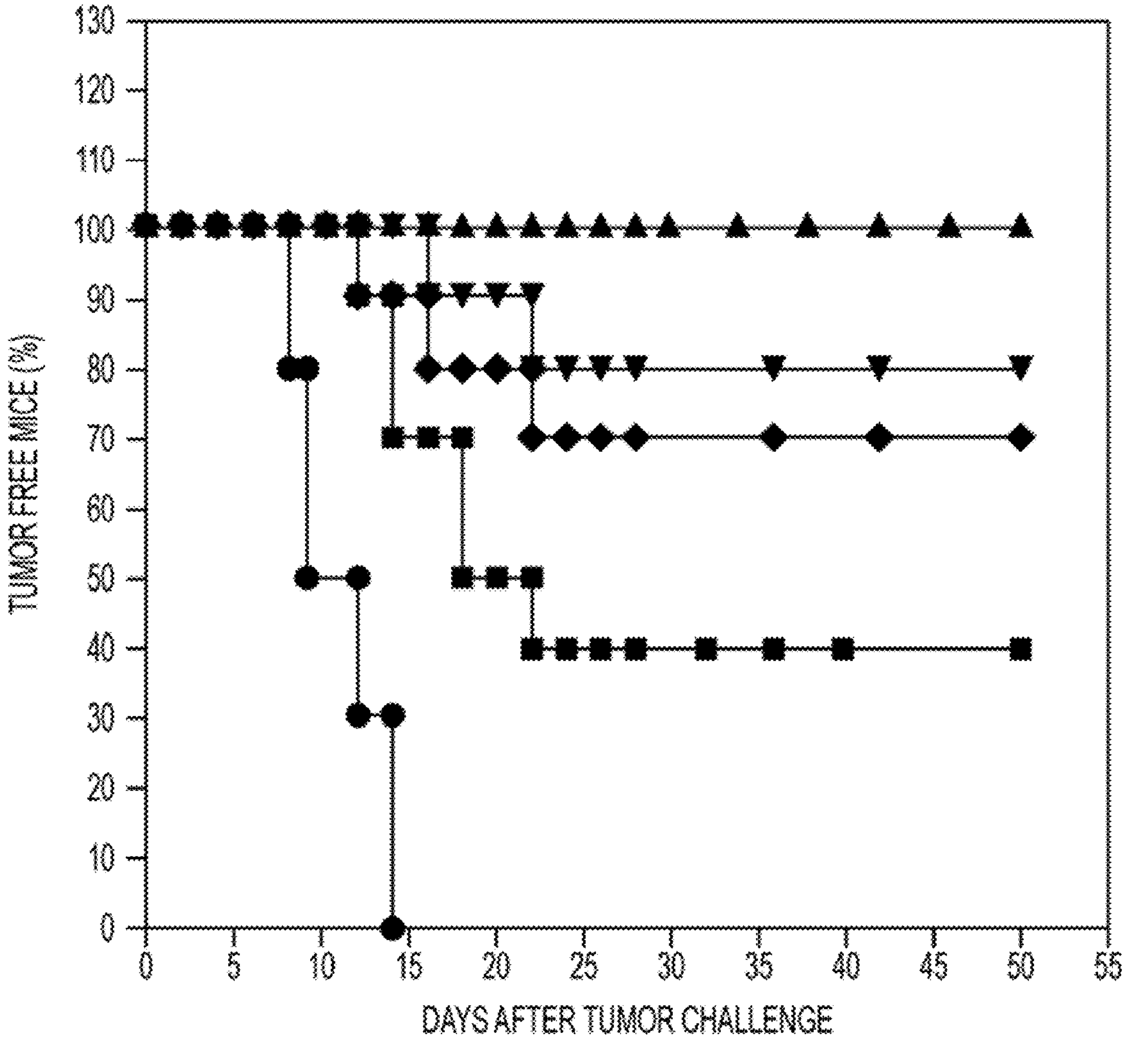

FIG. 33 is a graph showing the effect of co-injecting irradiated hsp110-overexpressing tumor vaccine and GM-CSF-secreting bystander cells on the response to wild-type CT26 tumor cell challenge. Mice were immunized subcutaneously with irradiated $5\times10^5$ tumor cells as follows: CT26-empty vector cells, CT26-vector cells plus B78H1GM-CSF cells (2:1 ratio; squares), CT26-hsp110 cells plus B78H1GM-CSF cells (2:1; upward triangles), CT26-hsp110 cells (downward triangles), CT26-hsp110 plus B78H1 cells (2:1; diamonds). Also shown are results for mice immunized only with PBS (circles). Mice were challenged at a separate site with CT26 wild-type cells and monitored every other day for the tumor development. Results are plotted as percent tumor free mice at the indicated number of days after tumor challenge.

Figure 34:
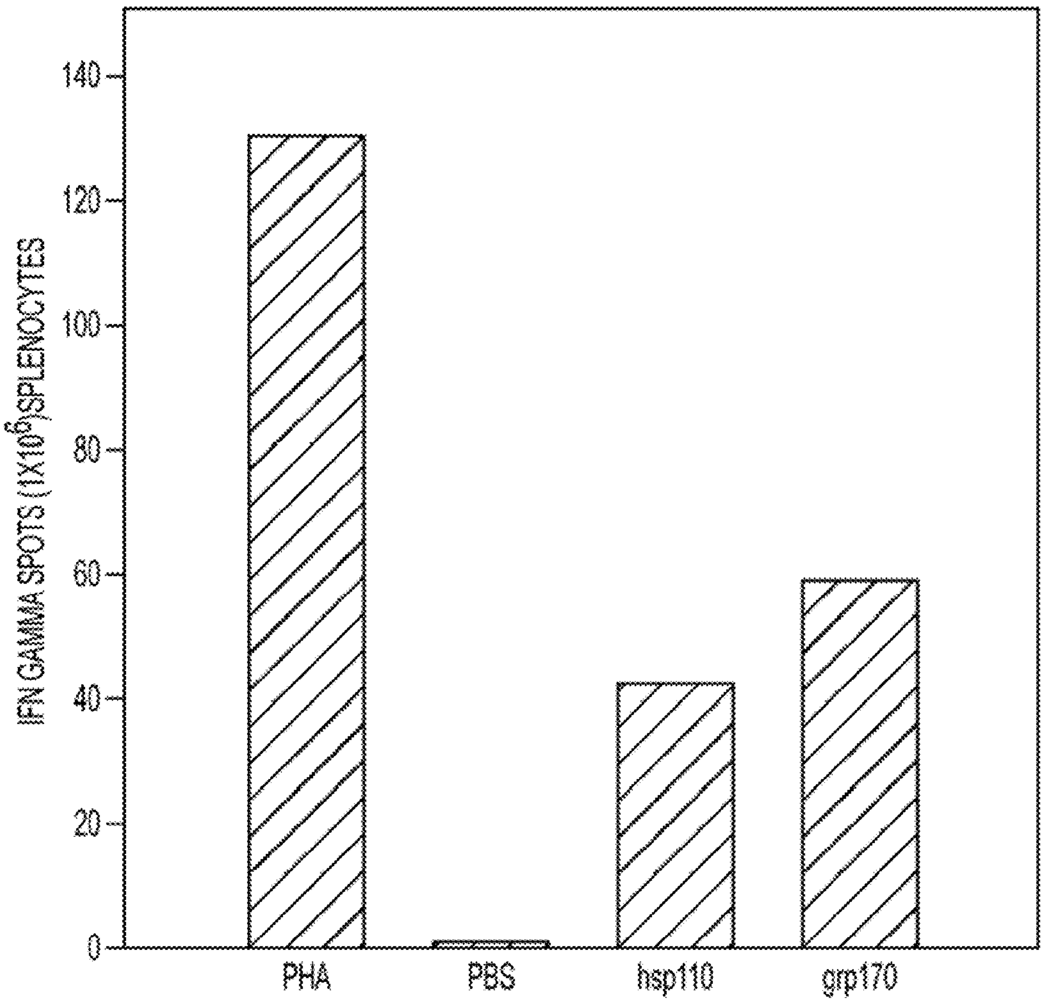

FIG. 34 is a bar graph showing that immunization with colon 26-derived hsp110 or grp170 stimulates interferon (IFN) gamma secretion. A week after mice were immunized with hsp110 or grp170, splenocytes were isolated for ELISPOT assay. Phytohemagglutinin (PHA) treated lymphocytes were used for positive control.

Figure 35:
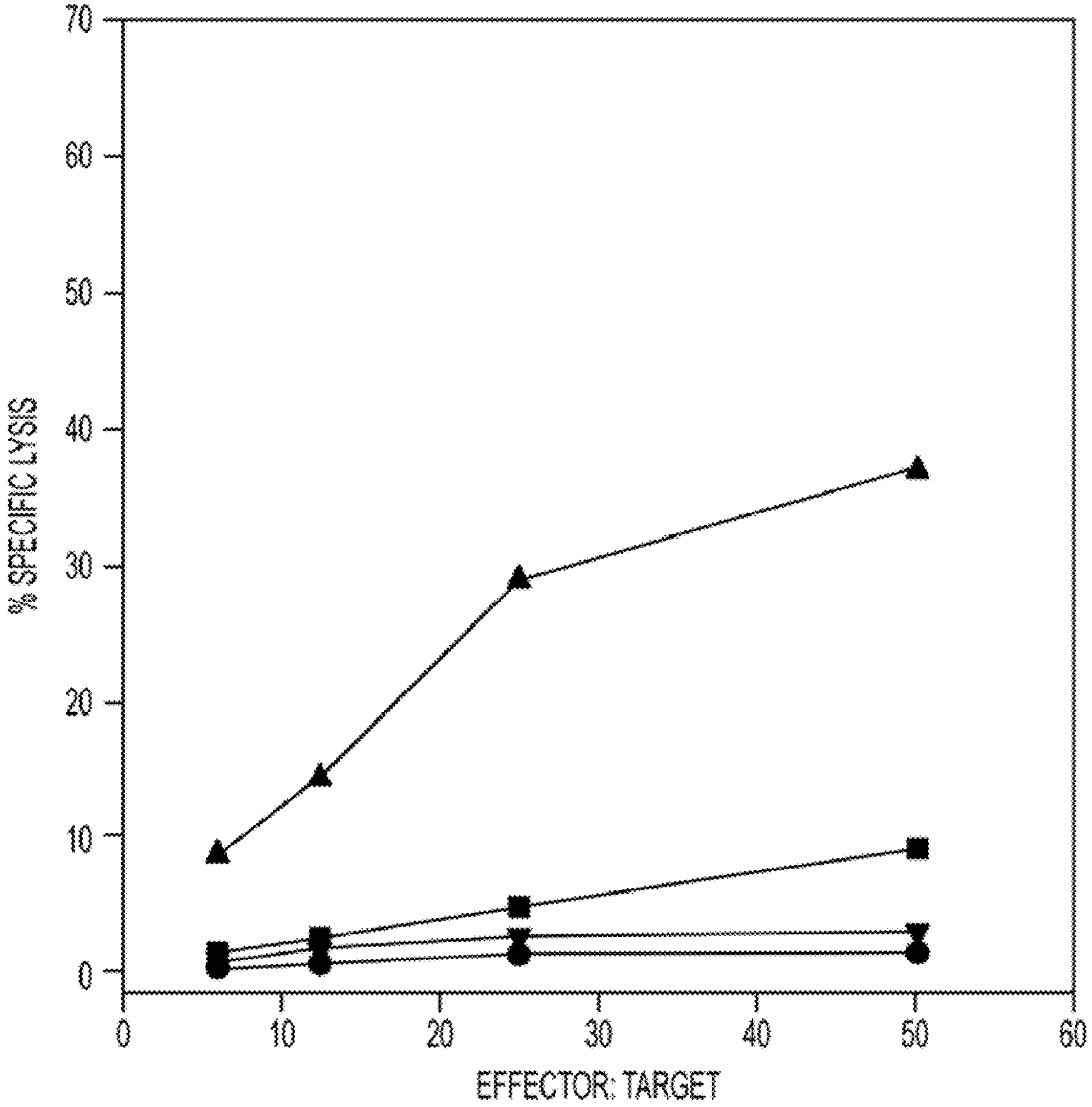

FIG. 35 is a graph showing tumor specific CTL response elicited by immunization with B16F10 tumor derived grp170. Mice were immunized twice with grp170 (40 μg) at weekly intervals. One week after the second immunization, splenocytes were isolated as effector cells and restimulated with irradiated B16F10 cells in vitro for 5 days. The lymphocytes were analyzed for cytotoxic activity using $^{51}$Cr-labeled B16F10 or Meth A cells as target cells. Results are plotted as percent specific lysis as a function of effector:target ratio for controls (circles), liver-derived grp170 (squares), B16F10-derived grp170 (upward triangles), and Meth A-derived grp170 (downward triangles).

Figure 36:
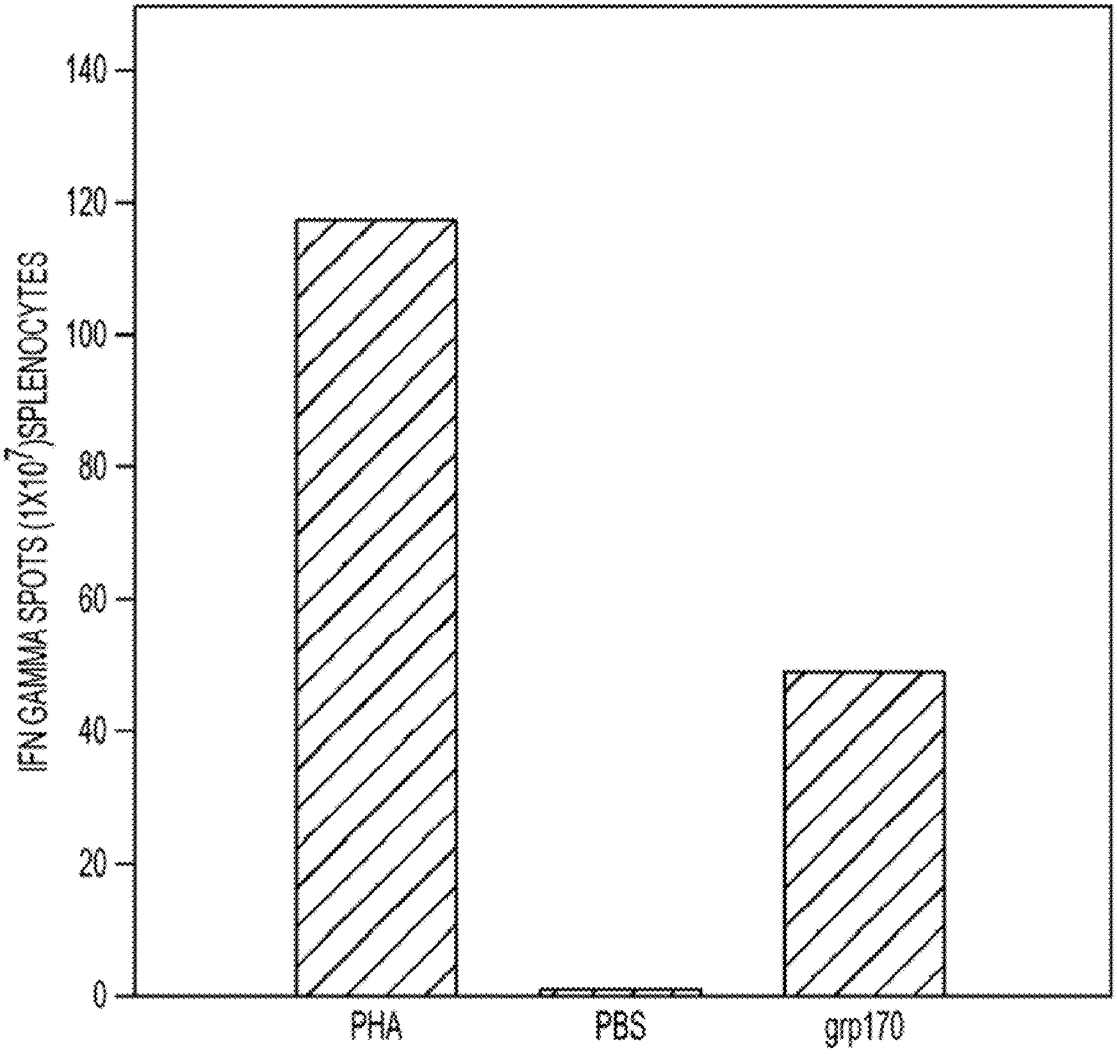

FIG. 36 shows immunization with B16F10-derived grp170 stimulates IFN gamma secretion. A week after mice were immunized with hsp110 or grp170, splenocytes were isolated for ELISPOT assay.

Figure 37:
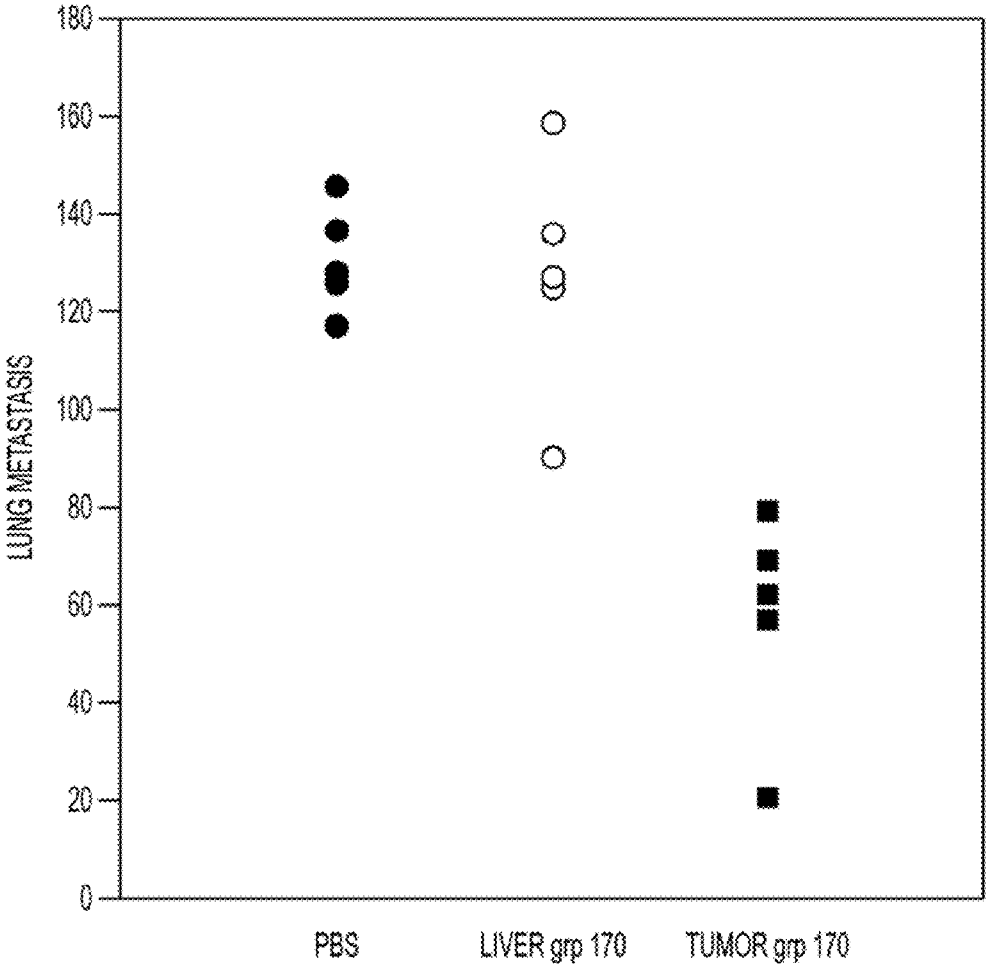

FIG. 37 shows lung metastases for mice in which $1\times10^5$ B16F10 cells were inoculated intravenously into the tail vein of each C57BL/6 mouse. 24 hr after tumor cell injection, mice were then treated with PBS (closed circles), liver-derived grp170 (open circles), or tumor-derived grp170 (40 μg). Three treatments were carried out during the whole protocol. The animals were killed 3 weeks after tumor injection, lungs were removed and surface colonies were counted.

Figure 38:
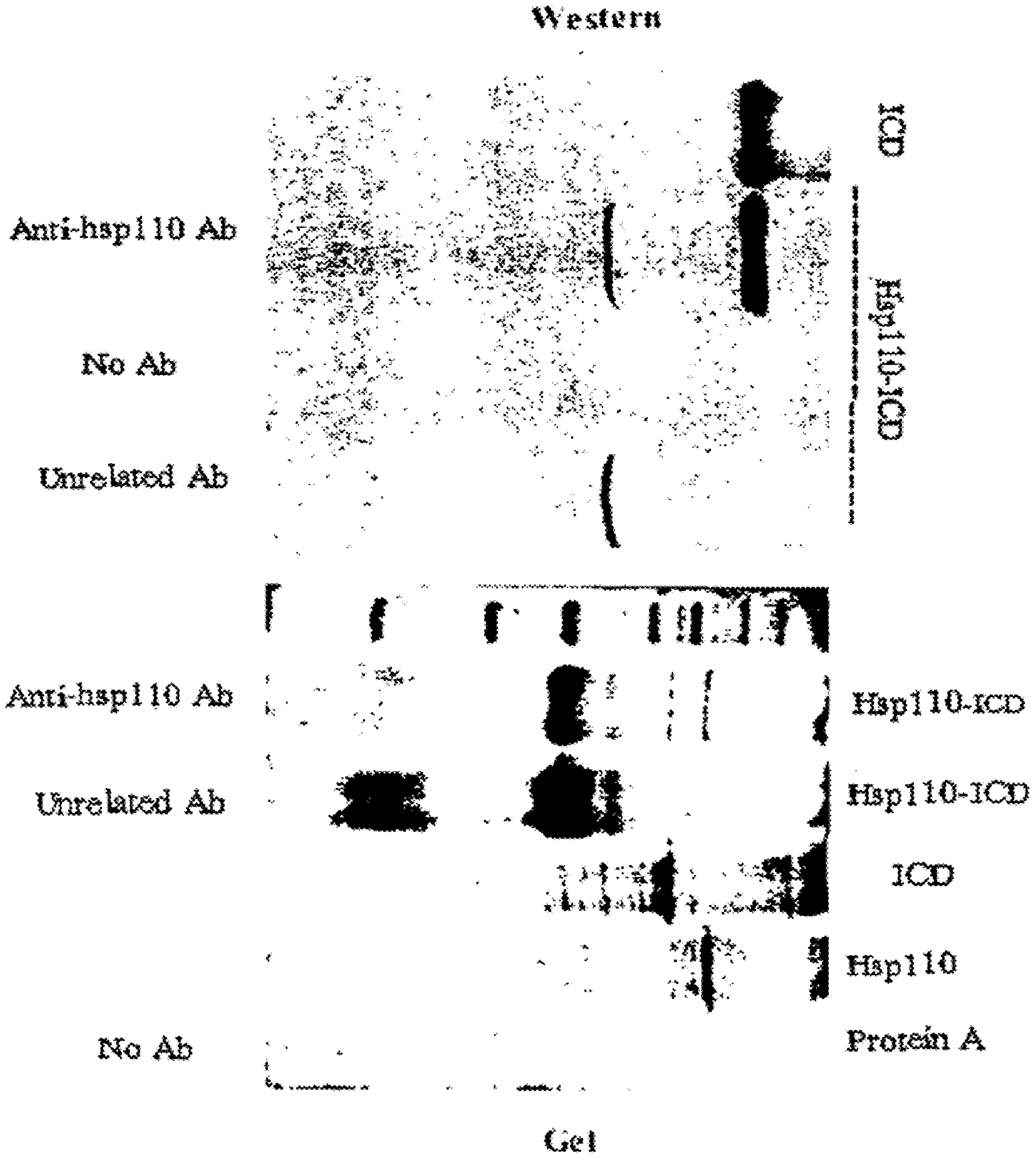

FIG. 38A-B is a western blot (38A) and corresponding gel (38B) showing formation of a non-covalent HSP110-ICD binding complex in vitro. Recombinant HSP110 (rHSP110) was incubated with recombinant intracellular domain of human HER-2/neu (rICD) at 43° C. for 30 min followed by further incubation at 37° C. for 1 hour in PBS. Different molar ratios of HSP110:ICD (1:4, 1:1, or 1:0.25) were used. The complexes were then immunoprecipitated by anti-HSP110 antiserum (1:200) or an unrelated Ab (1:100) using protein A sepharose and incubation at room temperature for 1 hour while rotating. The complexes were washed 8 times in a washing buffer at 4° C. and subjected to SDS-PAGE (10%). Gels were either stained with Gel-blue (38B) or subjected to western blot analysis (38A) using HRP-conjugated sheep anti-mouse IgG (1:5000) followed by 1 min incubation of the nitrocellulose membrane with chemiluminescence reagent and exposure to Kodak™ autoradiography film for 20 sec.

Figure 39:
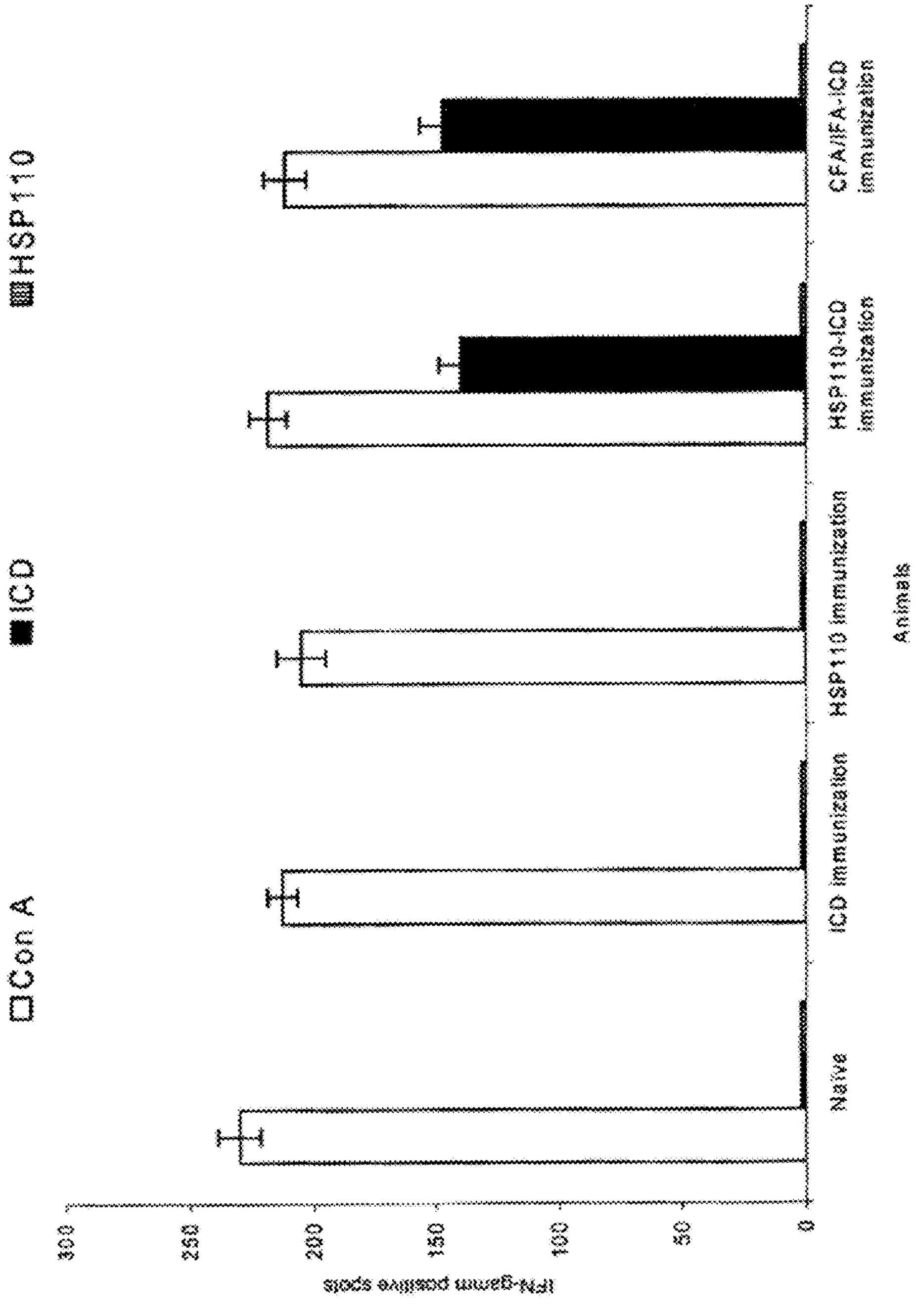

FIG. 39 is a bar graph showing frequency of IFN-γ producing T cells following immunization with different vaccine formulations. Five A2/Kb transgenic mice/group were immunized with 25 μg of the HSP110-ICD (i.p.), or CFA/IFA-ICD (s.c.) complexes. Animals were boosted after 2 weeks with the HSP110-ICD or IFA-ICD and sacrificed 2 weeks thereafter. Control groups were injected i.p. with 25 μg of the ICD, HSP110, or left non-immunized. The splenocytes ($10^7$ cells/ml) were cultured in vitro with Con A (5 μg/ml), or ICD (10-20 μg/ml) overnight and IFN-γ secretion was detected in an ELISPOT assay using biotinylated anti-IFN-γ antibody and BCIP/NBT substrate. Control wells were also pulsed with 20 μg/ml of HSP110. Data are presented after subtraction of background IFN-γ secretion upon in vitro stimulation with a control recombinant protein made in *E. Coli* (10-20 μg/ml).

Figure 40:
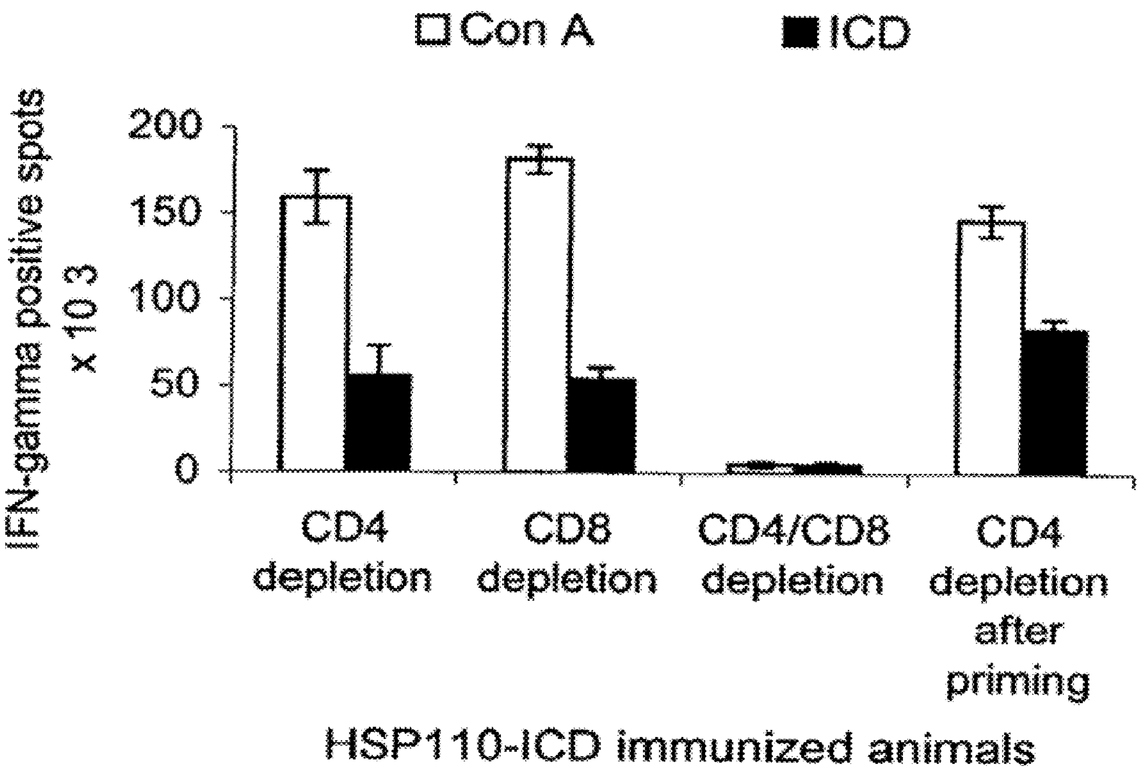

FIG. 40 is a bar graph showing frequency of IFN-γ producing $CD8^+$ and $CD4^+$ T cells following immunization with the HSP110-ICD complex. Five A2/Kb transgenic mice/group were depleted from $CD8^+$, $CD4^+$ or $CD8^+/CD4^+$ T cells on three sequential days before immunization followed by twice a week i.p. injections (250 μg) using mAbs 2.43 and/or GK1.5. Animals were also depleted from $CD4^+$ T cells one week after the booster to determine whether $CD4^+$ T cells helps to generate stronger antigen-specific CTL responses. They were primed i.p. with the HSP110-ICD (25 μg/mouse) and boosted 2 weeks later. The splenocytes ($10^7$ cells/ml) were cultured in vitro with Con A (5 μg/ml) or ICD (10-20 μg/ml) overnight and IFN-γ secretion was detected in an ELISPOT assay using biotinylated anti-IFN-γ antibody and BCIP/NBT substrate.

Figure 41A:
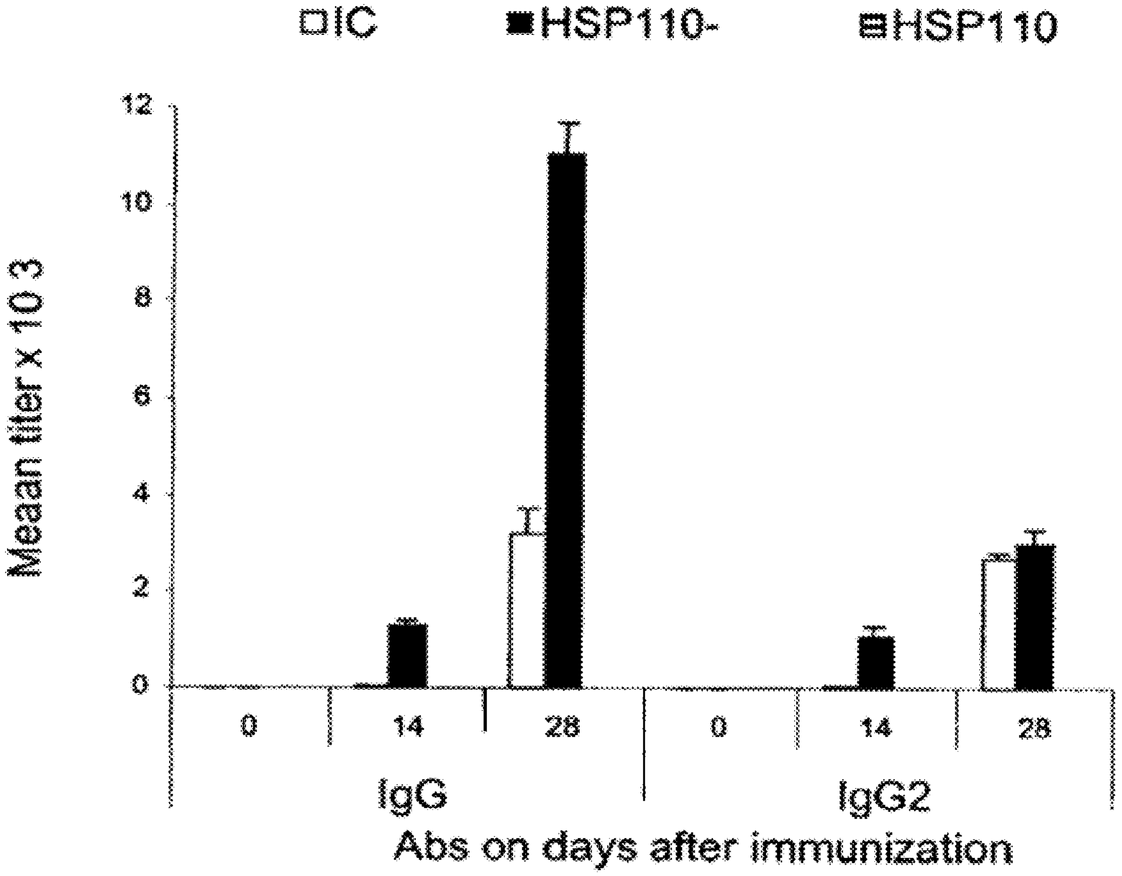

FIG. 41A is a bar graph showing isotype-specific antibody responses against the ICD following immunization with the HSP110-ICD complex or ICD. Five A2/Kb transgenic mice/group were immunized i.p. with 25 μg of the HSP110-ICD complex or ICD alone. Animals were boosted 2 weeks later and their blood samples were collected on days 0, 14 and 28 prior to each injection. The sera were prepared and subjected to ELISA using HRP-labeled anti-mouse IgG1, or IgG2a at dilutions recommended by manufacturers. The reactions were developed by adding TMB Microwell substrate, stopping the reaction by 2 M $H_2SO_4$ and reading at 450 nm.

Figure 41B:

FIG. 41B is a western blot. Sera were collected and pooled from the HSP110-ICD immunized animals and utilized to stain the ICD in a western blot. Lane 1 shows specific staining of the ICD with the immune serum (1:2000) and lane 2 shows the specific staining with mouse anti-human ICD antibody (1:10000).

Figure 42A:
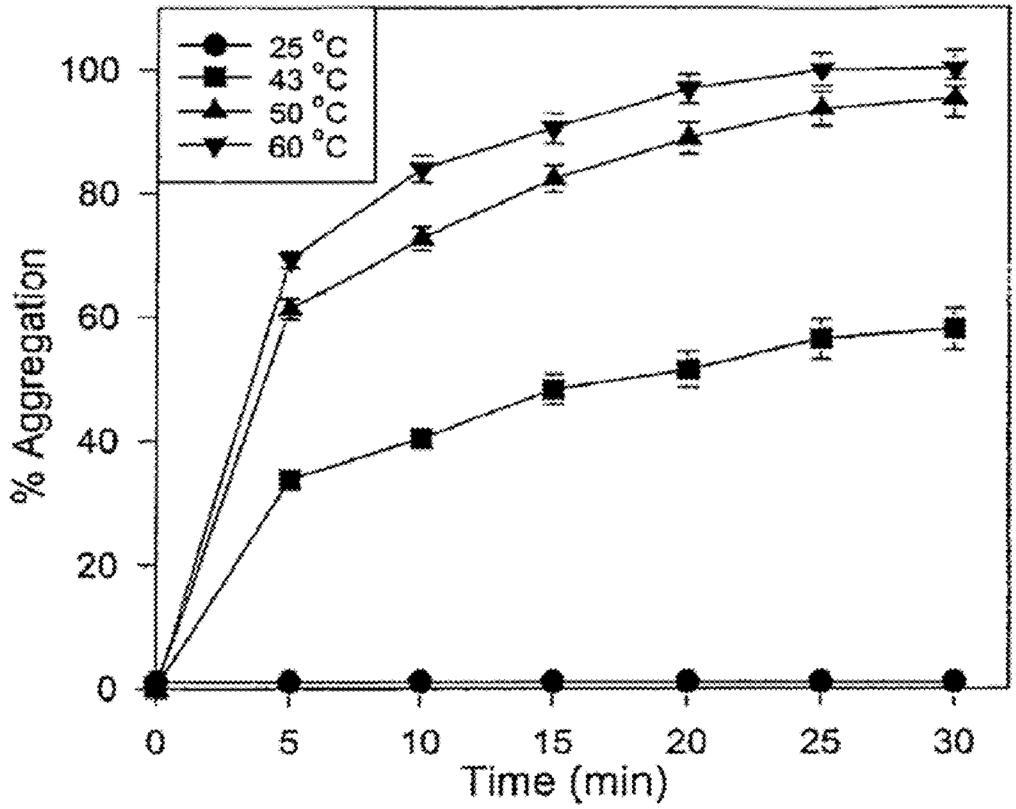
Figure 42B:
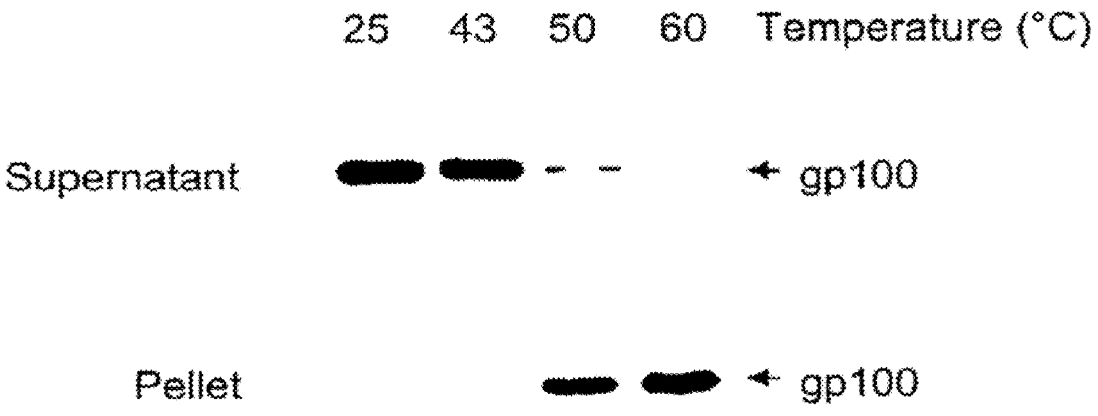

FIGS. 42A-B show aggregation of gp100 protein induced by heat shock at different temperature. FIG. 42A is a graph in which percent aggregation is plotted as a function of time. Recombinant human gp100 protein (150 uM) was incubated for 30 min at room temperature, 43° C., 50° C. and 60° C. in a thermostated cuvette. Optical density changes resulted from protein aggregation was measured at 320 um using a spectrophotometer. FIG. 42B is an immunoblot of samples after incubations at different temperature. Samples were separated into supernatant (soluble) and pellet (insoluble) fractions by centrifugation. Both fractions were resolved into SDS-PAGE and analyzed by immunoblot with anti-gp100 antibody.

Figure 43A:
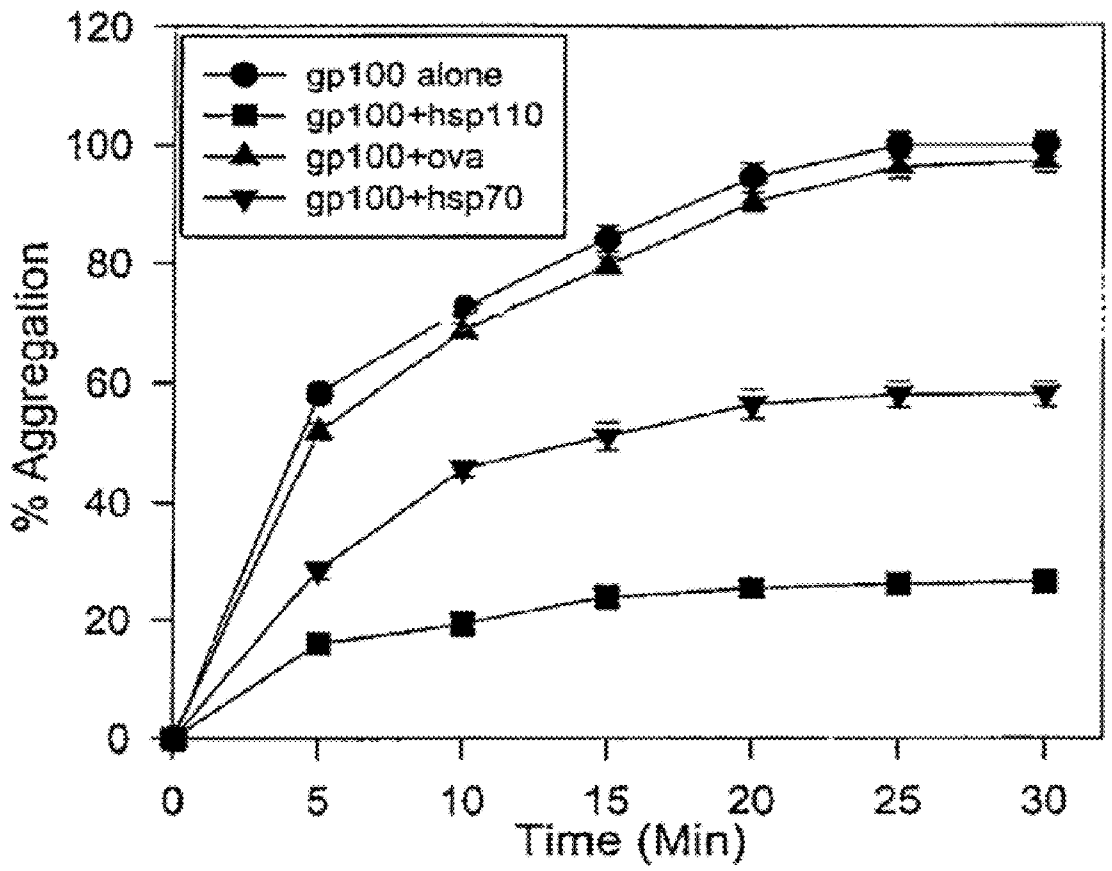
Figure 43B:
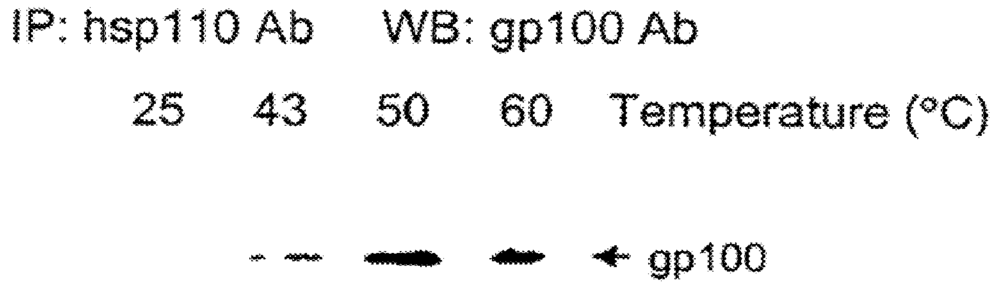

FIGS. 43A-B show that hsp110 protects gp100 from heat shock-induced aggregation by forming chaperone complexes with gp100. FIG. 43A is a graph, in which percent aggregation is plotted as a function of time, and demonstrates inhibition of heat induced gp100 aggregation by hsp110. Recombinant hsp110 and gp100 protein (1:1 molar ratio) were incubated at 50° C. and optical density changes were measured at 320 nm using a spectrophotometer. FIG. 43B is an immunoblot showing the results of an analysis of gp100 binding to the hsp110 at different temperatures. The hsp110 gp100 complexes formed at room temperature, 43° C., 50° C. and 60° C. were immunoprecipitated by anti-hsp110 serum (1:100). The immuno-complexes were subjected to western blot analysis using gp100 antibody.

Figure 44A:
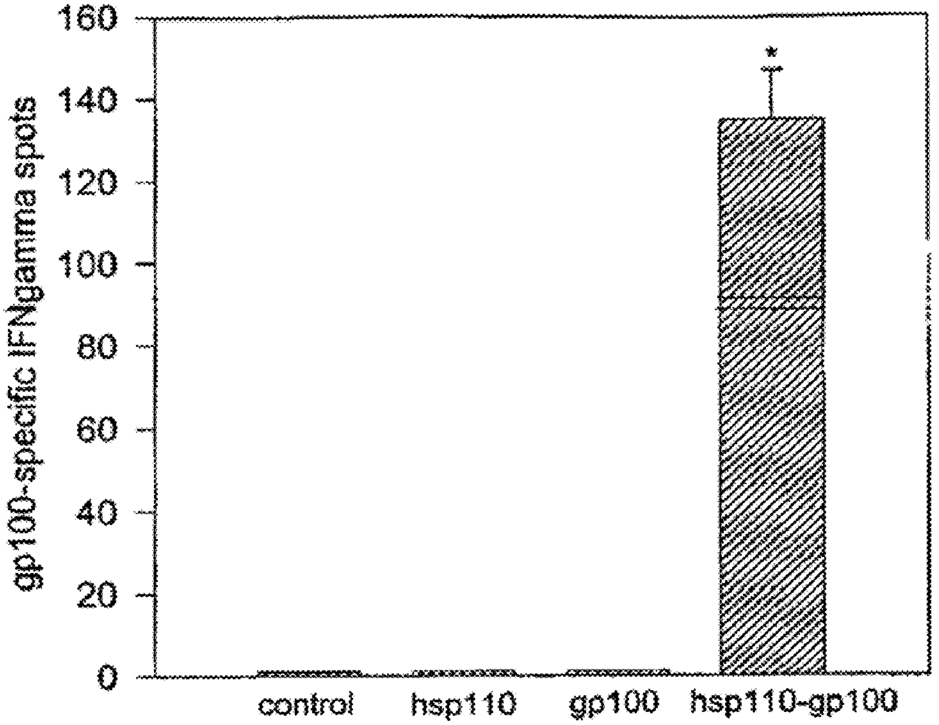
Figure 44B:
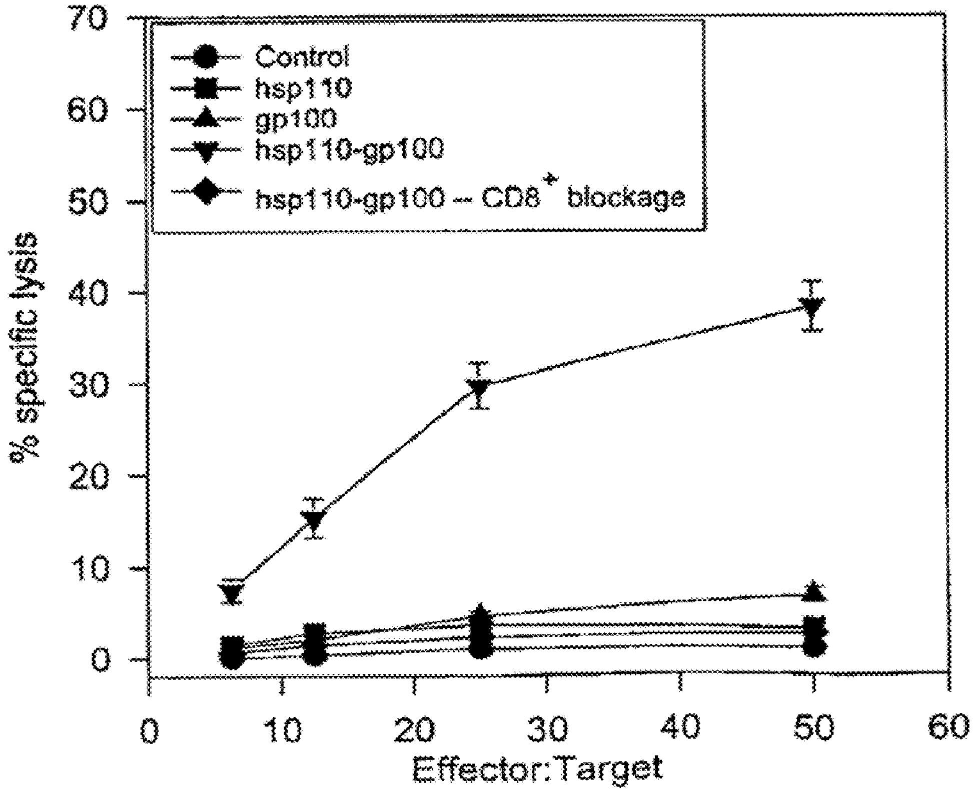
Figure 44C:
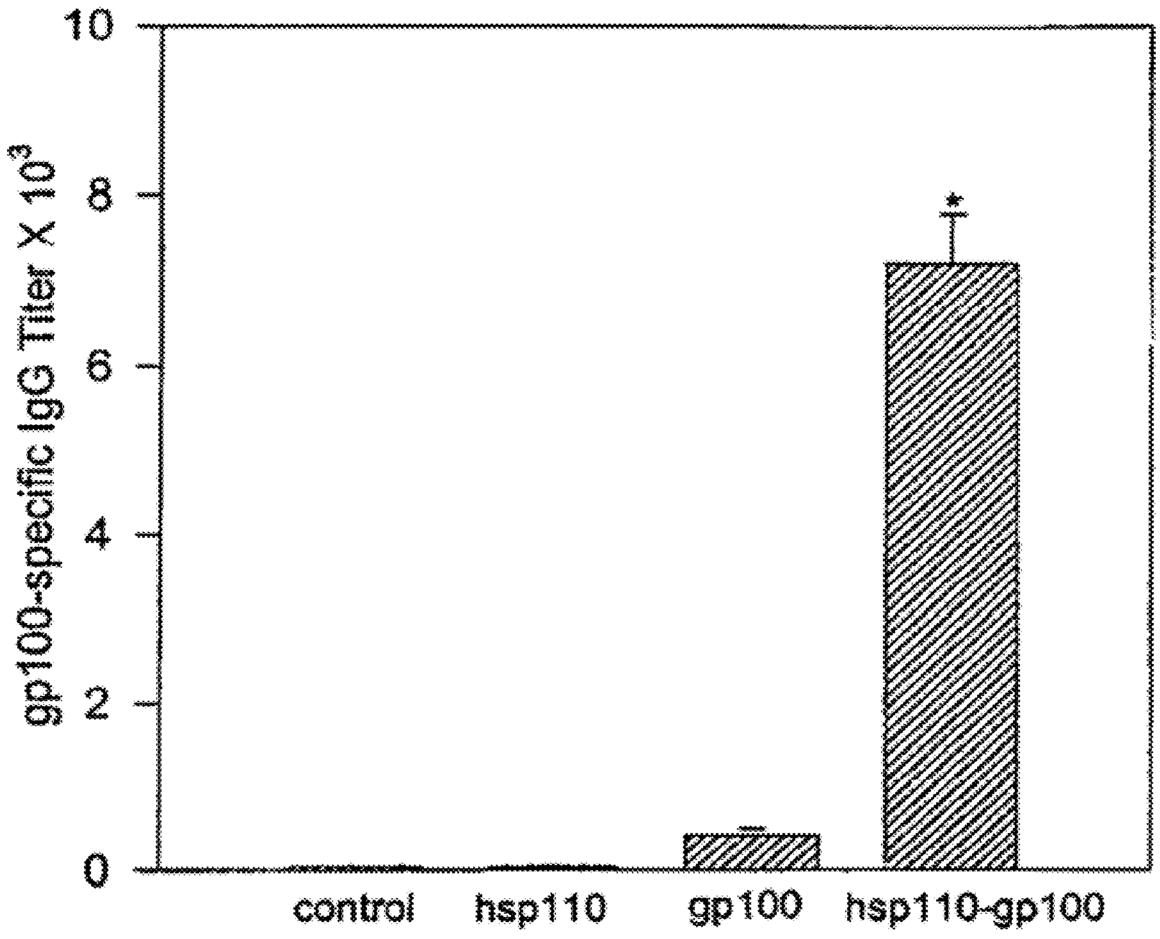

FIGS. 44A-C demonstrate that immunization with the hsp110-gp100 complexes elicits gp100-specific immune responses. C57BL/6 mice (5/group) were immunized i.p. with 30 μg of the hsp110-gp100 complexes, hsp110 alone, gp100 alone or left untreated. The vaccinations were repeated two weeks later. FIG. 44A is a bar graph showing the results of an ELISPOT assay. Two weeks after the booster, splenocytes ($5\times10^5$ cells/well) were isolated, cultured in vitro with gp100 (20 μg/rnl) overnight, and IFN-γ secretion was detected using ELISPOT. *. p<0.005 compared with splenocytes from naive mice by student's t test. FIG. 44B is a graph in which percent specific lysis is plotted as a function of effector:target ratio. Splenocytes were isolated as effector cells and re-stimulated with irradiated B16-gp100 in vitro for 5 days. The lymphocytes were analyzed for cytotoxic activity using $^{51}$Cr-labeled B16-gp100 cells as targets. For CD8+ mAb inhibition, effector cells were pre-incubated for 30 min with 20 μg/ml of the CD8-blocking antibody 2.43. FIG. 44C is a bar graph antigen-specific antibody titer. Mice were immunized with different vaccine formulations as described above. Three weeks after the booster, sera were collected and subjected to ELISA using HRP-labeled anti-mouse IgG. Data are presented as means±the standard error (SE). Similar results were obtained in three separate experiments. *. p<0.005 compared with sera from naive mice.

Figures 45A, 45B, 45C, 45D:
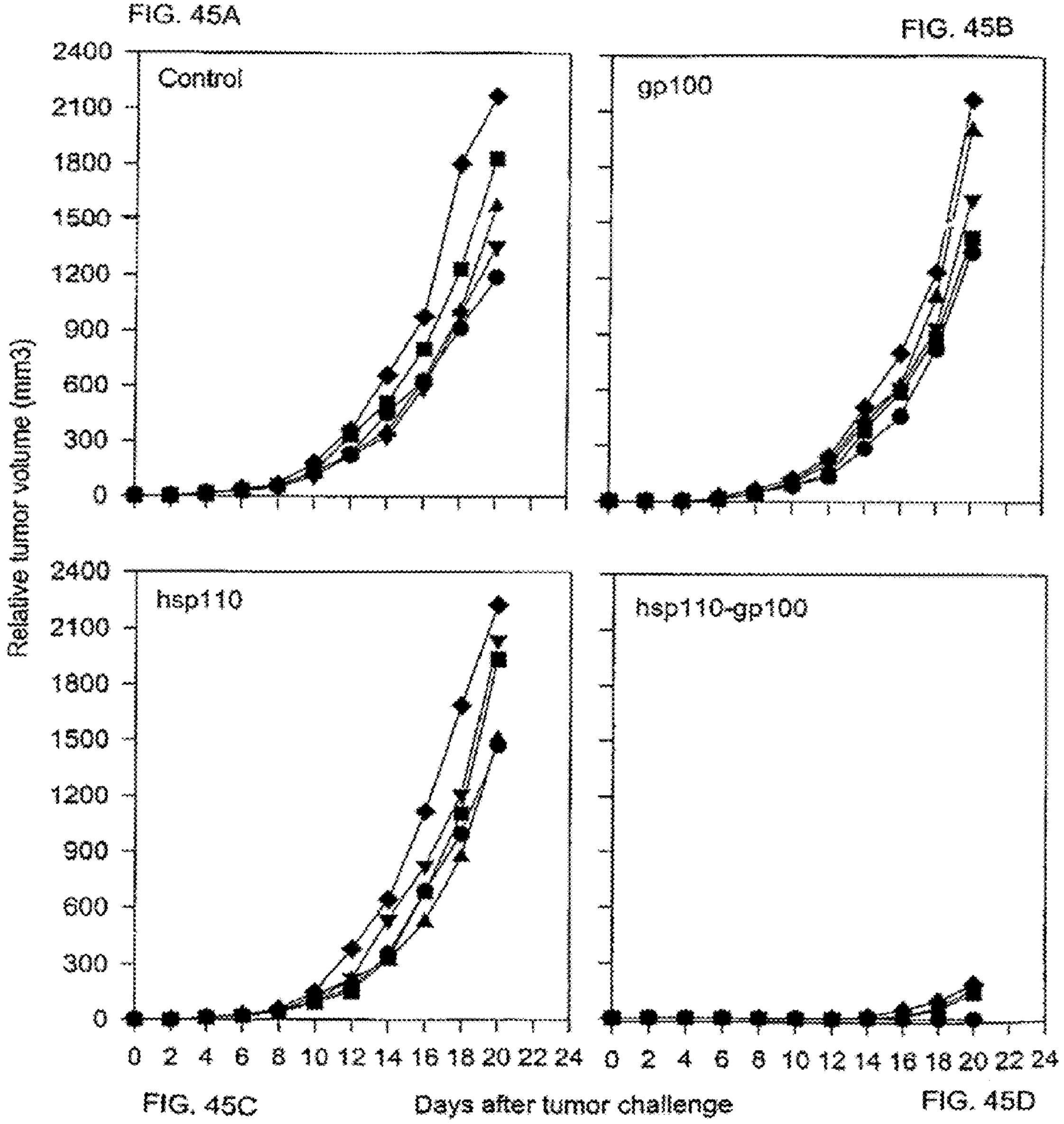

FIGS. 45A-D show that immunization with the hsp110-gp100 complexes protects mice against tumor challenge. Mice were immunized twice with 30 μg hsp110-gp100 complex (FIG. 45D), hsp110 alone (FIG. 45C), or gp100 alone (FIG. 45B) at the interval of two weeks, or left untreated (FIG. 45A). Two weeks after booster, mice were challenged with $1\times10^5$ B16 cells transduced with human gp100 (B16-gp100). Tumor growth was followed three times a week by measuring two diameters with a caliper. Each line represents data from one individual mouse. In these graphs, relative tumor volume, in cubic mm, is plotted against days following tumor challenge.

Figure 46A:
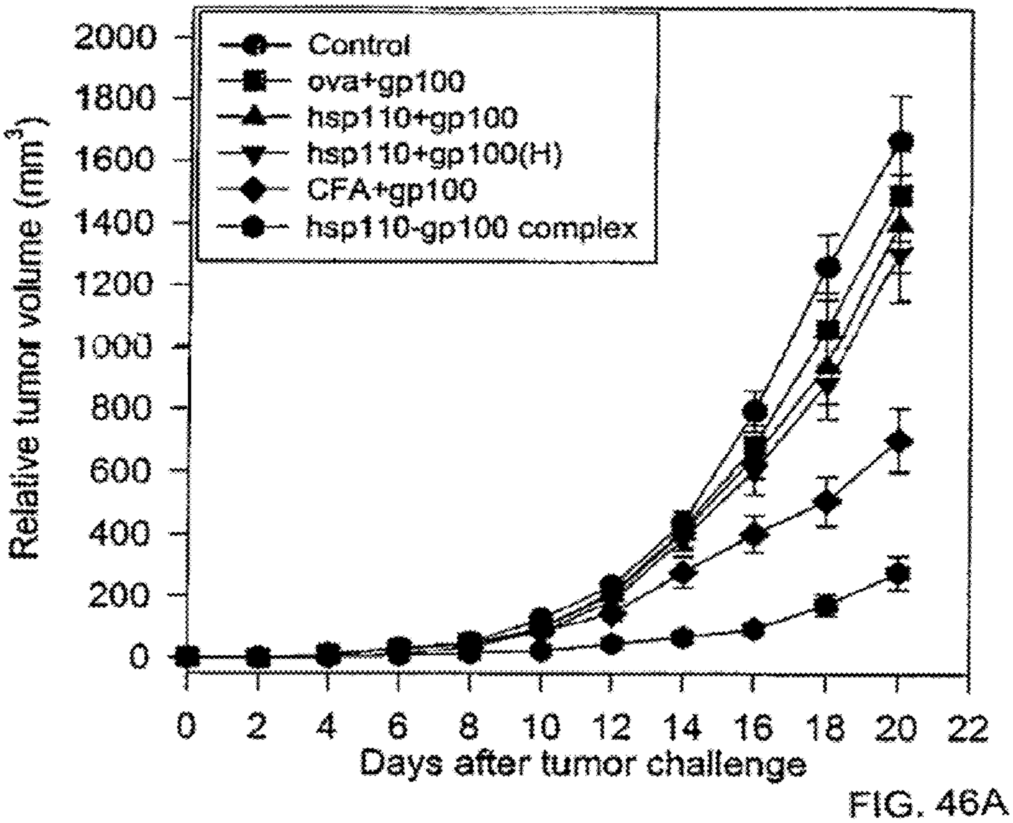
Figure 46B:
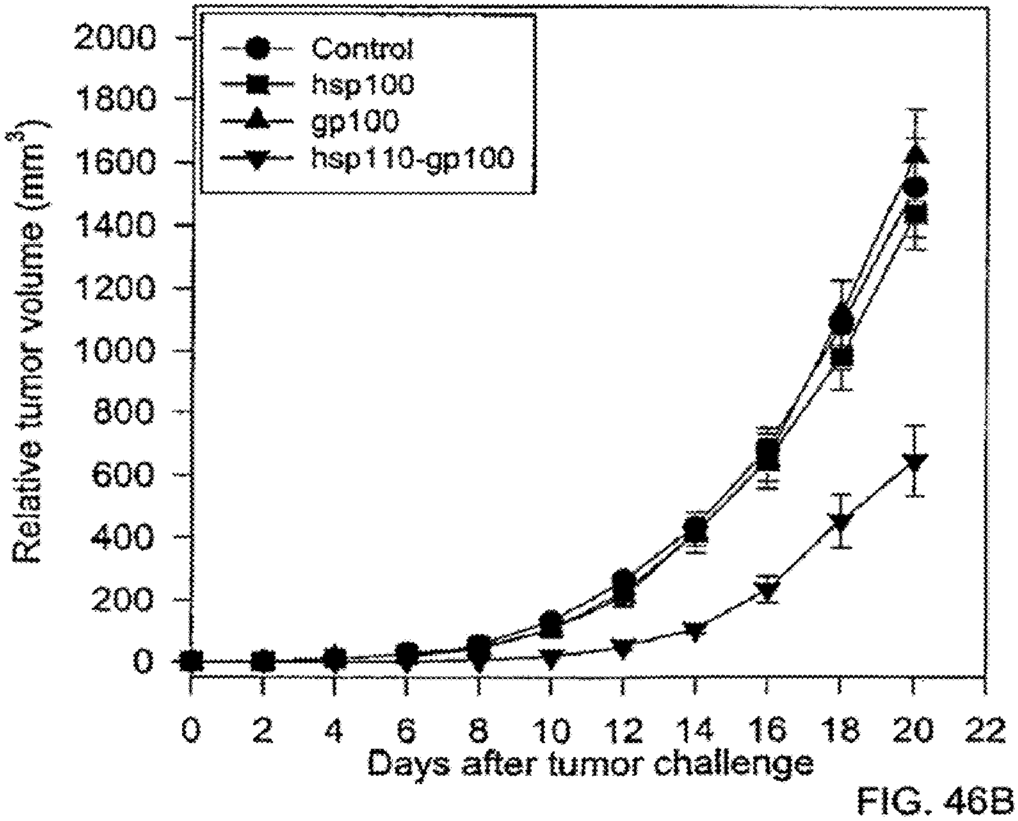

FIGS. 46A-B are graphs, in which relative tumor volume in cubic mm is plotted against days after tumor challenge, showing that hsp110-gp100 vaccine elicited anti-tumor immunity depends on the complex formation of hsp110 and gp100. FIG. 46A shows the results for mice immunized twice with different vaccine formulations: ova and gp100 treated with heat shock, hsp110 and gp100 mixture without heat shock, hsp110 mixed with heat-denatured gp100, CFA and gp100 mixture, hsp110-gp100 complexes. Two weeks after the booster, mice were challenged with $1\times10^5$ B16-gp100 tumor cells. Tumor growth was followed three times a week. FIG. 46B shows that administration of hsp110-gp100 vaccine results in the suppression of tumor growth in tumor-bearing mice. Mice were first inoculated with $5\times10^4$ B16-gp100 tumor cells on day 0. The hsp110 alone, gp100 alone, or hsp110-gp100 complexes were administered i.p. on day 4. This treatment was repeated on days 9, and 14 after tumor implantation. The size of tumor was measured ever other day.

Figure 47A:
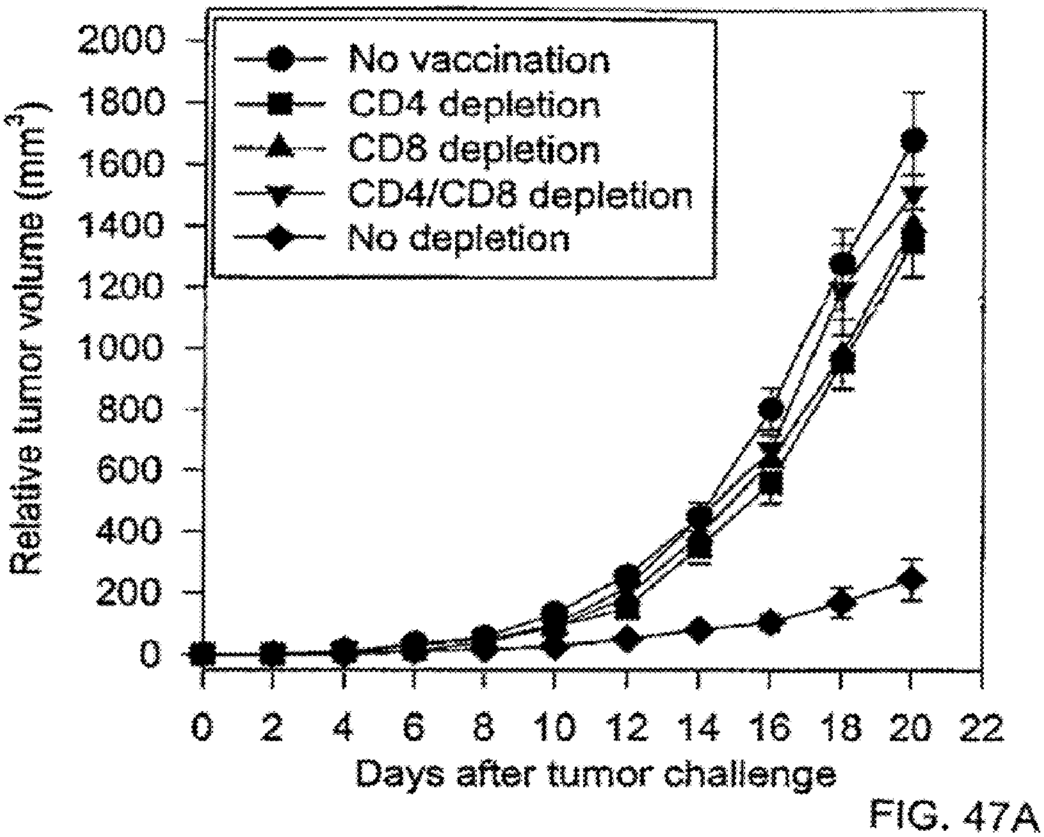
Figure 47B:
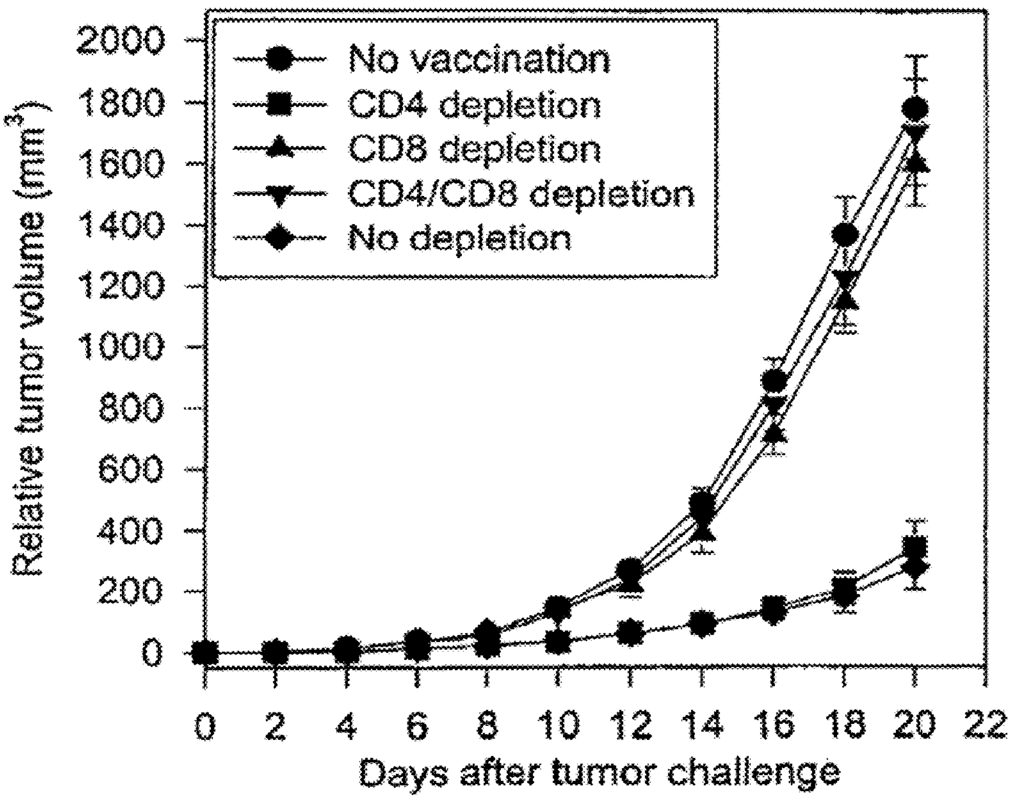

FIGS. 47A-B, also graphs plotting relative tumor volume against days after tumor challenge, show that both CD4+ and CD8+ T cells are involved in the anti-tumor immunity elicited by hsp110-gp100 vaccine. FIG. 47A shows the results for mice depleted of CD4+, CD8+ or CD4+ ICD8+ T cells before immunization, and maintained by weekly injections of anti-CD4 antibody (GKI-5), anti-CD8 antibody (2.43). The mice were then primed with the hsp110-gp100 complexes and boosted two weeks later. Two weeks after booster, mice were challenged with $1\times10^5$ B16-gp100 tumor cells and, monitored for tumor formation. FIG. 47B shows the result for mice first primed and boostered with the hsp110-gp100 complexes. CD4+ or CD8+ T cell subsets were then depleted before tumor challenge. Injections of depletion antibodies were repeated every week until the experiment was terminated.

Figure 48A:
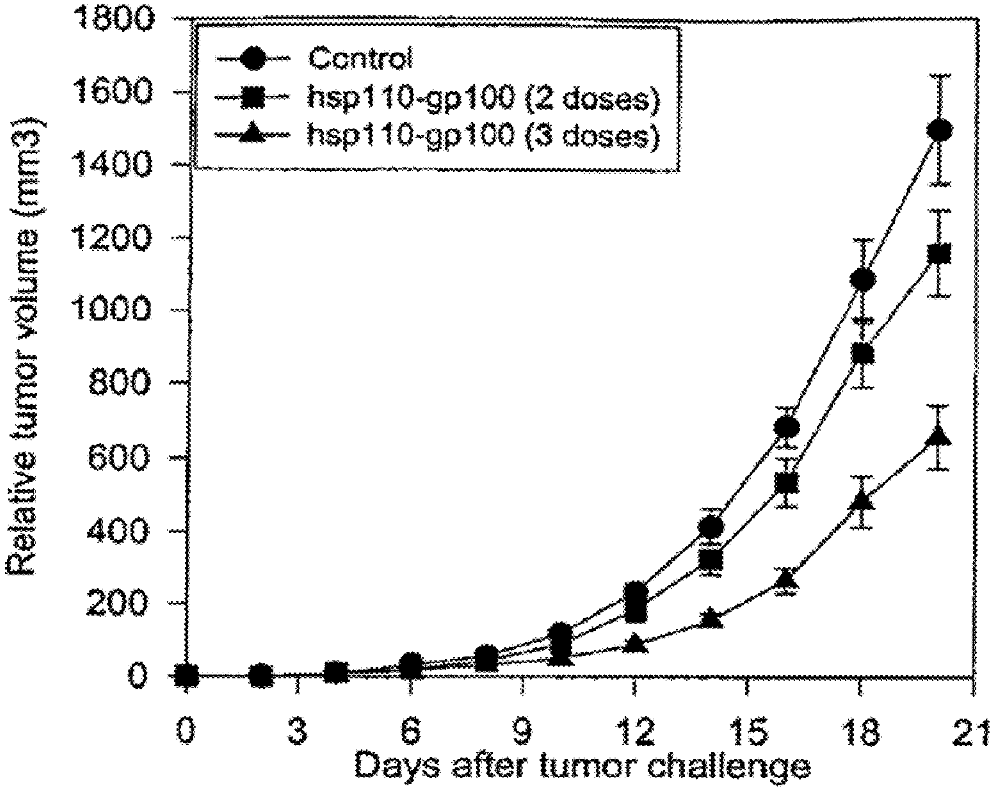
Figure 48B:
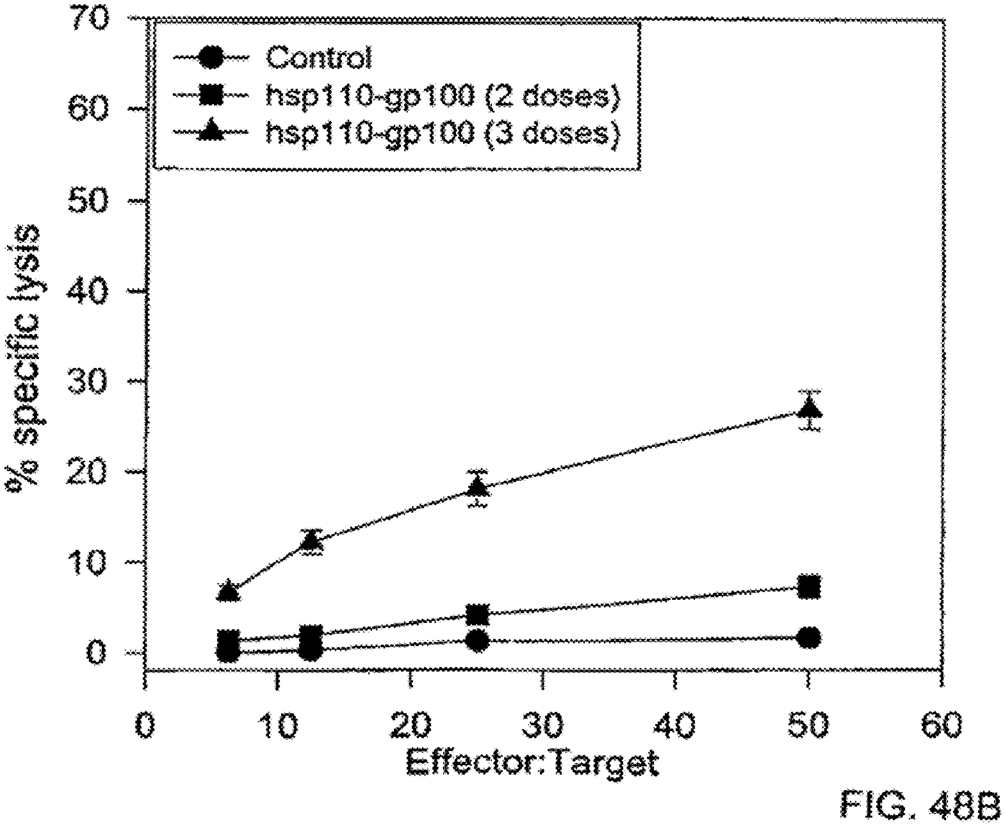

FIGS. 48A-B are graphs, again plotting relative tumor volume versus days after tumor challenge, showing that multiple immunizations with the hsp110-100 complexes inhibit growth of wild-type B16 tumor. Two vaccination protocols were employed to treat mice: the first group of mice was immunized with hsp110-gp100 complexes on days −28, −14; the second group was immunized on days −30, −20, and −10. All the immunized mice and nave mice were challenged i.d. with $5\times10^4$ wild-type B16 tumor on day 0. Tumor size was measured every other day, and the results are shown in FIG. 48A. In addition, splenocytes were isolated from naive mice and the mice treated with those two vaccination protocols, and re-stimulated with irradiated wild-type B16 cells in vitro for 5 days. The lymphocytes were then analyzed for cytotoxic activity using $^{51}Cr$-labeled wild-type B16 cells as targets. The results are shown in FIG. 48B.

DETAILED DESCRIPTION OF THE INVENTION

The present invention is based on the discovery that the stress proteins hsp110 and grp170, when complexed with tumor antigens, are remarkably effective as anti-tumor vaccines. The efficacy of these stress protein complexes has been demonstrated in both prophylactic and therapeutic contexts. The discovery of the ability of these stress proteins to facilitate an effective immune response provides a basis for their use in presenting a variety of antigens for use in prophylaxis and therapy of cancer and infectious disease. Because both hsp110 and grp170 have an enlarged peptide binding cleft and can stabilize unfolded peptide chains with greater efficiency relative to hsp70, these molecules can elicit different immunological reactions than previously obtained.

Overview of Stress Proteins hsp110 and grp170

While the expression of most cellular proteins is significantly reduced in mammalian cells exposed to sudden elevations of temperature, heat shock proteins exhibit increased expression under these conditions. Heat shock proteins, which are produced in response to a variety of stressors, have the ability to bind other proteins in the non-native states (e.g., denatured by heating or guanidium chloride treatment), and in particular the ability to bind nascent peptides emerging from ribosomes or extruded from the endoplasmic reticulum (Hendrick and Hartl, Ann. Rev. Biochem. 62:349-384, 1993; Hartl, Nature 381:571-580, 1996). Heat shock proteins have also been shown to serve a chaperoning function, referring to their important role in the proper folding and assembly of proteins in the cytosol, endoplasmic reticulum and mitochondria (Frydman et al., Nature 370:111-117, 1994).

Mammalian heat shock protein families include hsp28, hsp70, hsp90 and hsp110. These primary heat shock proteins are found in the cytoplasm and, to a lesser extent, in the nucleus. An additional set of stress proteins, known as glucose regulated proteins (grps), reside in the endoplasmic reticulum. The major families of glucose regulated proteins includes grp78, grp74 and grp170. This category of stress proteins lack heat shock elements in their promoters and are not inducible by heat, but by other stress conditions, such as anoxia.

Hsp110 is an abundant and strongly inducible mammalian heat shock protein. Human hsp110 is also known as KIAA0201, NY-CO-25, HSP105 alpha and HSP105 beta. Mouse hsp110 is also known as HSP105 alpha, HSP105 beta, 42° C.-specific heat shock protein, and hsp-E71. Hsp110 has an ATP binding beta sheet and alpha helical regions that are capable of binding peptides having greater size and different binding affinities as compared to hsp70. Hsp110 has also been shown to bind shorter peptides (12 mers) and a preferred consensus motif for binding to hsp110 has been determined (i.e., basic, polar, aromatic/basic, proline, basic, acidic, aromatic, aromatic, basic, aromatic, proline, basic, X (no preference), basic/aromatic). This sequence differs from preferred sequence motifs previously identified to bind to members of the hsp70 family.

Hsp110 is more efficient in stabilizing heat denatured proteins compared to hsp70, being four-fold more efficient on an equimolar basis. The peptide binding characteristics of hsp70 and hsp110 make them effective in inhibiting aggregation of denatured protein by binding to denatured peptide chain. Using two different denaturing conditions, heating and guanidium chloride exposure, hsp110 exhibits nearly total efficacy in inhibiting aggregation of these luciferase and citrate synthase when present in a 1:1 molar ratio. Hsp70 family members perform a similar function, but with significantly lower efficiency.

Grp170 is a strong structural homolog to hsp110 that resides in the endoplasmic reticulum (Lin et al., Mol. Biol. Cell 4:1109-19, 1993; Chen et al., FEBS Lett. 380:68-72, 1996). Grp170 exhibits the same secondary structural features of hsp110, including an enlarged peptide binding domain. Grp170 is predicted to contain a beta sheet domain near its center, a more C-terminal alpha-helical domain, and a loop domain connecting both that is much longer than the loop domain present in hsp110 (200 amino acids versus 100 amino acids in length) and absent in DnaK. In addition, grp170 is likely the critical ATPase required for protein import into the mammalian endoplasmic reticulum (Dierks et al., EMBO J. 15; 6931-42, 1996). Grp170 is also known as ORP150 (oxygen-regulated protein identified in both human and rat) and as CBP-140 (calcium binding protein identified in mouse). Grp170 has been shown to stabilize denatured protein more efficiently than hsp70.

The discovery disclosed herein that both grp170 and hsp110 function as vaccines provides the capability for novel and more effective vaccines for use in the treatment and prevention of cancer and infectious disease than previously available strategies.

A preferred embodiment of the invention disclosed herein utilizes the potent protein binding property of HSP110 to form a natural chaperone complex with the intracellular domain (ICD) of HER-2/neu as a substrate. This natural, non-covalent complex elicits cell-mediated immune responses against ICD, which are not obtained with ICD alone, as determined by antigen-specific IFN-γ production. The complex also significantly enhances the humoral immune response against ICD relative to that seen with ICD alone. In vivo depletion studies reveal that both $CD4^+$ and $CD8^+$ T cells are involved in antigen-specific IFN-γ production, and the $CD8^+$ T cell response is independent of $CD4^+$ T cell help. Although both IgG1 and IgG2a antibodies are observed following the HSP110-ICD immunization, IgG1 antibody titer is more vigorous than IgG2a antibody titer. Neither $CD8^+$ T cell nor antibody response is detected against the HSP110 itself. The use of HSP110 to form natural chaperone complexes with full-length proteins opens up a new approach for the design of protein-targeted vaccines.

Another preferred embodiment of the invention provides hsp110 complexed with the melanoma-associated antigen, gp100. Both gp100 and ICD of her2/neu, when complexed with hsp110, have demonstrated efficacy as anti-tumor agents.

DEFINITIONS

All scientific and technical terms used in this application have meanings commonly used in the art unless otherwise specified. As used in this application, the following words or phrases have the meanings specified.

As used herein, "polypeptide" includes proteins, fragments of proteins, and peptides, whether isolated from natural sources, produced by recombinant techniques or chemically synthesized. Polypeptides of the invention typically comprise at least about 6 amino acids.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, "antigen-presenting cell" or "APC" means a cell capable of handling and presenting antigen to a lymphocyte. Examples of APCs include, but are not limited to, macrophages, Langerhans-dendritic cells, follicular dendritic cells, B cells, monocytes, fibroblasts and fibrocytes. Dendritic cells are a preferred type of antigen presenting cell. Dendritic cells are found in many non-lymphoid tissues but can migrate via the afferent lymph or the blood stream to the T-dependent areas of lymphoid organs. In non-lymphoid organs, dendritic cells include Langerhans cells and interstitial dendritic cells. In the lymph and blood, they include afferent lymph veiled cells and blood dendritic cells, respectively. In lymphoid organs, they include lymphoid dendritic cells and interdigitating cells.

As used herein, "modified" to present an epitope refers to antigen-presenting cells (APCs) that have been manipulated to present an epitope by natural or recombinant methods. For example, the APCs can be modified by exposure to the isolated antigen, alone or as part of a mixture, peptide loading, or by genetically modifying the APC to express a polypeptide that includes one or more epitopes.

As used herein, "tumor protein" is a protein that is expressed by tumor cells. Proteins that are tumor proteins also react detectably within an immunoassay (such as an ELISA) with antisera from a patient with cancer.

As used herein, a "heat-inducible stress polypeptide" means a stress polypeptide or protein whose expression is induced by elevated temperature. One example of a heat-inducible stress polypeptide comprises a stress protein that contains one or more heat shock elements in its promoter.

An "immunogenic polypeptide," as used herein, is a portion of a protein that is recognized (i.e., specifically bound) by a B-cell and/or T-cell surface antigen receptor. Such immunogenic polypeptides generally comprise at least 5 amino acid residues, more preferably at least 10, and still more preferably at least 20 amino acid residues of a protein associated with cancer or infectious disease. Certain preferred immunogenic polypeptides include peptides in which an N-terminal leader sequence and/or transmembrane domain have been deleted. Other preferred immunogenic polypeptides may contain a small N- and/or C-terminal deletion (e.g., 1-30 amino acids, preferably 5-15 amino acids), relative to the mature protein.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences,* 18th edition, A. Gennaro, ed., Mack Publishing Co., Easton, Pa., 1990).

As used herein, to "prevent" or "treat" a condition means to decrease or inhibit symptoms indicative of the condition or to delay the onset or reduce the severity of the condition.

As used herein, "adjuvant" includes those adjuvants commonly used in the art to facilitate an immune response. Examples of adjuvants include, but are not limited to, helper peptide; aluminum salts such as aluminum hydroxide gel (alum) or aluminum phosphate; Freund's Incomplete Adjuvant and Complete Adjuvant (Difco Laboratories, Detroit, Mich.); Merck Adjuvant 65 (Merck and Company, Inc., Rahway, N.J.); AS-2 (Smith-Kline Beecham); QS-21 (Aquilla Biopharmaceuticals); MPL or 3d-MPL (Corixa Corporation, Hamilton, Mont.); LEIF; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; muramyl tripeptide phosphatidyl ethanolamine or an immunostimulating complex, including cytokines (e.g., GM-CSF or interleukin-2, -7 or -12) and immunostimulatory DNA sequences. In some embodiments, such as with the use of a polynucleotide vaccine, an adjuvant such as a helper peptide or cytokine can be provided via a polynucleotide encoding the adjuvant.

As used herein, "a" or "an" means at least one, unless clearly indicated otherwise.

Polynucleotides of the Invention

The invention provides polynucleotides, including a first polynucleotide that encodes one or more stress proteins, such as hsp110 or grp170, or a portion or other variant thereof, and a second polynucleotide that encodes one or more immunogenic polypeptides, or a portion or other variant thereof. In some embodiments, the first and second polynucleotides are linked to form a single polynucleotide that encodes a stress protein complex. The single polynucleotide can express the first and second proteins in a variety of ways, for example, as a single fusion protein or as two separate proteins capable of forming a complex.

Preferred polynucleotides comprise at least 15 consecutive nucleotides, preferably at least 30 consecutive nucleotides and more preferably at least 45 consecutive nucleotides, that encode a portion of a stress protein or immunogenic polypeptide. More preferably, the first polynucleotide encodes a peptide binding portion of a stress protein and the second polynucleotide encodes an immunogenic portion of an immunogenic polypeptide. Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a stress protein, immunogenic polypeptide or a portion thereof) or may comprise a variant of such a sequence. Polynucleotide variants contain one or more substitutions, additions, deletions and/or insertions such that the immunogenicity of the encoded polypeptide is not diminished, relative to a native stress protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native stress protein or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor. 11:105; Santou, N., Nes, M. (1987) Mol. Biol. Evol. 4:406-425; Sneath, P. H. A. and Sokal, R. R. (1973) Numerical Taxonomy the Principles and Practice of Numerical Taxonomy, Freeman Press, San Francisco, Calif.; Wilbur, W. J. and Lipman, D. J. (1983) Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native stress protein (or a complementary sequence). Suitable moderately stringent conditions include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques known in the art. DNA encoding a stress protein may be obtained from a cDNA library prepared from tissue expressing a stress protein mRNA. Accordingly, human hsp110 or grp170 DNA can be conveniently obtained from a cDNA library prepared from human tissue. The stress protein-encoding gene may also be obtained from a genomic library or by oligonucleotide synthesis. Libraries can be screened with probes (such as antibodies to the stress protein or oligonucleotides of at least about 20-80 bases) designed to identify the gene of interest or the protein encoded by it. Illustrative libraries include human liver cDNA library (human liver 5' stretch plus cDNA, Clontech Laboratories, Inc.) and mouse kidney cDNA library (mouse kidney 5'-stretch cDNA, Clontech laboratories, Inc.). Screening the cDNA or genomic library with the selected probe may be conducted using standard procedures, such as those described in Sambrook et al., *Molecular Cloning: A Laboratory Manual* (New York: Cold Spring Harbor Laboratory Press, 1989). An alternative means to isolate the gene encoding hsp110 or grp170 is to use PCR methodology (Sambrook et al., supra; Dieffenbach et al., *PCR Primer: A Laboratory Manual* (Cold Spring Harbor Laboratory Press, 1995)).

The oligonucleotide sequences selected as probes should be sufficiently long and sufficiently unambiguous that false positives are minimized. The oligonucleotide is preferably labeled such that it can be detected upon hybridization to DNA in the library being screened. Methods of labeling are well known in the art, and include the use of radiolabels, such as $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs, which employ various algorithms to measure homology.

Nucleic acid molecules having protein coding sequence may be obtained by screening selected cDNA or genomic libraries, and, if necessary, using conventional primer extension procedures as described in Sambrook et al., supra, to detect precursors and processing intermediates of mRNA that may not have been reverse-transcribed into cDNA.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding a stress protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding a stress polypeptide, and administering the transfected cells to the patient).

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and to permit expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Stress Polypeptides and Immunogenic Polypeptides

Within the context of the present invention, stress polypeptides and stress proteins comprise at least a peptide binding portion of an hsp110 and/or grp170 protein and/or a variant thereof. Polypeptides as described herein may be of any length. Additional sequences derived from the native protein and/or heterologous sequences may be present, and such sequences may, but need not, possess further peptide binding, immunogenic or antigenic properties. In some embodiments, the stress polypeptide further includes all or a portion of a member of the hsp70, hsp90, grp78 and grp94 stress protein families.

Functional domains and variants of hsp110 that are capable of mediating the chaperoning and peptide binding activities of hsp110 are identified in Oh, H J et al., J. Biol. Chem. 274(22):15712-18, 1999. Functional domains of grp170 parallel those of hsp110. Candidate fragments and variants of the stress polypeptides disclosed herein can be identified as having chaperoning activity by assessing their ability to solubilize heat-denatured luciferase and to refold luciferase in the presence of rabbit reticulocyte lysate (Oh et al., supra).

In some embodiments, the immunogenic polypeptide is associated with a cancer or precancerous condition. One example of an immunogenic polypeptide associated with a cancer is a her-2/neu peptide (Bargmann et al., 1986, Nature 319(6050):226-30; Bargmann et al., 1986, Cell 45(5):649-57). Examples of her-2/neu peptides include, but are not limited to, the intracellular domain of her-2/neu (amino acid residues 676-1255; see Bargmann et al. references above), p369 (also known as E75; KIFGSLAFL; SEQ ID NO: 6) of the extracellular domain of her-2/neu, ECD-PD (see WO02/12341, published Feb. 14, 2002, and WO00/44899, published Aug. 3, 2000), and p546, a transmembrane region of her-2/neu (VLQGLPREYV; SEQ ID NO: 5). Another example of an immunogenic polypeptide associated with a cancer is gp100, a melanoma-associated antigen (see Example 17 below). In other embodiments, the immunogenic polypeptide is associated with an infectious disease. One example of an immunogenic polypeptide associated with an infectious disease is an antigen derived from *M. tuberculosis*, such as *M. tuberculosis* antigens Mtb 8.4 (Coler et al., 1998, J. Immunol. 161(5):2356-64), Mtb 39 (also known as Mtb39A; Dillon et al., 1999, Infect. Immun. 67(6):2941-50), or TbH9, the latter being an example of a tuberculosis antigen whose ability to form complexes with hsp110 has been confirmed.

The immunogenic polypeptide may be known or unknown. Unknown immunogenic polypeptides can be obtained incidentally to the purification of hsp110 or grp170 from tissue of a subject having cancer or a precancerous condition or having an infectious disease. In other embodiments, the immunogenic polypeptide comprises a known antigen.

Immunogenic polypeptides may generally be identified using well known techniques, such as those summarized in Paul, Fundamental Immunology, 4th ed., 663-665 (Lippincott-Raven Publishers, 1999) and references cited therein. Such techniques include screening polypeptides for the ability to react with antigen-specific antibodies, antisera and/or T-cell lines or clones. As used herein, antisera and antibodies are antigen-specific if they specifically bind to an antigen (i.e., they react with the protein in an ELISA or other immunoassay, and do not react detectably with unrelated proteins). Such antisera and antibodies may be prepared using well known techniques. An immunogenic polypeptide can be a portion of a native protein that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, Antibodies: A Laboratory Manual, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

Stress protein complexes of the invention can be obtained through a variety of methods. In one example, a recombinant hsp110 or grp170 is mixed with cellular material (e.g., lysate), to permit binding of the stress polypeptide with one or more immunogenic polypeptides within the cellular material. Such binding can be enhanced or altered by stress conditions, such as heating of the mixture. In another example, target cells are transfected with hsp110 or grp170 that has been tagged (e.g., HIS tag) for later purification. This example provides a method of producing recombinant stress polypeptide in the presence of immunogenic material. In yet another example, heat or other stress conditions are used to induce hsp110 or grp170 in target cells prior to purification of the stress polypeptide. This stressing can be performed in situ, in vitro or in cell cultures).

In some embodiments, the invention provides a stress protein complex having enhanced immunogenicity that comprises a stress polypeptide and an immunogenic polypeptide, wherein the complex has been heated. Such heating, particularly wherein the stress polypeptide comprises a heat-inducible stress protein, can increase the efficacy of the stress protein complex as a vaccine. Examples of heat-inducible stress proteins include, but are not limited to, hsp70 and hsp110. In one embodiment, heating comprises exposing tissue including the stress protein complex to a temperature of at least approximately 38° C., and gradually increasing the temperature, e.g. by 1° C. at a time, until the desired level of heating is obtained. Preferably, the temperature of the tissue is brought to approximately 39.5° C., ±0.5° C. At the time of heating, the tissue can be in vivo, in vitro or positioned within a host environment.

A stress protein complex of the invention can comprise a variant of a native stress protein. A polypeptide "variant," as used herein, is a polypeptide that differs from a native stress protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1-30 amino acids, preferably 5-15 amino acids) has been removed from the N- and/or C-terminal of the mature protein.

Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein that co-translationally or post-translationally directs transfer of the protein. The polypeptide may also be conjugated to a linker or other sequence for ease of synthesis, purification or identification of the polypeptide (e.g., poly-FEs), or to enhance binding of the polypeptide to a solid support. For example, a polypeptide may be conjugated to an immunoglobulin Fc region.

Polypeptides may be prepared using any of a variety of well known techniques, including the purification techniques described in Example 1 below. In one embodiment, the stress polypeptide(s) and immunogenic polypeptide(s) are co-purified from tumor cells or cells infected with a pathogen as a result of the purification technique. In some embodiments, the tumor cells or infected cells are stressed prior to purification to enhance binding of the immunogenic polypeptide to the stress polypeptide. For example, the cells can be stressed in vitro by several hours of low-level heating (39.5-40° C.) or about 1 to about 2 hours of high-level heating (approximately 43° C.). In addition, the cells can be stressed in vitro by exposure to anoxic and/or ischemic or proteotoxic conditions. Tumors removed from a subject can be minced and heated in vitro prior to purification.

In some embodiments, the polypeptides are purified from the same subject to whom the composition will be administered. In these embodiments, it may be desirable to increase the number of tumor or infected cells. Such a scale up of cells could be performed in vitro or in vivo, using, for example, a SCID mouse system. Where the cells are scaled up in the presence of non-human cells, such as by growing a human subject's tumor in a SCID mouse host, care should be taken to purify the human cells from any non-human (e.g., mouse) cells that may have infiltrated the tumor. In these embodiments in which the composition will be administered to the same subject from whom the polypeptides are purified, it may also be desirable purify both hsp110 and grp170 as well as additional stress polypeptides to optimize the efficacy of a limited quantity of starting material.

Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast, insect cells or a mammalian cell line such as COS or CHO. Supernatants from suitable host/vector systems that secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of polypeptides is commercially available from suppliers such as Perkin Elmer/Applied BioSystems Division (Foster City, Calif.), and may be operated according to the manufacturers instructions.

Polypeptides can be synthesized on a Perkin Elmer/Applied Biosystems Division 430A peptide synthesizer using FMOC chemistry with HPTU (O-BenzotriazoleN,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid: ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%-60% acetonitrile (containing 0.1% TFA) in water may be used to elute the peptides. Following lyophilization of the pure fractions, the peptides may be characterized using electrospray or other types of mass spectrometry and by amino acid analysis.

Fusion Proteins

In some embodiments, the polypeptide is a fusion protein that comprises multiple polypeptides as described herein, or that comprises at least one polypeptide as described herein and an unrelated sequence. In some embodiments, the fusion protein comprises a stress polypeptide of hsp110 and/or grp170 and an immunogenic polypeptide. The immunogenic polypeptide can comprise all or a portion of a tumor protein or a protein associated with an infectious disease.

Additional fusion partners can be added. A fusion partner may, for example, serve as an immunological fusion partner by assisting in the provision of T helper epitopes, preferably T helper epitopes recognized by humans. As another example, a fusion partner may serve as an expression enhancer, assisting in expressing the protein at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

Fusion proteins are also provided that comprise a polypeptide of the present invention together with an unrelated immunogenic protein. Preferably the immunogenic protein is capable of eliciting a memory response. Examples of such proteins include tetanus, tuberculosis and hepatitis proteins (see, for example, Stoute et al., New Engl. J. Med. 336:86-91, 1997).

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenza virus, NS I (hemaglutinin).

Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAR This property has been exploited for the development of *E. coli* CLYTA expressing plasmids useful for expression of fusion proteins. Purification of hybrid proteins containing the C-LYTA fragment at the amino terminus has been described (see Biotechnology 10:795-798, 1992). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides (including fusion proteins) and polynucleotides as described herein are isolated. An "isolated" polypeptide or polynucleotide is one that is removed from its original environment. For example, a naturally occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

T Cells

Immunotherapeutic compositions may also, or alternatively, comprise T cells specific for a stress protein complexed with an immunogenic polypeptide ("stress protein complex"). Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the ISOLEX™ magnetic cell selection system, available from Nexell Therapeutics, Irvine, Calif. (see also U.S. Pat. No. 5,536,475); or MACS cell separation technology from Miltenyi Biotec, including Pan T Cell Isolation Kit, CD4+ T Cell Isolation Kit, and CD8+ T Cell Isolation Kit (see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a stress protein complex, polynucleotide encoding a stress protein complex and/or an antigen presenting cell (APC) that expresses such a stress protein complex. The stimulation is performed under conditions and for a time sufficient to permit the generation of T cells that are specific for the polypeptide. Preferably, a stress polypeptide or polynucleotide is present within a delivery vehicle, such as a microsphere, to facilitate the generation of specific T cells.

T cells are considered to be specific for a stress polypeptide if the T cells kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065-1070, 1994.

Detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a stress protein complex (100 ng/ml-100 μg/ml, preferably 200 ng/ml-25 μg/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a stress polypeptide, polynucleotide or polypeptide-expressing APC may be CD4+ and/or CD8+. T cells can be expanded using standard techniques.

Within preferred embodiments, the T cells are derived from either a patient or a related, or unrelated, donor and are administered to the patient following stimulation and expansion. For therapeutic purposes, CD4+ or CD8+ T cells that proliferate in response to a stress polypeptide, polynucleotide or APC can be expanded in number either in vitro or in vivo. Proliferation of such T cells in vitro may be accomplished in a variety of ways. For example, the T cells can be re-exposed to a stress polypeptide complexed with an immunogenic polypeptide, with or without the addition of T cell growth factors, such as interleukin-2, and/or stimulator cells that synthesize a stress protein complex. Alternatively, one or more T cells that proliferate in the presence of a stress protein complex can be expanded in number by cloning. Methods for cloning cells are well known in the art, and include limiting dilution.

Pharmaceutical Compositions and Vaccines

The invention provides stress protein complex polypeptides, polynucleotides, T cells and/or antigen presenting cells that are incorporated into pharmaceutical compositions, including immunogenic compositions (i.e., vaccines). Pharmaceutical compositions comprise one or more such compounds and, optionally, a physiologically acceptable carrier. Vaccines may comprise one or more such compounds and an adjuvant that serves as a non-specific immune response enhancer. The adjuvant may be any substance that enhances an immune response to an exogenous antigen. Examples of adjuvants include conventional adjuvants, biodegradable microspheres (e.g., polylactic galactide), immunostimulatory oligonucleotides and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds that may be biologically active or inactive. For example, one or more immunogenic portions of other tumor antigens may be present, either incorporated into a fusion polypeptide or as a separate compound, within the composition or vaccine.

A pharmaceutical composition or vaccine can contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15:143-198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope.

In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., Proc. Natl. Acad. Sci. USA 86:317-321, 1989; Flexner et al., Ann. N.Y. Acad. Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art. The DNA may also be "naked," as described, for example, in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of adjuvants may be employed in the vaccines of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quil A. Cytokines, such as GM CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-$\alpha$, IL-2 and IL-12) tend to favor the induction of cell mediated immune responses to an administered antigen. In contrast, high levels of Th2-type cytokines (e.g., IL-4, IL-5, IL-6, IL-10 and TNF-$\beta$) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145-173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Hamilton, Mont.) (see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 313MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Another adjuvant that may be used is AS-2 (Smith-Kline Beecham). Any vaccine provided herein may be prepared using well known methods that result in a combination of antigen, immune response enhancer and a suitable carrier or excipient.

A stress polypeptide of the invention can also be used as an adjuvant, eliciting a predominantly Th1-type response as well. The stress polypeptide can be used in conjunction with other vaccine components, including an immunogenic polypeptide and, optionally, additional adjuvants.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/ or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Antigen Presenting Cells

Any of a variety of delivery vehicles may be employed within pharmaceutical compositions and vaccines to facilitate production of an antigen-specific immune response that targets tumor cells or infected cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor or anti-infective effects per se and/or to be immunologically compatible with the receiver (i.e., matched BLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245-251, 1998) and have been shown to be effective as a physiological adjuvant for eliciting prophylactic or therapeutic antitumor immunity (see Timmerman and Levy, Ann. Rev. Med. 50:507-529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II NMC, adhesion molecules (e.g., CD54 and CD11) and co-stimulatory molecules (e.g., CD40, CD80 and CD86).

APCs may generally be transfected with a polynucleotide encoding a stress protein (or portion or other variant thereof) such that the stress polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and Cell Biology 75:456-460, 1997. Antigen loading of dendritic cells may be achieved by incubating dendritic cells or progenitor cells with the stress polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Therapeutic and Prophylactic Methods

The stress protein complexes and pharmaceutical compositions of the invention can be administered to a subject, thereby providing methods for inhibiting *M. tuberculosis*-infection, for inhibiting tumor growth, for inhibiting the development of a cancer, and for the treatment or prevention of cancer or infectious disease.

Treatment includes prophylaxis and therapy. Prophylaxis or therapy can be accomplished by a single direct injection at a single time point or multiple time points to a single or multiple sites. Administration can also be nearly simultaneous to multiple sites.

Patients or subjects include mammals, such as human, bovine, equine, canine, feline, porcine, and ovine animals. The subject is preferably a human, and may or may not be afflicted with cancer or disease.

In some embodiments, the condition to be treated or prevented is cancer or a precancerous condition (e.g., hyperplasia, metaplasia, dysplasia). Example of cancer include, but are not limited to, fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, multiple myeloma, Waldenström's macroglobulinemia, and heavy chain disease.

In some embodiments, the condition to be treated or prevented is an infectious disease. Examples of infectious disease include, but are not limited to, infection with a pathogen, virus, bacterium, fungus or parasite. Examples of viruses include, but are not limited to, hepatitis type B or type C, influenza, varicella, adenovirus, herpes simplex virus type I or type II, rinderpest, rhinovirus, echovirus, rotavirus, respiratory syncytial virus, papilloma virus, papova virus, cytomegalovirus, echinovirus, arbovirus, hantavirus, coxsachie virus, mumps virus, measles virus, rubella virus, polio virus, human immunodeficiency virus type I or type II. Examples of bacteria include, but are not limited to, *M. tuberculosis, mycobacterium, mycoplasma, neisseria* and *legionella*. Examples of parasites include, but are not limited to, *rickettsia* and *chlamydia*.

Accordingly, the above pharmaceutical compositions and vaccines may be used to prevent the development of a cancer or infectious disease or to treat a patient afflicted with a cancer or infectious disease. A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors or infected cells with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8+ cytotoxic T lymphocytes and CD4+ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. In a preferred embodiment, dendritic cells are modified in vitro to present the polypeptide, and these modified APCs are administered to the subject. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy.

In particular, antigen-presenting cells, such as dendritic, macrophage, monocyte, fibroblast and/or B cells, can be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Cultured effector cells can be induced to grow in vivo and to survive long term in substantial numbers by repeated stimulation with antigen supplemented with IL-2 (see, for example, Cheever et al., Immunological Reviews 157:177, 1997).

Alternatively, a vector expressing a polypeptide recited herein can be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumoral administration.

Administration and Dosage

The compositions are administered in any suitable manner, often with pharmaceutically acceptable carriers. Suitable methods of administering cells in the context of the present invention to a subject are available, and, although more than one route can be used to administer a particular cell composition, a particular route can often provide a more immediate and more effective reaction than another route.

The dose administered to a patient, in the context of the present invention, should be sufficient to effect a beneficial therapeutic response in the patient over time, or to inhibit infection or disease due to infection. Thus, the composition is administered to a subject in an amount sufficient to elicit an effective immune response to the specific antigens and/or to alleviate, reduce, cure or at least partially arrest symptoms and/or complications from the disease or infection. An amount adequate to accomplish this is defined as a "therapeutically effective dose."

Routes and frequency of administration of the therapeutic compositions disclosed herein, as well as dosage, will vary from individual to individual, and may be readily established using standard techniques. In general, the pharmaceutical compositions and vaccines may be administered, by injection (e.g., intracutaneous, intratumoral, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. In one embodiment, 2 intradermal injections of the composition are administered 10 days apart.

A suitable dose is an amount of a compound that, when administered as described above, is capable of promoting an anti-tumor immune response, and is at least 10-50% above the basal (i.e., untreated) level. Such response can be monitored, for example, by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to nonvaccinated patients. In general, for pharmaceutical compositions and vaccines comprising one or more polypeptides, the amount of each polypeptide present in a dose ranges from about 100 μg to 5 mg per kg of host. Suitable volumes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

EXAMPLES

The following examples are presented to illustrate the present invention and to assist one of ordinary skill in making and using the same. The examples are not intended in any way to otherwise limit the scope of the invention.

Example 1

Purification of hsp110, grp170 and grp78

This example describes the procedure for purification of hsp110 and grp170, as well as for grp78. The results confirm the identity and purity of the preparations.

Materials and Methods

A cell pellet or tissue was homogenized in 5 vol. of hypotonic buffer (30 mM sodium bicarbonate, pH7.2, 1 mM PMSF) by Dounce homogenization. The lysate was centrifuged at 4500 g and then 100,000 g to remove unbroken cells, nuclei, and other tissue debris. The supernatant was further centrifuged at 100,000 g for 2 hours. Supernatant was applied to concanavalin A-sepharose beads (1 ml bed volume/ml of original material), previously equilibrated with 20 mM Tris-HCl, 50 mM NaCl, 1 mM MgCl2, 1 mM CaCl2, 1 mM $MnCl_2$. The bound proteins were eluted with binding buffer A containing 15% a-D-methylmannoside (a-D-MM).

For purification of Hsp110, ConA-sepharose unbound material was applied to a Mono Q (Pharmacia) 10/10 column equilibrated with 20 mM Tris-HCl, pH 7.5, 200 mM NaCl. The bound proteins were eluted with the same buffer by a linear salt gradient up to 500 mM sodium chloride (FR: 3 ml/min, 40%-60% B/60 min). Fractions were collected and analyzed by SDS-PAGE followed by immunoblotting with an anti-hsp110 antibody. Pooled fractions containing hsp110 (270 mM-300 mM) were concentrated by Centriplus (Amicon, Beverly, Mass.) and applied on a Superose 12 column. Proteins were eluted by 40 mM Tris HCl, pH 8.0, 150 mM NaCl with flow rate of 0.2 ml/min. Fractions were tested by immunoblot and silver staining.

For purification of Grp170, Con A-sepharose bound material, eluted by 10% αmethylmannoside, was first applied on MonoQ column equilibrated with 20 mM Tris HCl, pH 7.5, 150 mM NaCl and eluted by 150~500 mM NaCl gradient. Grp170 was eluted between 300 mM-350 mM NaCl. Pooled fractions were concentrated and applied on the Superose 12 column. Fractions containing homogeneous grp170 were collected, and analyzed by SDS-PAGE followed by immunoblotting with an anti-grp170 antibody.

For purification of Grp78 (Bip), ConA-sepharose unbound proteins were loaded on an ADP-agarose column (Sigma Chemical Co., St. Louis, Mo.) equilibrated with binding buffer B (20 mM Tris-acetate, pH 7.5, 20 mM NaCl, 15 mM β-mercaptoethanol, 3 mM MgCl2, 0.5 mM PMSF). The column was washed with binding buffer B containing 0.5 M NaCl, and incubated with buffer B containing 5 mM ADP at room temperature for 30 min. Protein was subsequently eluted with the same buffer (~5 times bed volume). The elute was resolved on a FPLC system using MonoQ column and eluted by a 20-500 mM NaCl gradient. Grp78 was present in fractions eluted between 200 mM-400 mM salt. For purification of Hsp or Grps from liver, the 100,000 g supernatant was first applied to a blue sepharose column (Pharmacia) to remove albumin. All protein was quantified with a Bradford assay (BioRad, Richmond, Calif.), and analyzed by SDS-PAGE followed by immunoblotting with antibodies to grp78 obtained from StressGen Biotechnologies Corp. (Victoria, BC, Canada).

Results

Figure 1A:
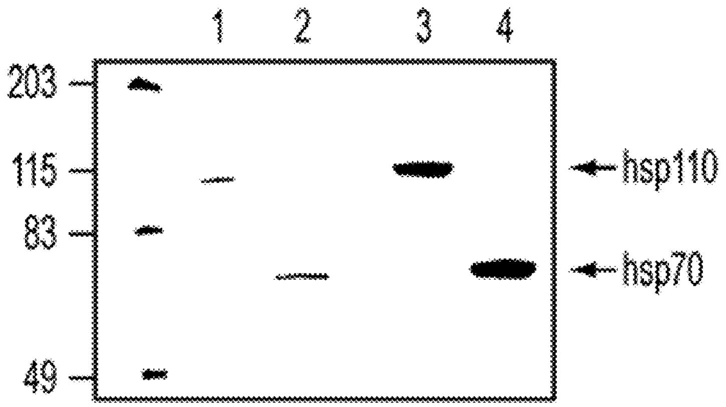
FIG. 1A shows silver staining and analysis of purified hsp proteins. Gel staining of hsp110 and hsp70 from tumor are shown in lanes 1 and 2, respectively. Lanes 3 and 4 show results of an immunoblot analysis with hsp110 antibody and hsp70 antibody, respectively.
Figure 1B:
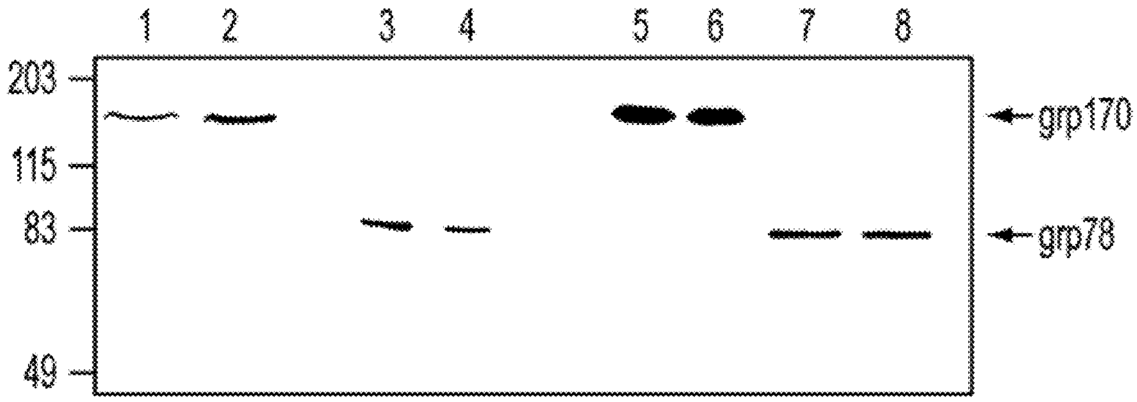
FIG. 1B shows silver staining and analysis of purified grp proteins, with gel staining of grp170 from tumor in lane 1, of grp170 from liver in lane 2, grp78 from tumor in lane 3, grp78 from liver in lane 4. Results of an immunoblot analysis with grp170 antibody and grp78 antibody, respectively, are shown in lanes 5-6 and 7-8.

Proteins hsp110, grp170 and grp78 were purified simultaneously from tumor and liver. Homogeneous preparations for these three proteins were obtained and they were recognized by their respective antibodies by immunoblotting. The purity of the proteins was assessed by SDS-PAGE and silver staining (FIG. 1).

Example 2

Tumor Rejection Assays

This example demonstrates that immunization with tumor derived hsp110 and grp170 protects mice against tumor challenge. The results show tumor growth delay with prophylactic immunization as well as longer survival times with therapeutic immunization.

Materials and Methods

BALB/cJ mice (viral antigen free) were obtained from The Jackson Laboratory (Bar Harbor, Me.) and were maintained in the mouse facilities at Roswell Park Cancer Institute. Methylcholanthrene-induced fibrosarcoma (Meth A) was obtained from Dr. Pramod K. Srivastava (University of Connecticut School of Medicine, Farmington, Conn.) and maintained in ascites form in BALB/cJ mice by weekly passage of 2 million cells.

Mice (6-8-week-old females; five mice per group) were immunized with PBS or with varying quantities of tumor or liver derived hsp110 or grp170, in 200 μl PBS, and boosted 7 days later. Seven days after the last immunization, mice were injected subcutaneously on the right flank with $2\times10^4$ colon 26 tumor cells (viability>99%). The colon 26 tumor exemplifies a murine tumor model that is highly resistant to therapy. In other experiments, the mice were challenged 7 days after the second immunization with intradermal injections of MethA tumor cells. Tumor growth was monitored by measuring the two diameters.

Results

Figure 2A:
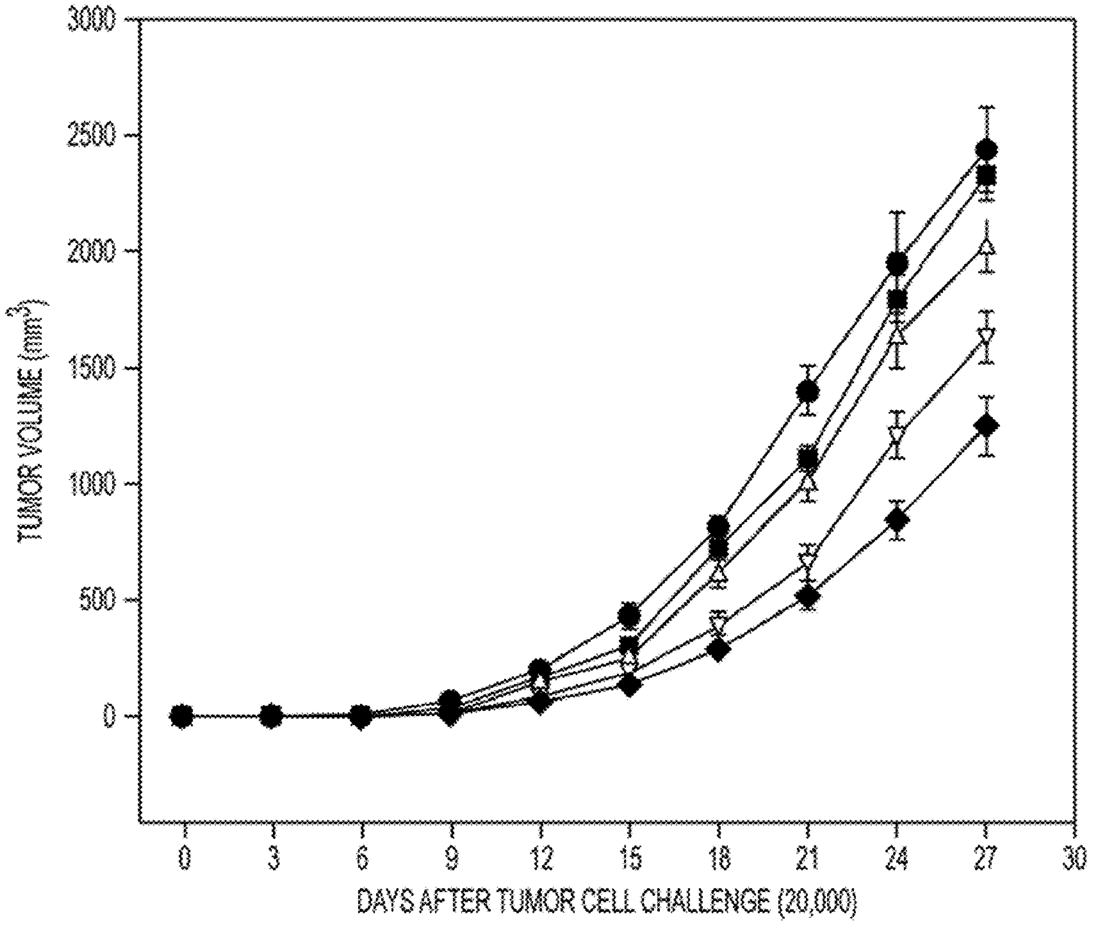
FIG. 2A shows tumor growth after immunization with purified hsp110. Tumor volume, in cubic millimeters, is plotted against the number of days after challenge with 20,000 colon 26 tumor cells, for mice immunized with PBS (circles), 40 μg of liver-derived hsp110 (squares), 20 μg of tumor derived hsp110 (upward triangles), 40 μg of tumor derived hsp110 (downward triangles) and 60 μg of tumor derived hsp110 (diamonds).
Figure 2B:
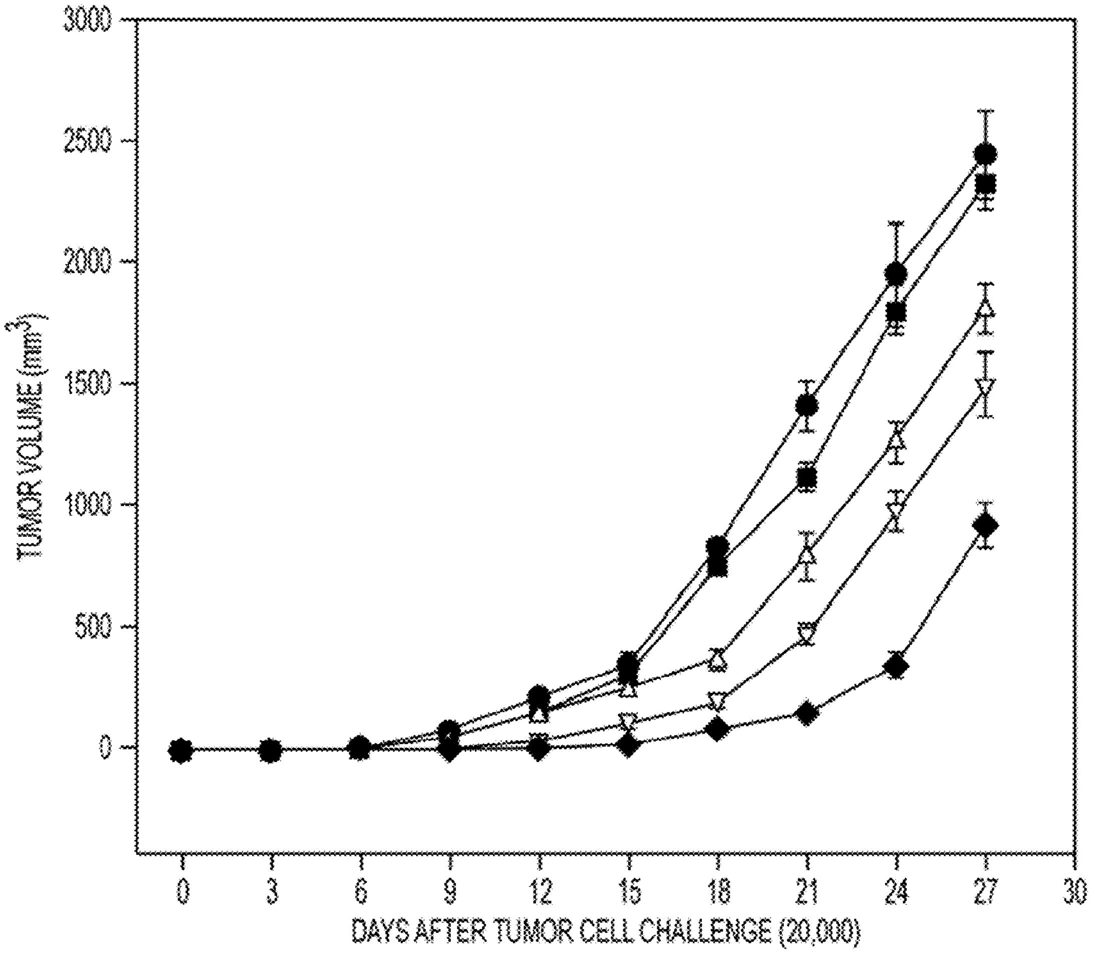
FIG. 2B shows tumor growth after immunization with purified grp170. Tumor volume, in cubic millimeters, is plotted against the number of days after challenge with 20,000 colon 26 tumor cells, for mice immunized with PBS (circles), 40 μg of liver-derived grp170 (squares), 20 μg of tumor derived grp170 (upward triangles), 40 μg of tumor derived grp170 (downward triangles) and 60 μg of tumor derived grp170 (diamonds).

The results of vaccination with hsp110 and grp170 are presented in FIGS. 2A and 2B, respectively. All mice that were immunized with PBS and liver derived hsp110 or grp170 developed rapidly growing tumors. In contrast, mice immunized with tumor derived hsp110 and grp170 showed a significant tumor growth delay. Thus, hsp110 or grp170 that is complexed with tumor proteins significantly inhibits tumor growth.

The inhibition effect was directly dependent on the dose of tumor derived hsp110 or grp170. Mice immunized with 20 μg (per injection) of hsp110 or grp170 showed slight or no inhibition of colon 26 tumor growth, while those immunized with 40 or 60 μg of hsp110 or grp170 showed increasingly significant tumor growth delay. On each day examined (15, 21, 27 days after challenge), the mean volumes of the tumors that developed in mice immunized with hsp110 and grp170 at doses of 40 and 60 μg were significantly smaller than those of control mice ($p<0.01$, student's t test). However, the differences in the mean volumes of the groups injected with PBS or liver derived hsp preparations did not reach statistical significance.

Additional tumor rejection assays were performed by challenging mice with larger quantities of tumor cells (50,000 and 100,000). Similar inhibitory results were obtained for tumor derived hsp110 or grp170, although, as expected, these tumors grew more rapidly. Although grp170 was purified by conA-sepharose column, a contamination with conA can be ruled out because the protective immunity could only be observed in the mice immunized with grp170 preparations from tumor but not normal liver tissue.

On an equal molar, quantitative basis, grp170 appears to be more immunogenic than hsp110. The immunogenicity of grp78 was also tested by injecting 40 μg of protein, but no tumor growth delay was observed. These results indicate that grp78 is either not immunogenic, or is so at a low level only.

To test the generality of those observations in other systems, the immunogenicity of hsp110 and grp170 were tested in the methylcholanthrene-induced (MethA) fibrosarcoma. Based on the immunization data in colon 26 tumor model, mice were immunized twice with 40 μg hsp110 or grp170, and challenged with 100,000 MethA cells introduced by intradermal injection.

Figure 4A:
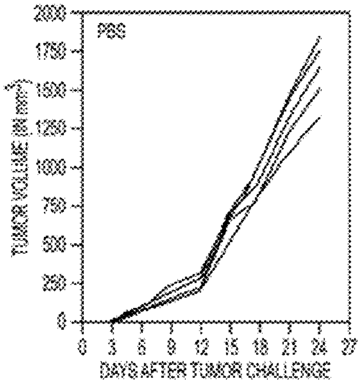
FIG. 4A is a graph depicting tumor size as a function of days after tumor challenge in mice immunized with PBS (control). Individual lines represent individual mice to show variations between animals.
Figure 4B:
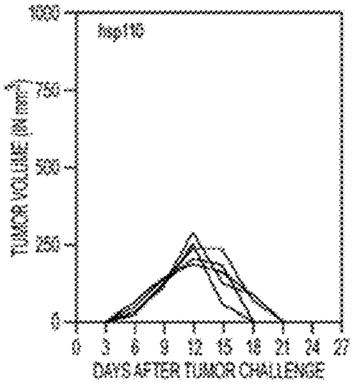
FIG. 4B is a graph depicting tumor size as a function of days after tumor challenge in mice immunized with hsp110 derived from MethA-induced tumor. Individual lines represent individual mice to show variations between animals.
Figure 4C:
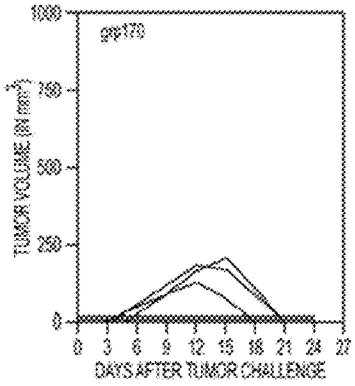
FIG. 4C is a graph depicting tumor size as a function of days after tumor challenge in mice immunized with grp170 derived from MethA-induced tumor. Individual lines represent individual mice to show variations between animals.
Figure 5A:
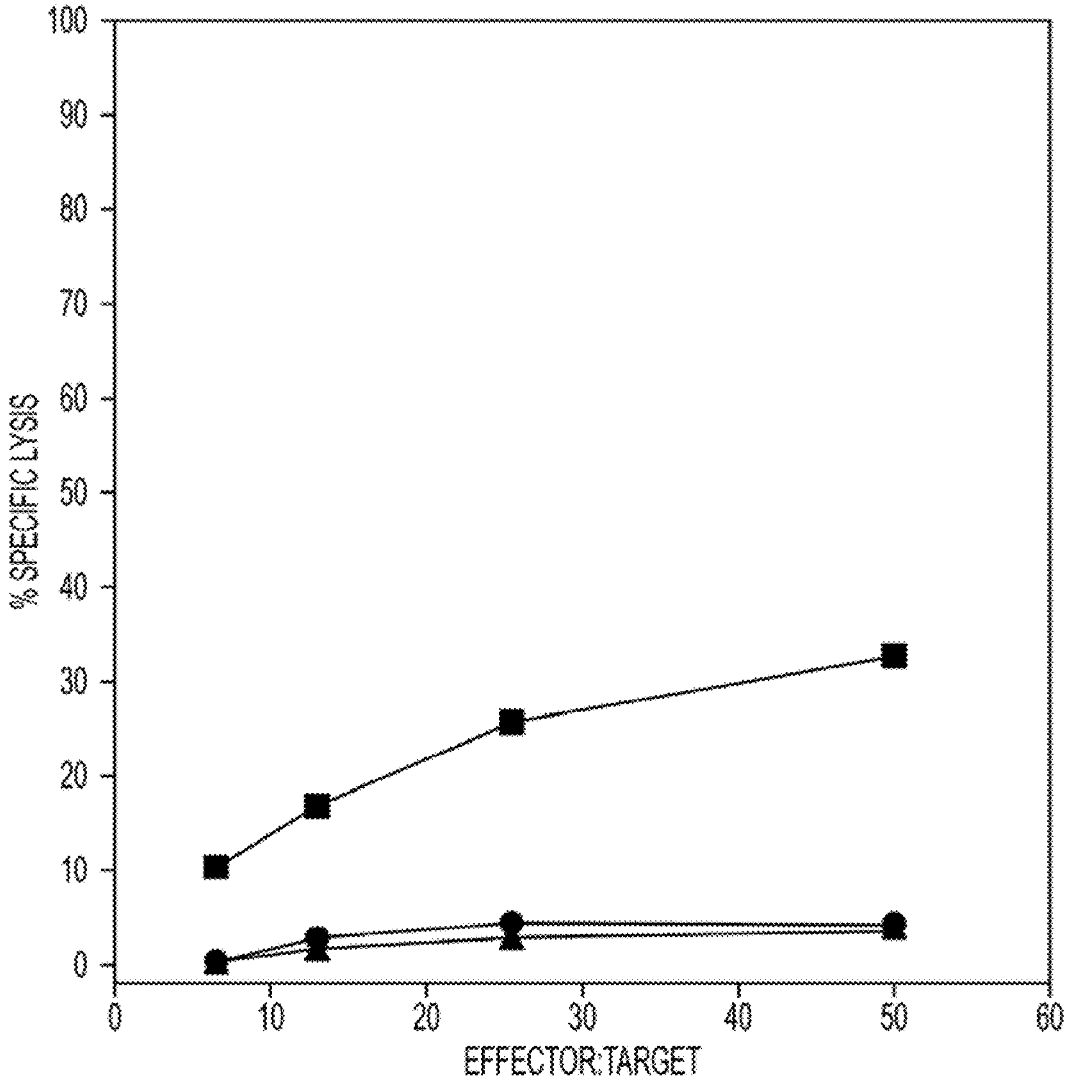
FIG. 5A is a graph showing results of a CTL assay targeting colon 26 tumor cells. Percent specific lysis is plotted as a function of effector:target ratio for control T cells (circles), T cells directed against hsp110 derived from colon 26 tumor cells (squares), and T cells directed against hsp110 derived from MethA tumor cells.
Figure 5C:
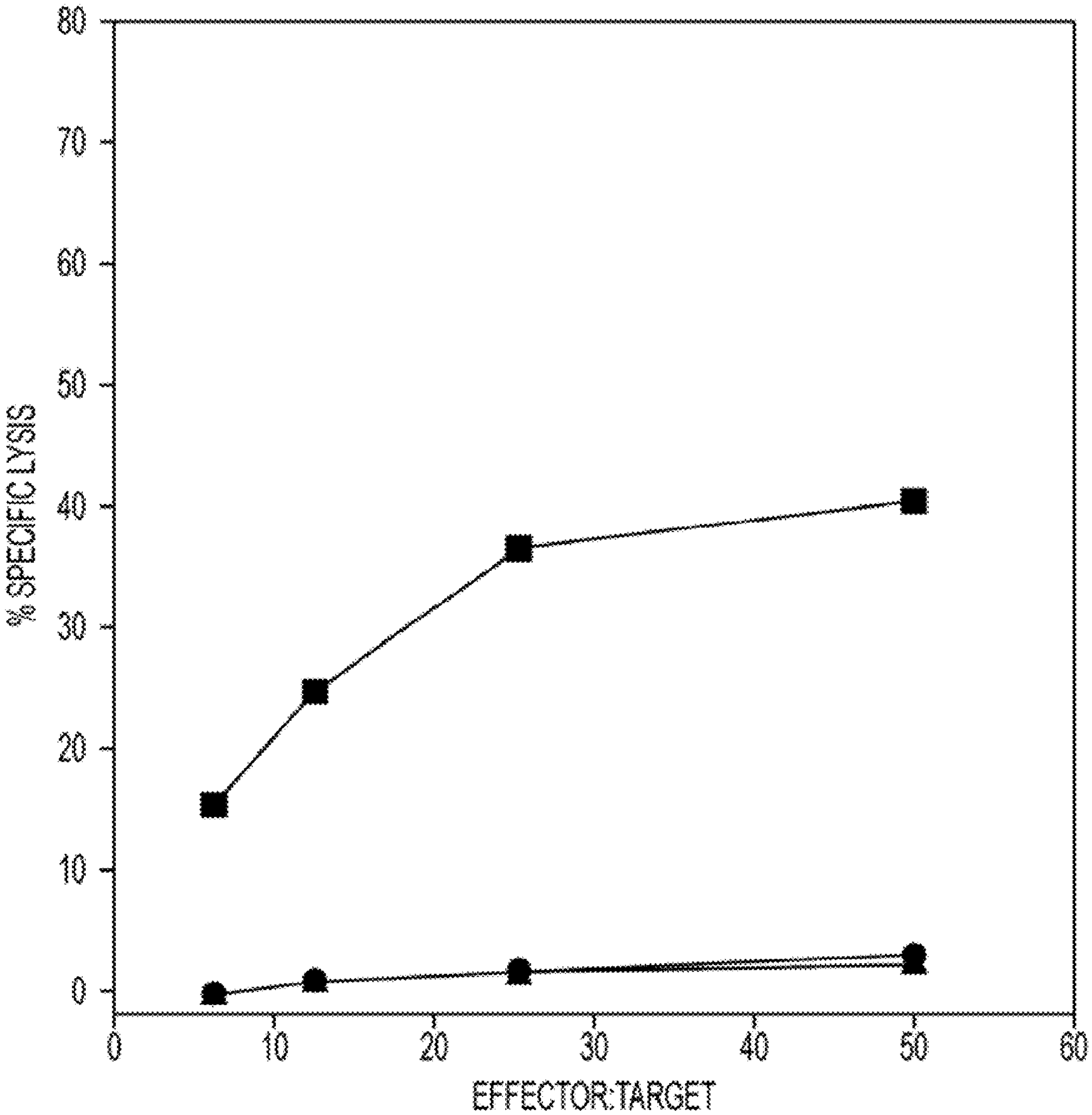
FIG. 5C is a graph showing results of a CTL assay targeting MethA tumor cells. Percent specific lysis is plotted as a function of effector:target ratio for control T cells (circles), T cells directed against hsp110 derived from colon 26 tumor cells (squares), and T cells directed against hsp110 derived from MethA tumor cells.
Figure 5D:
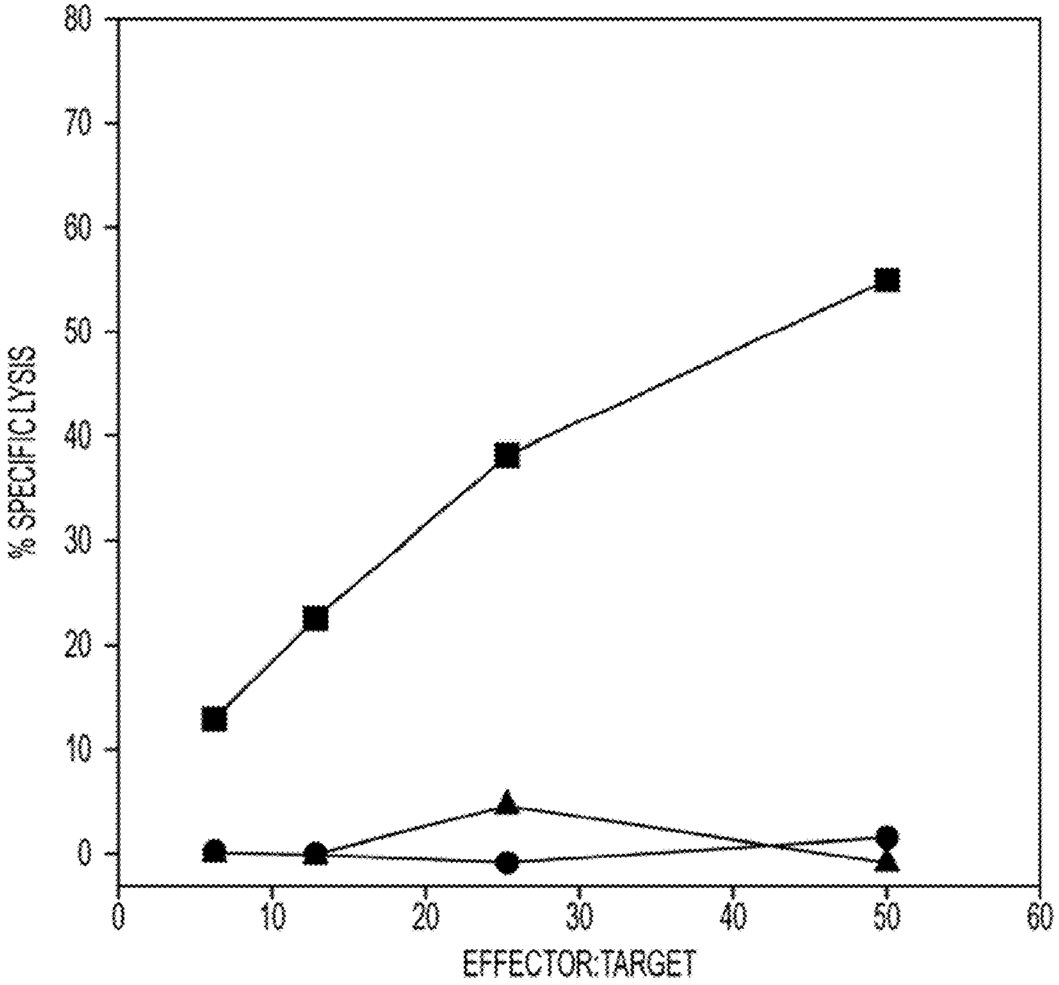
FIG. 5D is a graph showing results of a CTL assay targeting MethA tumor cells. Percent specific lysis is plotted as a function of effector:target ratio for control T cells (circles), T cells directed against grp170 derived from colon 26 tumor cells (squares), and T cells directed against grp170 derived from MethA tumor cells.

Line representations in FIGS. 4A-4C show the kinetics of tumor growth in each individual animal. Notable differences between individuals in tumor growth in response to immunization was observed in the grp170 group. Mice immunized with PBS developed MethA tumors (FIG. 4A). However, mice immunized with hsp110 (FIG. 4B) or grp170 (FIG. 4C) were protected. While most animals initially developed tumors, the tumors later disappeared. In the mice that were immunized with grp170, two of five mice completely failed to develop a palpable tumor (FIG. 4C).

Therapeutic Immunization

The aggressive colon 26 tumor was also examined in a therapy model. Tumor cells (500,000) were injected into the flank area and mice (10 per group) were vaccinated two times (separated by 7 days) with liver or colon 26 derived hsp110 or grp170, starting when the tumor was visible and palpable (e.g., day 6). The survival of mice was recorded as the percentage of mice surviving after the tumor challenge at various times.

Figure 3A:
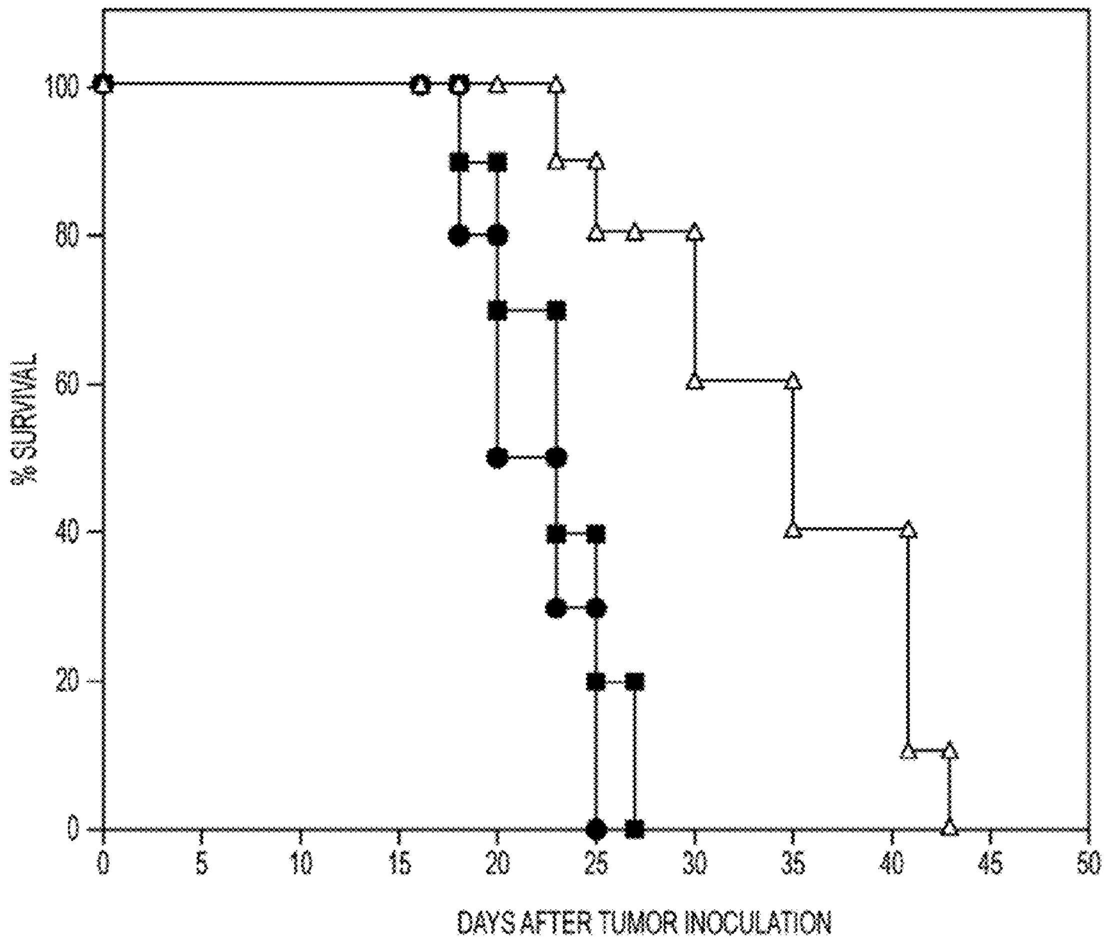
FIG. 3A is a plot showing the survival of Balb/C mice bearing colon 26 tumors after immunization with tumor derived hsp110. Percent survival is plotted as a function of days after tumor inoculation for mice immunized with PBS (control, circles), 40 μg liver-derived hsp110 (squares), and 40 μg tumor derived hsp110 (triangles).
Figure 3B:
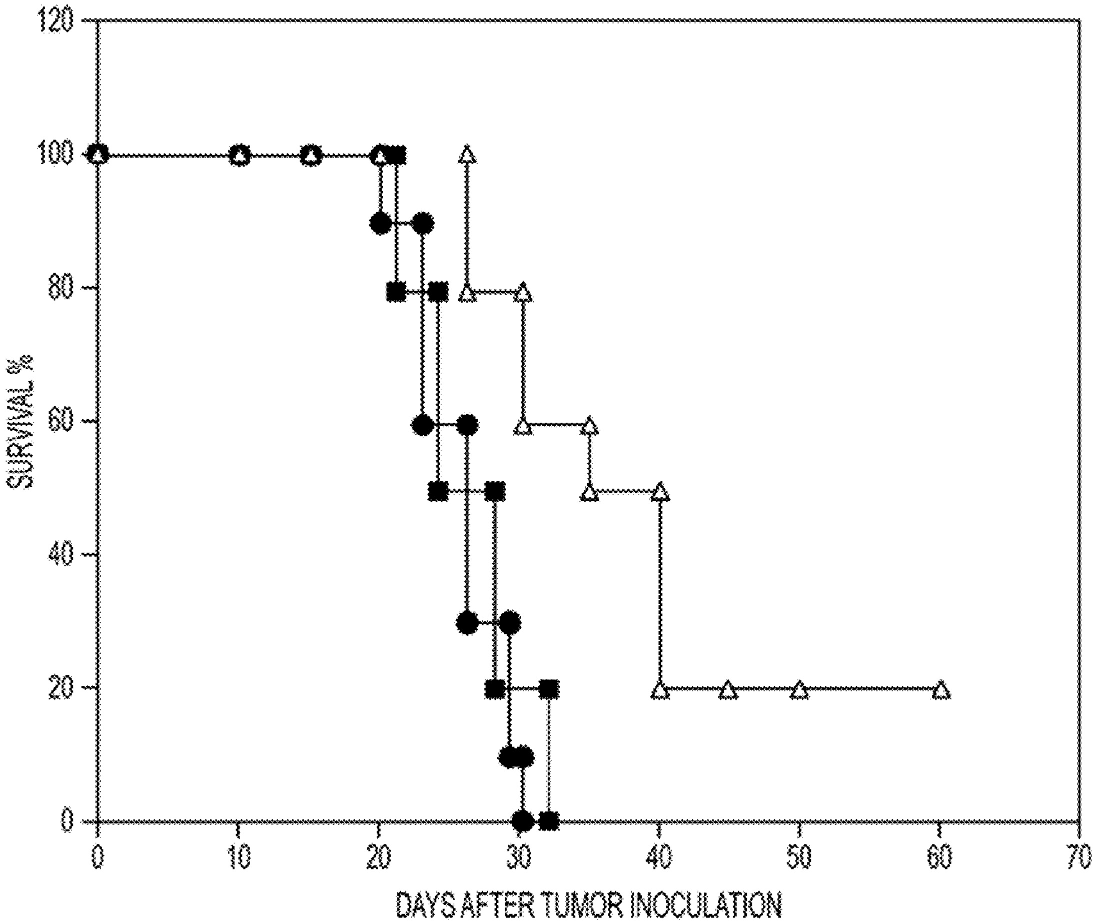
FIG. 3B is a plot showing the survival of Balb/C mice bearing colon 26 tumors after immunization with tumor derived grp170. Percent survival is plotted as a function of days after tumor inoculation for mice immunized with PBS (control, circles), 40 μg liver-derived grp170 (squares), and 40 μg tumor derived grp170 (triangles).
Figure 5B:
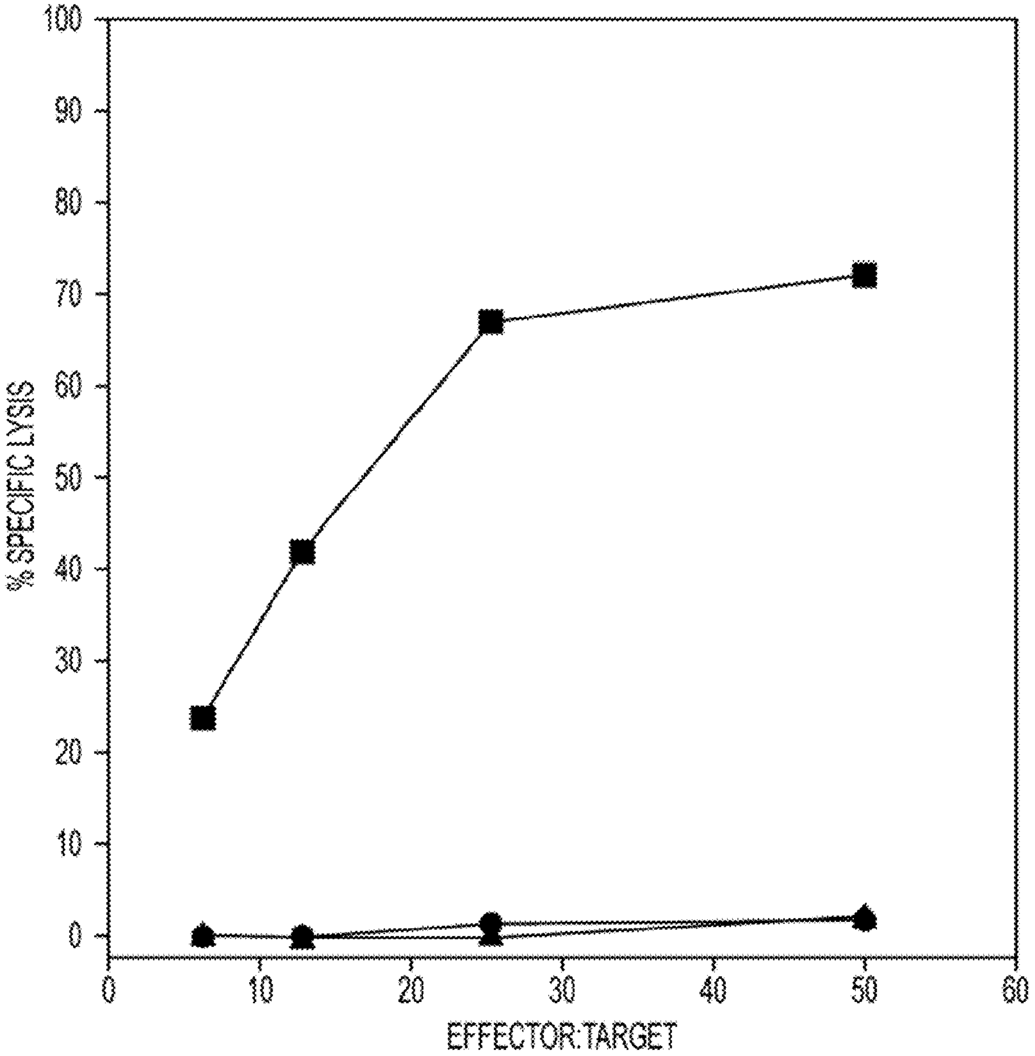
FIG. 5B is a graph showing results of a CTL assay targeting colon 26 tumor cells. Percent specific lysis is plotted as a function of effector:target ratio for control T cells (circles), T cells directed against grp170 derived from colon 26 tumor cells (squares), and T cells directed against grp170 derived from MethA tumor cells.

The results are shown in FIGS. 3A and 3B. Tumor bearing mice treated with autologous hsp110 (FIG. 3A) or grp170 (FIG. 3B) preparations showed significantly longer survival times compared to the untreated mice or mice immunized with liver derived hsp110 or grp170. All the control animals died within 30 days, but approximately one-half of each group survived to 40 days, and 20% of grp170 treated mice survived to 60 days. These results are consistent with the data obtained from the tumor injection assay, and again indicate that grp170 and hsp110 are effective anti-cancer vaccines. These data also show that grp170 appears to be the more efficient of the two proteins on an equal molar basis.

Example 3

CTL Assay

Because cellular immunity appears to be critical in mediating antitumor effects, a cytotoxic T lymphocyte (CTL) assay was performed to analyze the ability of tumor derived hsp110 or grp170 preparations to elicit a CD8+ T cell response. The results show that vaccination with tumor derived hsp110 or grp170 elicits an effective tumor specific CTL response.

Materials and Methods

Mice were immunized twice as described above. Ten days after the second immunization, spleens were removed and spleen cells ($1\times10^7$) were co-cultured in a mixed lymphocyte-tumor culture (MLTC) with irradiated tumor cells ($5\times10^5$) used for immunization for 7 days, supplemented with 10% FCS, 1% penicillin/streptomycin, 1 mM sodium pyruvate and 50 μM 2-mercaptoethanol. Splenocytes were then purified by Ficoll-Paque (Pharmacia) density centrifugation and utilized as effector cells. Cell-mediated lysis was determined in vitro using a standard $^{51}$Chromium-release assay. Briefly, effector cells were serially diluted in 96 V-bottomed well plates (Costar, Cambridge, Mass.) in triplicate with varying effector: target ratios of 50:1, 25:1, 12.5:1 and 6.25:1. Target cells ($5\times10^6$) were labeled with 100 μCi of sodium [$^{51}$Cr]chromate at 37° C. for 1-2 h. $^{51}$Cr-labeled tumor cells (5,000) were added to a final volume of 200 μl/well.

Wells that contained only target cells, with either culture medium or 0.5% Triton X-100, served as spontaneous or maximal release controls, respectively. After 4 h incubation at 37° C. and 5% $CO_2$, 150 μl supernatant was analyzed for radioactivity in a gamma counter. Percentage of specific lysis was calculated by the formula: percent specific lysis=100× (experimental release−spontaneous release)/(maximum release−spontaneous release). The spontaneous release was <10% of maximum release.

Results

As shown in FIG. 5, tumor-specific cytotoxicity against the tumor that was used for grp170 or hsp110 purification was observed. However, cells from naive mice were unable to lyse target cells. Furthermore, splenocytes from mice immunized with colon 26 derived hsp110 or grp170 preparations showed specific lysis for colon 26 tumor, but not MethA tumor cells. Likewise, MethA derived hsp 10 or grp170 showed specific lysis for MethA but not colon 26 cells. These results demonstrate that vaccination with tumor derived hsp110 or grp170 elicits an effective tumor specific CTL response.

Example 4

Vaccination with Dendritic Cells Pulsed with Tumor Derived Protein

This example demonstrates the capacity of antigen presenting cells to play a role in the anti-tumor response elicited by hsp110 or grp170 immunization. The results show the ability of dendritic cells (DCs) to represent the hsp110 or grp170 chaperoned peptides. Moreover, immunotherapy with hsp110 or grp170 pulsed DC was more efficient than direct immunization with protein.

Materials and Methods

Bone marrow was flushed from the long bones of the limbs and depleted of red cells with ammonium chloride. Leukocytes were plated in bacteriological petri dishes at $2\times10^6$ per dish in 10 ml of RPMI-10 supplemented with 200 U/ml (=20 ng/ml) murine GM-CSF (R&D System), 10 mM HEPES, 2 mM L-glutamine, 100 U/ml penicillin, 100 μg/ml streptomycin, 50 mM 2-mercaptoethanol. The medium was replaced on days 3 and 6. On day 8, the cells were harvested for use. The quality of DC preparation was characterized by cell surface marker analysis and morphological analysis. DCs ($1\times10^7$/ml) were pulsed with tumor derived hsp110 or grp170 (200 μg) for 3 hrs at 37° C. The cells were washed and resuspended in PBS ($10^6$ pulsed DCs in 100 μl PBS per mouse) for intraperitoneal injection. The entire process was repeated 10 days later, for a total of two immunizations per treated mouse. Ten days after the second immunization, mice were challenged with colon 26 tumor cells ($2\times10^4$).

Results

Figure 6:
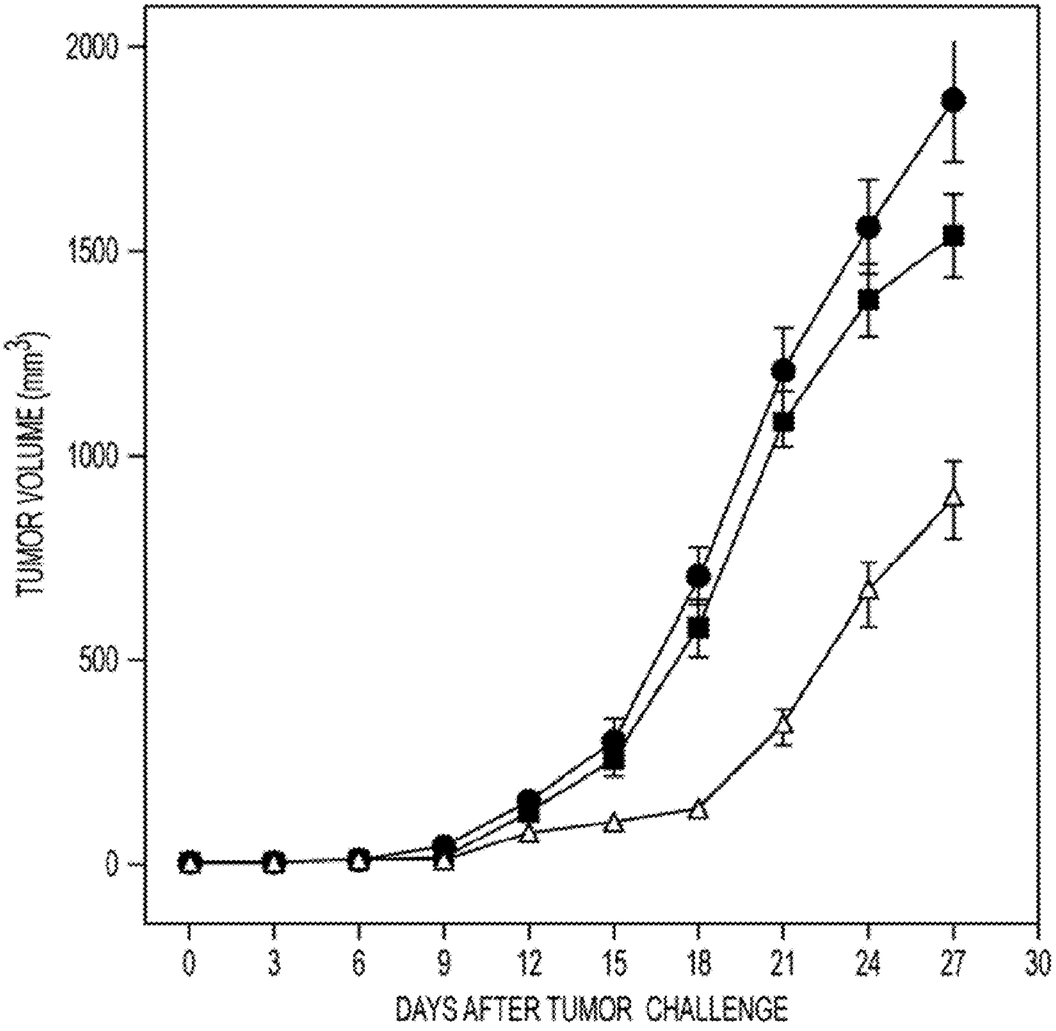
FIG. 6 is a graph showing tumor volume, in cubic millimeters, as a function of days after tumor challenge in mice immunized with grp170-pulsed dendritic cells (triangles), control dendritic cells (squares), or PBS (circles).

Tumors grew aggressively in the mice that received PBS or dendritic cells alone (FIG. 6). However, in mice immunized with tumor derived hsp110 or grp170 pulsed DCs, a significant slowing of tumor growth was observed. These results parallel the direct immunization studies with hsp110 or grp170. Comparison of direct immunization with protein (2 subcutaneous injections of 40 μg protein) versus immunization with pulsed DCs ($10^6$ DCs pulsed with 20 μg protein) suggests that pulsed DC based immunotherapy is more efficient, as it was more effective and used less protein.

Example 5

Production of More Effective Vaccines Through Heat Treatment

This example demonstrates that stress proteins purified from heat-treated tumors are even more effective at reducing tumor size than stress proteins purified from non-heat-treated tumors. This increased efficacy may reflect improved peptide binding at higher temperatures as well as other heat-induced changes.

Mice were first inoculated subcutaneously with 100,000 colon 26 tumor cells on the flank area. After the tumors reached a size of approximately ⅓ cm, WBH was carried out as described before. Briefly, mice were placed in microisolator cages preheated to 38° C. that contained food, bedding and water. The cages were then placed in a gravity convection oven (Memmert model BE500, East Troy, Wis.) with preheated incoming fresh air. The body temperature was gradually increased 1° C. every 30 minutes until a core temperature of 39.5° C. (±0.5 C) was achieved. Mice were kept in the oven for 6 hours. The core temperature of the mice was monitored with the Electric laboratory Animal Monitoring system Pocket Scanner (Maywood, N.J.). Tumors were removed on the next day for purification of hsp110, grp170 and hsp70. Immunizations were performed as above, twice at weekly intervals, using PBS, 40 μg hsp110 derived from tumors, 40 μg hsp110 derived from WBH-treated tumor, 40 μg grp170 derived from tumors, 40 μg grp170 derived from WBH-treated tumor, 40 μg hsp70 derived from tumors, or 40 μg hsp70 derived from WBH-treated tumor. Mice were then challenged with 20,000 live colon 26 tumor cells. Tumor volume, in $mm^3$, was measured at 0, 3, 6, 9, 12, 15, 18 and 21 days after tumor challenge.

Figure 7:
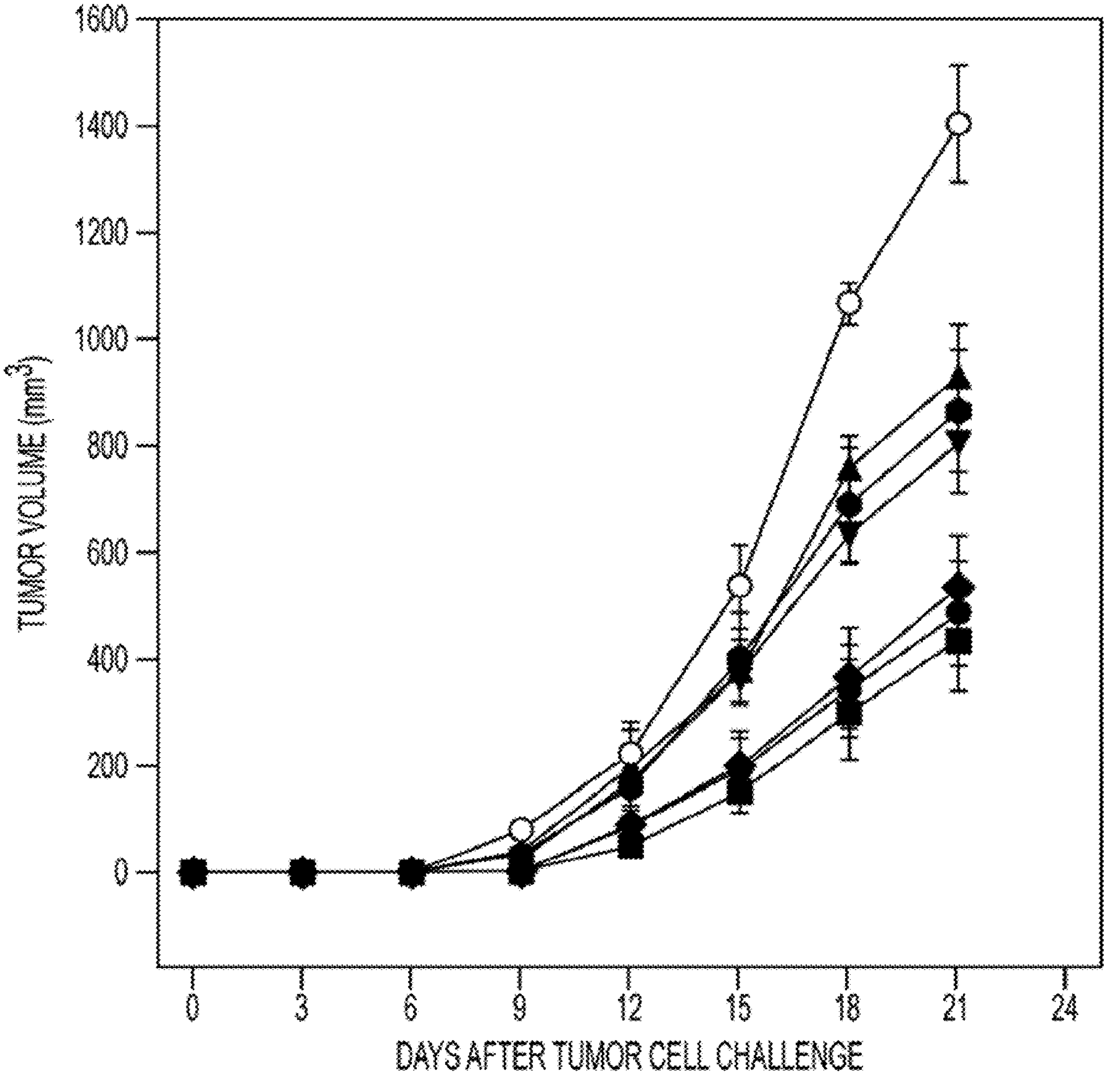
FIG. 7 is a graph showing tumor volume, in cubic millimeters, as a function of days after tumor challenge in mice immunized with PBS (open circles), grp170 derived from tumors (squares), grp170 derived from tumors of whole body heat-treated mice (upward triangles), hsp110 derived from tumors (downward triangles), hsp110 derived from tumors of whole body heat-treated mice (diamonds), hsp70 derived from tumors (hexagons), hsp70 derived from tumors of whole body heat-treated mice (solid circles).

The results are shown in FIG. 7. At 12 and 15 days after tumor challenge, both of the hsp110- and hsp70-treated groups showed significantly reduced tumor volume relative to PBS-treated mice. By 15 days following tumor challenge, hsp110 or hsp70 purified from WBH-treated tumor was significantly more effective at reducing tumor volume as compared to hsp110 or hsp70 purified from non-heat-treated tumor. However, by 15 days, grp170 purified from non-heat-treated tumor was more effective than grp170 from WBH-treated tumor.

These data indicate that fever-like exposures can influence the antigen presentation pathway and/or peptide binding properties of these two (heat inducible) hsps purified from colon 26 tumors but not a heat insensitive grp. Thus, the vaccine potential of hsp70 and hsp110 are significantly enhanced following fever level therapy. This could result from enhanced proteosome activity, enhanced peptide binding of the hsp, altered spectrum of peptides bound to the hsp, or other factors. Because the hsps were purified 16 hours after the 8-hour hyperthermic exposure, the effect is maintained for some time at 37° C. The factors leading to this enhanced immunogenicity likely derive from an altered and/or enhanced antigenic profile of hsp bound peptides. Stability following the hyperthermic episode suggests up-stream changes in antigen processing that are still present many hours later, e.g. stimulation of proteosome activity. Another feature of fever-like hyperthermia is the highly significant induction of hsps in colon 26 tumors. Therefore, fever-like heating not only provides a more efficient vaccine in the case of the hsps examined, but also a lot more of it. Finally, it is intriguing that the observed increase in vaccine efficiency resulting from hyperthermia is seen only for hsp110 and hsc70. Grp170, which is regulated by an alternative set of stress conditions such as anoxia and other reducing states, but not heat, is diminished in its vaccine potential by heat.

In addition to these observations, the data shown in FIG. 7 illustrate that grp170 purified from unheated, control tumors (mice) is significantly more efficient in its vaccine efficiency when compared on an equal mass basis to either hsp70 or hsp110 (without heat). This increased efficiency of grp170 compared to hsp110 is also reflected in the studies described above. This comparison is based on administration of equal masses of these proteins and the enhanced efficiency of grp170 is further exacerbated when molecular size is taken into account (i.e. comparisons made on a molar basis). Third, hsp70 is seen here to be approximately equivalent in its vaccine efficiency (again, on an equal mass but not equal molar basis) to hsp110.

Example 6

Chaperoning Activity of Grp170 and Hsp110

This example demonstrates, through a protein aggregation assay, the ability of grp170 and hsp110 to chaperone protein and prevent aggregation. The results show the increased efficiency of grp170 and hsp110 as compared to that demonstrated for hsp70 (Oh et al., 1997, J. Biol. Chem. 272:31636-31640).

The ability of the stress proteins to prevent protein aggregation induced by heat treatment was assessed by the suppression of the increase in light scattering obtained upon heat treatment in the presence of a reporter protein, firefly luciferase. Luciferase was incubated with equimolar amounts of hsp110 or grp170 at 43° C. for 30 minutes. Aggregation was monitored by measuring the increase of optical density at 320 nm. The optical density of the luciferase heated alone was set to 100%.

Figure 8:
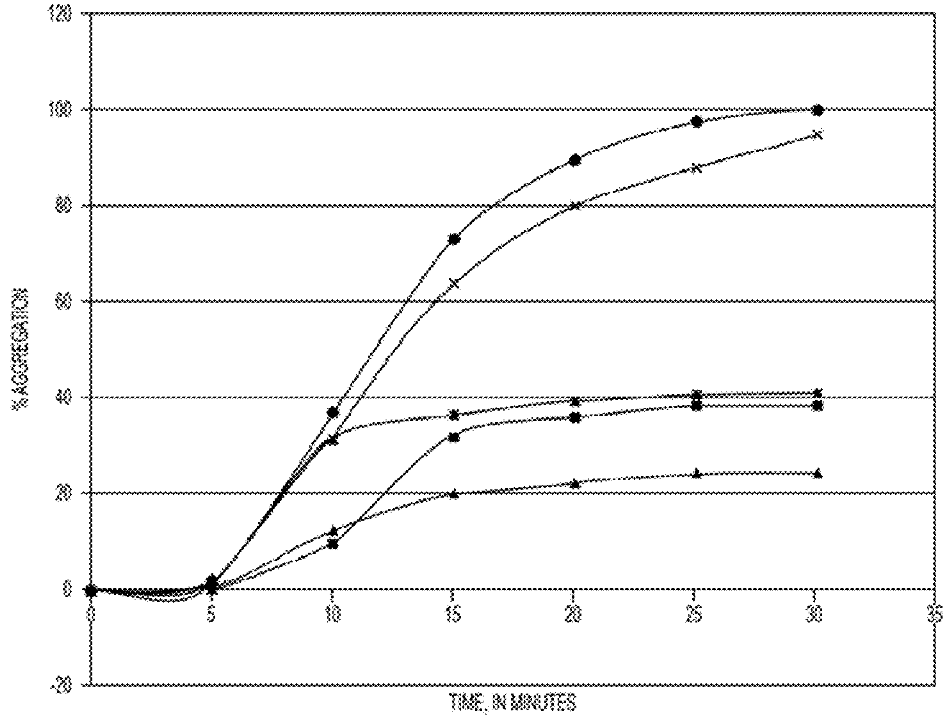
FIG. 8 is a graph showing percent protein aggregation (determined by light scattering) as a function of time, in minutes, for luciferase incubated with hsp110+hsp70+hsp25 at a molar ratio of 1:1:1:1 (squares), hsp110 at 1:1 (triangles), hsp25 at 1:1 (X's), grp170 at 1:1 (asterisks), or luciferase alone (circles).

The results are shown in FIG. 8. Hsp110 in a 1:1 molar ratio with luciferase limited aggregation to approximately 20% as compared to the 100% aggregation observed with luciferase alone. Grp170 in a 1:1 molar ratio with luciferase resulted in approximately 40% aggregation. These are the same conditions as used by Oh et al., 1997, J. Biol. Chem. 272:31636-31640, which resulted in 70% aggregation with hsp70 in a 1:1 molar ratio with luciferase. Thus, both grp170 and hsp110 demonstrate a greater efficiency than hsp70 in binding protein and preventing aggregation. Based on studies in which the loop domain of hsp110 was deleted (Oh et al., 1999, J. Biol. Chem. 272(22):15712-15718), this increased efficiency in chaperoning activity is likely attributable to the larger loop domain found in both hsp110 and grp170.

Hsp110 and grp170 both appear to exhibit a peptide binding cleft. However, hsp110 and grp170 differ dramatically from the hsp70s in their C-terminal domains which, in the case of hsp70 proteins, appears to function as a lid for the peptide binding cleft and may have an important influence on the properties of the bound peptide/protein and/or the affinity for the associated peptide/protein. Both hsp110 and grp170 appear to be more significantly efficient in binding to and stabilizing thermally denatured proteins relative to hsc70. This may reflect these structural differences and influence peptide binding properties, a factor in the ability of stress proteins to function as vaccines. While hsp70 and hsp110 are approximately similar in vaccine efficiency, they may bind differing subsets of peptides, i.e. hsp110 may carry antigenic epitopes that do not readily bind to hsc70, i.e. they may exhibit differing vaccine potential if not differing (mass) efficiencies. A similar argument can be made for grp170. The significant differences in molar efficiencies of these stress proteins may result from differing peptide binding affinities, differing properties of peptides bound to each stress protein family, or differing affinities of antigen presenting cells to interact with each of these four stress protein groups. Also noteworthy is that grp170, the most efficient vaccine in this group, is the only glycoprotein of the group.

Example 7

Interaction of hsp110 with hsp25 and hsp70

This example demonstrates the native interactions of hsp110, which protein was found to reside in a large molecular complex. Immunoblot analysis and co-immunoprecipitation studies identified two other heat shock proteins as components of this complex, hsp70 and hsp25. When examined in vitro, purified hsp25, hsp70 and hsp110 were observed to spontaneously form a large complex and to directly interact with one another. When luciferase was added to this in vitro system, it was observed to migrate into this chaperone complex following heat shock. Examination of two deletion mutants of hsp110 demonstrated that its peptide-binding domain is required for interaction with hsp25, but not with hsp70. The potential function of the hsp110-hsp70-hsp25 complex is discussed.

Materials & Methods

Reagents

The rabbit anti-hsp110 antibody has been characterized by Lee-Yoon, D. et al., 1995, J. Biol. Chem. 270, 15725-15733. Affinity purified mouse anti-hsc70 monoclonal antibody, rabbit anti-murine hsp25 antibody, rat anti-hsp90 antibody and rat anti-TCP-1a monoclonal antibody, as well as recombinant hsc70 and murine hsp25 were all obtained from StressGen Biotechnological Corp (Victoria, Canada). Anti-His Antibody was purchased from Amersham. Colon 26 tumor cells were cultured in DMEM supplemented with 10% calf serum in 5% $CO_2$ incubator.

Plasmid Construction and Expression

Purification of recombinant His-tagged hsp110 and two deletion mutants used here have been described by Oh, H. J. et al., 1997, J. Biol. Chem. 272, 31696-31640; and Oh, H. J. et al., 1999, J. Biol. Chem. 274, 15712-15718. Briefly, for the construction of hsp110 mutants, primers 5'-GCTAGAGGATCCTGTGCATTGCAGTGTGC AATT (SEQ ID NO: 1) –/–CAGCGCAAGCTTACTAGTCCAGGTCCATATTGA-3' (SEQ ID NO: 2) (Mutant #1, a.a. 375-858) and 5'-GACGACGGATCCTCTGTCGAGGCAGACATGGA (SEQ ID NO: 3)–/–CAGCGCAAGCTTACTAGTCCAGGTCCATATTGA-3' (SEQ ID NO: 4) (mutant #2, a.a. 508-858) were used in the polymerase chain reaction. The PCR products were cloned into pRSETA vector (Invitrogen), and a $His_6$-(enterokinase recognition sequence) and additional Asp-Arg-Trp-Gly-Ser (for mutant #1) or Asp-Arg-Trp (for mutant #2) were added to the N-terminal of hsp110 mutants. Plasmids were transformed into *E. coli* strain JM109 (DE3) and expression products were purified by Ni2-nitrilotriacetic acid-agarose column (QIAGEN, Inc.). The protein concentration was measured using the Bio-Rad protein assay kit.

Purification of Native hsp110

Cells were washed with phosphate-buffered saline and homogenized with a Teflon homogenizer with 5 volumes of buffer (30 mM $NaHCO_3$, pH7.5, 1 mM phenylmethylsulfonyl fluoride). The homogenates were centrifuged for 20 min at 12,000×g, supernatant were further centrifuged for 2 h at 100,000×g. Cell extracts were first applied to Con A-sepharose column, unbound proteins were collected and loaded on ion exchange column (Mono Q, Pharmacia) equilibrated with 20 mM Tris.HCl, pH 7.5, 200 mM NaCl, 0.1 mM dithiothreitol. Bound proteins were eluted with a linear salt gradient (200 mM~350 mM NaCl). Hsp110 pooled fractions were concentrated using centricon 30 (Amicon) and applied to size exclusion column (superose 6, Pharmacia) for high performance chromatography (HPLC) equilibrated with 20 mM Tris-HCl, pH8.0, 150 mM NaCl, 1 mM DTT), then eluted with at a flow rate of 0.2 ml/min. Thyroglobulin (669 kDa), ferritin (440 kDa), catalase (158 kDa), albumin (67 kDa) and ovalbumin (43 kDa) were used as protein markers.

Western Blot Analysis

Cells were washed with PBS and lysed in 50 mM Tris.HCl, pH 7.5, 150 mM NaCl, 2 mM EDTA, 1% Triton X-100 and protease inhibitors. After incubation on ice for 30 min, cell extracts were boiled with equal volume of SDS sample buffer (50 mM Tris-HCl, pH 6.8, 5% β-mercaptoethanol, 2% SDS, 10% glycerol) for 10 min and centrifuged at 10,000 g for 20 min. Equivalent protein samples were subjected to 7.5-10% SDS-PAGE and electro-transferred onto immobilon-P membrane (Millipore Ltd., UK). Membrane were blocked with 5% non-fat milk in TBST (20 mM Tris-HCl, pH 7.4, 137 mM NaCl, 0.05% Tween-20) for 1 h at room temperature, and then incubated for 2 h with primary antibodies diluted 1:1000 in TBST. After washing, membranes were incubated with horseradish peroxidase-conjugated goat anti-rabbit IgG or goat anti-mouse IgG diluted 1:2,000 in TBST. Immunoreactivity was detected using the Enhanced Chemiluminescence detection system (Amersham, Arlington Heights, Ill.).

Immunoprecipitation

Cells were washed 3 times with cold PBS and lysed in Buffer (10 mM Tris-HCl, pH 7.4, 150 mM NaCl, 2 mM EDTA, 0.5% Sodium Deoxycholate, 0.1% SDS, 1% NP40, 10 μg/ml leupeptin, 25 μg/ml aprotinin, 1 mM ABESF, 0.025% NaN3). The lysates were centrifuged and supernatant was presorbed with 0.05 volume preimmune serum together with 30 ml protein A beads for 1 h. The lysates were incubated overnight at 4° C. with hsp110 antibody (1:100) or hsc70 antibody (1:200) or hsp25 antibody (1:100). For in vitro analysis of interaction within chaperones, recombinant wild-type hsp110 and hsp110 mutants first were incubated with hsc70 or hsp25 at 30° C. Then hsc70 antibody or hsp25 antibody were added and further incubated overnight at 4° C. Immune complex were precipitated with Protein A-agarose (30 μl) for 2 h. Precipitates were washed 3 times with 50 mM Tris.HCl, pH 7.5, 150 mM NaCl, 0.1% SDS, 0.5% sodium deoxycholate, 1% NP40, 30-40 μl SDS sample buffer was added and boiled for 5 min. Supernatant were loaded to 7.5-12% SDS-PAGE and analyzed by immunoblotting.

Interaction Between Luciferase and HSPs

Luciferase (Boehringer Mannheim) was incubated with hsp110, hsc70 and hsp25 (150 nM each) in 25 mM Hepes, pH 7.9, 5 mM magnesium acetate, 50 mM KCl, 5 mM b-mercaptoethanol, and 1 mM ATP at room temperature or 43° C. for 30 min. The solution was centrifuged at 16,000 g for 20 min, the supernatant was loaded on the Sephacryl S-300 column (Pharmacia) equilibrated with 20 mM Tris.HCl, pH 7.8, 150 mM NaCl and 2 mM DTT. The protein was eluted at the flow rate of 0.24 ml/min at 4° C. Fractions were collected and analyzed by western blotting.

Results

Existence of hsp110 as a Large Complex Containing hsc70 and hsp25

Figure 9A:
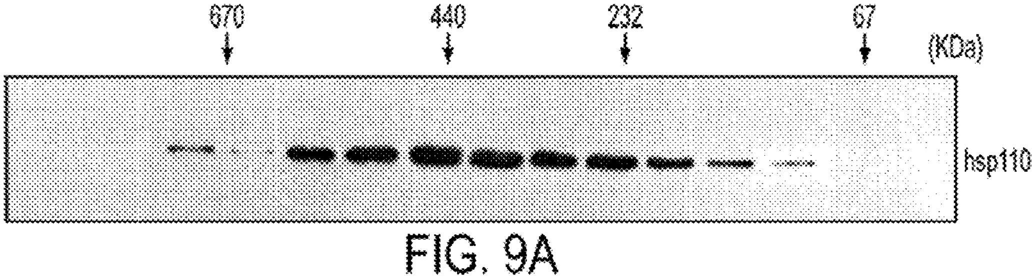
FIG. 9A shows chromatography profiles of native hsp110 separated by size exclusion column for FPLC for characterization of hsp110 complex. Hsp110 was partially purified by successive chromatography on Con-A sepharose and mono Q column. Pooled fraction was loaded on the superose 6 column, proteins in each fraction were detected by immunoblotting with antibodies for hsp110, hsc70 and hsp25 (1:1000).

Characterization of native hsp110 in Colon26 cells was performed to investigate the physiological role of hsp110. After cell extracts were applied to successive chromatography on Con-A sepharose and Mono Q columns, partially purified hsp110 fraction was loaded onto the Superose 6 size exclusion column (maximum resolution of 5,000 kDa). It was observed that the ConA and ion exchange purified hsp110 fraction eluted from the Superose column in those fractions of size range between 200 to 700 kDa (FIG. 9A). Work was repeated using sephacryl 300 (allyl dextran/bisacrylamide matrix) column and analysis provided similar data.

Figure 9B:
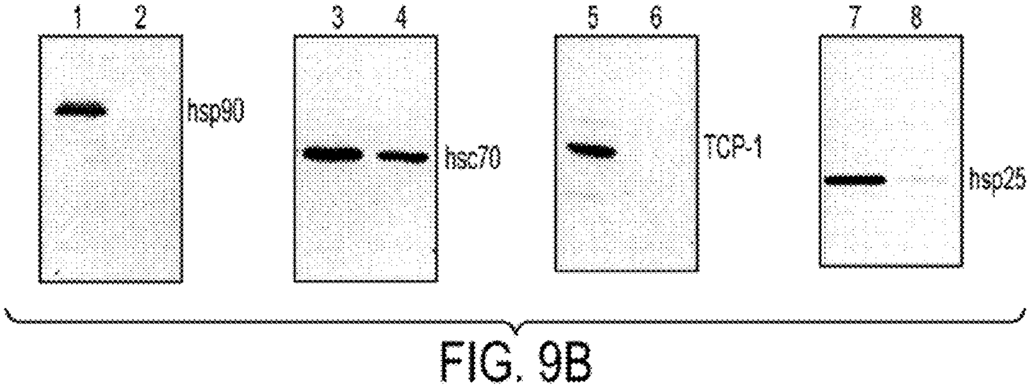
FIG. 9B is an immunoblot that shows composition analysis of native hsp110 complex. Purified hsp110 fraction was detected by antibodies for hsp90 (lane 1, 2), hsc70 (lane 3, 4), TCP-1 (lane 5, 6) and hsp25 (lane 7, 8). Total cell extracts was also used as a positive control (lane 1, 3, 5, 7).

Since hsp110 was eluted as one broad peak of high molecular mass, it is reasonable that this large in situ hsp110 complex might also contain additional components, potentially including other molecular chaperones and/or cellular substrates that may interact with hsp110. To investigate this possibility, the purified hsp110 fraction derived from both ion exchange and size exclusion columns was examined by immunoblotting for other HSPs using available antibodies. As shown in FIG. 9B, antibodies for hsp90, hsc70, T-complex polypeptide1 (TCP-1) and hsp25 were used. All four proteins were readily detectable in the total cell lysate (lanes 1, 3, 5, and 7). When the hsp110 fraction was examined, TCP-1 and hsp90 were not observed (lane 2 and 6). However, both hsc70 and hsp25 were found to co-purify with hsp110 with a significantly greater fraction of total cellular hsc70 present than of hsp25. Chromatography profile of hsc70 and hsp25 from size exclusion column also showed the similar pattern as that of hsp110 (FIG. 9A).

Figures 10A, 10B, 10C:
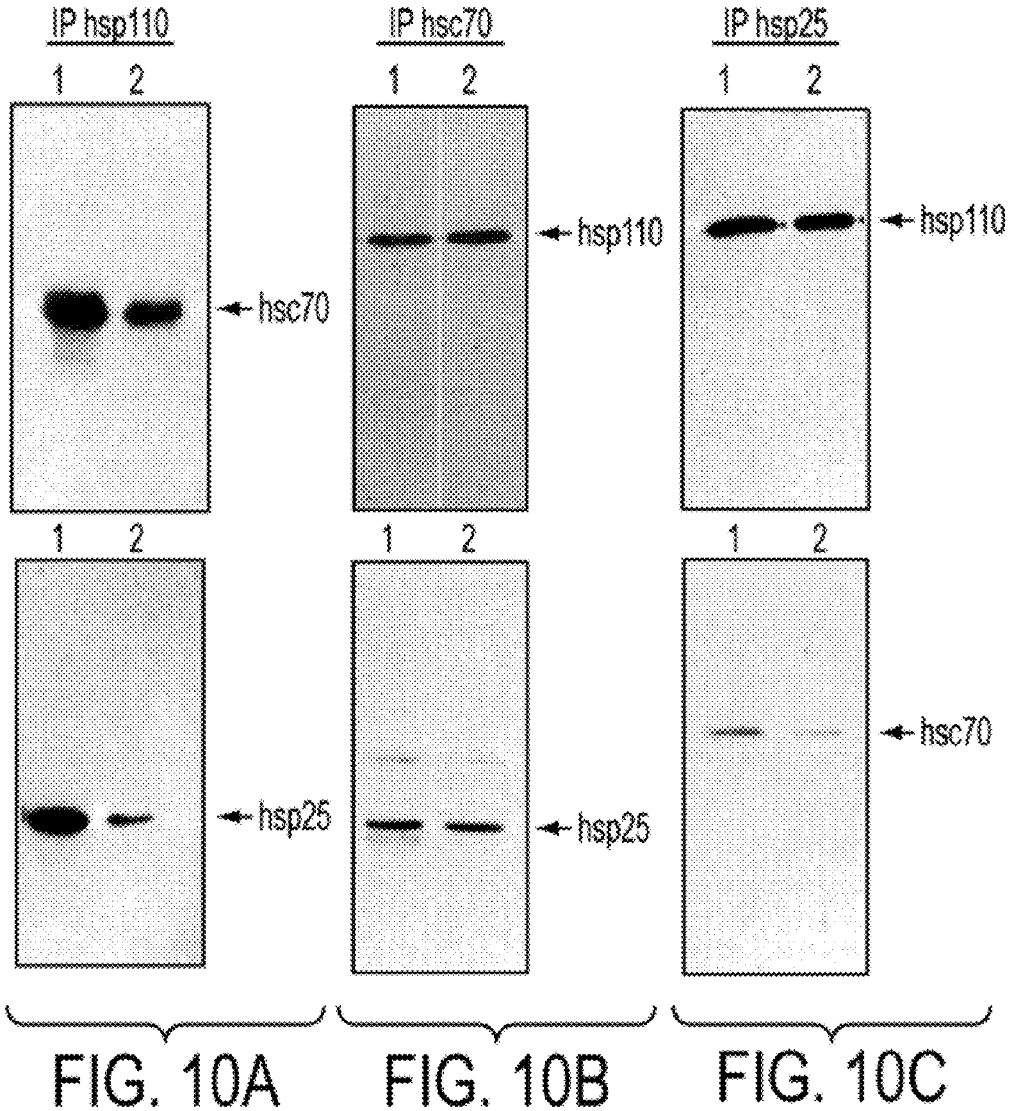
FIGS. 10A-C are immunoblots showing reciprocal immunoprecipitation between hsp110 and hsp70, hsp25. Following incubation with the indicated antibodies, protein A-sepharose was added and further incubated at 4° C. overnight, immunoprecipitates were examined by immunoblotting with hsp110, hsp70 and hsp25 antibodies. Total cell extracts was also used as a positive control (lane 1).

To determine whether this co-purification also reflected an interaction between these three molecular chaperones, a reciprocal co-immunoprecipitation analysis was conducted with Colon26 cell extracts and hsp110 fractions. Hsc70 and hsp25 were shown to precipitate with hsp110 using an anti-hsp110 antibody (FIG. 10A). Conversely, hsp110 was co-precipitated by an anti-hsc70 antibody or anti-hsp25 antibody (FIGS. 10B and 10C, top). Pre-immune serum was also used to perform immunoprecipitation as a negative control with a correspondingly negative outcome. Finally, interaction between hsc70 and hsp25 was analyzed by using antibodies for hsc70 and hsp25. Again, these two proteins were observed to co-immunoprecipitate with one (FIGS. 10B and 10C, bottom). From the above study, one can conclude that hsp110, hsc70 and hsp25 interact in situ, either directly or indirectly.

Analysis of Interaction of hsp 110 with hsc70 and hsp25 in vitro

To determine whether hsp110, hsc70 and hsp25 interact in vitro, and whether they are capable of forming a large molecular weight complex by using purified protein components, luciferase was added as a potential substrate to this mixture. It has been shown that hsp110 can solubilize this reporter protein following heat denaturation. Luciferase, with hsp110, hsc70 and hsp25 mix (at 1:1 molar ratio) were incubated at room temperature or at 43° C. for 30 minutes. The soluble fractions were loaded onto a Sephacryl S-300 column, eluted fractions were run on SDS-PAGE and analyzed by immunoblotting with antibodies for hsp110, hsc70, hsp25 and luciferase.

Figure 11A:
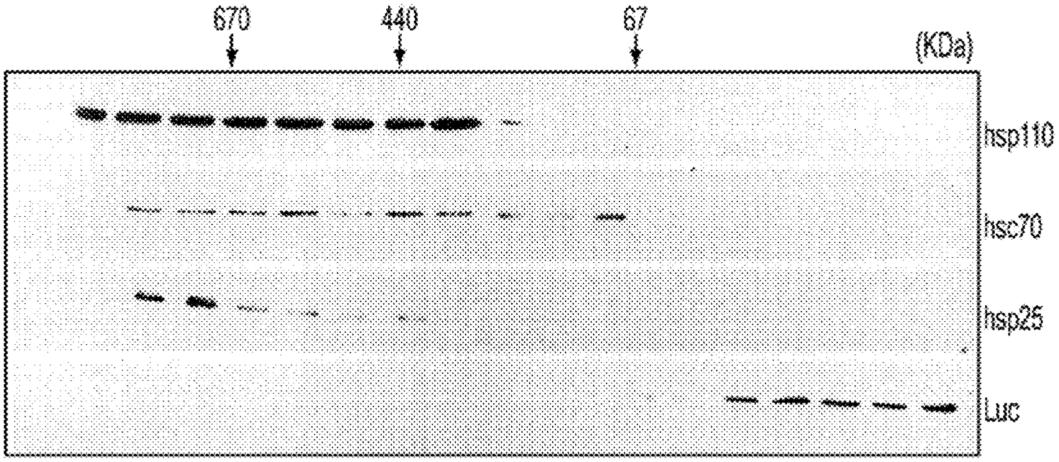
FIG. 11A shows immunoblots prepared when luciferase and Hsps were incubated at room temperature for 30 min, and soluble fraction after centrifugation at 16,000 g was loaded on Sephacryl S-300 column. The eluted fractions were analyzed by immunoblotting with antibodies for Hsps and luciferase.
Figure 11B:
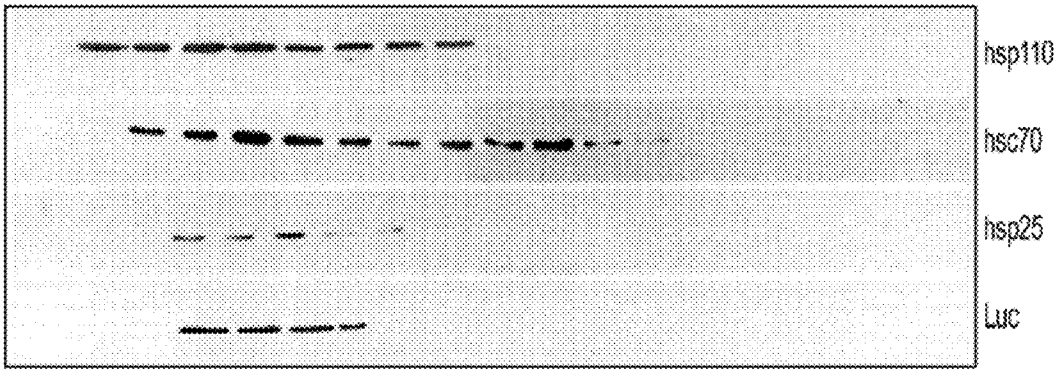
FIG. 11B shows immunoblots prepared when luciferase and Hsps were incubated at 43° C. for 30 min, and soluble fraction after centrifugation at 16,000 g was loaded on Sephacryl S-300 column. The eluted fractions were analyzed by immunoblotting with antibodies for Hsps and luciferase.

The results of this study are presented in FIGS. 11A and 11B. It was found that hsp110, hsc70 and hsp25 are again present in high molecule weight fractions, however these fractions were eluted at a significantly larger molecular size than that seen in vivo (FIG. 11A). Moreover, it was seen that heat treatment does not change elution pattern for hsp110, hsc70 or hsp25. However, luciferase, which does not co-elute with the hsp110 complex prior to heating (being present as a monomer), was observed to move into high molecule weight structure after the heat exposure (FIG. 11B). Almost all of the luciferase was sustained in a soluble form in these experiments. When heated alone, luciferase became rapidly insoluble. Heat shock did not affect the solubility of the three hsp110, hsc70 or hsp25.

Figure 12:
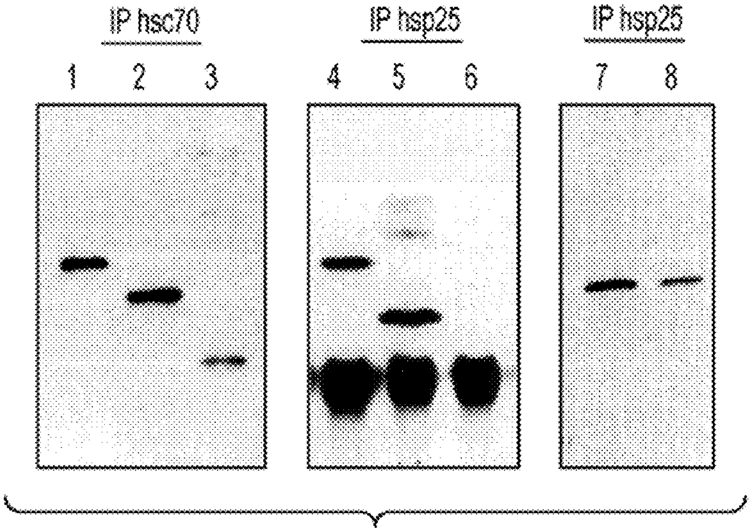
FIG. 12 shows the results of interaction analysis of hsp110 mutants and hsp70, hsp25 in vitro. *E. coli* expressed full-length hsp110 (lane 1, 4) and mutant #1 (lane 2, 5), mutant #2 (lane 3, 6) were incubated with hsc70 or hsp25 at 30° C. for 1 hour, then anti-hsc70 or anti-hsp25 antibodies were added. Immunoprecipitates were detected by anti-His antibody. In vitro interaction between hsc70 and hsp25 was also analyzed by the same method described above; hsc70 antibodies were used to test immunoprecipitate (lane 8). Total cell lysate was used as a positive control (lane 7). Equal amount of protein (2 μg) for wild-type hsp110, hsp110 mutants, hsc70 and hsp25 were included in each assay.

The above data indicate that hsp110, hsc70, and hsp25 co-purify in a large molecular weight structure in vitro, as does luciferase (if present) after heating. This does not indicate how these proteins interact themselves or that any two of them interact at all. That heated luciferase remains soluble, however, is evidence for its interaction with at least one of the chaperones. To determine how these proteins interact, co-immunoprecipitation experiments were performed again using the pairs of purified proteins. Hsc70 and hsp110 were found to interact in the absence of hsp25 (FIG. 12, lane 1) and correspondingly hsp110 was observed to precipitate with hsp25 alone, in the absence of hsc70 (lane 4). Lastly, hsc70 and hsp25 also co-precipitate in the absence of hsp110 (lane 8).

Finally, this in vitro study defining the interactions between hsp110, hsc70 and hsp25 was extended by examining two deletion mutants of hsp110 that have previously been shown to represent the most simplistic (i.e. functional and non-functional) forms of this chaperone (Oh, H-J. et al., 1999, J. Biol. Chem. 274, 15712-15718). The first mutant examined (#1) lacks the N-terminal ATP binding domain of hsp110, but contains the remaining sequence: i.e. the adjacent beta sheet peptide binding domain and other C-terminal sequences (size: 75 kDa and containing amino acids 375-858). This mutant has been shown to be fully functional in its ability to stabilize heat denatured luciferase in a folding competent state. The second mutant used here (#2), again lacked the ATP binding domain as well as the adjacent beta sheet (peptide binding) domain, but contained the remaining C terminal sequence (size: 62 kDa and containing amino acids 508-858). This mutant has recently been shown to be incapable of performing the chaperoning function of sustaining heat denatured luciferase in a soluble state.

Mutant #1 (no ATP binding domain) was observed to co-precipitate with both hsp70 (lane 2) and hsp25 (lane 5), indicating that these interactions do not involve its ATP binding domain. However, mutant #2 (lacking both the ATP region and the peptide-binding region of hsp110) was observed to only associate with hsp70 (lane 3). This indicates that hsp25 and hsp70 can interact with hsp110 at different sites and that the association of hsp110 with hsp25 requires the peptide-binding domain of hsp110.

Discussion

This example describes investigations into the native interactions of hsp110 in Colon26 cells. The results show that hsp110 co-purifies with both hsc70 and hsp25 and further, that the three proteins can be co-immunoprecipitated. To determine that the co-immunoprecipitation results can reflect direct interactions between these chaperones and to also define these interactions, in vitro studies using purified hsp110, hsc70 and hsp25 were undertaken. It was found that these three chaperones also spontaneously form a large molecular complex in vitro. Moreover, this complex forms in the absence of an added substrate, but substrate (luciferase) can be induced to migrate into the complex by a heat stress.

It is also shown that each pair of these proteins can interact directly, i.e. hsc70 with hsp110, hsc70 with hsp25, and hsp110 with hsp25. This, together with the co-precipitation data obtained from cell lysates, strongly argues that these interactions naturally occur in situ. Moreover, use of two deletion mutants of hsp110 demonstrate that its peptide-binding domain is required for hsp25 binding, but not for hsc70 binding, and that its ATP binding domain is not required for the interaction with either hsc70 or hsp25. This suggests that hsp110 binds to hsp25 through its peptide-binding domain. That hsc70-hsp110 binding occurs in the absence of the hsp110 peptide-binding domain suggests that hsc70 may be actively binding to hsp110 through its (i.e. hsc70's) peptide-binding domain, but does not exclude the possibility that the two proteins interact via the involvement of other C-terminal domains.

These interactions between hsp110 and hsc70 raise possibilities as to how these proteins may function cooperatively. Since the peptide-binding domain of hsc70 and hsp110 appears to represent the "business end" of these chaperones in performing chaperoning functions, one might expect that their peptide binding domains would be actively associated with substrate and not one another. This raises the possibility that this complex represents a chaperone "storage compartment" that awaits cellular requirements. However, the migration of heat denatured luciferase into this fraction following heat shock argues for an active chaperoning activity of the complex itself. It is possible that hsc70 may piggy-back hsp110 in a manner that allows transfer of substrate from hsp110 to hsc70 with subsequent folding in conjunction with DnaJ homologs and other chaperones.

Hsp110 has not yet been shown to have a folding function in conjunction with DnaJ co-chaperones, as is the case with hsc70 (Oh, H. J. et al., 1997, J. Biol. Chem. 272, 31696-31640; Oh, H. J. et al., 1999, J. Biol. Chem. 274, 15712-15718). However, hsp110 exhibits different ATP binding properties than do the hsp70s, and possible co-chaperones of hsp110 may be awaiting discovery. Previous in vitro studies have demonstrated that while sHSPs (e.g. hsp25) bind normative protein, refolding still requires the presence of hsp70 (Lee, G. J. et al., 1997, EMBO J. 16, 659-671; Jakob, U. et al., 1993, J. Biol. Chem. 268, 7414-7421; Merck, K. B. et al., 1993, J. Biol. Chem. 268, 1046-1052; Kampinga, H. H et al., 1994, Biochem. Biophys. Res. Commun. 204, 170-1177; Ehrnsperger, M. et al., 1997, EMBO J. 16, 221-229). Hsp110 and sHSPs may act in the differential binding of a broad variety of substrates for subsequent shuttling to hsp70-DnaJ containing chaperone machines.

That these three chaperones interact may represent a general phenomenon. Plesofsky-Vig and Brambl have recently shown that the small HSP of *Neurospora crassa*, called hsp30, binds to two cellular proteins, hsp70 and hsp88. Cloning and analysis of hsp88 has shown that it represents the hsp110 of *Neurospora crassa* (Plesofsky-Vig, N. and Brambl, R., 1998, J. Biol. Chem. 273, 11335-11341), suggesting that the interactions described here are phylogenetically conserved. In addition, Hatayama has described an interaction between hsp110 (referred to as hsp1105) and hsp70 in FM3A cells (Hatayama, T et al., 1998, Biochem. Biophys. Res. Comm. 248, 394-401). The size of the hsp110 complex and the interaction with hsc70 observed in the present example (which also employed the added step of ion exchange chromatography) are clearly similar to, and in excellent agreement with this recent report. Finally, hsp90 and TCP-1 were not observed in the hsp110 complex in the present study, despite its previously identified association with hsc70 and other proteins in the steroid hormone receptor. However, it has recently been shown that SSE1 encoding a yeast member of the hsp110 family is required for the function of glucocorticoid receptor and physically associates with the hsp90 (Liu, X. D. et al., 1999, J. Biol. Chem. 274, 26654-26660).

The data presented in this example suggest that this complex offers an enhanced capacity to hold a greater variety of substrate proteins in a folding competent state and/or to do so more efficiently. The results further suggest that there may be an enhanced ability gained to refold denatured proteins in the presence of additional chaperones.

Example 8

In Vitro Formation and Stability of Stress Polypeptide Complexes

This example demonstrates that complexes of stress polypeptides with immunogenic polypeptides can be generated in vitro and that such complexes remain stable following freezing and thawing. Moreover, hsp110 and grp170 are both capable of forming complexes with different peptides that include antigens associated with both cancer and infectious disease.

Figure 13:
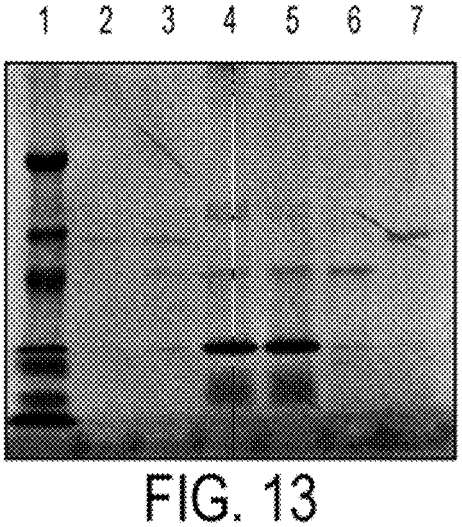
FIG. 13 shows the results of immunoprecipitation of her2/neu intracellular domain (ICD) with anti-hsp110 and anti-grp170 antibodies after formation of binding complexes in vitro. Lane 1 is a protein standard from 205 kDa to 7.4 kDa; lane 2 is hsp110+anti-hsp110 antibody; lane 3 is hsp110+ICD; lane 4 is grp170+ICD (in binding buffer); lane 5 is grp170+ICD (in PBS); lane 6 is ICD; and lane 7 is hsp110.

FIG. 13 shows the results of immunoprecipitation of her-2/neu intracellular domain (ICD) with anti-hsp110 and anti-grp170 antibodies after formation of binding complexes in vitro. Lane 1 is a protein standard from 205 kDa to 7.4 kDa; lane 2 is hsp110+anti-hsp110 antibody; lane 3 is hsp110+ICD; lane 4 is grp170+ICD (in binding buffer); lane 5 is grp170+ICD (in PBS); lane 6 is ICD; and lane 7 is hsp110.

Figure 14:
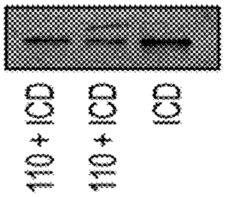
FIG. 14 is a western blot showing hsp110-ICD complex in both fresh (left lane) and freeze-thaw (center lane) samples, after immunoprecipitation of the complexes with anti-hsp110 antibody. The right lane is ICD.

FIG. 14 is a western blot showing hsp110-ICD complex in both fresh (left lane) and freeze-thaw (center lane) samples, after immunoprecipitation of the complexes with anti-hsp110 antibody. The right lane is ICD. These results show that hsp110-ICD complexes are stable after freezing and thawing.

Figure 15:
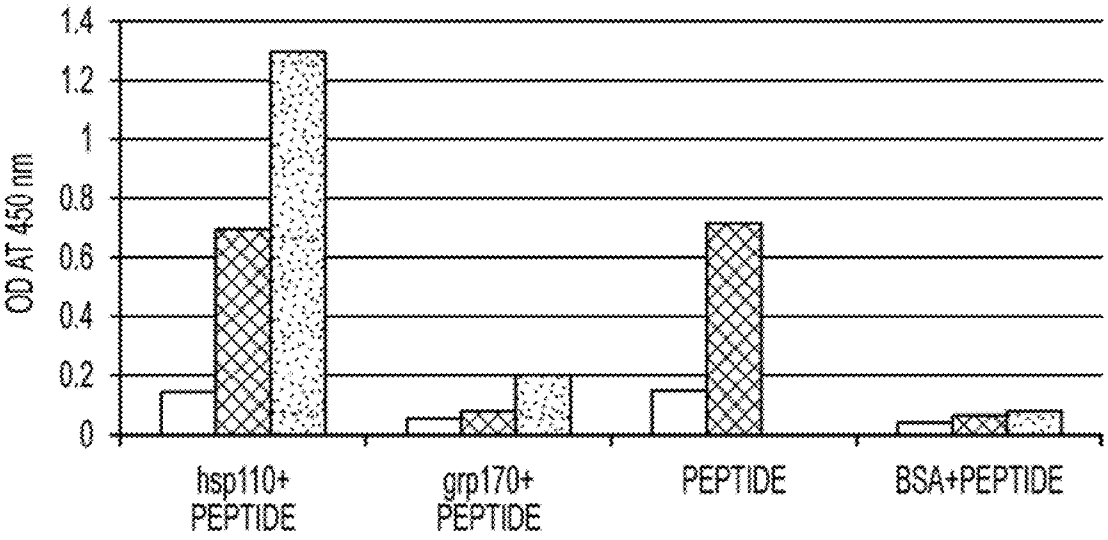
FIG. 15 is a bar graph showing hsp-peptide binding using a modified ELISA and p546, a 10-mer peptide of her-2/neu, selected for its HLA-A2 binding affinity and predicted binding to hsp110. The peptide was biotinylated and mixed with hsp110 in vitro. Purified mixture concentrations were 1 μg/ml (white bars), 10 μg/ml (cross-hatched bars), and 100 μg/ml (dark stippled bars).

FIG. 15 is a bar graph showing hsp-peptide binding using a modified ELISA and p546, a 10-mer peptide (VLQGLPREYV; SEQ ID NO: 5) of a her-2/neu transmembrane domain, selected for its HLA-A2 binding affinity and predicted binding to hsp110. The peptide was biotinylated and mixed with hsp110 in vitro (60 μg peptide and 60 μg hsp110 in 150 μl PBS). The mixtures were incubated at 43° C. for 30 minutes and then at 37° C. for 1 hour. The mixtures were purified using a Centricon-10 centrifuge to remove the unbound peptide. BSA (1%) was also incubated with 100 μg of the biotinylated peptide at the same conditions, and purified. Wells were coated with different concentrations of the purified mixtures, biotinylated peptide (positive control), or BSA (negative control) in a coating buffer. After incubation at 4° C. overnight, wells were washed 3 times with PBS-Tween 20 (0.05%) and blocked with 1% BSA in PBS for 1 hour at room temperature. After washing, 1:1000 streptavidin-HRP was added into the wells and plates were incubated at room temperature for 1 hour. The color was developed by adding the TMB substrate and reading the absorbance at 450 nm. Purified mixture concentrations were 1 μg/ml (white bars), 10 μg/ml (cross-hatched bars), and 100 μg/ml (dark stippled bars).

Figure 16:
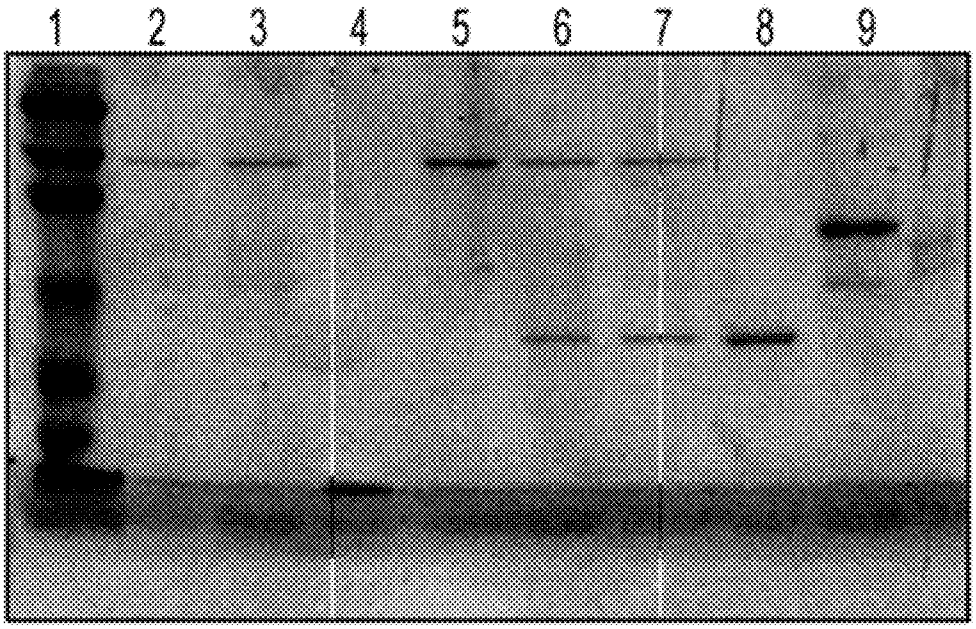
FIG. 16 shows the results of immunoprecipitation of *M. tuberculosis* antigens Mtb8.4 and Mtb39 with anti-hsp110 antibody after formation of binding complexes in vitro, using both fresh samples and samples that had been subjected to freezing and thawing. Lane 1 is a protein standard from 205 kDa to 7.4 kDa; lane 2 is hsp110+Mtb8.4; lane 3 is hsp110+Mtb8.4 (after freeze-thaw); lane 4 is Mtb8.4; lane 5 is hsp110; lane 6 is hsp110+Mtb39; lane 7 is hsp110+Mtb39 (after freeze-thaw); lane 8 is Mtb39; and lane 9 is anti-hsp110 antibody.

FIG. 16 shows the results of immunoprecipitation of *M. tuberculosis* antigens Mtb8.4 and Mtb39 with anti-hsp110 antibody after formation of binding complexes in vitro, using both fresh samples and samples that had been subjected to freezing and thawing. Lane 1 is a protein standard from 205 kDa to 7.4 kDa; lane 2 is hsp110+Mtb8.4; lane 3 is hsp110+Mtb8.4 (after freeze-thaw); lane 4 is Mtb8.4; lane 5 is hsp110; lane 6 is hsp110+Mtb39; lane 7 is hsp110+Mtb39 (after freeze-thaw); lane 8 is Mtb39; and lane 9 is anti-hsp110 antibody.

Example 9

Stress Polypeptide Complexes Elicit Cellular Immune Responses

This example demonstrates that hsp110 complexed with a peptide from her-2/neu, including the intracellular domain (ICD; amino acid residues 676-1255), extracellular domain (ECD; p369; KIFGSLAFL; SEQ ID NO: 6), or transmembrane region (p546) of her-2/neu, is immunogenic, as determined by gamma interferon (IFN-gamma) production by stimulated CTLs. The data show that hsp110 complexed with ICD generates a stronger CTL response than hsp110 complexed with the other peptides of her-2/neu.

FIG. 17 is a bar graph showing IFN-gamma production (determined by number of spots in an ELISPOT assay) by T cells of A2/Kb transgenic mice (5 animals per group) after i.p. immunization with 25 μg of recombinant mouse hsp110-ICD complex. These mice are transgenic for a hybrid human/mouse class I molecule such that the animals are capable of HLA-A2 presentation, as well as retaining the murine poly-α3 domain, providing for additional cell surface protein interactions. Animals were boosted after 2 weeks, and sacrificed 2 weeks thereafter. Control groups were injected with 25 μg of ICD or hsp110, or not immunized. CD8 T cells were depleted using Dynabeads coated with anti-CD8 antibody and magnetic separation. Total splenocytes or depleted cells ($5\times10^6$ cells/ml) were cultured in vitro with 25 μg/ml PHA (checkered bars) or 20 μg/ml ICD (dark stippled bars) overnight and IFN-gamma secretion was detected using the ELISPOT assay.

FIG. 18 is a bar graph showing immunogenicity of hsp110-peptide complexes reconstituted in vitro, as determined by number of positive spots in an ELISPOT assay for IFN-gamma secretion. Recombinant hamster hsp110 (100 μg) was incubated with 100 μg of the 9-mer her-2/neu peptide p369, an HLA-A2 binder, at 43° C. for 30 minutes, followed by incubation at room temperature for 60 minutes. The complex was purified using a Centricon-10 centrifuge to remove unbound peptides. Eight-week old HLA-A2 transgenic mice (n=4) were immunized i.p. with 60 μg of either hsp110+peptide complex (group A, cross-hatched bars) or peptide alone (group B, dark stippled bars) in 200 μl PBS and boosted 2 weeks later. Animals were sacrificed 2 weeks after the last injection and their splenocytes ($10^7$ cells/ml) were stimulated in vitro with PHA (positive control), immunizing peptide, or hsp110 when added with 15 U/ml of human recombinant IL-2. Counts for the non-stimulated cells (negative controls) were <40 and were subtracted from the counts for stimulated cells.

FIG. 19 is a bar graph showing immunogenicity of hsp110-peptide complexes reconstituted in vitro, as determined by number of positive spots in an ELISPOT assay for IFN-gamma secretion. Recombinant hamster hsp110 (100 μg) was incubated with 100 μg of the 10-mer her-2/neu peptide p546, an HLA-A2 binder, at 43° C. for 30 minutes, followed by incubation at room temperature for 60 minutes. The complex was purified using a Centricon-10 centrifuge to remove unbound peptides. Eight-week old HLA-A2 transgenic mice (n=2) were immunized i.p. with 60 μg of either hsp110+peptide complex (group A, cross-hatched bars) or peptide alone (group B, dark stippled bars) in 200 μl PBS and boosted 2 weeks later. Animals were sacrificed 2 weeks after the last injection and their splenocytes ($10^7$ cells/ml) were stimulated in vitro with PHA (positive control), immunizing peptide, or hsp110 when added with 15 U/ml of human recombinant IL-2. Counts for the non-stimulated cells (negative controls) were <40 and were subtracted from the counts for stimulated cells.

Example 10

Stress Polypeptide Complexes Elicit Specific Antibody Responses

This example demonstrates that immunization with an hsp110-her2/neu ICD complex elicits antibody responses in A2/Kb transgenic mice. This response is specific, and the response is significantly greater than occurs with administration of her2/neu ICD alone. Thus, stress protein complexes of the invention are capable of stimulating both cellular and humoral immunity.

FIG. 20 is a graph showing specific anti-hsp110 antibody response in A2/Kb transgenic mice following i.p. immunization with the hsp110-ICD (her2/neu) complex. ELISA results are plotted as optical density (OD) at 450 nm as a function of serum and antibody dilutions. Results are shown for the positive control of anti-hsp110 (solid squares), the negative control of unrelated antibody (open circles), and serum at day 0 (closed circles), day 14 (open squares, dashed line), and day 28 (open squares, solid line). These results confirm that the mice did not develop an autoimmune response to hsp110.

FIG. 21 is a graph showing specific anti-ICD antibody response in A2/Kb transgenic mice following i.p. immunization with the hsp110-ICD complex. ELISA results are plotted as optical density (OD) at 450 nm as a function of serum and antibody dilutions. Results are shown for the positive control of anti-ICD (solid squares), the negative control of unrelated antibody (open diamonds), and serum at day 0 (closed circles), day 14 (open squares, dashed line), and day 28 (open squares, solid line). These results confirm that the mice developed a specific antibody response to ICD of her2/neu after immunization with the stress protein complex.

FIG. 22 is a bar graph comparing specific anti-ICD antibody responses in A2/Kb transgenic animals 2 weeks after priming with different vaccine formulas. Results are plotted as OD at 450 nm for the various serum and antibody dilutions and bars represent data for animals primed with hsp110-ICD (stippled bars), the positive control of ICD in complete Freund's adjuvant (CFA; checkered bars), ICD alone (cross-hatched bars), anti-ICD antibody (dark stippled bars), and the negative control of unrelated antibody (open bars).

FIG. 23 is a bar graph comparing specific anti-ICD antibody generation 2 weeks after s.c. or i.p. priming of A2/Kb transgenic with hsp110-ICD complex. Results are plotted as OD at 450 nm for the various serum and antibody dilutions and bars represent serum at day 0 (stippled bars), serum i.p. at day 14 (checkered bars), serum s.c. at day 14 (cross-hatched bars), anti-ICD antibody (dark stippled bars), and the negative control of unrelated antibody (open bars).

Example 11

Tumor Cells Transfected with an Hsp110 Vector Over-Express Hsp110

This example provides data characterizing colon 26 cells (CT26) transfected with a vector encoding hsp110 (CT26- hsp110 cells). These CT26-hsp110 cells overexpress hsp110, as demonstrated by both immunoblot and immunofluorescence staining.

FIG. 24A is an immunoblot showing that CT26-hsp110 cells exhibit increased hsp110 expression relative to untransfected CT26 cells and CT26 cells transfected with an empty vector (CT26-vector). Equivalent protein samples from CT26 (lane 1), CT26-vector (lane 2), and CT26-hsp110 (lane 3) were subjected to 10% SDS PAGE and transferred onto immobilon-P membrane. Membranes were probed with antibodies for hsp110. After washing, membranes were incubated with horseradish peroxidase-conjugated goat anti-rabbit IgG or goat anti-mouse IgG diluted 1:2,000 in TBST. Immunoreactivity was detected using the Enhanced Chemiluminescence detection system.

FIG. 24B shows that CT26-hsp110 cells do not exhibit enhanced hsc70 expression relative to untransfected CT26 cells or CT26 cells transfected with an empty vector. Equivalent protein samples from CT26 (lane 1), CT26-vector (lane 2), and CT26-hsp110 (lane 3) were prepared as for FIG. 24A, except that membranes were probed with antibodies for hsc/hsp70.

FIG. 25A is a photomicrograph showing immunofluorescence staining of hsp110 in CT26 cells. Cells were seeded on the cover slips one day before the staining. Cover slips were then incubated with rabbit anti-hsp110 antibody (1:500 dilution) followed by FITC-labeled dog anti-rabbit IgG staining. Normal rabbit IgG was used as negative control.

FIG. 25B is a photomicrograph showing immunofluorescence staining of hsp 110 in empty vector transfected CT26 cells. Cells were prepared and immunostained as in FIG. 25A.

FIG. 25C is a photomicrograph showing immunofluorescence staining of hsp110 in hsp110 over-expressing cells. Cells were prepared and immunostained as in FIG. 25A.

Example 12

Growth Properties of Tumor Cells Over-Expressing Hsp110

This example provides data characterizing the in vivo and in vitro growth properties of CT26-hsp110 cells.

FIG. 26 is a graph demonstrating in vitro growth properties of wild type and hsp110-transfected cell lines, plotted as cell number at 1-5 days after seeding. Cells were seeded at a density of $2\times10^4$ cells per well. 24 hours later cells were counted (assigned as day 0). Cells from triplicate wells were counted on the indicated days. The results are means±SD of three independent experiments using wild type CT26 cells (circles), CT26 cells transfected with empty vector (squares), and hsp110-transfected CT26 cells (triangles).

FIG. 27 is a bar graph showing the effect of hsp110 overexpression on colony forming ability in soft agar. Wild-type CT26 cells, empty vector transfected CT26-vector cells and hsp110 over-expressing CT26-hsp110 cells were plated in 0.3% agar and analyzed for their ability to form colonies (≧0.2) in soft agar. $P<0.05$, compared with CT26-vector, as assessed by student's t test.

FIG. 28 is a graph showing in vivo growth properties of wild-type and hsp110 transfected CT26 cell line. $5\times10^4$ cells were inoculated s.c. into flank area of balb/c mice. Tumor growth was recorded twice a week measuring both the longitudinal and transverse diameter with a caliper. Tumor volume, in cubic mm, is plotted as a function of days after tumor implantation for CT26 wild type cells (circles), CT26 cells transfected with empty vector (squares), CT26 cells transfected with hsp110, $5\times10^4$ (upward triangles), and CT26 cells transfected with hsp110, $5\times10^5$ (downward triangles).

Example 13

Immunization with CT26-Hsp110 Cells Protects Against Tumor Challenge

This example demonstrates that mice immunized with irradiated hsp110 over-expressing CT26 cells are protected against subsequent challenge with live CT26 cells. In addition, immunization with CT26-hsp110 cells elicits tumor specific CTL and antibody responses.

FIG. 29 is a plot showing the effect of injection with irradiated hsp110-overexpressing cells on the response to challenge with live CT26 cells. Mice were injected with $5\times10^5$ irradiated (9,000 rad) CT26-hsp110 cells subcutaneously in the left flank. Two weeks later, mice were challenged on the right flank with live CT26 cells. Growth of tumor in mice without preimmunization was also shown. Results are plotted as percent tumor free mice as a function of days after tumor challenge for mice immunized with PBS and challenged with $5\times10^4$ CT26 cells (circles); irradiated CT26 cells with empty vector/$5\times10^5$ CT26 cells (squares); irradiated CT26 cells with empty vector/$5\times10^6$ CT26 cells (upward triangles); irradiated CT26-hsp110 cells/$5\times10^5$CT26 cells (downward triangles); and irradiated CT26-hsp110 cells/$5\times10^6$ CT26 cells (diamonds).

FIG. 30 is a graph showing tumor specific CTL response elicited by immunization with tumor derived hsp110. Mice were injected with $5\times10^5$ irradiated (9,000 rad) CT26-empty vector and CT26-hsp 110 cells subcutaneously. Two weeks later, splenocytes were isolated as effector cells and re-stimulated with irradiated Colon 26 in vitro for 5 days. The lymphocytes were analyzed for cytotoxic activity using $^{51}$Cr-labeled Colon 26 as target cells. Meth A tumor cells were also used as target in the experiment, and no cell lysis was observed. Results are plotted as percent specific lysis as a function of effector:target ratio for control (circles), irradiated CT26 cells (squares), and irradiated CT26-hsp110 cells (triangles).

FIG. 31 is a graph showing antibody response against CT26 cells following immunization with irradiated hsp110-overexpressing cells. Mice were injected with $5\times10^5$ irradiated (9,000 rad) CT26 empty vector and CT26-hsp110 cells subcutaneously. Two weeks later, serum was collected and assayed for antibody response using ELISA. Results are plotted as OD at 450 nm as a function of serum dilution for control (circles), CT26-empty vector (squares), and CT26-hsp110 (triangles).

Example 14

GM-CSF-Secreting Cells Enhance Protective Effect of CT26-Hsp110 Cells

This example demonstrates that cells transfected with a GM-CSF gene, when co-injected with CT26-hsp110 cells, provide enhanced protection against tumor challenge that leaves all mice treated with the combined therapy free of tumors.

FIG. 32 is a graph showing the effect of GM-CSF from bystander cells on the growth of hsp110 overexpressing cells. Mice were injected subcutaneously with $5\times10^4$ live tumor cells as follows: CT26-empty vector cells (circles), CT26-vector cells plus irradiated B78H1GM-CSF cells (2:1 ratio; squares), CT26-hsp110 cells plus irradiated B78H1GM CSF cells (2:1 ratio; upward triangles), CT26-hsp110 cells (downward triangles), CT26-hsp110 plus irradiated B78H1 cells (2:1 ratio; diamonds). The B78H1GM-CSF are B16 cells transfected with CM-CSF gene, while B78H1 are wild type cells. Tumor growth was recorded by measuring the size of tumor, and is plotted as tumor volume in cubic mm as a function of days after implantation.

FIG. 33 is a graph showing the effect of co-injecting irradiated hsp110-overexpressing tumor vaccine and GM-CSF-secreting bystander cells on the response to wild-type CT26 tumor cell challenge. Mice were immunized subcutaneously with irradiated $5\times10^5$ tumor cells as follows: CT26-empty vector cells, CT26-vector cells plus B78H1GM-CSF cells (2:1 ratio; squares), CT26-hsp110 cells plus B78H1GM-CSF cells (2:1; upward triangles), CT26-hsp110 cells (downward triangles), CT26-hsp110 plus B78H1 cells (2:1; diamonds). Also shown are results for mice immunized only with PBS (circles). Mice were challenged at a separate site with CT26 wild-type cells and monitored every other day for the tumor development. Results are plotted as percent tumor free mice at the indicated number of days after tumor challenge.

Example 15

Immunization with Tumor-Derived Stress Protein Complexes Stimulates Cellular Immunity and Inhibits Metastatic Tumor Growth This example demonstrates that tumor-derived stress protein complexes of the invention can be used to stimulate cellular immunity and inhibit metastatic tumor growth. Interferon-gamma secretion was stimulated by immunization with colon 26 tumor-derived hsp110 and grp170, as well as with B16F10-derived grp170. Immunization with B16F11-derived grp170 was also shown to elicit a tumor-specific CTL response and a reduction in lung metastases.

FIG. 34 is a bar graph showing that immunization with colon 26-derived hsp110 or grp170 stimulates interferon (IFN) gamma secretion. A week after mice were immunized with hsp110 or grp170, splenocytes were isolated for ELISPOT assay. Phytohemagglutinin (PHA) treated lymphocytes were used for positive control.

FIG. 35 is a graph showing tumor specific CTL response elicited by immunization with B16F1 tumor-derived grp170. Mice were immunized twice with grp170 (40 μg) at weekly intervals. One week after the second immunization, splenocytes were isolated as effector cells and restimulated with irradiated B16F10 cells in vitro for 5 days. The lymphocytes were analyzed for cytotoxic activity using $^{51}$Cr-labeled B16F10 or Meth A cells as target cells. Results are plotted as percent specific lysis as a function of effector:target ratio for controls (circles), liver-derived grp170 (squares), B16F10-derived grp170 (upward triangles), and Meth A-derived grp170 (downward triangles).

FIG. 36 shows immunization with B16F10-derived grp170 stimulates IFN gamma secretion. A week after mice were immunized with hsp110 or grp170, splenocytes were isolated for ELISPOT assay.

FIG. 37 shows lung metastases for mice in which $1\times10^5$ B16F10 cells were inoculated intravenously into the tail vein of each C57BL/6 mouse. 24 hr after tumor cell injection, mice were then treated with PBS (closed circles), liver-derived grp170 (open circles), or tumor-derived grp170 (40 μg). Three treatments were carried out during the whole protocol. The animals were killed 3 weeks after tumor injection, lungs were removed and surface colonies were counted.

Example 16

Further Development of a Recombinant HSP110HER-2/neu Vaccine Using the Chaperoning Properties of HSP110

HER-2/neu has been selected as a protein antigen of choice since it is clinically relevant to breast cancer and could well be applicable to other tumor systems such as ovarian, prostate, lung, and colon cancers expressing this protein. Importantly, some patients with breast cancer have preexisting cellular and humoral immune responses directed against intracellular domain (ICD) of HER-2/neu. Thus, an effective cancer vaccine targeting HER-2/neu, ICD in particular, would be able to boost this immunity to potentially therapeutic levels in humans. Moreover, the results from clinical trials targeting HER-2/neu have been promising.

This example demonstrates the ability of this novel approach, which uses HSP110, to elicit both cell-mediated and humoral immune responses against this bound protein antigen. Shown herein is that HSP110 is as efficient as Complete Freund's Adjuvant (CFA) in eliciting an antigen-specific $CD8^+$ T cell response both in a $CD4^+$-dependent and in a $CD4^+$-independent fashion with no indication of anti-HSP110 cell-mediated or humoral immune responses.

Materials and Methods

Mice. Studies were performed in A2/Kb transgenic animals purchased from Harlan Sprague Dawley (La Jolla, Calif.). This model was used for comparison of data obtained in the present study with peptide immunization approach using the HSP110-peptide complex (HLA-A2 epitopes from HER-2/neu) underway in a separate investigation. In addition, studies were reproduced using C57/BL6 mice (obtained from the Department of Laboratory Animal Resources at Roswell Park Cancer Institute) in a confirmatory experiment. Data obtained using A2/Kb mice is presented. All animals used in this study were 6-8 week old females.

Recombinant proteins. Recombinant mouse HSP110 is routinely prepared using pBacPAK.His vector (CLONTECH Laboratories Inc., CA). This vector carrying HSP110 gene was co-transfected with BacPAK6 viral DNA into Sf21 insect cells using a BacPAK™ Baculovirus Expression System Kit (CLONTECH Laboratories Inc. CA) followed by amplification of the recombinant virus and purification of HSP110 protein using Ni-NTA-Agarose (QIAGEN, Germany). Concentration of the recombinant HSP110 was determined using Bio-Rad protein assay Kit. Highly purified recombinant human ICD was provided by Corixa Corp. This protein was produced in *E. coli* and purified from solubilized inclusion bodies via High Q anion exchange followed by Nickel resin affinity chromatography. A control recombinant protein was also made in *E. coli* and purified in a similar way as the ICD.

In vitro HSP110-antigen binding. The HSP110-ICD complex (3-6 μg each in 1 ml PBS) was generated by incubation of the mixture in a 1:1 molar ratio at 43° C. for 30 min and then at 37° C. for 1 h. The binding was evaluated by immunoprecipitation as previously described (Oh, H. J., et al. *J. Biol. Chem.,* 272:31636-31640, 1997), with some modifications. Briefly, the HSP110-ICD complex was incubated with either rabbit anti-mouse HSP110 antiserum (1:200) or rabbit anti-mouse GRP170 antiserum (1:100), as a specificity control, at room temperature for 1-2 h. The immune complexes were then precipitated by incubation with Protein-A Sepharose™ CL-4B (20 μl/ml; Amersham Pharmacia Biotech AB, Upsala Sweden) and rocking for 1 h at room temperature. All proteins were spun for 15 min at 4° C. to precipitate any aggregation before use. Samples were then washed 8 times with washing buffer (1 M Tris-Cl pH 7.4, 5 M NaCl, 0.5 M EDTA pH 8.0, 0.13% Triton X-100) at 4° C. to remove any non-specific binding of the recombinant proteins to protein-A sepharose. The beads were then added with 2×SDS sample buffer, boiled for 5 min, and subjected to SDS-PAGE (10%) followed by either Gel-blue staining or probing with mouse anti-human ICD antiserum (1:10000, provided by Corixa Corp.) in a western blotting analysis using HRP-conjugated sheep anti-mouse IgG (1:5000, Amersham Pharmacia Biotech, NJ) and 1 min incubation of the nitrocellulose membrane with Chemiluminescence reagent followed by exposure to Kodak autoradiography film for 20 sec.

Immunizations. Preliminary studies showed that s.c. and i.p. routes of injection of the HSP110-ICD complex stimulated comparable levels of cell-mediated immune responses, but i.p. injection was better than s.c. injection in eliciting antibody responses. Thus, all groups were injected i.p. except for mice immunized s.c. with ICD together with CFA and boosted together with Incomplete Freund's Adjuvant (IFA). Mice (5/group) were injected with 25 μg of the HSP110-ICD complex in 200 μl PBS on days 0 and 14. Control groups were injected with 25 μg of the HSP110, ICD, ICD together with CFA/IFA, or left unvaccinated. The splenocytes were removed 14 days after the booster and subjected to ELISPOT assay to evaluate CTL responses. Sera were also collected on days 0, 14, and 28 to measure isotype-specific antibodies (IgG1 and IgG2a) against the ICD or HSP110 using ELISA technique. Groups of animals (5/group) were also depleted from $CD8^+$, $CD4^+$, or $CD4^+/CD8^+$ T cells either 4 days prior to vaccination followed by twice a week injections or one week after the priming. The splenocytes were then subjected to ELISPOT assay.

In vivo antibody depletion. In vivo antibody depletions were carried out as previously described (Lin, K. Y., et al. *Cancer Res.* 56:21-26, 1996). The GK1.5, anti-CD4 and 2.43, anti-CD8 hybridomas were kindly provided by Dr. Drew Pardoll (John Hopkins University) and the ascites were generated in SCID mice. The depletions were started 4 days before vaccination. Each animal was injected i.p. with 250 μg of the monoclonal antibodies (mAbs) on 3 subsequent days before and twice a week after immunization. Animals were depleted from $CD4^+$, $CD8^+$, or $CD4^+/CD8^+$ T cells. Depletion of the lymphocyte subsets was assessed on the day of vaccination and weekly thereafter by flow cytometric analysis of spleen cells stained with mAbs GK1.5 or 2.43 followed by FITC-labeled rat anti-mouse IgG (Pharmingen, San Diego Calif.). For each time point analysis, >98% of the appropriate subset was achieved. Percent of $CD4^+$ T cells did not change after $CD8^+$ T cell depletion, and neither did percent of $CD8^+$ T cells change after $CD4^+$ T cell depletion. Representative data are shown in Table 1.

TABLE 1

Flow cytometric analysis of the presence of T cell subsets following in vivo antibody depletion.

| Animals | T cell subsets CD4 | CD8 |
|---|---|---|
| Wild type | 22% | 14% |
| CD4 depletion | <2% | 15% |
| CD8 depletion | 20% | <2% |
| CD4/CD8 depletion | <2% | <2% |

Depletion of $CD4^+$ or $CD8^+$ T cells was accomplished by i.p. injection of GK1.5 or 2.43 antibodies (250 μg), respectively. The $CD4^+/CD8^+$ T cells were also depleted by i.p. injection of both GK1.5 and 2.43 antibodies (250 μg of each). The depletion was performed on 3 subsequent days prior to immunization, and followed by twice a week injections. Spleen cells were stained for $CD4^+$ or $CD8^+$ T cells using FITC-labeled rat anti-mouse IgG and subjected to flow cytometry showing that almost 98% of the lymphocyte subsets were depleted without any affect on other T cell subsets.

Enzyme-linked immunosorbent spot (ELISPOT) assay. Generation of CTL responses by the immunized animals were evaluated using ELISPOT assay as described by others (Chen, C. H., et al. *Cancer Res.* 60:1035-1042, 2000). Briefly, the 96-well filtration plates (Millipore, Bedford, Mass.) were coated with 10 μg/ml of rat anti-mouse IFN-γ antibody (clone R4-6A2, Pharmingen, San Diego, Calif.) in 50 μl PBS. After overnight incubation at 4° C., the wells were washed and blocked with RPMI-1640 medium containing 10% fetal bovine serum (RF10). Red cells were lysed by incubation of the splenocytes with Tris-$NH_4Cl$ for 5 min at room temperature followed by two times washing in RF10. Fifty μl of the cells ($10^7$ cells/ml) were added into the wells and incubated with 50 μl of the ICD (10-20 μg/ml) or HSP110 (20 μg/ml) at 37° C. in a atmosphere of 5% $CO_2$ for 20 h. Positive control wells were added with Con-A (5 μg/ml) and background wells were added with RF10. A control recombinant protein made in *E. Coli* was also used (10-20 μg/ml) in a confirmatory experiment using the HSP110-ICD or ICD immunized animals. The plates were then washed extensively (10 times) and incubated with 5 μg/ml biotinylated IFN-γ antibody (clone XMG1.2, Pharmingen, San Diego Calif.) in 50 μl PBS at 4° C. overnight. After six times washing, 0.2 U/ml alkaline phosphatase avidin D (Vector Laboratories, Burlingame Calif.) in 50 μl PBS, was added and incubated for 2 h at room temperature, and washed on the following day (the last wash was carried out with PBS without Tween-20). IFN-γ spots were developed by adding 50 μl BCIP/NBT solution (Boehringer Mannheim, Indianapolis, Ind.) and incubating at room temperature for 20-40 min. The spots were counted using a dissecting microscope.

Enzyme-linked immunosorbent assay (ELISA). ELISA technique was carried out as described elsewhere (Longenecker, B. M., et al. *Adv. Exp. Med. Biol.* 353:105-124, 1994). Briefly, 96-well ELISA plates were coated with ICD (20 μg/ml) or HSP110 (20 μg/ml), and then blocked with 1% BSA in PBS after incubation at 4° C. overnight. After washing with PBS-0.05% Tween-20, wells were added with five-fold serial dilutions of the sera starting at 1:50, then incubated at room temperature for 1 h, washed 3 times and added with HRP-labeled goat anti-mouse IgG1 or IgG2a Ab (Caltag laboratories, Burlingame Calif.). The reactions were developed by adding 100 μl/well of the TMB Microwell peroxidase substrate (KPL, Maryland) and reading at 450 nm after stopping the reaction with 50 μl of 2 M $H_2SO_4$. Specificity of the binding was assessed by testing the pre-immune sera or staining of the ICD with the pooled immune sera (1:2000), collected from the HSP111-CD immunized animals, in a western blot. Data are presented as mean values for each antibody isotype.

Statistical analysis: Unpaired two-tailed Student's t test was used to analyze the results. Data are presented as the ±SE. $p \leqq 0.05$ was considered significant.

Results

Non-covalent binding of the HSP110 to ICD at 43° C. Based on the previous finding that HSP110 binds to Luciferase and Citrate Synthase at a 1:1 molar ratio at 43° C., next was examined whether the same condition was applicable for binding of HSP110 to ICD. Different molar ratios of HSP110 and ICD (1:4, 1:1, 1:0.25) were used and the samples were run on SDS-PAGE. The bands were developed by either Gel-blue staining or western blot analysis using mouse anti-human ICD antiserum and HRP-conjugated sheep anti-mouse IgG. It was found that excess ICD over HSP110 did not improve the binding efficiency nor did excess HSP110 over the ICD. Approximately a 1:1 molar ratio of the HSP110 to ICD was again found to be optimal for formation of the complex. Thus, a 1:1 molar ratio was used to generate the HSP110-ICD binding complex (FIG. 38A-B).

Vaccination with the HSP110-ICD complex induces antigen-specific IFN-γ production. ELISPOT assay is a sensitive functional assay used to measure IFN-γ production at the single-cell level, which can thus be applied to quantify antigen-specific CD8+ or CD4+ T cells. Depletion of T cell subsets was also performed to determine the source of IFN-γ production. First explored was whether the HSP110-ICD complex, without any adjuvant, could elicit antigen-specific IFN-γ production. FIG. 39 demonstrates that the HSP110-ICD-immunized animals elicited significant IFN-γ production upon stimulation with ICD in vitro. No IFN-γ spot was detected in the background wells. The HSP110-ICD complex was as efficient as the CFA-ICD, i.e. there was no significant difference between the two vaccines in their ability to induce IFN-γ production. This shows that IFN-γ production was specific for ICD. Splenocytes collected from all groups did not produce IFN-γ upon in vitro stimulation with rHSP110. Mice that immunized with ICD only did not show IFN-γ production upon stimulation with the antigen.

Vaccination with the HSP110-ICD complex induces both $CD8^+$ and $CD4^+$ T cell-mediated immune responses. To identify which cell populations were involved in the antigen-specific IFN-γ production, in vivo lymphocyte subset depletion was performed with injections of the mAb 2.43 or GK1.5 to deplete $CD8^+$ or $CD4^+$ T cells, respectively. A group of animals were also depleted from both $CD8^+$ and $CD4^+$ T cells. FIG. 40 shows that all animals vaccinated with the HSP110-ICD complex and depleted from the $CD8^+$ or $CD4^+$ T cells showed IFN-γ production upon in vitro stimulation with the antigen. Animals depleted from both $CD8^+$ and $CD4^+$ T cells did not show any IFN-γ production upon either ICD or Con A stimulation in vitro. There was also no significant difference between the $CD8^+$-depleted cells and $CD4^+$-depleted cells to produce antigen-specific IFN-γ in vitro (p=0.95).

To further explore whether activation of $CD4^+$ T cells may promote activation of $CD8^+$ T cells, $CD4^+$ T cell depletion in the HSP110-ICD immunized animals was carried out one week after the booster. Although frequency of IFN-γ producing cells was slightly higher in these animals than that in animals depleted from CD4+ T cells prior to vaccination, this difference was not statistically significant ($p \geqq 0.16$).

Vaccination with the HSP110-ICD complex induces both IgG1 and IgG2a antibody responses against the ICD. It has been reported that non-covalent binding of HSPs with a peptide could elicit a potent T cell responses to the bound peptide whereas the covalent binding complexes elicit the potent antibody responses. Therefore, the next step was to examine whether in vitro loading of HSP110 with a large tumor antigen, ICD, in a form of non-covalent complex may be able to elicit antibody responses in addition to cell-mediated immunity. Blood was collected from animals that were utilized to monitor cell-mediated immunity by ELISPOT assay. Sera were prepared and tested for antigen specific antibody responses by ELISA. Using HRP-labeled anti-mouse isotype specific antibodies, IgG1 or IgG2a, both IgG1 and IgG2a Abs were found to be elevated remarkably in the immunized animals (FIG. 41A). Both IgG1 and IgG2a Ab levels were significantly higher in the HSP110-ICD immunized animals than those in the ICD immunized animals 14 days after immunization ($p \leqq 0.0001$). However, IgG2a Ab reached the same levels in the two groups on day 28. The IgG1 was the major antibody, which stayed significantly higher in the HSP110-ICD immunized animals than in the ICD-immunized animals 28 days after immunization ($p \leqq 0.0001$). Western blot analysis of the pooled immune sera collected from the HSP110-ICD immunized animals revealed specificity of the Ab for the ICD (FIG. 42B, lane 1). Mouse anti-human ICD Ab (1:10000) was used as a control to stain the ICD (FIG. 42B, lane 2). No anti-HSP 110 antibody was detected before or after immunization.

Discussion

It was recognized approximately twenty years ago that there are only a few major HSPs in mammalian cells. One of these, HSP110, has only recently been cloned and only a few recent studies of its properties have appeared. It has been found that HSP110 and its mammalian and non-mammalian relatives are distantly related to HSP70, but do not fall into the previously defined HSP70 "family". Indeed HSP110 is representative of a family of heat shock proteins conserved from *S. cerevisiae* and *S. pombe* to man. Since HSP110 exists in parallel with HSP70 in the cytoplasm of (apparently) all eukaryotic cells, it is expected that HSP110 would carry out functions not performed by members of the HSP70 family. Initial characterization of the chaperoning properties of HSP110 demonstrate that it indeed exhibits major functional differences when compared to HSP70. While HSP70 avidly binds ATP, HSP110 does not. Secondly, in protein binding studies it has been found that HSP110 is significantly more efficient (i.e. approximately four fold more efficient) compared to HSP70 in forming natural chaperone complexes with denatured reporter proteins. Surprisingly HSP110 complexes with reporter proteins and totally inhibits their heat induced aggregation at a 1:1 molar ratio.

This unexpected protein binding property of HSP110 is the basis of a new approach for the development of protein vaccines, which uses the binding of the protein antigen to HSP110 in a natural chaperone complex by heat shock. The protein antigen used here was ICD, which is a 84 kDa protein. One advantage of the Her-2/neu antigen is its involvement in the malignant phenotype of the tumor. Therefore, in the case of tumor escape by antigen loss due to the treatment, it would still be beneficial to patients since HER-2/neu negative cancers are less aggressive than those that overexpress the neu protein and are associated with a more favorable prognosis.

As with previous studies using reporter proteins, HSP110 is again found to efficiently bind ICD at approximately a 1:1 molar ratio as seen in FIG. 38A-B. This strong protein binding capacity of HSP110 may be a typical and unique property of this stress protein. Immunization with this heat shock HSP110-ICD complex was found to be as potent as adding CFA to the ICD in eliciting specific IFN-γ production in immunized animals. On the other hand, neither naïve nor ICD-immunized animals showed a IFN-γ production upon in vitro stimulation with the ICD. Importantly, mice immunized with HSP110 did not show any IFN-γ production upon in vitro stimulation with the HSP110, indicating that this heat shock protein, as a self-protein, did not elicit an autoimmune response.

The ability of HSP110 to chaperone and present the ICD of HER-2/neu to the immune system and the strong response indicates that ICD is processed via an intracellular pathway, which requires degradation of ICD in antigen presenting cells (APCs) into a repertoire of antigenic peptides. This would facilitate the presentation of both $CD8^+$ as well as $CD4^+$ T cell epitopes from ICD by APCs since immunization with the HSP110-ICD complex was able to induce both $CD8^+$ and $CD4^+$ T cells to produce IFN-γ. Depletion studies showed that NK cells were not involved in the antigen-specific IFN-γ production since mice depleted of both $CD8^+$ and $CD4^+$ T cells did not produce IFN-γ. Elevation of these T cell subsets were comparable and also antigen specific, but not due to alteration in the percent of T cell subsets following depletion. The finding is consistent with previous studies showing that HSPs are able to route exogenous antigens into an endogenous presentation pathway for presentation by MHC class I molecules.

Depletion studies also demonstrated that stimulation of the $CD8^+$ T cells did not require help of $CD4^+$ T cells. This finding is consistent with previous studies showing that depletion of $CD4^+$ T cells in the priming phase did not abrogate the immunity elicited by gp96. Udono et al. also showed that depletion of macrophages by treatment of mice with carrageenan during the priming phase resulted in loss of gp96-elicited immunity. One explanation for this phenomenon is that HSPs may replace $CD4^+$ T cells help to convert APCs into the cells that are fully competent to prime $CD8^+$ T cells. These findings indicate the central role that HSP-APC may play in activation of $CD8^+$ T cells via expression of CD40 molecule, which may interact with CD40 ligand and provide help for $CD8^+$ T cell activation. This pathway does not necessarily require activation of $CD4^+$ T cells for $CD8^+$ T cell priming. It has been shown that HSP-APCs interaction leads to activation of APCs, and induces proinflammatory cytokines secretion by activated DCs.

Evaluation of the ICD-specific antibody responses in the immunized animals revealed that the HSP110-ICD complex could elicit both $T_h1$ and $T_h2$ cells as evaluated by production of IgG2a and IgG1 antibodies, respectively. This finding was consistent with the results obtained from the ELISPOT assay showing that HSP110-ICD complex could provide the immune system with the $CD4^+$ T cell epitopes. Earlier and more vigorous anti-ICD antibody responses in the HSP110-ICD immunized animals than in the ICD-immunized animals may be due to the chaperon activity of HSP110 to facilitate antibody responses by a better presentation of the antigen through MHC class II molecules and thereby to provide help for B-cells through activation of CD4+ T cells. Western blot analysis of the immune sera revealed the specificity of the antibody for ICD. Elevation of IgG Ab isotype against ICD is important since Herceptin, an anti-HER-2/neu antibody being used to treat breast cancer patients overexpressing HER-2/neu, is also of IgG isotype.

While this HSP110-protein vaccine lacks some of the polyvalent benefits of the tumor-derived HSPs, which presumably carries a spectrum of unknown peptides, it also offers important benefits: 1) Since HSP110 is able to efficiently bind large proteins at approximately an equivalent molar ratio, a highly concentrated vaccine would be presented to the immune system compared to a tumor derived HSP/GRP where only a very small fraction of the HSP/GRP would be expected to carry antigenic epitopes. This vaccine would include numerous peptide epitopes (a single copy of each represented in each full-length protein) bound to every HSP110. Thus, such a preparation would not only be "partially polyvalent" as well as being targeted against a specific tumor protein antigen but may also provide both CD4 and CD8 antigenic epitopes. The vaccine would also circumvent HLA restriction since a large reservoir of potential peptides would be available. 2) Such a recombinant protein vaccine would not be an individual specific vaccine, as are the tumor-derived HSP vaccines, but could be applied to any patient with a tumor expressing that tumor antigen.

Further, if an antigenic protein is shared among several tumors, the HSP110-protein complex could well be applied to all cancers expressing that protein. For example, in the case of HER-2/neu, HSP110-her-2 vaccines would be applicable to the treatment of numerous patients with breast cancer as well as ovarian, prostate, lung and colon cancers. 3) Lastly, preparation of such protein vaccines would be much less labor intensive than purification of tumor-derived HSP from a surgical specimen. Indeed, a surgical specimen is not required to prepare such a vaccine. The vaccine would also be available in unlimited quantity and a composite vaccine using more than a single protein antigen (e.g. gp100, MART1, etc for melanoma) could be easily prepared.

HSPs have been proposed to be "danger signals" which alarm the immune system of the presence of tumor or damaged tissues. This hypothesis envisions the release of HSPs, carrying peptides, from necrotic or damaged cells and their uptake by APCs, thereby providing the immune system with both a "signal 1" (peptide presentation) and a "signal 2" (upregulation of co-stimulatory molecules). Indeed, several studies indicated that HSPs are able to activate APCs. HSP110 can induce maturation of DCs, up-regulate MHC class II surface expression, and up-regulate the expression of pro-inflammatory cytokines tumor necrosis factor-alpha (TNF-α) and IL-6 in mouse DCs. However, in addition to peptides, it has long been understood that HSPs/GRPs are also essential to protein folding and assembly events within cells and also bind damaged and mutant proteins in vivo. It is not clear what fraction of an HSP/GRP family (e.g. HSP70 or HSP110) is actually complexed with peptides relative to that fraction complexed with full-length proteins. Thus, the release of HSP as a putative danger signal would also encompass the presentation of HSP-protein complexes, as disclosed herein, in addition to peptide complexes.

Aluminum adjuvants, together with calcium phosphate and a squalene formulation are the only adjuvants approved for human vaccine use. These approved adjuvants are not effective in stimulating cell-mediated immunity but rather stimulate a good Ab response. Shown here is that HSP110 is a safe mammalian adjuvant in molecular targeting of a well-known tumor antigen, ICD of HER-2/neu, being able to activate both arms of the immune system. In addition, neither CTL nor antibody responses was found against HSP110 itself. This property of HSP110 is particularly interesting in light of the paucity of adjuvants judged to be effective and safe for human use. Studies of HER-2/neu transgenic mouse using HSP110-ICD complex as an immunogen demonstrate that HSP110-ICD complex may inhibit spontaneous breast tumor formation in this transgenic animal model.

Example 17

Targeted Immunotherapy Using in vitro Reconstituted Chaperone Complexes of hsp110 and Melanoma Associated Antigen gp100

This example describes a novel strategy for antigen-specific vaccination for cancer immunotherapy, which uses human melanoma-associated antigen, gp100, naturally complexed to the highly efficient molecular chaperone, hsp1100. This example demonstrates that hsp110 can effectively protect against heat shock induced aggregation of gp100 through direct interaction. Hsp110-gp100 complexes generated in vitro by heat shock are immunogenic, as determined by their ability to elicit CD8+ T cell activity and antigen specific antibody responses. Immunization with the hsp110-gp100 complexes protected mice against subsequent challenge with human gp100-transduced B16 melanoma, which requires both CD4+ and CD8+ T cells. Administration of the hsp110-gp100 vaccine to the mice bearing established tumor also resulted in significant suppression of tumor growth. Furthermore, multiple vaccinations with the hsp1-gp100 complexes exhibited an anti-tumor effect against the wild-type B16 tumor, indicating that the immune response cross-reacts with mouse gp100. Thus, this antigen-targeted vaccine, which utilizes the natural chaperone complexes of hsp110 with antigens like gp100, provides a powerful new approach for inducing antigen specific immune response and can be applied for the treatment of cancer as well as other infectious diseases.

The recent identification of genes encoding tumor-associated Antigens (TAA) has created new possibilities for the development of cancer vaccines. The melanoma-associated antigen, gp100, which is a melanocyte differentiation antigen, is expressed at low levels in melanocytes and is highly expressed in about 80% of HLA-A2 positive malignant melanomas. gp100 can be specifically recognized by cytotoxic T lymphocytes (CTLs) as well as antibodies derived from melanoma patients. The human gp100 gene, which is about 75% identical to its mouse homologue, has been shown to induce protective immunity in mice after immunization using adenovirus-mediated gene transfer. In addition, gp100 has also been defined as a tumor rejection antigen in mice, and the adoptive transfer of gp100-reactive, tumor-infiltrating lymphocytes (TIL) or gp01-derived peptide vaccines can induce an anti-tumor immune response in some melanoma patients. Thus, gp100 is an attractive candidate for vaccine development.

Besides the abilities to bind short peptides, HSPs can also bind to and stabilize large proteins. They have been implicated in the folding and translocation of newly synthesized proteins, the assembly and disassembly of multiunit protein complexes and the folding of misfolded proteins. The study described here uses a novel approach to improve cancer vaccine formulations, taking advantage of the strong chaperone properties of heat shock protein hsp110 to bind and chaperone large protein substrates with high efficiency. To do this, a recombinant tumor antigen (e.g. gp100) is non-covalently complexed with hsp110 during heat shock in vitro. This recombinant HSP-based vaccine formulation targets the tumor-associated antigen (gp100). This HSP-protein vaccine can be applied to any patient with a tumor expressing the antigen used in the vaccine complex. This approach presents a highly concentrated tumor-associated antigen chaperoned by the immunologically functional HSP, as shown in Example 16 herein, using Her-2/neu as an antigen of choice.

This example demonstrates that the natural hsp110-gp100 complexes, reconstituted by heat shock in vitro, are able to elicit both cell-mediated and humoral immune responses against the gp100 antigen. Most importantly, immunization with the hsp110-gp100 complexes results in a strong anti-tumor immunity, which involves both CD4+ and CD8+ T cells.

Material and Methods

Mice and cell lines. 8 to 12-week-old female C57BL/6 mice purchased from Taconic (Germantown, N.Y.) were housed under pathogen-free conditions. All experiments involving the use of mice were performed in accordance with protocols approved by the Animal Care and Use Committee of Roswell Park Cancer Institute. Human gp100-transduced B16 cells (B16-gp100) and parental B16 melanoma cells were kindly provided by Dr. Alexander Rakhmilevich (University of Wisconsin-Madison) (Rakhmilevich, A. L., et al. 2001, Cancer Res. 7: 952-961). All cells were maintained in RPMI 1640, supplemented with 10% heat-inactivated fetal bovine serum (FBS) (Life Technologies, Grand Island, N.Y.), 2 mM L-glutamine, 100 U/ml penicillin, and 100 μg/ml streptomycin.

Expression and purification of recombinant protein. Recombinant mouse hsp110 cDNA was subcloned into pBacPAK-his vector and co-transfected with BacPAK6 viral DNA into Sf21 insect cells using a BacPAK™ baculovirous Expression System kit (Clontech laboratories Inc., CA) followed by amplification of the recombinant virus and purification of hsp110 protein using nickel nitriloacetic acid (Ni-NTA)-agarose (Qiagen, Germany). Human gp100 cDNA provided by Dr. Nicholas Restifo (National Cancer Institute, Bethesda, Md.) was subcloned into SpeI/XbaI sites of pRSETA vector (Invitrogen). Plasmid was transformed into *Escherichia coli* JM 109 (DE3) cells and purified using a Ni-NTA-agarose column following the manufacturer's instructions. Protein concentration was determined using a Bio-Rad protein assay kit.

Thermal Aggregation Experiments. 150 nM gp100 alone or in the presence of 1:1 molar ratio of ovalbumin, hsp110 or hsp70 were equilibrated to room temperature in 25 mM Hepes, pH 7.4, 5 mM magnesium acetate, 50 mM KCl, 5 mM β-mercaptoethanol followed by incubation at the indicated temperature in a thermostated cuvette. Light scattering by protein aggregation was determined by measuring the increase of optical density at 320 nm with a spectrophotometer. The samples were then transferred to microcentrifuge tubes and centrifuged for 15 min at 16,000×g at 4° C., and supernatant and pellet were separated and run on SDS-polyacrylamide gel electrophoresis, and probed with anti-gp100 antibody HMB45 (Adema 1996). Hsp110-antigen Binding. Hsp110 and gp100 were mixed in a 1:1 molar ratio and incubated for 30 min at the indicated temperatures in PBS. The samples were then incubated for 30 min at room temperature. The binding was evaluated by immunoprecipitation as previously described (Manjili 2002). Briefly, the samples were incubated with rabbit hsp110 antiserum (1:100) at room temperature for 1 h. The immune complexes were then precipitated using Protein-A Sepharose™ CL-4B (20 μl/ml; Amersham Pharmacia Biotech, Upsala, Sweden) and washed 6 times with phosphate-buffered saline containing 500 mM NaCl, 1% Nonidet P-40. The pellet was resolved in SDS-PAGE and subjected to western analysis with anti-gp100 antibody.

Western blot analysis. Equivalent protein samples were subjected to 10% SDS-PAGE and transferred onto immobilon-P membrane (Millipore Ltd., UK). Membranes were blocked with 5% non-fat milk in TBST (20 mM Tris-HCl, pH 7.4, 137 mM NaCl, 0.05% Tween-20) for 1 h at room temperature, and then incubated for 1 h with mAb for gp100, HMB45 (NeoMakers, Fremont, Calif.) diluted 1:500 in TBST. After washing, membranes were incubated with horseradish peroxidase-conjugated goat anti-mouse 1 gG diluted 1:4,000 in TBST at room temperature for 1 h. The protein was visualized using the enhanced chemiluminescence detection system according to manufacturer instructions (Amersham, Arlington Heights, Ill.).

Enzyme-linked immunosorbent spot (ELISPOT) assay. The ELISPOT assay was used to determine antigen-specific IFN-γ secreting T cells. Briefly, the 96-well filtration plates (Millipore, Bedford, Mass.) were coated with 10 μg/ml rat anti-mouse IFN-γ (clone R4-6A2, Pharmingen, San Diego, Calif.) in 50 μl of PBS. After overnight incubation at 4° C., the wells were washed and blocked with culture medium containing 10% FBS. Splenocytes were isolated from the mice 2 weeks after vaccination. Red cells were lysed by incubation of the splenocytes with Tris-$NH_4Cl$ for 5 min at room temperature and then washed twice. Splenocytes ($5\times10^5$/well) were added to the wells and incubated with 50 μl of the gp100 (20 μg/ml) or HSP110 (20 μg/rnl) at 37° C. in an atmosphere of 5% $CO_2$ for 24 h. The plates were then extensively washed (8 times) and incubated with 5 μg/ml biotinylated IFN-γ antibody (clone XMGI.2, Pharmingen, San Diego Calif.) in 50 μl PBS at 4° C. overnight. After six washes, 0.2 U/ml avidin-alkaline phosphatase D (Vector Laboratories, Burlingame Calif.) in 50 μl PBS was added and incubated for 2 h at room temperature. After washing, spots were developed by adding 50 μl of 5-bromo-4-chloro-3-indolyl phosphatase/Nitro Blue Tetrazolium (Boehringer Mannheim, Indianapolis, Ind.) and incubated at room temperature for 20 minutes. The spots were counted using a dissecting microscope.

$^{51}$Cr release assay. Splenocytes were harvested 2 weeks following immunization and stimulated in vitro with irradiated B16-gp100 cells (12,000 rad) for 5 days. Splenocytes were then serially diluted in 96 V-bottomed well plates (Costar, Cambridge, Mass.) in triplicate with varying E: T ratios. $^{51}$Cr-labeled tumor cells ($1\times10^4$) were added to a final volume of 200 μl/well. Wells containing target cells, with either culture medium alone or with 0.5% Triton X-100, served as spontaneous and maximal release controls, respectively. After 5 h incubation at 37° C., 150 μl supernatant was analyzed for radioactivity using a gamma counter (Packard, Downers Grove, Ill., USA) and the percentage of specific lysis was calculated by the formula: percent specific lysis=100×(experimental release−spontaneous release)/(maximum release−spontaneous release). In some experiments, the re-stimulated effector cell populations were incubated with the anti-CD8 antibodies (20 μg/ml) for 30 min at 4° C. to block CD8+ T cells before cytotoxicity assays.

Enzyme-linked immunosorbent assay (ELISA). Briefly, 96-well microtiter plates were coated overnight at 4° C. with gp100 (20 μg/ml) or hsp110 (20 μg/ml). Plates were then blocked with 1% BSA in PBS for 2 h at 37° C. After washing with PBS containing 0.05% Tween-20, 5-fold serial dilutions of the sera starting at 1:200 were added, and incubated at room temperature for 2 h. Plates were washed 3 times and horseradish peroxidase (HRP)-conjugated goat anti-mouse IgG (Boehringer Mannheim, Indianapolis, II) was added. The colorimetric reactions were developed by adding 100 μl/well of the TMB Microwell peroxidase substrate (KPL, Maryland). After the reactions were stopped with 50 μl of 2 M $H_2SO_4$, the wells were read at 490 nm in a Titertek Multiscan MCC/340 plate scanner. Specificity of the binding was also assessed by western analysis using the pre-immune sera or the pooled immune sera (1:2000), collected from the hsp110-gp100 complexes immunized animals.

Tumor challenge Assays. Mice were immunized i.p. with 30 μg of hsp110 alone, gp100 alone or the hsp110-gp100 complex on days −28 and −14, with the exception of the mice that were immunized s.c. with 30 μg gp100 together with Complete Freund's Adjuvant (CFA) and boosted together with Incomplete Freund's Adjuvant (IFA). Two weeks after second immunization (on day 0), mice were injected i.d. with $1\times10^5$ B16-gp100 cells in 50 μl of PBS. For therapeutic treatment of tumor bearing animals, mice were first inoculated i.d. with $5\times10^4$ B16-gp100 tumor cells. The hsp110-gp100 vaccine was then administered i.p. on days 4, 9 and 14 after tumor implantation. Tumor growth was monitored every two days by measuring perpendicular tumor diameters using an electronic digital caliper. The relative tumor volume is calculated using the formula V=(The shortest diameter$^2$×the longest diameter)/2.

In vivo antibody depletion. Anti-CD4 hybridoma (GK1.5 cells and anti-CD8 hybridoma (2.43 cells) were obtained from the American Type Culture Collection (Rockville, Md.). Anti-CDR mAb and anti-CD8 mAb were produced from ascites of SCID mice injected i.p. with GK1.5 and 2.43 hybridomas. Depletion of CD4+, CD8+ T cell subsets was accomplished by i.p. injection of 200 μg GK1.5 (anti-CD4+), 2.43 (anti-CD8+) mAb respectively, given every other day for 5 days before vaccination or tumor challenge. Effective depletion of cell subsets was confirmed by FACS analysis of splenocytes 1 day after the third injection and maintained by continuing the antibody injections once a week for the duration of the tumor challenge experiment. Isotype-matched antibodies were also used as control, and no effect on the tumor growth was observed.

Data analysis. All experiments were repeated a minimum of three times. The data in each figure is from one representative experiment. Each group has at least 5 mice. The unpaired Student's t-test was performed for statistical analysis and data are presented as mean±standard error (SE). Values of $p<0.05$ were considered statistically significant using the unpaired Student's t-test.

Results

Characterization of in vitro "Natural Chaperone Complexes" of hsp110-gp100

To characterize the molecular chaperoning function of hsp110, the melting temperature of gp100 antigen was determined using an in vitro aggregation assay. Recombinant human gp100 protein was incubated for up to 30 min at room temperature, 43° C., 50° C., 55° C. or 60° C. in a thermostated cuvette. Light scattering at 320 nm by protein aggregation vas measured using a spectrophotometer (FIG. 42A). Optical density changes of the gp100 indicated that the melting temperature of this antigen is at around 50° C. Furthermore, after incubations at different temperatures, the samples were separated into supernatant (soluble) and pellet (insoluble) fractions by centrifugation. Both fractions were resolved into sodium dodecyl sulfate-polyacrylamide gel electrophoresis (SDS-PAGE) and analyzed by immunoblot with anti-gp100 antibody (FIG. 42B). It was observed that gp100 protein become insoluble in a temperature-dependent manner. The amount of gp100 protein in the insoluble fraction reached maximum around 50° C., which is consistent with light scattering measurements shown in FIG. 42A. Thus, 50° C. was used in this model as the temperature to characterize the chaperoning functions of hsp110.

To determine whether hsp110 can protect heat induced denaturation of gp100, aggregation studies were performed at 50° C. (FIG. 43A). It was seen that, when presented in a 1:1 molar ratio, hsp110 is efficient in inhibiting the heat-induced aggregation of gp100 in vitro. However, gp100 aggregation was not prevented in the presence of ovalbumin. For comparative purposes, chaperoning function of hsp70 was also examined in parallel, as hsp110 shares sequence similarities with the hsp70 family. It was found that, although hsp70 as a molecular chaperone is also capable of inhibiting the gp100 aggregation, it is less efficient than hsp110 in holding larger proteins, such as gp100 (FIG. 43A). The co-immunoprecipitation was then used to examine binding of hsp110 and gp100. Hsp110 and gp100 mixtures (1:1) were incubated at different temperatures for 30 min, followed by 30 min incubation at room temperature. Afterward, anti-hsp110 antibody was added to precipitate hsp110 using protein A-sepharose beads. The immune complexes were then analyzed using anti-gp100 antibody. It was observed that gp100 co-precipitates with hsp110 indicating that the protective effect of hsp110 is due to its direct interaction with gp100. Furthermore, gp100 protein was seen to associate with hsp110 in a temperature-dependent manner, with optimal binding at 50° C. (FIG. 43B). Thus, this condition was used to generate the hsp110-gp 100 complexes in vitro.

Immunization with the hsp110-gp100 Complexes Induces Both CT'L Activity and Antibody Response Immunogenicity of hsp110-gp100 complexes reconstituted in vitro was first examined using ELISPOT, which is a sensitive functional assay for measuring IFN-γ production at the single-cell level. Mice were immunized twice with hsp110 alone, gp100 alone and hsp110-gp100 complexes at the interval of two weeks. Two weeks after second immunization, splenocytes were isolated and stimulated with gp100 in vitro. It was found that splenocytes derived from the hsp110-gp100 complex immunized mice showed significant IFN-γ production upon stimulation with gp100, while immunization with hsp110 alone or gp100 alone did not elicit gp100 specific IFN-γ production (FIG. 44A). Most notably, splenocytes from all groups did not generate IFN-γ spot when stimulated with hsp110.

To determine the ability of hsp110-gp100 vaccine to elicit CTL responses, chromium release assays were carried out after immunization. Splenocytes obtained from the nice immunized with hsp110-gp100 complexes demonstrated a significant lytic activity against the B16-gp100 cells, whereas cells from mice immunized with hsp110 alone or gp100 alone showed no cytotoxic activity. This specific killing was completely inhibited by blocking of CD8+ T cells with an anti-CD8 antibody, indicating that CD8+ T cells were responsible for the observed CTL activity (FIG. 44B).

In addition, sera were also collected from mice three weeks after the immunization and examined for antigen specific antibody responses by ELISA. As indicated in FIG. 44C, gp100 specific IgG levels were remarkably elevated in the mice immunized with hsp110-gp100 complexes compared to that of the animals immunized with gp100 alone. Specificity of the antibody for the gp100 was also confirmed by Western blot analysis using pooled sera from these animals. Sera obtained from the experimental animals did not recognized hsp110 regardless of vaccine formulation used.

Vaccination with the hsp110-gp100 Complexes Elicits Anti-Tumor Immunity Against B16-gp100 Tumor Challenge Tumor challenge assays were used to determine the capacity of the hsp110-gp100 complexes to induce protective anti-tumor immunity. C57BL/6 mice were immunized twice with hsp110 alone, gp100 alone, hsp110-gp100 complexes, or left untreated. Two weeks after second immunization, mice were challenged intradermally with $1\times10^5$ B16 murine melanoma cells transduced with human gp100 cDNA (B16-gp100). Naive mice and mice receiving only hsp110 or gp100 exhibited no protection from tumor challenge, and all of these mice developed aggressively growing tumors. However, mice immunized with hsp110-gp100 complexes were protected from subsequent challenge with B16-gp100 melanoma (FIG. 45D), and 20% of mice remained tumor free for at least 2 months. Among the animals that developed tumors, relative tumor volumes in mice immunized with hsp110-gp100 complexes were markedly smaller than those of animals immunized with hsp110 alone or gp100 alone.

To further characterize immunogenicity of the hsp110-gp100 complexes, different vaccine formulations were used in tumor challenge studies. Mice were immunized twice with different vaccine formulations: OVA plus gp100 treated with heat shock, hsp110 plus gp100 without heat shock, hsp110 plus heat-denatured gp100, CFA plus gp100, or hsp110-gp100 complexes. Two weeks after the booster, mice were challenged with $1\times10^5$ B16-gp100 tumor cells (FIG. 46A). Only the hsp110-gp100 complex vaccine elicited a strong anti-tumor immunity, indicating that immunogenicity of the vaccine depends on formation of a complex between gp100 and hsp110 by heat shock. Although adding CFA to the gp100 could inhibit tumor growth to some degree, CFA+gp100 is far less efficient than the hsp110-gp100 complex.

To evaluate this vaccination strategy in a model that is more analogous to the clinical setting, the therapeutic efficacy of the hsp110-gp100 complex was examined in mice bearing established tumors. Mice were first inoculated with $5\times10^4$ B16-gp100 tumor cells on day 0. The hsp110 alone, gp100 alone, or hsp1-gp100 complexes were administered i.p. on day 4. This treatment was repeated on days 9 and 14 after tumor implantation. Treatment with hsp110-gp100 vaccine significantly inhibited the growth of established tumor, while treatments with hsp110 or gp100 alone did not exhibit any anti-tumor effects (FIG. 46B). The effect of therapeutic treatment against established tumor was further confirmed by evaluating the survival tine of mice. Survival time for the animals was calculated based on the time it took for tumors to reach a diameter of 15 mm. It was seen that tumor-bearing mice without treatment and mice treated with hsp110 or gp100 showed mean survival time of 21.8±0.86, 22.5±1.12 and 23.6±1.32 days, respectively, whereas hsp1-gp100 complex-treated mice showed survival tune of 36.2±3.58 days ($p<0.005$).

Both CD4+ and CD8+ T Cells are Involved in the Antitumor Immunity Elicited by hsp110-gp100 Complexes To evaluate the contribution of T-cell subsets to protective immunity mediated by the hsp110-gp100 vaccine, in vivo antibody depletion was performed during immunization. Mice were first depleted of CD4+, CD8+ or both CD4+ and CD8+ T cell subsets before vaccination with hsp110-gp100 complexes. The depletion of T cell subsets was maintained by injection of the antibodies weekly. All the mice were then challenged with the B16-gp100 tumor cells two weeks after the booster (FIG. 47A). All naive mice and mice depleted of CD4+ T cells, CD8+ T cells or both CD4+ and CD8+ T cells developed aggressively growing tumors after the challenge.

To further examine the role of the two T-cell subsets, antibody depletion was carried out during the challenge phase. Mice were first primed and boosted with the hsp110-gp100 complexes. CD4+ or CD8+ T cell subsets were then depleted before tumor cells were inoculated into the mice (FIG. 47B). Injections of depleting antibodies were repeated every week after tumor challenge until the experiment was terminated. Depletion of CD8+ T cells or both CD4+ and CD8+ T cells abrogated the anti-tumor effect of vaccination. In contrast, when mice were depleted of CD4+ T cells at the challenge phase, tumor immunity elicited by the hsp110-gp100 complexes was intact. These data suggest that CD8+ T cells are the primary effectors in the anti-tumor response, while CD4+ T cells are required for priming the induction of effective antigen-specific ant-tumor responses.

Multiple Vaccinations with hsp110-gp100 Complexes Inhibit Growth of Wild-Type B16 Tumor Further studies were undertaken to determine whether immunization of mice with human gp100 chaperoned by hsp110 could break tolerance against mouse gp100 and protect mice against wild-type B16 tumor that expresses the murine gp100. Two immunization schedules were tested. One group of mice was immunized with hsp110-gp100 complexes on days −28, −14; another group was immunized on days −30, −20, and −10. Mice were challenged with wild-type B16 tumor on day 0. Although two immunizations with hsp110-gp100 complexes revealed marginal inhibition of the wild-type B16 tumor cells, three vaccinations with the same regimen induced a statistically significant inhibition of wild-type B16 tumor compared to the control mice (FIG. 48A).

Furthermore, CTL assay using splenocytes derived from vaccinated or unvaccinated animals also indicated that multiple immunizations with the hsp110-gp100 complexes resulted in an increased cytolytic activity against B16 tumor cells relative to the two-immunization protocol (FIG. 48B).

Discussion

This example describes a novel approach for cancer vaccine development, which takes advantage of the natural chaperoning function of certain HSPs (e.g. hsp110). This strategy utilizes the molecular chaperone hsp110 as an antigen delivery vehicle that readily forms non-covalent complexes with protein substrates (e.g. gp100) during heat shock. The data presented here demonstrate that the hsp110-gp100 complexes reconstituted in vitro by heat shock elicit gp01-specific immunity while either the hsp110 molecule alone, or the gp100 alone, do not. This observation indicates that the hsp110-gp100 protein complex exhibits immunological activities similar to the HSP-peptide complexes derived from tumor. This example is also consistent with other examples herein using the intracellular domain (ICD) of Her-2/neu as the antigen. Further studies described herein test different regimens (hsp110-gp100 mixture without heat shock, hsp110 mixed with heated gp100, or ova-gp100 mixture with heat shock) for comparison with the actual hsp110-gp100 complex as a vaccine. The results demonstrate that non-covalent formation of the hsp110-gp100 complex is important for its immunogenicity. Immunization with gp100 chaperoned by hsp110, but not other (non-heat shock) proteins such as OVA, is necessary to generate antigen-specific immunity.

It is well known that interaction of HSPs and denatured protein substrates within the cells is an important natural function of these molecular chaperones. Thus, complexes between HSP and substrate protein as used in this example reflect chaperone complexes present naturally. In agreement with previous studies showing that hsp110 is far more efficient than hsp70 in protecting luciferase from heat induced aggregation, the data presented herein show that hsp110 is significantly more efficient in maintaining heat-damaged gp100 protein in a soluble state than its evolutionary relative, hsp70. Hsp110, is much more efficient in binding and holding large proteins (e.g. luciferase, Citrate Synthase and gp100), although the conditions for generation of hsp110-protein complexes differ. In the case of gp100, it is associated with hsp110 in a temperature-dependent manner and the optimal binding occurs at around 50° C. The differences might be attributed to the different biochemical properties of the protein antigens used. Thus, those skilled in the art will appreciate the value of optimization using the characterization protocols described herein when a protein antigen is selected for complexing with hsp110.

This example demonstrates that immunization with human melanoma antigen gp100 chaperoned by heat shock protein hsp110 results in a strong immunity against gp100, which is evidenced by antigen-specific CTL activity and antibody responses. These data are consistent with other examples herein showing that immunization with hsp 10-ICD complexes can induce both CD8+ and CD4+ T cells to produce IFN-γ, as well as ICD specific antibody response. It is possible that antigen presentation of gp100 is mediated through cross-priming, where hsp110-antigen complexes are taken up through receptor mediated endocytosis and processed by APCs, which eventually present both CD8+ and CD4+ T-cell epitopes of gp100. The observations here also provide additional evidence that hsp110 is able to route exogenous antigens into an endogenous processing pathway for presentation by MHC class I molecules.

Mice immunized with hsp110 alone did not show any IFN-γ production upon in vitro stimulation with hsp110, consistent the studies of ICD (Example 16). This is not surprising since the mouse sequence for hsp110 was used in these studies. Indeed, this is one of the major advantages of this approach. Interestingly, this hsp110-gp100 complex is even more potent than vaccination with gp100 mixed with CFA, in terms of an anti-tumor response. These results demonstrate that hsp110 is an adjuvant with a number of unique characteristics: in contrast to other adjuvants which are not effective in stimulating cell-mediated immunity, the adjuvanticity of hsp110 generates both MHC class I-restricted T cell responses and antigen-specific antibody responses.

Compared with the tumor-derived HSPs, which presumably carry a spectrum of unknown antigenic peptides, only some of which would be immunogenic, the recombinant hsp110-protein vaccine approach described here provides a highly concentrated vaccine that targets a specific antigen. The entire natural antigen employed in this approach contains multiple MHC class I and class II epitopes and thereby allows the individual's own MHC alleles to select the appropriate epitope for presentation. Thus, vaccination with whole protein complexes may increase the chance of polyepitope-directed T and B cell responses. This approach would therefore circumvent HLA restriction and would not be an individual specific vaccine, as are the tumor-derived HSPs, but could be applied to any patient with a tumor expressing that antigen. Lastly, this vaccine can be generated in unlimited quantity and is less time-consuming to prepare than is required for purification of tumor-derived HSP vaccines. Most importantly, a tumor specimen is not required for vaccine preparation.

In vivo depletion studies demonstrated that both CD4+ and CD8+ T cells are required for the antigen-specific immune response elicited by hsp110-gp100 complexes. This is consistent with previous studies showing that either CD4+ or CD8+ depletion abrogated the anti-tumor effect of tumor-derived gp96, although other reports indicate that the CTL responses elicited by HSP fusion proteins are independent of CD4+ T cells. This discrepancy may be due to the different immunization approaches and vaccine formulations utilized. In the present system, using gp100 as a model antigen, CD8+ T cells are likely to be the primary effector cells as shown by the CTL assay in this example. However, induction of effective anti-tumor immunity by hsp110-gp100 vaccination also depends on the presentation of MHC class II-restricted epitopes to CD4+ T cells. In vivo activation of CD4+ T cells may produce enough cytokines or deliver helper signals for the proliferation and clonal expansion of CD8+ T cells, which are primed by immunization of hsp110-gp100 complexes. However, the precise contribution of CD4+ T cells to the observed anti-tumor immunity requires further investigation.

Also demonstrated in this example is that multiple immunizations (3 doses) with hsp110-gp100 complexes induce a distinct anti-tumor immunity against wild-type B16 melanoma, indicating that vaccination with the human gp100 breaks tolerance to the endogenous mouse gp100 expressed by the B16 tumor cells. It is proposed that nonhomologous regions of the full-length human gp100 could result in intramolecular epitope-spreading or facilitate antibody-mediated antigen capture by APCs, which could contribute to this cross-reaction. A similar cross-reactivity between the human and murine gp100 was also observed following immunization with recombinant vaccinia virus encoding human gp100. However, others demonstrated that CTL generated from human gp100 immunization specifically recognized human gp100 not mouse gp100. These differences may be due to the very low frequency of cross-reactive T cells or to the vaccination approaches used.

In a therapeutic setting against established tumor cells, the level of antitumor protection achieved with the hsp110-gp100 vaccine was reduced compared with that obtained in a preimmunization model. Nevertheless, treatment with the hsp110-gp100 vaccine resulted in a significant inhibition of tumor growth. Several approaches can be considered to improve this vaccination approach. For example, simultaneous immunization against two antigens might enhance the immune response and prevent the escape of tumor variants that may have lost antigen expression or express insufficient levels of the target antigen. Second, multiple administrations of hsp110-gp100 vaccines may enhance the therapeutic efficacy (e.g. anti-tumor response against wild-type B16 with three doses compared to two doses). Furthermore, using mouse gp100 as a booster may also expand the cross-reactive T cells generated by the hsp110-human gp100 complex.

The studies described herein indicate that hsp110-gp100 complexes can be reconstituted in vitro by using the natural chaperoning functions of a major heat shock protein, i.e. hsp110. These natural chaperone hsp110-gp100 complexes exhibit an active immunological activity indicated by the stimulation of both T cell and antibody responses. The antigen-specific immunity elicited by hsp110-gp100 complexes demonstrates significant protection against tumor challenge in both prophylactic and therapeutic models. Thus, the hsp110-based vaccine targeting specific antigens represents a powerful and novel approach for use in the immunotherapy of cancer.

Example 18

Anti-Tumor Efficacy of hsp70, hsp110, and hsp70-hsp110 Complexed with ICD

This example shows the efficacy of hsp70 and/or hsp110 complexed with ICD of her2/neu breast cancer antigen in reducing tumor incidence and tumor volume in treated mice. Tumor incidence was examined in FVBN202 mice after immunization at two-week intervals with hsp110-ICD. The percent tumor-free mice for naïve and hsp110-ICD immunized mice were compared. While none of the naïve mice remained tumor-free at 235 days, 60% of the immunized mice remained tumor free at this time-point, and 50% of the immunized mice were tumor-free through the full 260 days of the study. Immunization with hsp110-ICD delayed the onset of tumors as well as reducing the number of mice developing tumors. Naïve mice began to exhibit tumors at 185 days, while tumors were not observed in immunized mice prior to 210 days.

The anti-tumor efficacy of hsp70, hsp110 and hsp70 together with hsp110 when complexed with ICD was compared. Tumor volume, in cubic millimeters, was determined at days 7, 10, 13 and 16 after challenge for naïve mice as well as for mice treated with ICD only, hsp110-ICD, hsp70-ICD and hsp110/hsp70-ICD. The results show that complexing ICD with hsp70, hsp110 or both, dramatically increases the efficacy of ICD in reducing tumor volume. No significant differences were observed between naïve and ICD-immunized mice.

Example 19

Construction of Recombinant Heat Shock Proteins Fused to Antigens

This example describes the preparation of constructs for expression of recombinant stress protein complexes in *E. coli*. Large molecular weight heat shock proteins (hsp) are fused to antigens in an *E. coli* expression system using a modified pET28 system. DPV and TbH9 are used as model antigens with hsp1105 and grp170 as the representative stress proteins. Although specific constructs are described herein, those skilled in the art will appreciate that many variations are possible. For example, the fusions can be constructed in a different order, the his tags can be removed and/or several antigens can be fused at once to a particular hsp. These methods can also be adapted for construction of DNA vaccines.

GRP170 Expression in pPDM His

For pPDM His Expression, the open reading frame was PCR amplified with the following primers:

```
                                     (SEQ ID NO: 7)
PDM-716
5' gcagctacagtaaggaggcagaggcc 3'
Tm 64° C.

                                     (SEQ ID NO: 8)
PDM-717
5' cattgttagcggccgctcattacacgtgtagttcatcgttc 3'
Tm 68° C..
```

Using the following conditions:

10 μl 10×Pfu buffer; 1 μl 10 mM dNTPs; 2 μl 10 μM each oligo; 83 μl sterile water; 1.5 μl Pfu DNA polymerase (Stratagene, La Jolla, Calif.); 50 ηg DNA;

| | | |
|---|---|---|
| 96° C. 2 minutes | | |
| 96° C. 20 seconds | 65° C. 15 seconds | 72° C. 6 minutes × 40 cycles |
| 72° C. 4 minutes | | |

The PCR product was digested with NotI and cloned into pPDM His, (a modified pET28 vector), that had been digested with Eco72I and NotI. Constructs were confirmed through sequence analysis and then the pPDM GRP 170 construct was transformed into BLR pLys S and HMS 174 pLys S and checked for expression in *E. coli.*

DPV/GRP170 Fusion pPDM His

For the pPDM HSP105 fusion, the open reading frame was PCR amplified with the following primers:

```
                                        (SEQ ID NO: 9)
PDM-571
5' gatcccgtggacgcggtcattaacacc 3'
Tm 66° C.

                                        (SEQ ID NO: 10)
PDM-732
5' cttacagagcggccgctcatcaatagttgttgcaggag 3'
Tm 69° C..
```

Using the following conditions (referred to hereinafter as Conditions A): 10 μl 10×Pfu buffer; 1 μl 10 mM dNTPs; 2 μl 10 μM each oligo; 83 μl sterile water; 1.5 μl Pfu DNA polymerase (Stratagene, La Jolla, Calif.); 50 ηg DNA;

| | | |
|---|---|---|
| 96° C. 2 minutes | | |
| 96° C. 20 seconds | 65° C. 15 seconds | 72° C. 45 seconds × 40 cycles |
| 72° C. 4 minutes | | |

The PCR product was cleaned up and gel purified and cloned into the pPDM GRP 170 construct which has been cut with Eco72I. Constructs were confirmed through sequence analysis and the pPDM GRP 170 B DPV construct was transformed into BLR pLys S and HMS 174 pLys S cells.

DPV in pPDM HSP 105 A Fusion

For the pPDM HSP 105 A fusion, the open reading frame was PCR amplified with the following primers:

```
PDM-571
5' gatcccgtggacgcggtcattaacacc 3'   (SEQ ID NO: 11)
Tm 66° C.

PDM-679
5' ggaatagttgttgcaggagccggc 3'      (SEQ ID NO: 12)
Tm 61° C..
```

Using the conditions described above as Conditions A.

The PCR product was cleaned up and gel purified and then cloned into pPDM HSP 105 A that had been digested with Eco72I and dephosphorylated with CIP. The construct was confirmed through sequence analysis and then transformed into BLR pLys S and HMS 174 pLys S cells.

HSPI05 Fusion Construct (HSPI05 B) for Expression in pPDM His

For pPDM His Expression, the open reading frame was PCR amplified with the following primers:

```
                                        (SEQ ID NO: 13)
PDM-677
5' cactcggtggttgggctagacgtaggctc 3'
Tm 67° C.

                                        (SEQ ID NO: 14)
PDM-746
5' cagttgaattcatcacacgtgatccaggtccatgttg 3'
Tm 65° C..
```

Using the following conditions:

10 μl 10×Pfu buffer; 1 μl 10 mM dNTPs; 2 μl 10 μM each oligo; 83 μl sterile water; 1.5 μl Pfu DNA polymerase (Stratagene, La Jolla, Calif.); 50 ηg DNA;

| | | |
|---|---|---|
| 96° C. 2 minutes | | |
| 96° C. 20 seconds | 65° C. 15 seconds | 72° C. 5 minutes 20 seconds × 40 cylces |
| 72° C. 4 minutes | | |

The PCR product was digested with EcoRI and cloned into pPDM His (a modified pET28 vector) that had been digested with Eco72I and EcoRI. Constructs were confirmed through sequence analysis. This construct was then used to put antigens in at the C-terminus of the HSP 105 protein at the Eco72I and EcoRI sites.

DPV/HSP105 Fusion in pPDM His

For the pPDM HSP 105 fusion, the open reading frame was PCR amplified with the following primers:

```
                                        (SEQ ID NO: 15)
PDM-571   5' gatcccgtggacgcggtcattaacacc 3'
          Tm 66° C.

                                        (SEQ ID NO: 16)
PDM-614   5' cctagaattcatcaatagttgttgcaggag 3'
          Tm 59° C..
```

Using the conditions described above as Conditions A.

The PCR product was digested with EcoRI and cloned into the pPDM HSP 105 B insert which had been digested with Eco72I and EcoRI. Constructs were confirmed through sequence analyses and the pPDM construct was transformed into BLR pLys S and BLR CodonPlus cells.

TbH9/Heat Shock Fusions in pPDM His

For the pPDM HSP 105 fusion and the pPDM GRP 170 B fusion, PCR the open reading frame with the following primers:

```
                                        (SEQ ID NO: 17)
PDM-570 5' gtggatttcggggcgttaccaccggag 3'
        Tm 66° C.

                                        (SEQ ID NO: 18)
PDM-613 5' ccgaagaattctagaaggcacagcagatctggatcc 3'
        Tm 67° C..
```

PCR using the following conditions:

10 μl 10×Pfu buffer; 1 μl 10 mM dNTPs; 2 μl 10 μM each oligo; 83 μl sterile water; 1.5 μl Pfu DNA polymerase (Stratagene, La Jolla, Calif.); 50 ηg DNA;

| | | |
|---|---|---|
| 96° C. 2 minutes | | |
| 96° C. 20 seconds | 65° C. 15 seconds | 72° C. 2 minutes 20 seconds × 40 cylces |
| 72° C. 4 minutes | | |

Clean up and gel purify the PCR product and clone into pPDM HSP 105 B and pPDM GRP 170 B that has been digested with Eco 72I. Constructs were confirmed through sequence analyses and transformed into BLR pLys S and BLR CodonPlus cells.

Provided in the Sequence Listing, which forms a part of this application, are nucleic acid and amino acid sequences corresponding to constructs produced in accordance with this example. Included in these sequences are:

SEQ ID NO: 19: HSP B TbH9 coding region
SEQ ID NO: 20: HSP B DPV coding region
SEQ ID NO: 21: HSP A DPV coding region
SEQ ID NO: 22: HSP 105 coding region SEQ ID NO: 23: GRP B DPV coding region
SEQ ID NO: 24: GRP B coding region
SEQ ID NO: 25: GRP170 with His
SEQ ID NO: 26: GRP B DPV protein
SEQ ID NO: 27: HSP B TbH9
SEQ ID NO: 28: HSP B DPV
SEQ ID NO: 29: HSP A DPV
SEQ ID NO: 30: HSP 105 with His
SEQ ID NO:31: HSP_B_TbH9_coding_region.seq__1 (frame 1 from 1 to 1257)
SEQ ID NO:32: HSP_B_TbH9_coding_region.seq__2 (frame 2 from 17 to 94)
SEQ ID NO:33: HSP_B_TbH9_coding_region.seq__3 (frame 2 from 359 to 442)
SEQ ID NO:34: HSP_B_TbH9_coding_region.seq__4 (frame 2 from 493 to 597)
SEQ ID NO:35: HSP_B_TbH9_coding_region.seq__5 (frame 2 from 706 to 756)
SEQ ID NO:36: HSP_B_TbH9_coding_region.seq__6 (frame 2 from 837 to 918)
SEQ ID NO:37: HSP_B_TbH9_coding_region.seq__7 (frame 2 from 989 to 1040)
SEQ ID NO:38: HSP_B_TbH9_coding_region.seq__8 (frame 2 from 1156 to 1205)
SEQ ID NO:39: HSP_B_TbH9_coding_region.seq__9 (frame 3 from 1 to 72)
SEQ ID NO:40: HSP_B_TbH9_coding_region.seq__10 (frame 3 from 398 to 447)
SEQ ID NO:41: HSP_B_TbH9_coding_region.seq__11 (frame 3 from 456 to 536)
SEQ ID NO:42: HSP_B_TbH9_coding_region.seq__12 (frame 3 from 904 to 981)
SEQ ID NO:43: HSP_B_TbH9_coding_region.seq__13 (frame 3 from 983 to 1257)
SEQ ID NO:44: HSP_B_TbH9_coding_region.seq__14 (frame −1 from 1 to 385)
SEQ ID NO:45: HSP_B_TbH9_coding_region.seq__15 (frame −1 from 442 to 503)
SEQ ID NO:46: HSP_B_TbH9_coding_region.seq__16 (frame −1 from 505 to 580)
SEQ ID NO:47: HSP_B_TbH9_coding_region.seq__17 (frame −1 from 699 to 808)
SEQ ID NO:48: HSP_B_TbH9_coding_region.seq__18 (frame −1 from 810 to 946)
SEQ ID NO:49: HSP_B_TbH9_coding_region.seq__19 (frame −1 from 948 to 1010)
SEQ ID NO:50: HSP_B_TbH9_coding_region.seq__20 (frame −1 from 1046 to 1107)
SEQ ID NO:51: HSP_B_TbH9_coding_region.seq__21 (frame −1 from 1127 to 1207)
SEQ ID NO:52: HSP_B_TbH9_coding_region.seq__22 (frame −2 from 12 to 237)
SEQ ID NO:53: HSP_B_TbH9_coding_region.seq__23 (frame −2 from 239 to 294)
SEQ ID NO:54: HSP_B_TbH9_coding_region.seq__24 (frame −2 from 296 to 345)
SEQ ID NO:55: HSP_B_TbH9_coding_region.seq__25 (frame −2 from 544 to 669)
SEQ ID NO:56: HSP_B_TbH9_coding_region.seq__26 (frame −2 from 702 to 785)
SEQ ID NO:57: HSP_B_TbH9_coding_region.seq__27 (frame −2 from 806 to 921)
SEQ ID NO:58: HSP_B_TbH9_coding_region.seq__28 (frame −2 from 930 to 982)
SEQ ID NO:59: HSP_B_TbH9_coding_region.seq__29 (frame −2 from 984 to 1066)
SEQ ID NO:60: HSP_B_TbH9_coding_region.seq__30 (frame −2 from 1071 to 1161)
SEQ ID NO:61: HSP_B_TbH9_coding_region.seq__31 (frame −3 from 62 to 153)
SEQ ID NO:62: HSP_B_TbH9_coding_region.seq__32 (frame −3 from 155 to 255)
SEQ ID NO:63: HSP_B_TbH9_coding_region.seq__33 (frame −3 from 257 to 312)
SEQ ID NO:64: HSP_B_TbH9_coding_region.seq__34 (frame −3 from 314 to 380)
SEQ ID NO:65: HSP_B_TbH9_coding_region.seq__35 (frame −3 from 690 to 759)
SEQ ID NO:66: HSP_B_DPV_coding_region.seq__1 (frame 1 from 1 to 949)
SEQ ID NO:67: HSP_B_DPV_coding_region.seq__2 (frame 2 from 17 to 94)
SEQ ID NO:68: HSP_B_DPV_coding_region.seq__3 (frame 2 from 359 to 442)
SEQ ID NO:69: HSP_B_DPV_coding_region.seq__4 (frame 2 from 493 to 597)
SEQ ID NO:70: HSP_B_DPV_coding_region.seq__5 (frame 2 from 706 to 756)
SEQ ID NO:71: HSP_B_DPV_coding_region.seq__6 (frame 2 from 885 to 949)
SEQ ID NO:72: HSP_B_DPV_coding_region.seq__7 (frame 3 from 1 to 72)
SEQ ID NO:73: HSP_B_DPV_coding_region.seq__8 (frame 3 from 398 to 447)
SEQ ID NO:74: HSP_B_DPV_coding_region.seq__9 (frame 3 from 456 to 536)
SEQ ID NO:75: HSP_B_DPV_coding_region.seq__10 (frame 3 from 875 to 949)
SEQ ID NO:76: HSP_B_DPV_coding_region.seq__11 (frame −1 from 51 to 114)
SEQ ID NO:77: HSP_B_DPV_coding_region.seq__12 (frame −1 from 134 to 195)
SEQ ID NO:78: HSP_B_DPV_coding_region.seq__13 (frame −1 from 197 to 272)
SEQ ID NO:79: HSP_B_DPV_coding_region.seq__14 (frame −1 from 391 to 500)
SEQ ID NO:80: HSP_B_DPV_coding_region.seq__15 (frame −1 from 502 to 638)
SEQ ID NO:81: HSP_B_DPV_coding_region.seq__16 (frame −1 from 640 to 702)
SEQ ID NO:82: HSP_B_DPV_coding_region.seq__17 (frame −1 from 738 to 799)
SEQ ID NO:83: HSP_B_DPV_coding_region.seq__18 (frame −1 from 819 to 899)
SEQ ID NO:84: HSP_B_DPV_coding_region.seq__19 (frame −2 from 236 to 361)
SEQ ID NO:85: HSP_B_DPV_coding_region.seq__20 (frame −2 from 394 to 477)
SEQ ID NO:86: HSP_B_DPV_coding_region.seq__21 (frame −2 from 498 to 613)
SEQ ID NO:87: HSP_B_DPV_coding_region.seq__22 (frame −2 from 622 to 674)
SEQ ID NO:88: HSP_B_DPV_coding_region.seq__23 (frame −2 from 676 to 758)
SEQ ID NO:89: HSP_B_DPV_coding_region.seq__24 (frame −2 from 763 to 853)
SEQ ID NO:90: HSP_B_DPV_coding_region.seq__25 (frame −3 from 1 to 51)
SEQ ID NO:91: HSP_B_DPV_coding_region.seq__26 (frame −3 from 382 to 451)
SEQ ID NO:92: HSP_A_DPV_coding_region.seq__1 (frame 1 from 1 to 955)

SEQ ID NO:93: HSP_A_DPV_coding_region.seq__2 (frame 2 from 26 to 93)

SEQ ID NO:94: HSP_A_DPV_coding_region.seq__3 (frame 2 from 105 to 182)

SEQ ID NO:95: HSP_A_DPV_coding_region.seq__4 (frame 2 from 447 to 530)

SEQ ID NO:96: HSP_A_DPV_coding_region.seq__5 (frame 2 from 581 to 685)

SEQ ID NO:97: HSP_A_DPV_coding_region.seq__6 (frame 2 from 794 to 844)

SEQ ID NO:98: HSP_A_DPV_coding_region.seq__7 (frame 3 from 16 to 160)

SEQ ID NO:99: HSP_A_DPV_coding_region.seq__8 (frame 3 from 486 to 535)

SEQ ID NO:100: HSP_A_DPV_coding_region.seq__9 (frame 3 from 544 to 624)

SEQ ID NO:101: HSP_A_DPV_coding_region.seq__10 (frame −1 from 53 to 114)

SEQ ID NO:102: HSP_A_DPV_coding_region.seq__11 (frame −1 from 116 to 191)

SEQ ID NO:103: HSP_A_DPV_coding_region.seq__12 (frame −1 from 310 to 419)

SEQ ID NO:104: HSP_A_DPV_coding_region.seq__13 (frame −1 from 421 to 557)

SEQ ID NO:105: HSP_A_DPV_coding_region.seq__14 (frame −1 from 559 to 621)

SEQ ID NO:106: HSP_A_DPV_coding_region.seq__15 (frame −1 from 657 to 718)

SEQ ID NO:107: HSP_A_DPV_coding_region.seq__16 (frame −1 from 738 to 818)

SEQ ID NO:108: HSP_A_DPV_coding_region.seq__17 (frame −1 from 866 to 915)

SEQ ID NO:109: HSP_A_DPV_coding_region.seq__18 (frame −2 from 155 to 280)

SEQ ID NO:110: HSP_A_DPV_coding_region.seq__19 (frame −2 from 313 to 396)

SEQ ID NO:111: HSP_A_DPV_coding_region.seq__20 (frame −2 from 417 to 532)

SEQ ID NO:112: HSP_A_DPV_coding_region.seq__21 (frame −2 from 541 to 593)

SEQ ID NO:113: HSP_A_DPV_coding_region.seq__22 (frame −2 from 595 to 677)

SEQ ID NO:114: HSP_A_DPV_coding_region.seq__23 (frame −2 from 682 to 772)

SEQ ID NO:115: HSP_A_DPV_coding_region.seq__24 (frame −3 from 301 to 370)

SEQ ID NO:116: HSP_A_DPV_coding_region.seq__25 (frame −3 from 832 to 917)

SEQ ID NO:117: HSP__105_coding_region.seq__1 (frame 1 from 1 to 867)

SEQ ID NO:118: HSP__105_coding_region.seq__2 (frame 2 from 17 to 94)

SEQ ID NO:119: HSP__105_coding_region.seq__3 (frame 2 from 359 to 442)

SEQ ID NO:120: HSP__105_coding_region.seq__4 (frame 2 from 493 to 597)

SEQ ID NO:121: HSP__105_coding_region.seq__5 (frame 2 from 706 to 756)

SEQ ID NO:122: HSP__105_coding_region.seq__6 (frame 3 from 1 to 72)

SEQ ID NO:123: HSP__105_coding_region.seq__7 (frame 3 from 398 to 447)

SEQ ID NO:124: HSP__105_coding_region.seq__8 (frame 3 from 456 to 536)

SEQ ID NO:125: HSP__105_coding_region.seq__9 (frame − 1 from 53 to 114)

SEQ ID NO:126: HSP__105_coding region.seq__10 (frame − 1 from 116 to 191)

SEQ ID NO:127: HSP__105_coding_region.seq__11 (frame − 1 from 310 to 419)

SEQ ID NO:128: HSP__105_coding_region.seq__12 (frame − 1 from 421 to 557)

SEQ ID NO:129: HSP__105_coding_region.seq__13 (frame − 1 from 559 to 621)

SEQ ID NO:130: HSP__105_coding_region.seq__14 (frame − 1 from 657 to 718)

SEQ ID NO:131: HSP__105_coding_region.seq__15 (frame − 1 from 738 to 818)

SEQ ID NO:132: HSP__105_coding_region.seq__16 (frame − 2 from 155 to 280)

SEQ ID NO:133: HSP__105_coding_region.seq__17 (frame − 2 from 313 to 396)

SEQ ID NO:134: HSP__105_coding_region.seq__18 (frame − 2 from 417 to 532)

SEQ ID NO:135: HSP__105_coding_region.seq__19 (frame − 2 from 541 to 593)

SEQ ID NO:136: HSP__105_coding_region.seq__20 (frame − 2 from 595 to 677)

SEQ ID NO:137: HSP__105_coding_region.seq__21 (frame − 2 from 682 to 772)

SEQ ID NO:138: HSP__105_coding_region.seq__22 (frame − 3 from 301 to 370)

SEQ ID NO:139: GRP_B_DPV_coding_region.seq__1 (frame 1 from 1 to 1089)

SEQ ID NO:140: GRP_B_DPV_coding_region.seq__2 (frame 2 from 181 to 254)

SEQ ID NO:141: GRP_B_DPV_coding_region.seq__3 (frame 2 from 256 to 326)

SEQ ID NO:142: GRP_B_DPV_coding_region.seq__4 (frame 2 from 470 to 522)

SEQ ID NO:143: GRP_B_DPV_coding_region.seq__5 (frame 2 from 561 to 705)

SEQ ID NO:144: GRP_B_DPV_coding_region.seq__6 (frame 2 from 739 to 798)

SEQ ID NO:145: GRP_B_DPV_coding_region.seq__7 (frame 2 from 809 to 860)

SEQ ID NO:146: GRP_B_DPV_coding_region.seq__8 (frame 2 from 903 to 961)

SEQ ID NO:147: GRP_B_DPV_coding_region.seq__9 (frame 2 from 1025 to 1089)

SEQ ID NO:148: GRP_B_DPV_coding_region.seq__10 (frame 3 from 385 to 471)

SEQ ID NO:149: GRP_B_DPV_coding_region.seq__11 (frame 3 from 1015 to 1089)

SEQ ID NO:150: GRP_B_DPV_coding_region.seq__12 (frame −1 from 262 to 352)

SEQ ID NO:151: GRP_B_DPV_coding_region.seq__13 (frame −1 from 354 to 492)

SEQ ID NO:152: GRP_B_DPV_coding_region.seq__14 (frame −1 from 564 to 678)

SEQ ID NO:153: GRP_B_DPV_coding_region.seq__15 (frame −1 from 680 to 958)

SEQ ID NO:154: GRP_B_DPV_coding_region.seq__16 (frame −1 from 1004 to 1070)

SEQ ID NO:155: GRP_B_DPV_coding_region.seq__17 (frame −2 from 72 to 448)

SEQ ID NO:156: GRP_B_DPV_coding_region.seq__18 (frame −2 from 450 to 549)

SEQ ID NO:157: GRP_B_DPV_coding_region.seq__19 (frame −2 from 759 to 838)

SEQ ID NO:158: GRP_B_DPV_coding_region.seq__20 (frame −2 from 872 to 927)

SEQ ID NO:159: GRP_B_DPV_coding_region.seq__21 (frame −2 from 986 to 1083)
SEQ ID NO:160: GRP_B_DPV_coding_region.seq__22 (frame −3 from 1 to 51)
SEQ ID NO:161: GRP_B_DPV_coding_region.seq__23 (frame −3 from 78 to 141)
SEQ ID NO:162: GRP_B_DPV_coding_region.seq__24 (frame −3 from 338 to 441)
SEQ ID NO:163: GRP_B_DPV_coding_region.seq__25 (frame −3 from 687 to 743)
SEQ ID NO:164: GRP_B_coding_region.seq__1 (frame 1 from 1 to 1008)
SEQ ID NO:165: GRP_B_coding_region.seq__2 (frame 2 from 181 to 254)
SEQ ID NO:166: GRP_B_coding_region.seq__3 (frame 2 from 256 to 326)
SEQ ID NO:167: GRP_B_coding_region.seq__4 (frame 2 from 470 to 522)
SEQ ID NO:168: GRP_B_coding_region.seq__5 (frame 2 from 561 to 705)
SEQ ID NO:169: GRP_B_coding_region.seq__6 (frame 2 from 739 to 798)
SEQ ID NO:170: GRP_B_coding_region.seq__7 (frame 2 from 809 to 860)
SEQ ID NO:171: GRP_B_coding_region.seq__8 (frame 2 from 903 to 961)
SEQ ID NO:172: GRP_B_coding_region.seq__9 (frame 3 from 385 to 471)
SEQ ID NO:173: GRP_B_coding_region.seq__10 (frame −1 from 181 to 271)
SEQ ID NO:174: GRP_B_coding_region.seq__11 (frame −1 from 273 to 411)
SEQ ID NO:175: GRP_B_coding_region.seq__12 (frame −1 from 483 to 597)
SEQ ID NO:176: GRP_B_coding_region.seq__13 (frame −1 from 599 to 877)
SEQ ID NO:177: GRP_B_coding_region.seq__14 (frame −1 from 923 to 989)
SEQ ID NO:178: GRP_B_coding_region.seq__15 (frame −2 from 1 to 367)
SEQ ID NO:179: GRP_B_coding_region.seq__16 (frame −2 from 369 to 468)
SEQ ID NO:180: GRP_B_coding_region.seq__17 (frame −2 from 678 to 757)
SEQ ID NO:181: GRP_B_coding_region.seq__18 (frame −2 from 791 to 846)
SEQ ID NO:182: GRP_B_coding_region.seq__19 (frame −2 from 905 to 1002)
SEQ ID NO:183: GRP_B_coding_region.seq__20 (frame −3 from 1 to 60)
SEQ ID NO:184: GRP_B_coding_region.seq__21 (frame −3 from 257 to 360)
SEQ ID NO:185: GRP_B_coding_region.seq__22 (frame −3 from 606 to 662)

Example 20

Immunologically Enhancing Interactions Between HSPs and APCs

This example demonstrates the effects of HSPs on immunologically significant responses, including both innate and adaptive responses. The data presented in this example further support the advantages of using the stress protein complexes of the invention in vaccines and therapeutic methods.

Table 2 illustrates the stimulatory effects of hsp110 and grp170 on secretion of pro-inflammatory cytokines by dendritic cells (DCs).

TABLE 2

Hsp110 and grp170 stimulates secretion of pro-inflammatory cytokines by BMDC

| DC | IL-6 (pg/ml) | IL-12 (pg/ml) | TNF-α (pg/ml) |
|---|---|---|---|
| Control | 119 | 0 | 0 |
| hsp110 | 49038 | 883 | 1919 |
| grp170 | 46890 | 554 | 1333 |
| LPS | 36149 | 143 | 1371 |
| Luciferase | 540 | 0 | 0 |

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of producing a stress protein complex, the method comprising:

(a) transfecting a target cell that expresses an antigen of interest with a vector whose expression product is a hsp110 or grp170 polypeptide; and (b) maintaining the transfected target cell in conditions that permit formation of a stress protein complex;

wherein the stress protein complex comprises the hsp110 or grp170 polypeptide expressed by the vector, complexed with the antigen of interest by non-covalent interaction, and wherein the target cell is an infectious agent, and wherein the antigen of interest has been denatured by heating so as to enhance binding of the hsp110 or grp170 polypeptide to the antigen.

2. The method of claim 1, wherein the expression product of the vector is a hsp110 polypeptide.

3. The method of claim 1, wherein the expression product of the vector is a grp170 polypeptide.

4. The method of claim 2, wherein the hsp110 polypeptide comprises at least the peptide-binding domain of hsp110.

5. The method of claim 1, wherein the target cell is a bacterium.

6. The method of claim 5, wherein the bacterium is a mycobacterium.

7. The method of claim 1, further comprising isolating the stress protein complex from the target cell.

8. The method of claim 6, wherein the mycobacterium is *M. tuberculosis*.

9. A method of producing a stress protein complex, the method comprising:

(a) transfecting a target cell that expresses an antigen of interest with a vector whose expression product is a hsp110 or grp170 polypeptide; and (b) maintaining the transfected target cell in conditions that permit formation of a stress protein complex;

wherein the stress protein complex comprises the hsp110 or grp170 polypeptide expressed by the vector, complexed with the antigen of interest by non-covalent interaction, and wherein the antigen is associated with a mycobacterium.

10. The method of claim 9, wherein the antigen comprises a *M. tuberculosis* antigen.

11. The method of claim 10, wherein the *M. tuberculosis* antigen is Mtb8.4 or Mtb39.

12. The method of claim 9, wherein the antigen has been denatured by heating.

13. The method of claim 12, wherein the heating comprises incubation at a temperature of at least 43° C.

14. A method of producing a stress protein complex, the method comprising:

(a) transfecting a target cell that expresses an antigen of interest with a vector whose expression product is a grp170 polypeptide;

(b) maintaining the transfected target cell in conditions that permit formation of a stress protein complex; and (c) isolating the stress protein complex from the target cell;

wherein the stress protein complex comprises the grp170 polypeptide expressed by the vector, complexed with the antigen of interest by non-covalent interaction, and wherein the target cell is a cancer cell.

15. The method of claim 14, wherein the antigen of interest has been denatured so as to enhance binding of the grp170 polypeptide to the antigen.

16. The method of claim 15, wherein the antigen has been denatured by heating.

17. The method of claim 16, wherein the heating comprises incubation at a temperature of at least 43° C.

18. A method of producing a stress protein complex, the method comprising:

(a) transfecting a target cell that expresses an antigen of interest with a vector whose expression product is a grp170 polypeptide;

(b) maintaining the transfected target cell in conditions that permit formation of a stress protein complex; and (c) isolating the stress protein complex from the target cell;

wherein the stress protein complex comprises the grp170 polypeptide expressed by the vector, complexed with the antigen of interest by non-covalent interaction, and wherein the antigen is associated with a cancer.

19. The method of claim 18, wherein the antigen comprises a her-2/neu peptide.

20. The method of claim 19, wherein the her-2/neu peptide is derived from the extracellular domain of her-2/neu.

21. The method of claim 19, wherein the her-2/neu peptide is derived from the intracellular domain of her-2/neu.

22. The method of claim 18, wherein the antigen comprises a gp100 peptide.

23. A target cell that expresses an antigen of interest and that has been transfected with a vector whose expression product is a grp170 polypeptide;

wherein the target cell is a cancer cell; and wherein the target cell produces a stress protein complex that comprises the grp170 polypeptide expressed by the vector, complexed with the antigen of interest by non-covalent interaction.

24. A target cell that expresses an antigen of interest and that has been transfected with a vector whose expression product is a hsp110 or grp170 polypeptide;

wherein the target cell is a mycobacterium; and wherein the target cell produces a stress protein complex that comprises the hsp110 or grp170 polypeptide expressed by the vector, complexed with the antigen of interest by non-covalent interaction.

25. The target cell of claim 24, wherein the mycobacterium is *M. tuberculosis*.

26. A method of producing a stress protein complex, the method comprising:

(a) transfecting a target cell that expresses an antigen of interest with a vector whose expression product is a hsp110 polypeptide; and (b) maintaining the transfected target cell in conditions that permit formation of a stress protein complex;

wherein the stress protein complex comprises the hsp110 polypeptide expressed by the vector, complexed with the antigen of interest by non-covalent interaction, and wherein the antigen is associated with a fibrosarcoma, melanoma, breast cancer or a mycobacterium.

27. A method of producing a stress protein complex, the method comprising:

(a) transfecting a target cell that expresses an antigen of interest with a vector whose expression product is a grp170 polypeptide; and (b) maintaining the transfected target cell in conditions that permit formation of a stress protein complex;

wherein the stress protein complex comprises the grp170 polypeptide expressed by the vector, complexed with the antigen of interest by non-covalent interaction, and wherein the antigen is associated with a cancer or a mycobacterium.

28. A method of producing a stress protein complex, the method comprising:

(a) transfecting a target cell that expresses an antigen of interest with a vector whose expression product is a hsp110 polypeptide; and (b) maintaining the transfected target cell in conditions that permit formation of a stress protein complex;

wherein the stress protein complex comprises the hsp110 polypeptide expressed by the vector, complexed with the antigen of interest by non-covalent interaction, and wherein the target cell is an infectious agent, and wherein the antigen of interest has been denatured so as to enhance binding of the hsp110 polypeptide to the antigen.

29. A method of producing a stress protein complex, the method comprising:

(a) transfecting a target cell that expresses an antigen of interest with a vector whose expression product is a hsp110 or grp170 polypeptide; and (b) maintaining the transfected target cell in conditions that permit formation of a stress protein complex;

wherein the stress protein complex comprises the hsp110 or grp170 polypeptide expressed by the vector, complexed with the antigen of interest by non-covalent interaction, and wherein the target cell is a mycobacterium, and wherein the antigen of interest has been denatured so as to enhance binding of the hsp110 or grp170 polypeptide to the antigen.

30. A target cell that expresses an antigen of interest and that has been transfected with a vector whose expression product is a hsp110 or grp170 polypeptide;

wherein the target cell is a melanoma or breast cancer cell; and wherein the target cell produces a stress protein complex that comprises the hsp110 or grp170 polypeptide expressed by the vector, complexed with the antigen of interest by non-covalent interaction.

* * * * *